US010987430B2

(12) United States Patent
Shen et al.

(10) Patent No.: US 10,987,430 B2
(45) Date of Patent: Apr. 27, 2021

(54) DI-SUBSTITUTED MALEIC AMIDE LINKER FOR ANTIBODY DRUG CONJUGATING AND PREPARATION METHOD AND USE THEREOF

(71) Applicants: Mabwell (shanghai) Bioscience Co., Ltd., Shanghai (CN); Jiangsu Mabwell Health Pharmaceutical R&D Co., Ltd., Jiangsu (CN)

(72) Inventors: Jingkang Shen, Shanghai (CN); Tao Meng, Shanghai (CN); Lanping Ma, Shanghai (CN); Xin Wang, Shanghai (CN); Hongli Peng, Shanghai (CN); Yongliang Zhang, Shanghai (CN); Ting Yu, Shanghai (CN); Lin Chen, Shanghai (CN); Zhiyan Du, Shanghai (CN); Ying Wang, Shanghai (CN)

(73) Assignees: Mabwell (Shanghai) Bioscience Co., Ltd., Shanghai (CN); Jiangsu Mabwell Health Pharmaceutical R&D Co., Ltd., Jiangsu (CN)

( * ) Notice: Subject to any disclaimer, the term of this patent is extended or adjusted under 35 U.S.C. 154(b) by 0 days.

(21) Appl. No.: 16/464,211

(22) PCT Filed: Nov. 24, 2017

(86) PCT No.: PCT/CN2017/112958

§ 371 (c)(1),
(2) Date: May 24, 2019

(87) PCT Pub. No.: WO2018/095422

PCT Pub. Date: May 31, 2018

(65) Prior Publication Data

US 2019/0388555 A1 Dec. 26, 2019

(30) Foreign Application Priority Data

Nov. 25, 2016 (CN) ........................ 201611093699.6
Nov. 22, 2017 (CN) ........................ 201711169847.2

(51) Int. Cl.

| | |
|---|---|
| ***A61K 31/4015*** | (2006.01) |
| ***A61K 31/402*** | (2006.01) |
| ***A61K 31/4025*** | (2006.01) |
| ***A61K 31/5377*** | (2006.01) |
| ***C07D 207/456*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 413/12*** | (2006.01) |
| ***C07D 413/14*** | (2006.01) |
| ***A61K 47/68*** | (2017.01) |
| ***A61P 35/00*** | (2006.01) |
| ***A61K 31/195*** | (2006.01) |
| ***A61K 31/365*** | (2006.01) |
| ***A61K 31/40*** | (2006.01) |
| ***A61K 31/427*** | (2006.01) |
| ***A61K 31/437*** | (2006.01) |
| ***A61K 31/454*** | (2006.01) |
| ***A61K 31/496*** | (2006.01) |
| ***A61K 31/5383*** | (2006.01) |
| ***A61K 31/5517*** | (2006.01) |

(52) U.S. Cl.

CPC ........ *A61K 47/6889* (2017.08); *A61K 31/195* (2013.01); *A61K 31/365* (2013.01); *A61K 31/40* (2013.01); *A61K 31/427* (2013.01); *A61K 31/437* (2013.01); *A61K 31/454* (2013.01); *A61K 31/496* (2013.01); *A61K 31/5383* (2013.01); *A61K 31/5517* (2013.01); *A61K 47/6803* (2017.08); *A61P 35/00* (2018.01); *C07D 207/456* (2013.01); *C07D 401/14* (2013.01); *C07D 403/14* (2013.01); *C07D 413/14* (2013.01)

(58) Field of Classification Search

CPC .............. A61K 31/4015; A61K 31/402; A61K 31/4025; A61K 31/5377; C07D 207/456; C07D 401/12; C07D 401/14; C07D 403/12; C07D 403/14; C07D 413/12; C07D 413/14

USPC ........ 514/425, 427, 428, 422, 429; 548/549, 548/548, 547; 544/541; 546/278.7

See application file for complete search history.

(56) References Cited

FOREIGN PATENT DOCUMENTS

WO WO-2014197871 A2 * 12/2014 ......... A61K 47/6845

* cited by examiner

*Primary Examiner* — Joseph R Kosack
*Assistant Examiner* — Sagar Patel
(74) *Attorney, Agent, or Firm* — Lewis Roca Rothgerber Christie LLP

(57) ABSTRACT

Provided in the present invention are a di-substituted maleic amide linker conjugated to an antibody and a preparation method and use thereof. In particular, the present invention conjugates a strongly cytotoxic active substance to a biomacromolecule through a class of new linkers. The class of linkers can selectively act simultaneously with disulphide chains, so as to greatly improve the substance homogeneity of a conjugate. The conjugate prepared by the linker of the present invention has a high inhibitory activity on a cell strain expressing the corresponding antigen. Also provided is a method for preparing the above-mentioned conjugate and the use.

28 Claims, 21 Drawing Sheets a)
Pertuzumab
Naked antibody b)ADC-I c) ADC-II d) ADC-III e) ADC-IV f) ADC-V g) ADC-VI h) ADC-VII Trend chart of the secondary hydrolyzates produced

| | Day 0 | Day 2 | Day 4 | Day 7 |
|---|---|---|---|---|
| Control ADC | 61779.22 | 1335141.055 | 2876314.43 | 4805336.565 |
| ADC-I | 12978.85 | 513796.83 | 1204614.135 | 1933475.96 |
| ADC-VIII | 24559.086 | 679689.286 | 1561582.255 | 3061651.06 |
| ADC-II | 0 | 11842.82 | 34018.8 | 79192.725 |

DI-SUBSTITUTED MALEIC AMIDE LINKER FOR ANTIBODY DRUG CONJUGATING AND PREPARATION METHOD AND USE THEREOF

CROSS-REFERENCE TO RELATED APPLICATION(S)

This application is a U.S. National Phase patent application of International Application Number PCT/CN2017/112958, filed on Nov. 24, 2017, which claims priority of Chinese Patent Application Number 201611093699.6, filed on Nov. 25, 2016, and Chinese Patent Application Number 201711169847.2, filed on Nov. 22, 2017, the entire contents of all of which are incorporated herein by reference.

TECHNICAL FIELD

The present invention relates to a class of novel cross-linking agents for disulfide bond bridging, macromolecules, therapeutic conjugates and synthesis methods thereof. Specifically, the present invention relates to conjugates obtained by crosslinking cytotoxic drugs and macromolecules via substituted maleamide-based crosslinking agents for disulfide bond bridging, preparation methods and uses thereof.

BACKGROUND OF THE INVENTION

Improving delivery efficiency of drugs or other agents to target cells, tissues or tumors so as to achieve maximal efficacy and minimal toxicity has been the focus of considerable researches for many years. Though many attempts have been made to develop effective methods for importing biologically active molecules into cells, both in vivo and in vitro, none has proved to be entirely satisfactory. Optimizing the association of a drug with its intracellular target, while minimizing intercellular redistribution of the drug, e.g., to neighboring cells, is often difficult or inefficient.

Currently, most agents administered parenterally to patients are not targeted, resulting in systemic delivery of the agents to body cells and tissues where they are unnecessary. This may result in adverse drug side effects, and often limits the dose of a drug (e.g., chemotherapeutic (anti-cancer), cytotoxic, enzyme inhibitory, and antiviral or antimicrobial drugs) that can be administered. Although oral administration is considered to be a convenient and economical administration mode, by contrast, it shares the concern of non-specific toxicity to unaffected cells once the drug has been absorbed into the systemic circulation. Further complications involve problems with oral bioavailability and residence of drug in internal organs leading to additional exposure of the internal organs to the drug and hence risk of producing toxicities therein. Accordingly, a major goal of developing (drug delivery) methods has been specifically targeting agents to cells and tissues. The benefits of such treatment include avoiding the general physiological effects resulted from inappropriate delivery of the agents to other cells and tissues, such as uninfected cells. Intracellular targeting may be achieved by methods, compounds and formulations which allow accumulation or retention of biologically active agents, i.e. active metabolites, inside cells.

The use of antibody-drug conjugates (ADCs), i.e. immunoconjugates, for the local delivery of cytotoxic or cytostatic agents, i.e. drugs to kill or inhibit tumor cells in the treatment of cancers, allows targeted delivery of the drug moiety to tumors, and intracellular accumulation therein, while systemic administration of these unconjugated drugs may result in unacceptable level of toxicity to normal cells, along with tumor cells sought to be eliminated. Efforts to improve therapeutic index, i.e. maximal efficacy and minimal toxicity of ADCs have focused on the selectivity of polyclonal and monoclonal antibodies (mAbs) as well as drug-linking and drug-releasing properties.

As novel targeted therapeutic agents, antibody drug conjugates (ADCs) open a new era for the treatment of tumors. The basic design philosophy originated from the concepts of “Magic bullet” and “Drug targeting”, i.e. delivering drugs to the diseased areas via suitable carriers, which were firstly proposed by Paul Ehrlich in 1931. However, because of limited technologies of antibody and high potency cytotoxic drug, it was not until 2000 that the first ADC drug, Malotarg™ (for the treatment of acute myleocytic leukemia, AML), was approved by FDA. Recently, FDA approved two ADC drugs, Adcetris™ (2011) developed by Seattle Genetics for the treatment of Hodgkin lymphoma (HL)/anaplastic large cell lymphoma (ALCL), and Kadcyla™ (2013) developed by Genentech for the treatment of breast cancer, indicating that a rapid development stage of ADCs used for tumor treatment is coming.

An antibody drug conjugate is generally composed of three parts: antibody or antibody-like ligand, small molecule drug, and linker that conjugates the drug to the ligand. In structures of antibody drug conjugates that have entered clinical trial stage, highly-potent cytotoxic drugs are generally linked, via linkers, to lysine residues on the surface of the ligands or cysteine residues (obtained through partial reduction of inter-chain disulfide bonds) in the hinge region of the antibodies, and the optimal drug to antibody ratio (DAR) is 2-4. The large number of lysine residues (more than 80) on the surface of the antibody and a non-selective conjugation mode lead to an uncertainty of conjugation sites and numbers, which in turn leads to heterogeneity of antibody drug conjugates produced. For example, T-DM1 (with an average DAR of 3.5) has a DAR distribution ranging from 0 to 8. Similarly, although an antibody contains only four inter-chain disulfide bonds in its hinge region, which must be partially reduced to achieve an optimal average DAR 2-4. As general reducing agents (DTT, TCEP, etc) cannot selectively reduce inter-chain disulfide bonds, conjugates obtained are not homogeneous products, but composed of different components with DARs of 0, 2, 4, 6 and 8. And even for a conjugate with a specific DAR value, it may be composed of isomers due to different conjugation sites. The heterogeneity of ADC products may ultimately lead to different PK, efficacy, and toxicity properties for different conjugates. For example, conjugates with higher DAR are cleared more rapidly and may result in more toxicity in the body.

To overcome the problem of high heterogeneity with antibody drug conjugates, site-directed conjugation technologies which control the conjugation between the antibodies and drugs both in sites and number have been hot spots recently. Despite controllable sites and number of conjugated drugs can be achieved by the technologies, the antibodies or proteins used are all obtained by gene recombination. As for gene recombination technology, substantial work and precise design are needed to screen antibodies or proteins with favorable sites for drug conjugation or pegylation. However, antibodies/proteins upon site-directed modification obtained through current gene recombination technologies have low expression levels. In this regard, a large-scale preparation and production may be time consuming and the cost of research and development and final industrialization is very high. What's more, additional work on the modified antibodies/proteins is needed to verify their efficacy and safety in vivo.

Considering the above problems in the conjugation technologies, achieving site-directed conjugation on current antibodies via simple chemistry methods may save a lot of manpower, material and financial resources and thus is more attractive. Existing related studies include: a conjugation technology reported by POLYTHERICS LIMITED in patent application No. CN200480019814.4; technical solutions reported in international publication No. WO2014197871A2 filed by Igenica Biotherapeutics; technical solutions reported in patent application No. CN201380025774.3 filed by CONCORTIS BIOSYSTEMS CORP; technical solutions reported in patent application No. CN201310025021.4 filed by NEWBIO THERAPEUTICS, INC.; and the like. However, the technologies described above have many defects as follows: synthesis routes for coupling reagents are too long, chemical stability of coupling reagents is poor, electropherograms of the obtained antibody conjugates are messy, indicating that side reactions may exist during the coupling process, and exchanging of sulfhydryl groups (a reverse Michael addition reaction) in the circulation of the body is not avoided by those available solutions.

Therefore, there is still a need for highly efficient, simple, and practical chemical conjugation methods which can achieve the purpose of site-directed conjugation and improve the stability, safety and other properties of the obtained antibody-drug conjugates simultaneously.

SUMMARY OF THE INVENTION

One purpose of the present invention is to provide a linker which can simply couple with most antibodies.

In the first aspect, the present invention provides a substituted maleamide linker as shown in Formula Ia, (Ia)

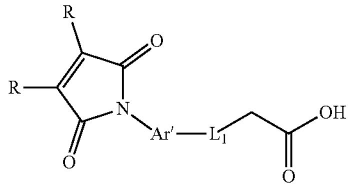

wherein, R is X or ArS—,

X is selected from halogen, preferably bromine or iodine;

Ar is selected from the group consisting of substituted or unsubstituted $C_6$-$C_{10}$ aryl and substituted or unsubstituted 5-12 membered heteroaryl; preferably, Ar is selected from the group consisting of phenyl, halogen-substituted phenyl, $C_1$-$C_4$ alkylphenyl, $C_1$-$C_4$ alkoxyphenyl, 2-pyridyl, 2-pyrimidinyl, 1-methylimidazol-2-yl, and

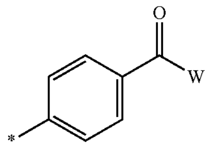

in which W is amido $R^1$ attached to carbonyl, and $R^1$ is selected from the group consisting of —$NH_2$,

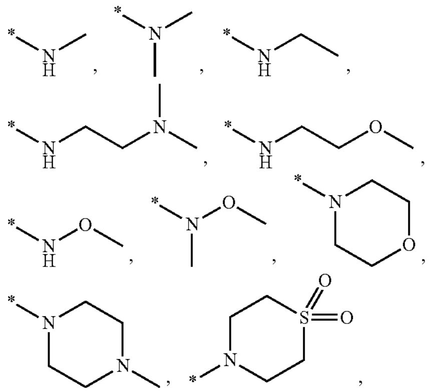

and the like; wherein $C_1$-$C_4$ alkylphenyl is preferably 4-methylphenyl; and wherein $C_1$-$C_4$ alkoxyphenyl is preferably 4-methoxylphenyl.

Ar' is selected from the group consisting of substituted or unsubstituted $C_6$-$C_{10}$ arylene, and substituted or unsubstituted 5-12 membered heteroarylene; preferably, Ar' is selected from the group consisting of substituted or unsubstituted phenylene and substituted or unsubstituted pyridyl; and the substitution means that hydrogen atom on the group is substituted by one or more substituents selected from the group consisting of: halogen, $C_1$-$C_4$ alkyl, $C_1$-$C_4$ alkoxy, trifluoromethyl, cyano, amide group, and the like.

$L_1$ is —$O(CH_2CH_2O)_n$— linked to Ar', in which n is any integer between 1 and 20, preferably any integer between 1 and 10.

In another preferred embodiment, the linker has a structure selected from the group consisting of:

Formula 1

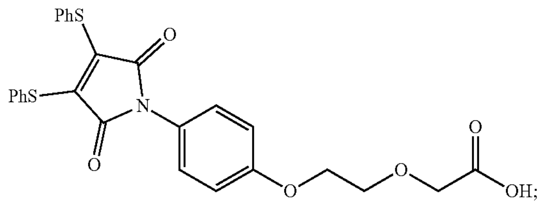

Formula 2

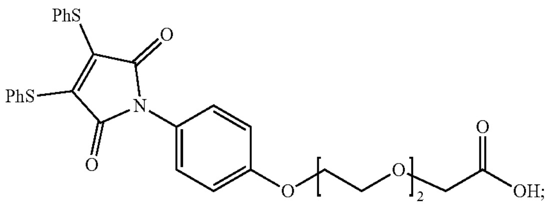

-continued
Formula 3
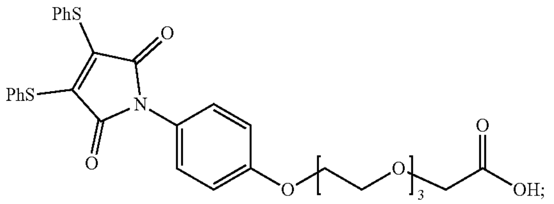
Formula 4
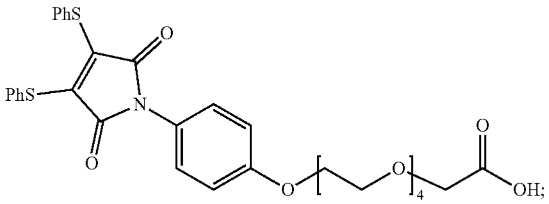
Formula 5
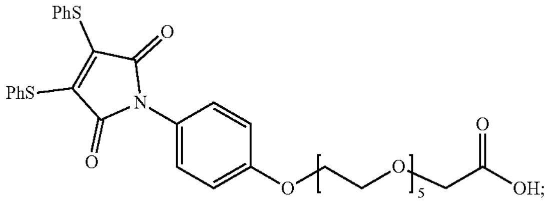
Formula 6
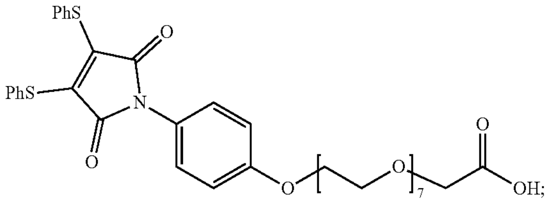
Formula 7
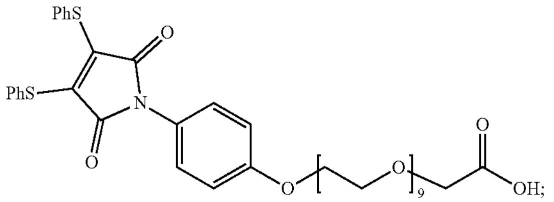
Formula 8
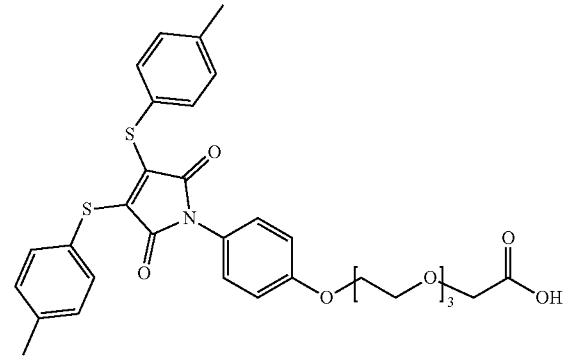
;
Formula 9
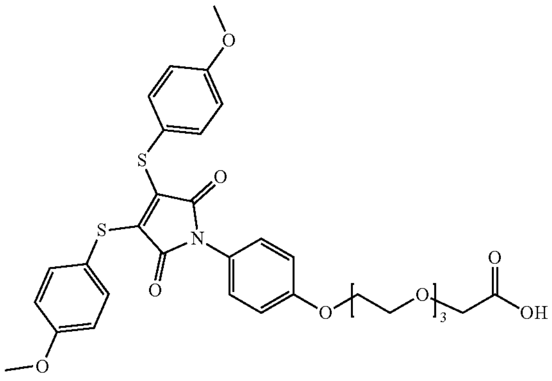
;
Formula 10
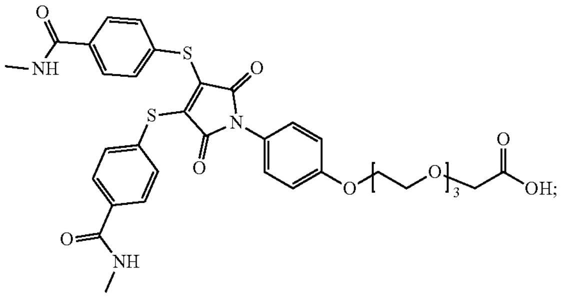
Formula 11
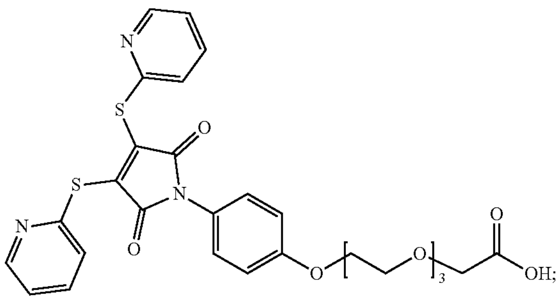
Formula 12
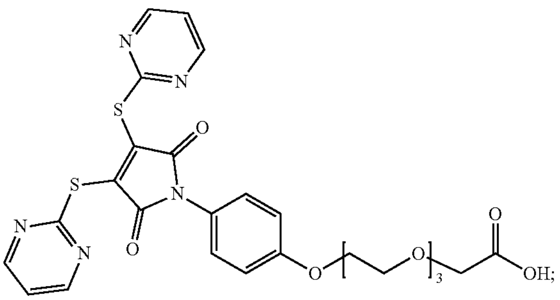

-continued
Formula 13
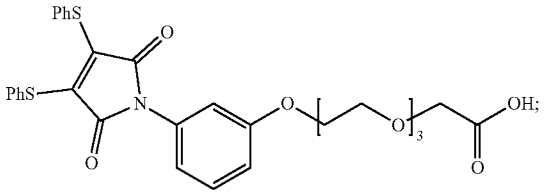
Formula 14
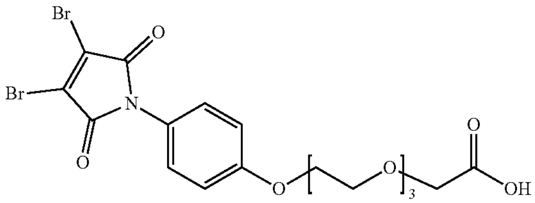
;
Formula 15
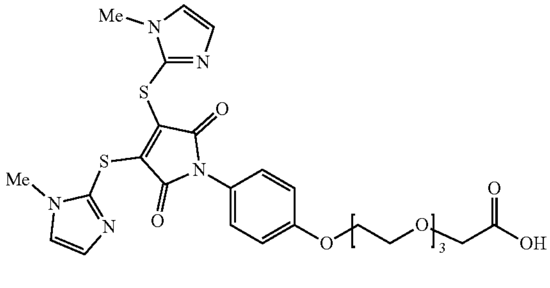
;
Formula 16
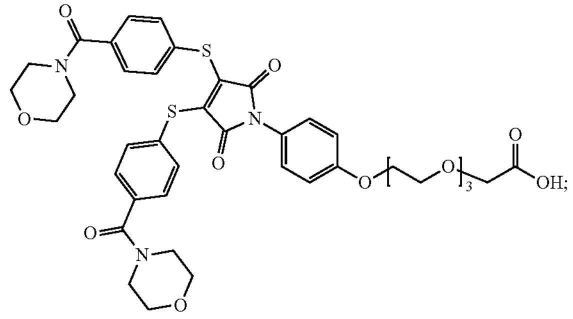
Formula 17
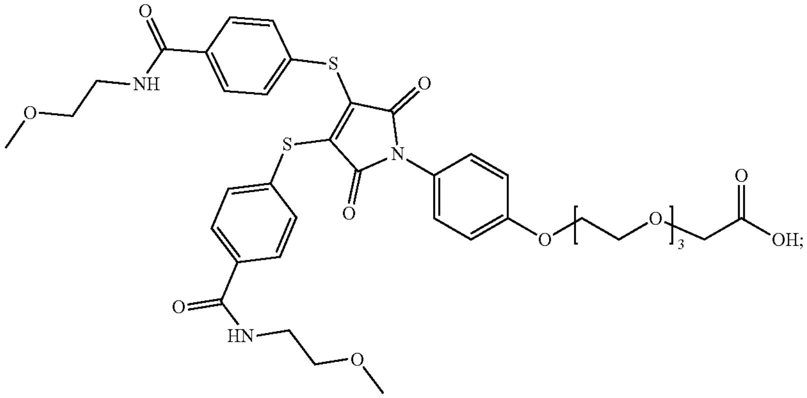
Formula 18
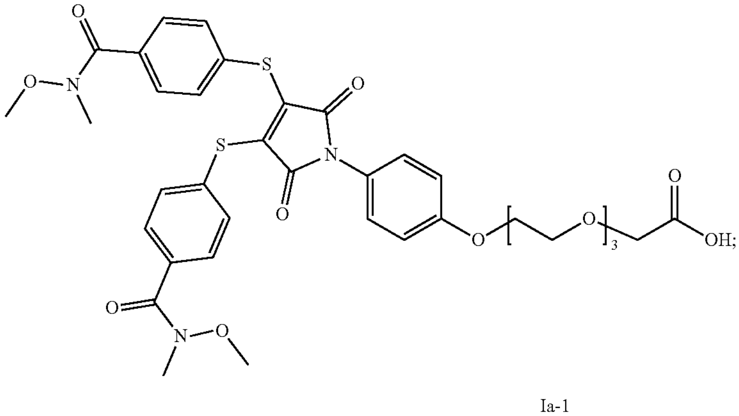
Ia-1
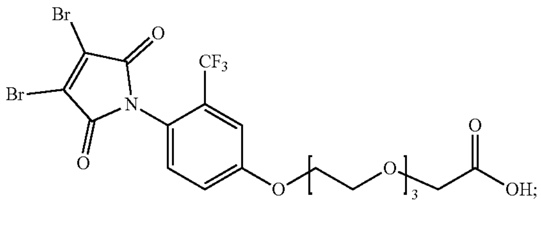
Ia-2
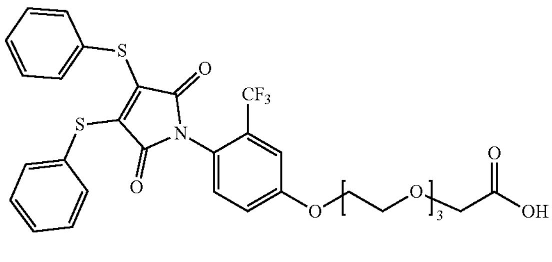
;

-continued
Ia-3
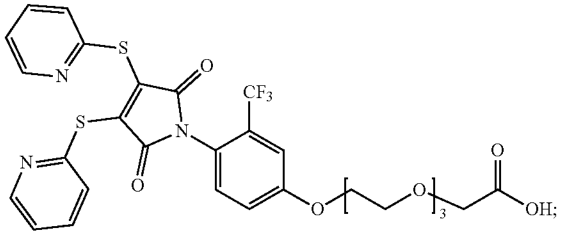
Ia-4
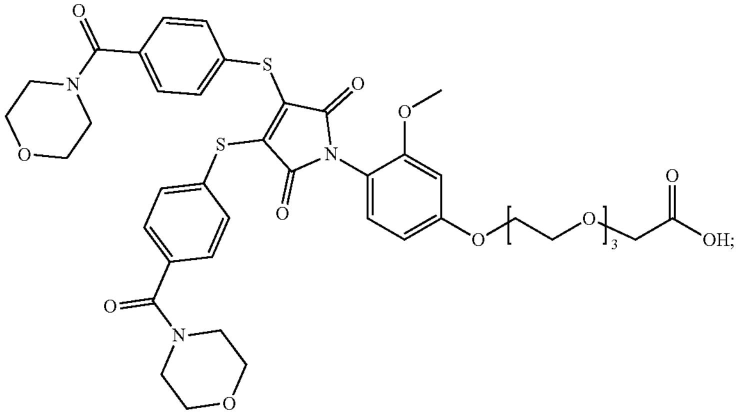
Ia-5
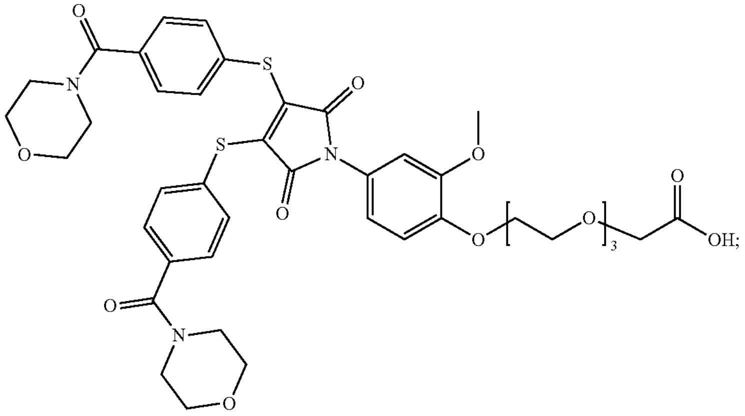
Ia-6
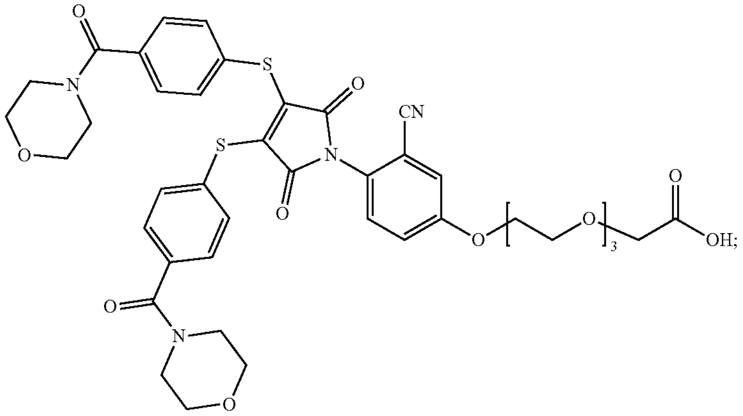

-continued
Ia-7
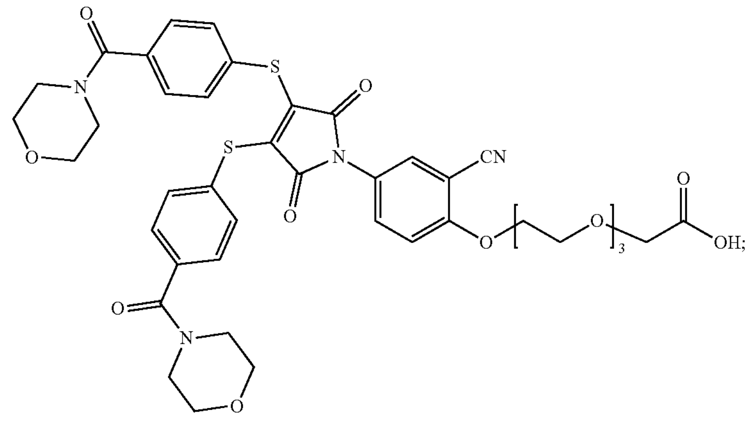
Ia-8
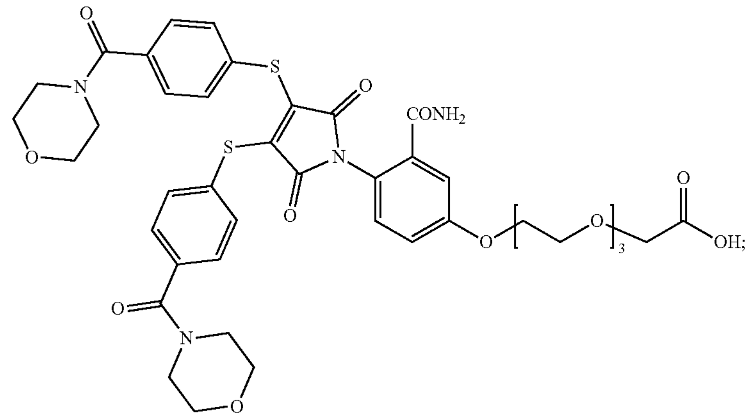
Ia-9
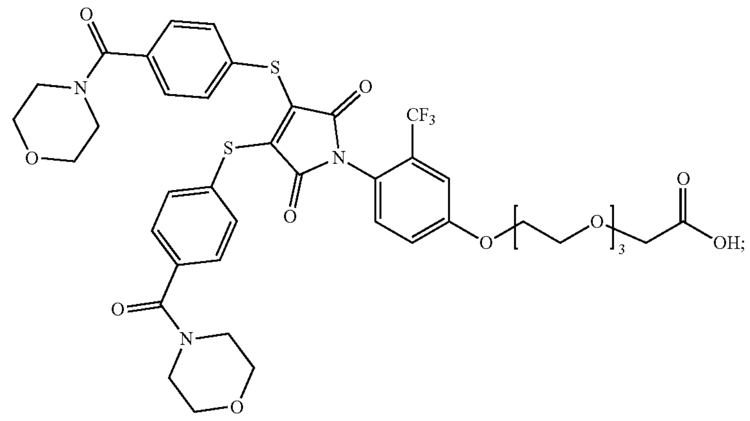

-continued
Ia-10
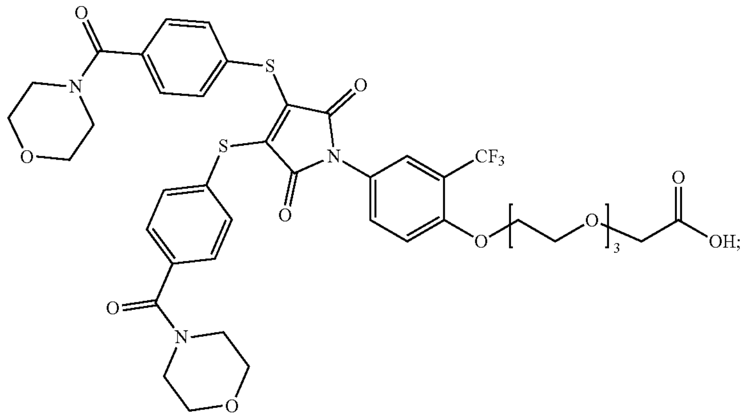
Ia-11
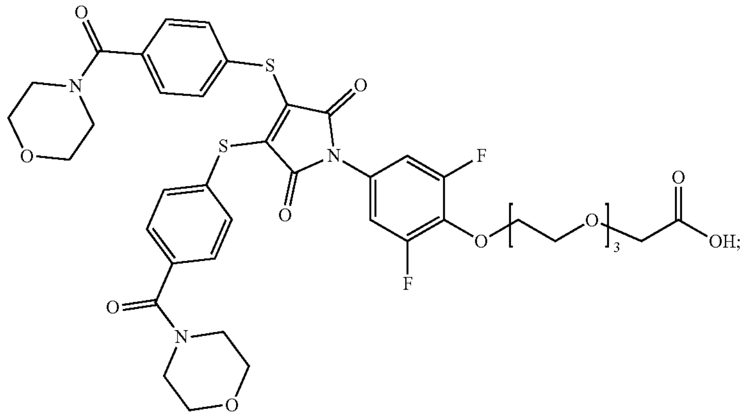
Ia-12
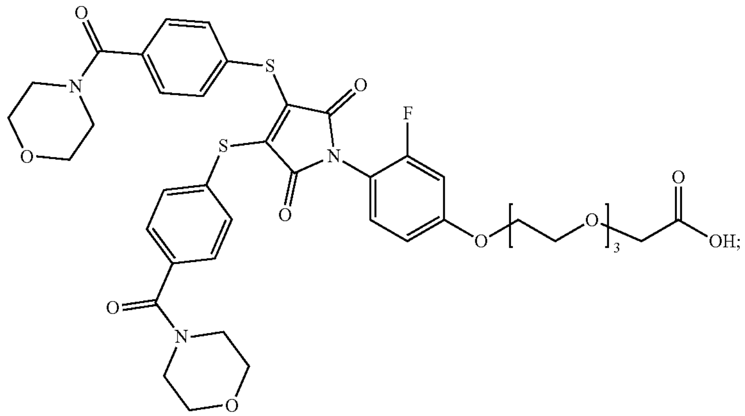

-continued
Ia-13
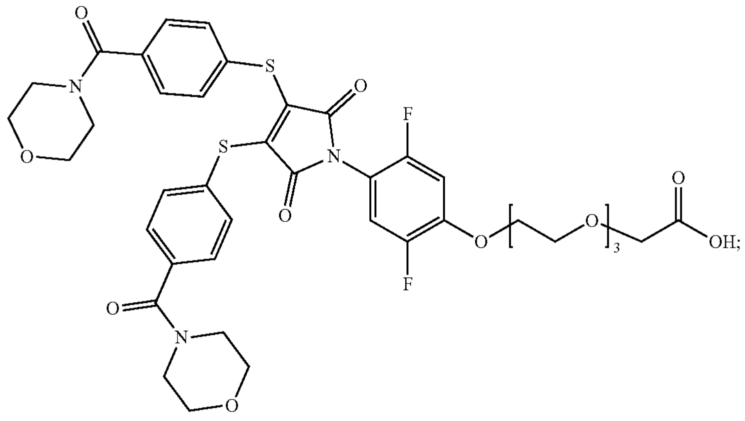
Ia-14
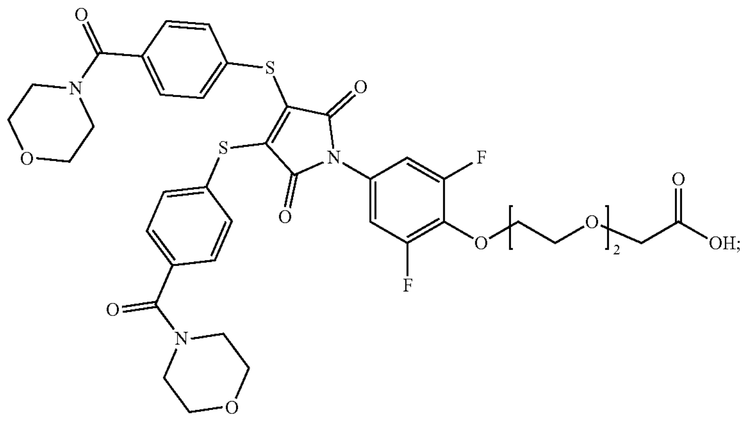
Ia-15
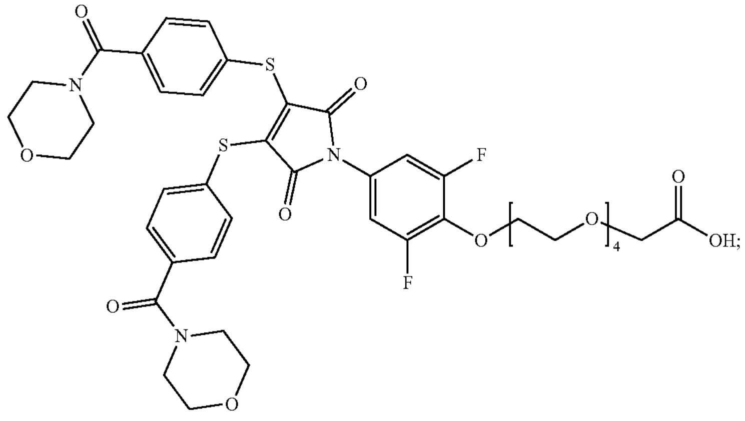

-continued
Ia-16
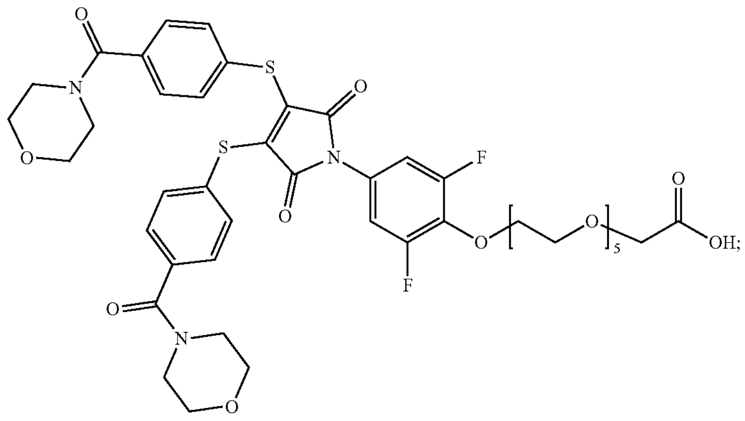
Ia-17
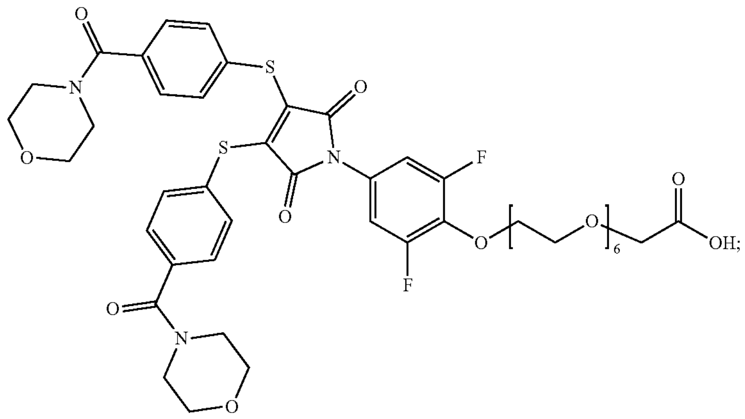
Ia-18
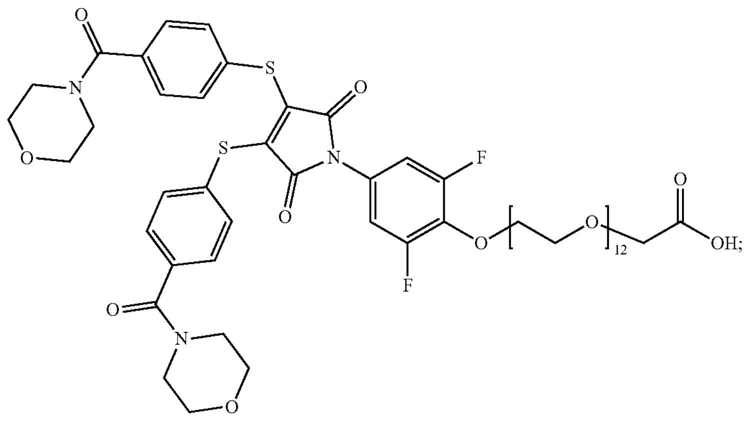

-continued
Ia-19
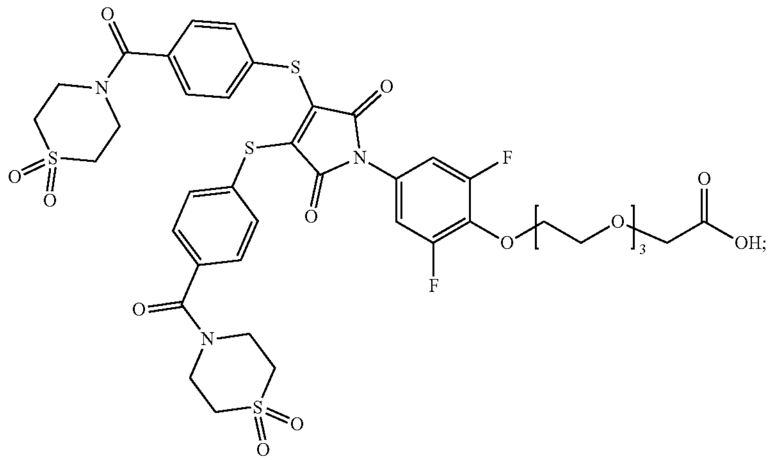
Ia-20
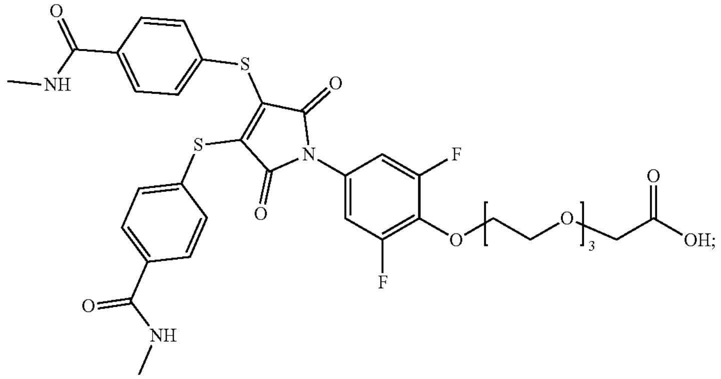
Ia-21
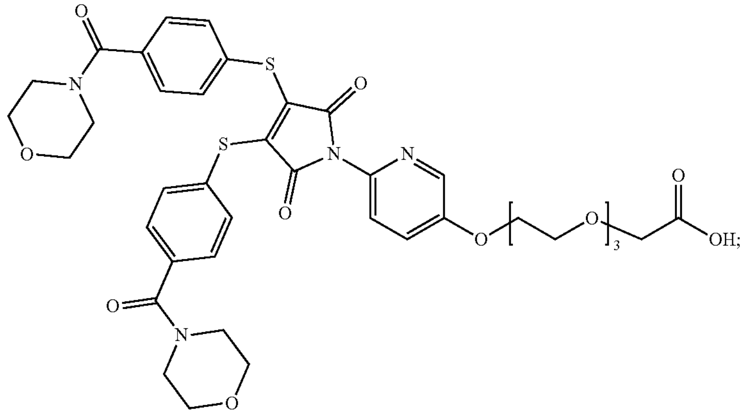

-continued

Ia-22

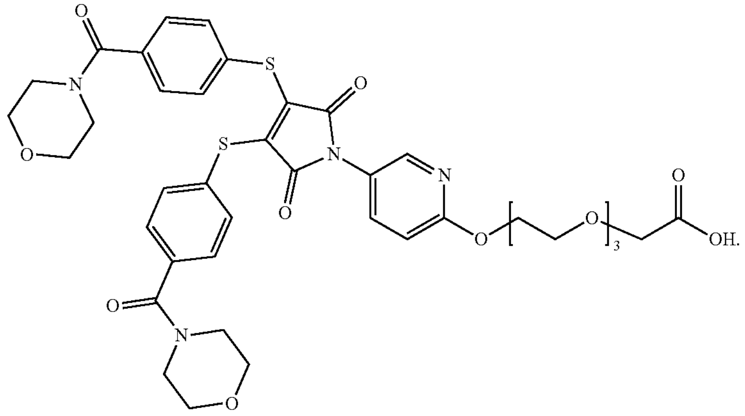

In the second aspect, the present invention provides a substituted maleamide linker-drug conjugate containing the linker as shown in Formula Ia described in the first aspect, or a pharmaceutically acceptable salt or solvate thereof, the conjugate having a structure as shown in Formula Ib:

(Ib)

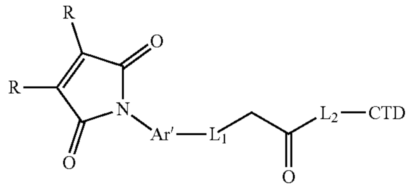

wherein R, Ar', and $L_1$ are defined as above;

$L_2$ is a chemical bond or has a structure of AA-PAB, in which AA is a dipeptide or tripeptide fragment (i.e. a fragment formed by linking 2-3 amino acids through peptide bonds), preferably, AA is selected from the group consisting of Val-Cit (valine-citrulline), Val-Ala (valine-glycine), Phe-Lys (phenylalanine-lysine), Ala-Ala-Asn (glycine-glycine-asparagine), D-Ala-Phe-Lys (D-glycine-phenylalanine-lysine), and the like; and PAB is p-aminobenzylcarbamoyl.

CTD is a cytotoxic small molecule drug and/or a drug for treating autoimmune disease and/or inflammation, which is bonded to $L_2$ via an amide bond; preferably, CTD is selected from the group consisting of tubulin inhibitor, topoisomerase inhibitor and DNA binding agent; more preferably, the tubulin inhibitor is selected from the group consisting of maytansine or its derivatives, Monomethyl auristatin E, Monomethylauristatin F, Monomethyl Dolastatin 10, Tubulysin or its derivatives, Cryptophycin or its derivatives, and Taltobulin; preferably, the DNA binding agent is selected from the group consisting of PBD or its derivatives and duocarmycin or its derivatives; preferably, the topoisomerase inhibitor is selected from the group consisting of metabolite PNU-159682 of Doxorubicin or its derivatives, metabolite SN38 of irinotecan or its derivatives, and Exatecan.

More specifically, the CTD has a molecular structure selected from the group consisting of D1-D13 and D13' as follows:

D1

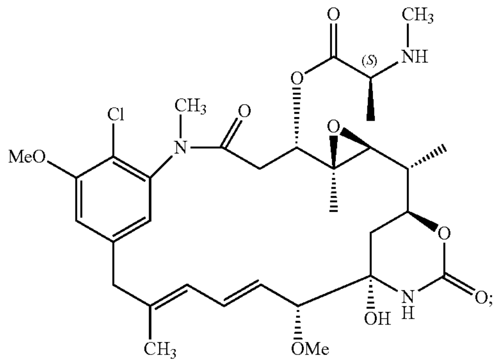

-continued
D2
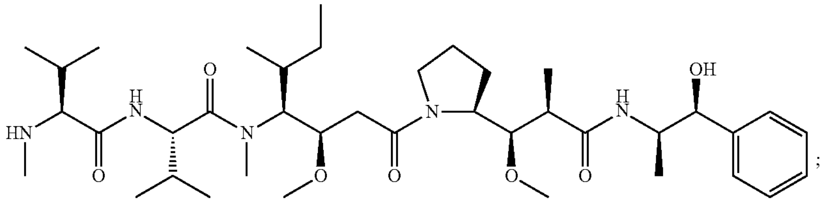
D3
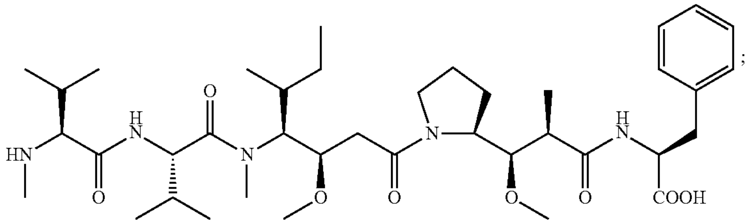
D4
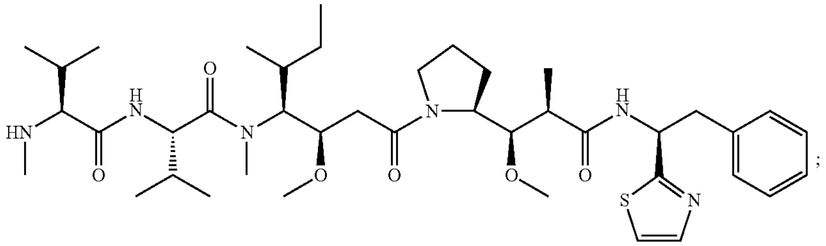
D5
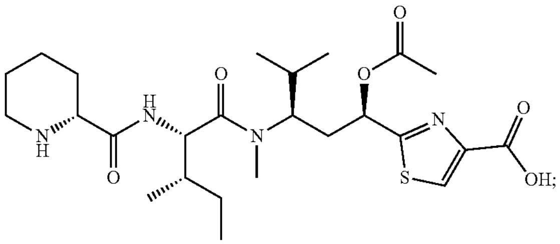
D6
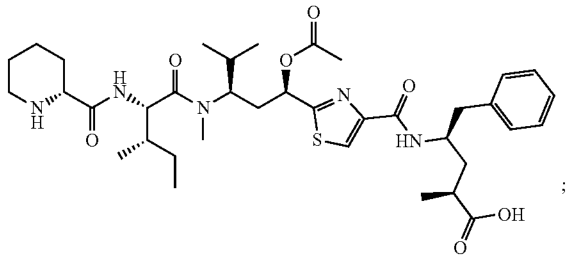
D7
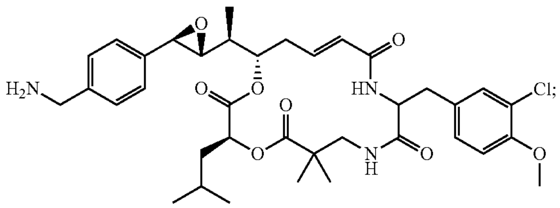
D8
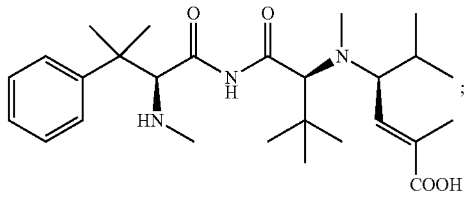
D9
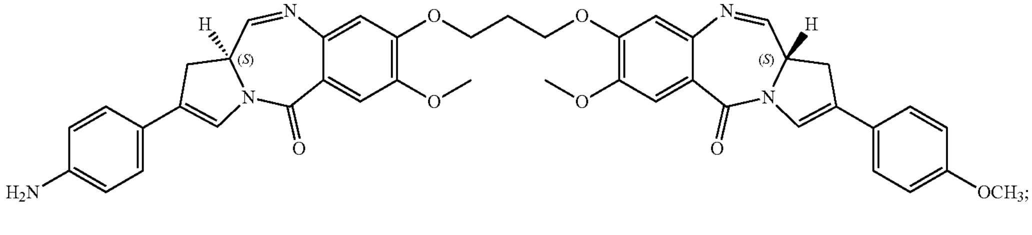

-continued
D10
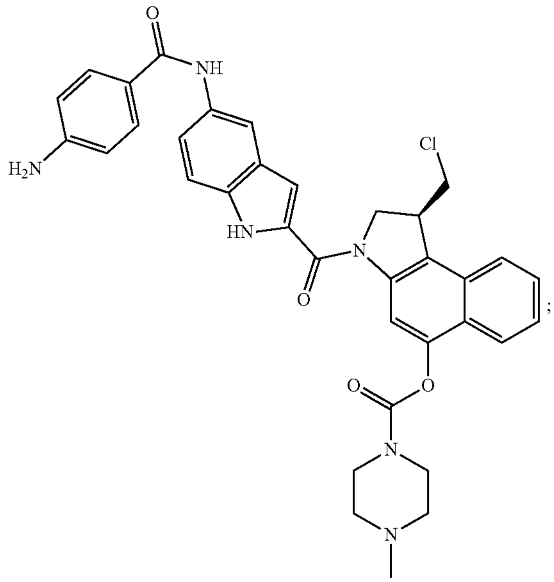
;
D11
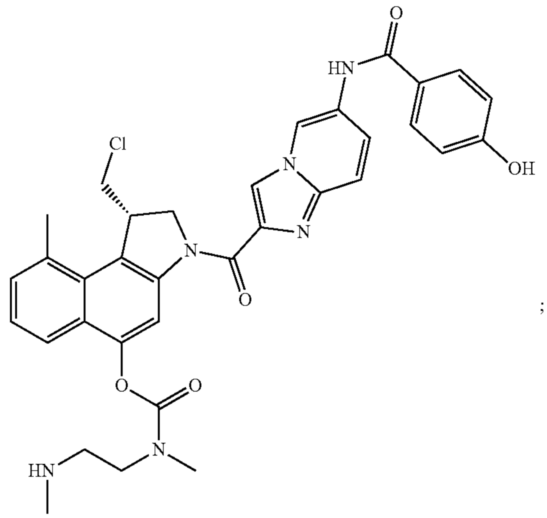
;
D12
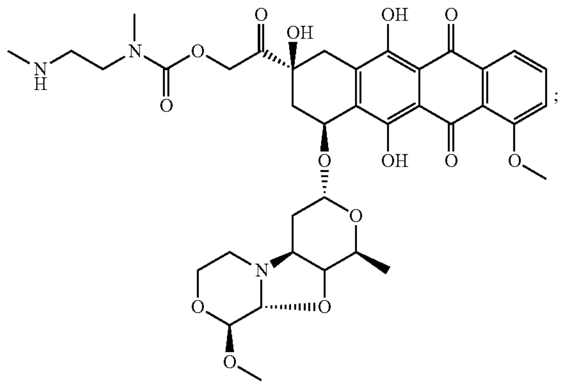
;
D13
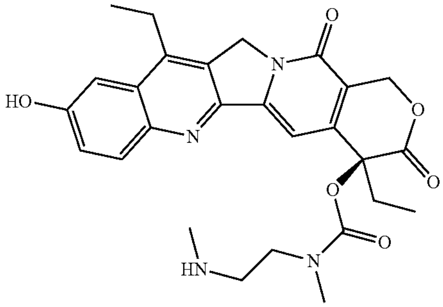
D13′
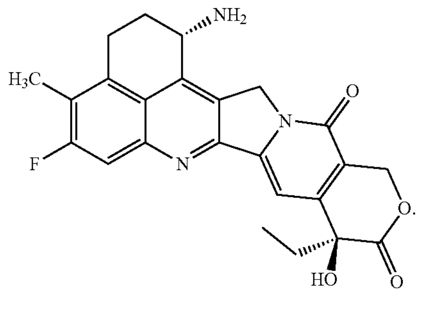

In another preferred embodiment, the conjugate as shown in Formula Ib is selected from the group consisting of:
Formula 19
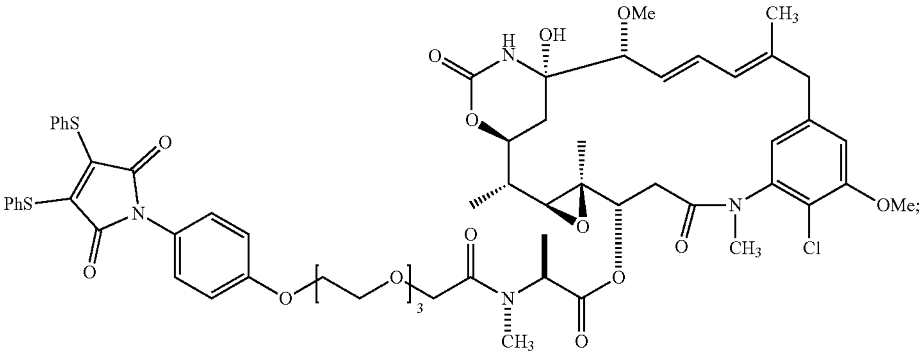
Formula 20
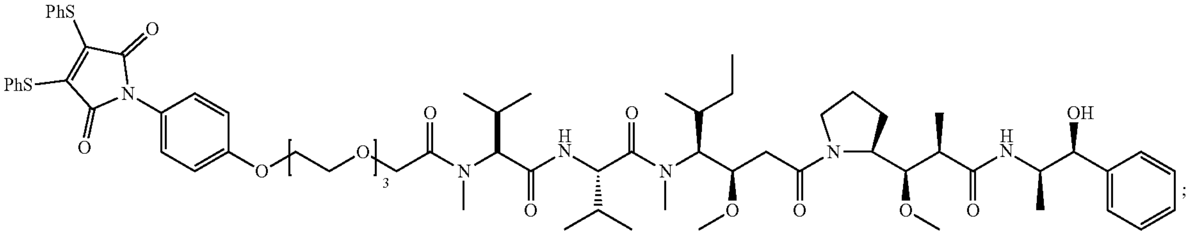
Formula 21
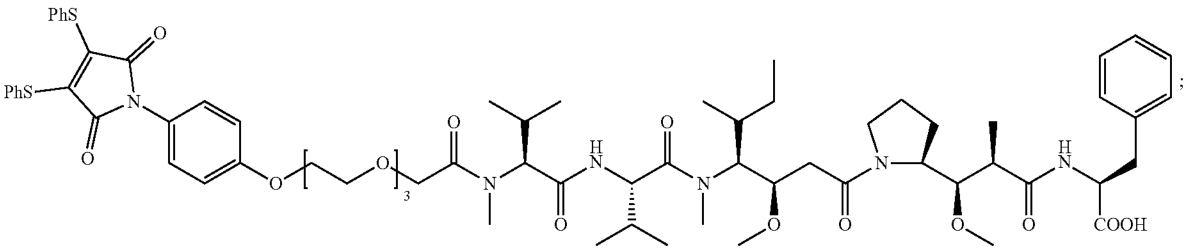
Formula 22
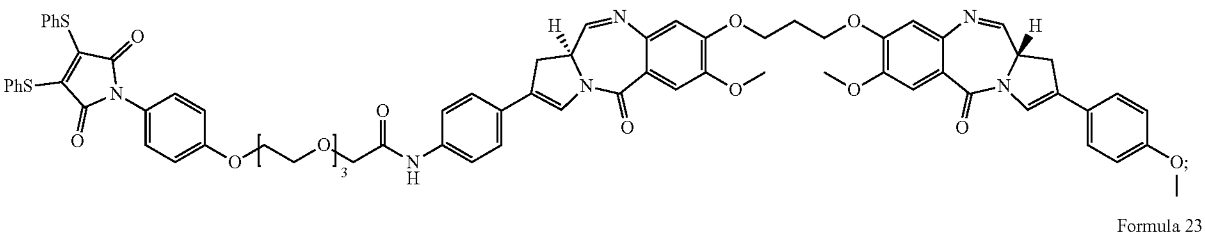
Formula 23
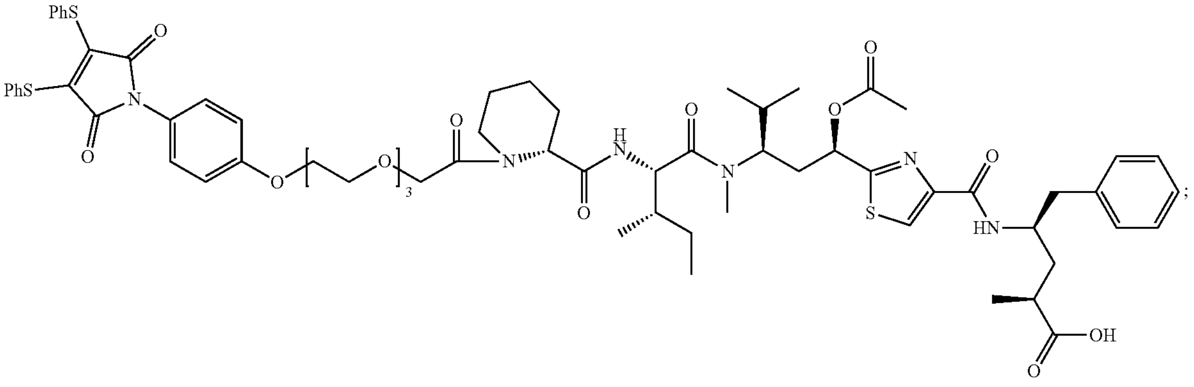

-continued
Formula 24
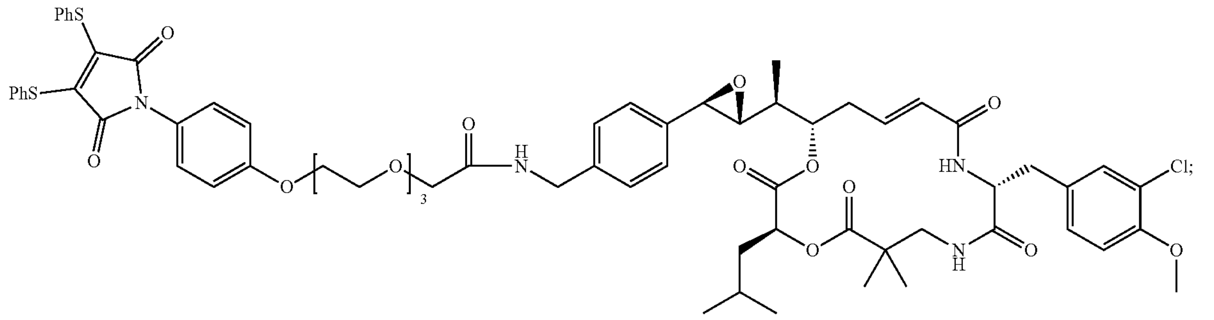
Formula 25
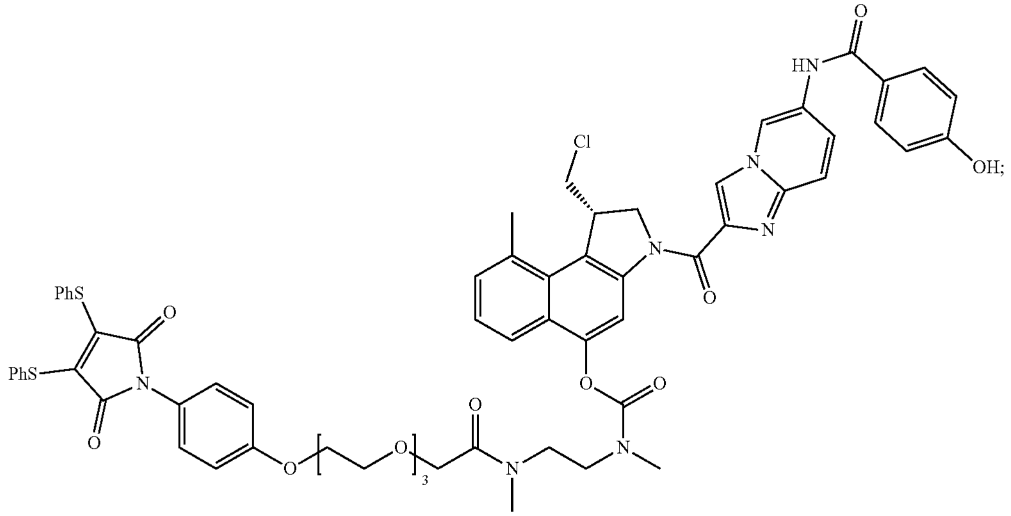
Formula 26
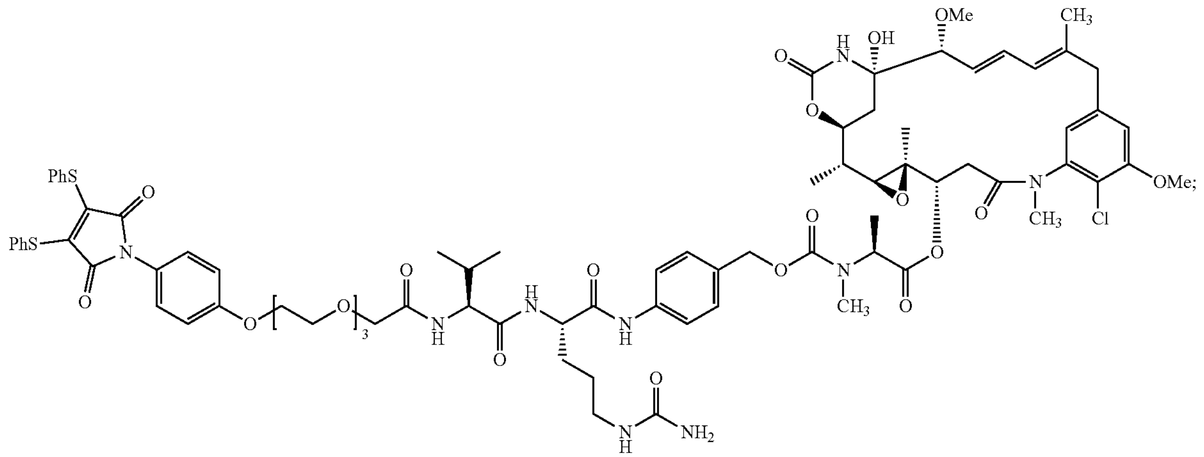
Formula 27
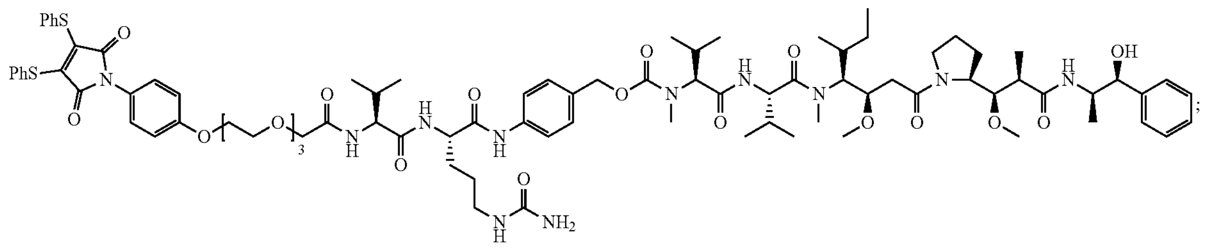

-continued
Formula 28
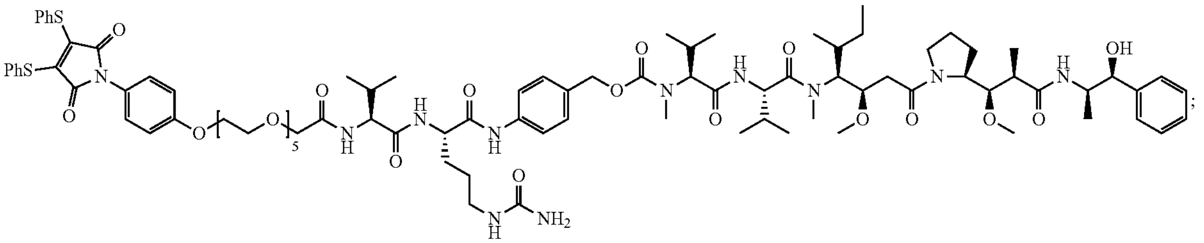
Formula 29
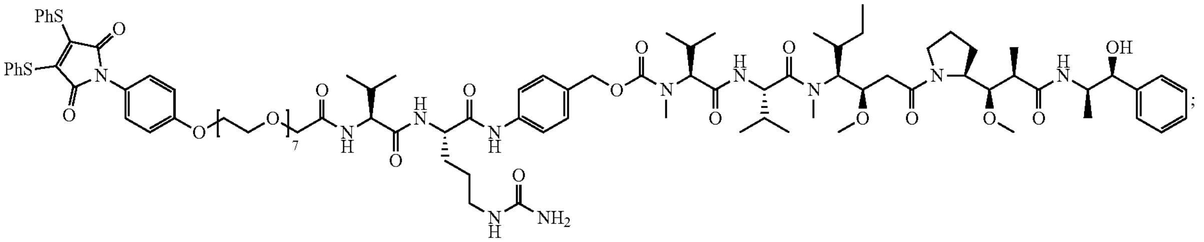
Formula 30
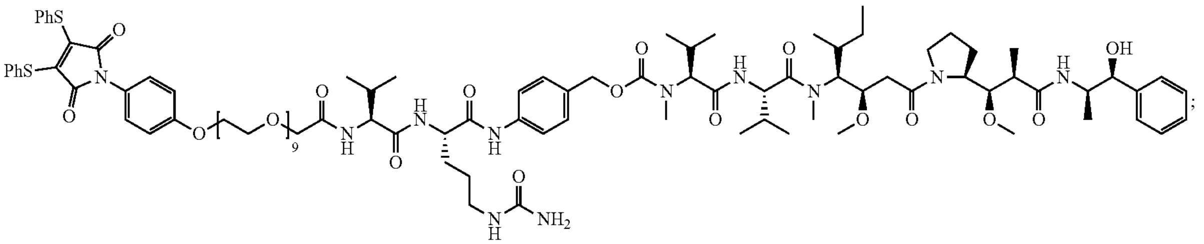
Formula 31
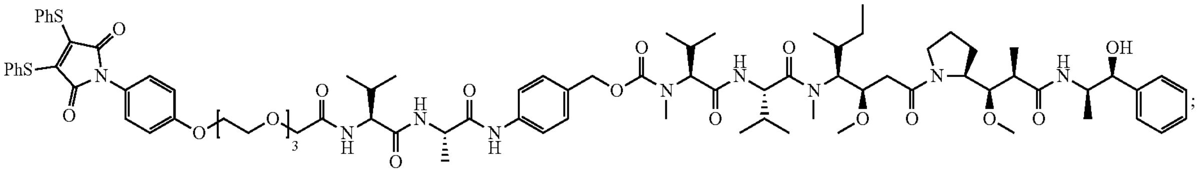
Formula 32
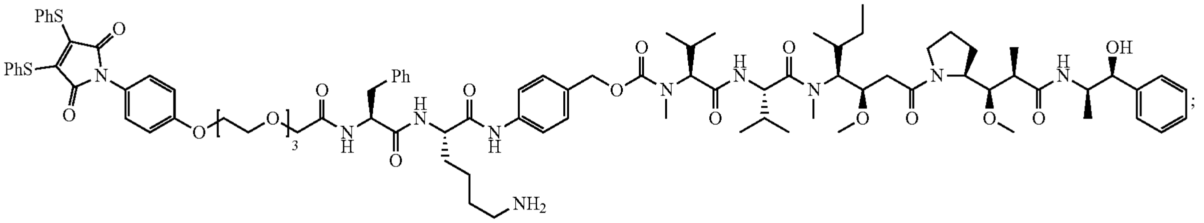
Formula 33
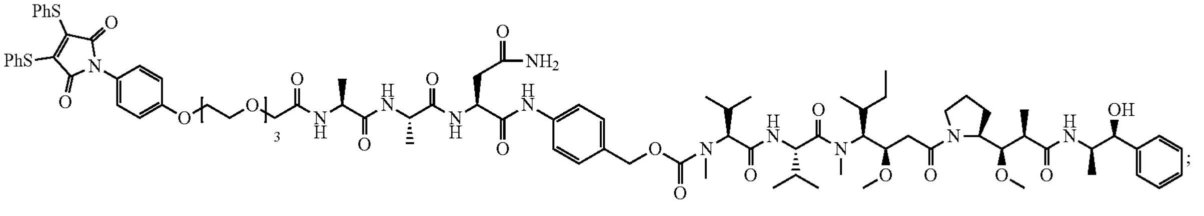

-continued
Formula 34
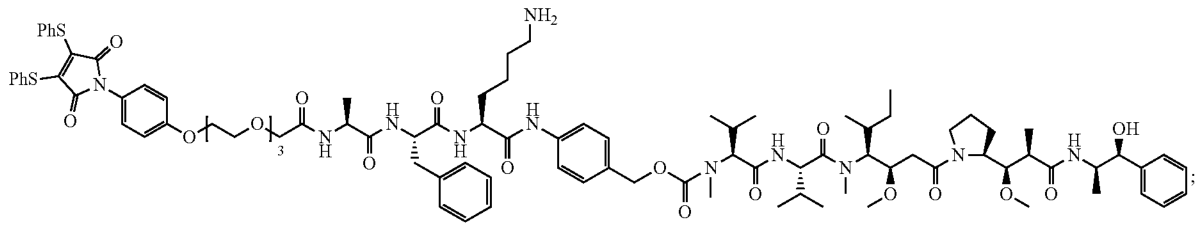
Formula 35
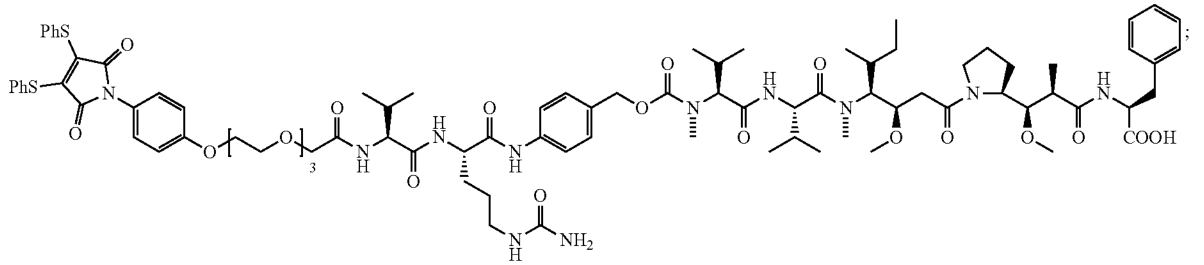
Formula 36
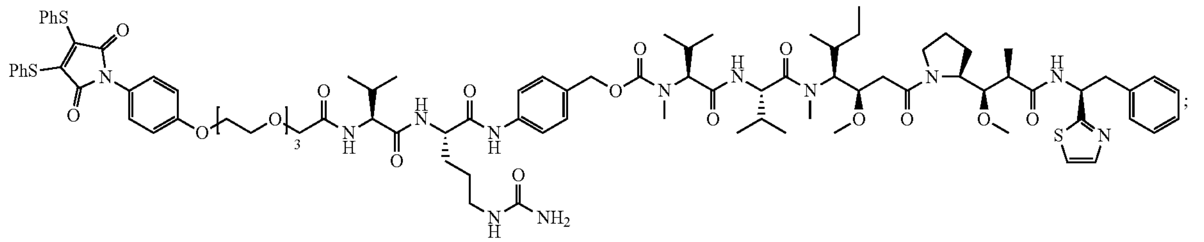
Formula 37
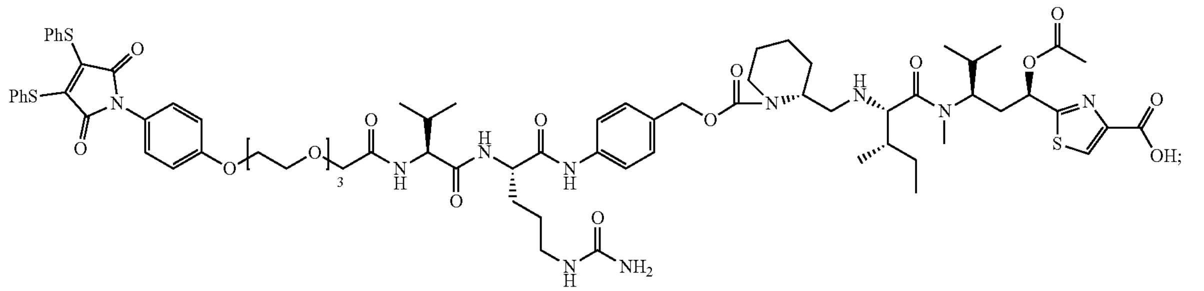
Formula 38
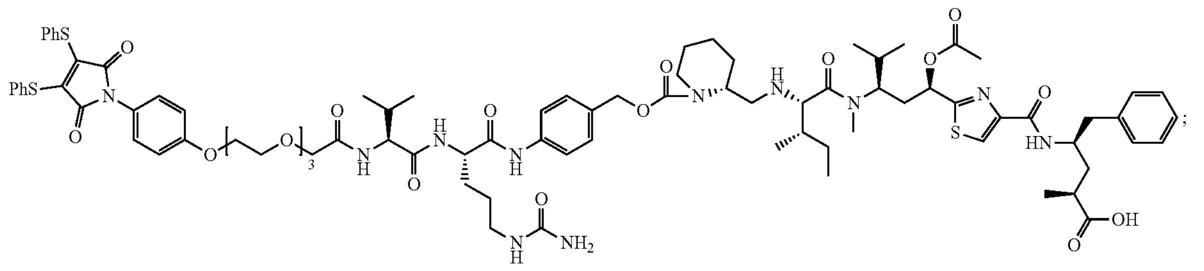

-continued
Formula 39
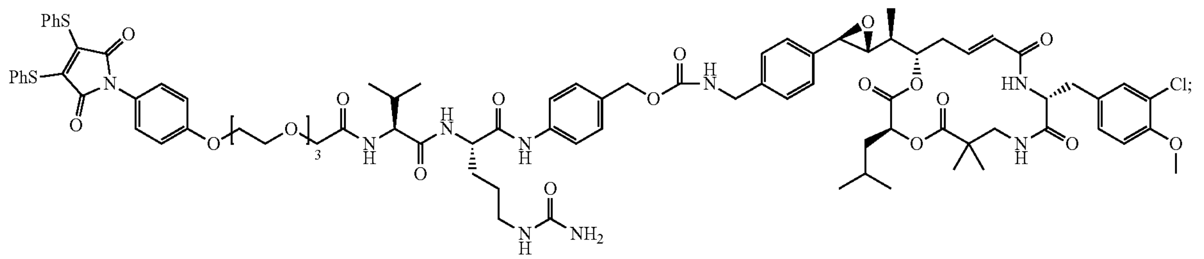
Formula 40
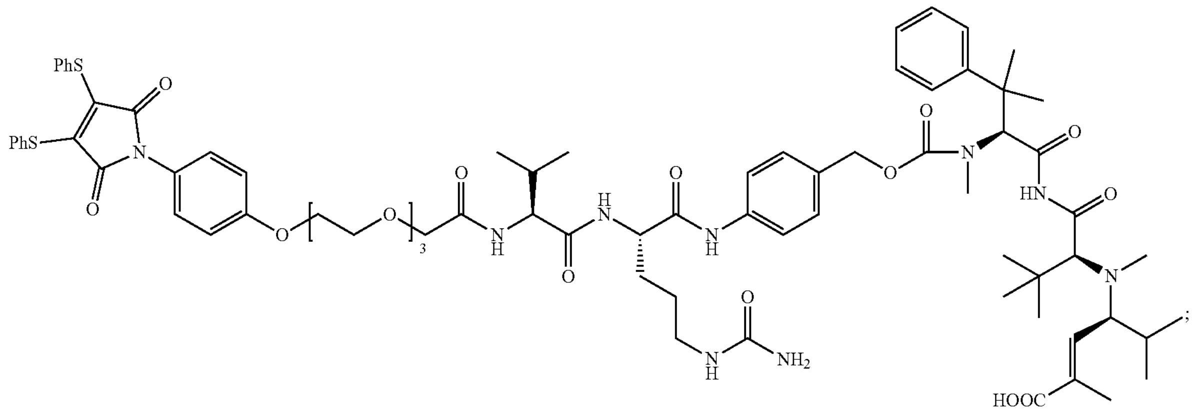
Formula 41
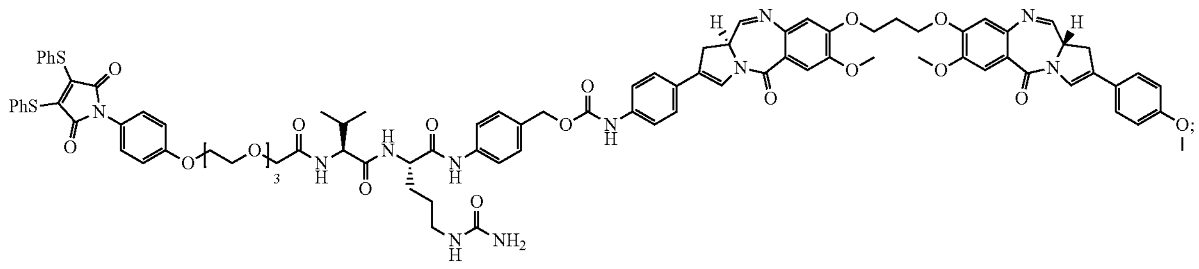
Formula 42
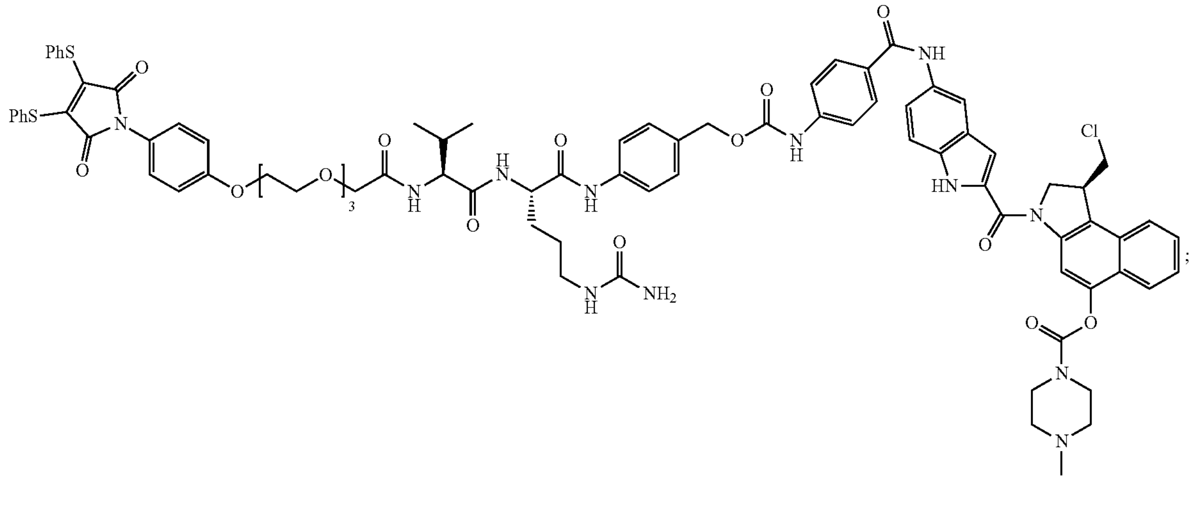

-continued
Formula 43
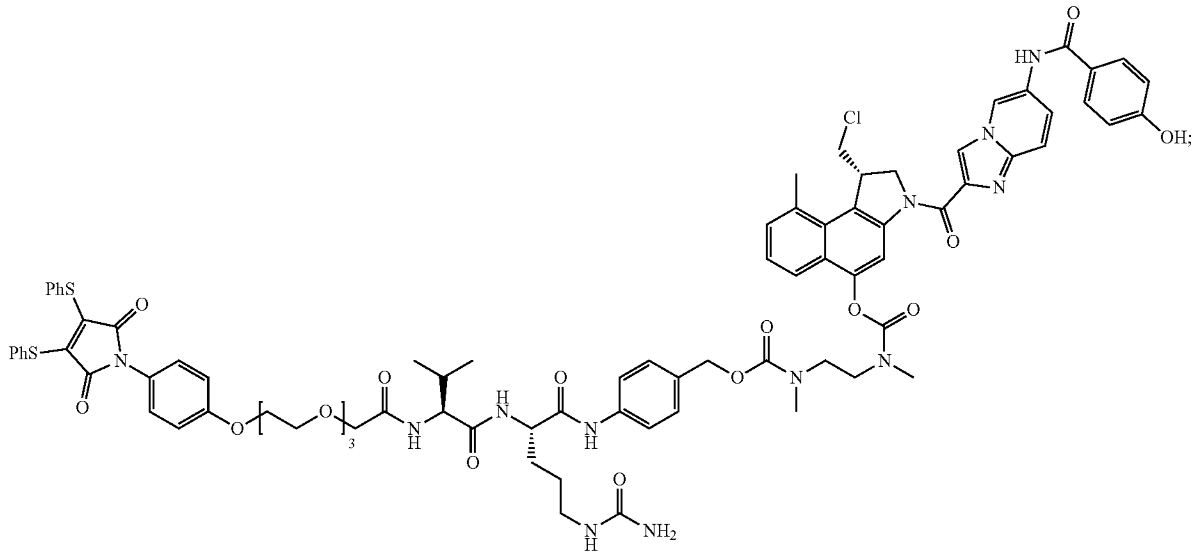
Formula 44
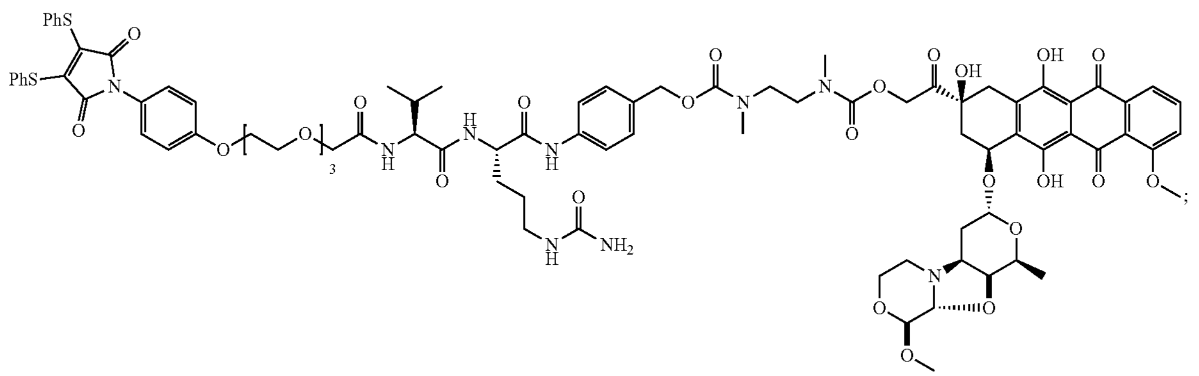
Formula 45
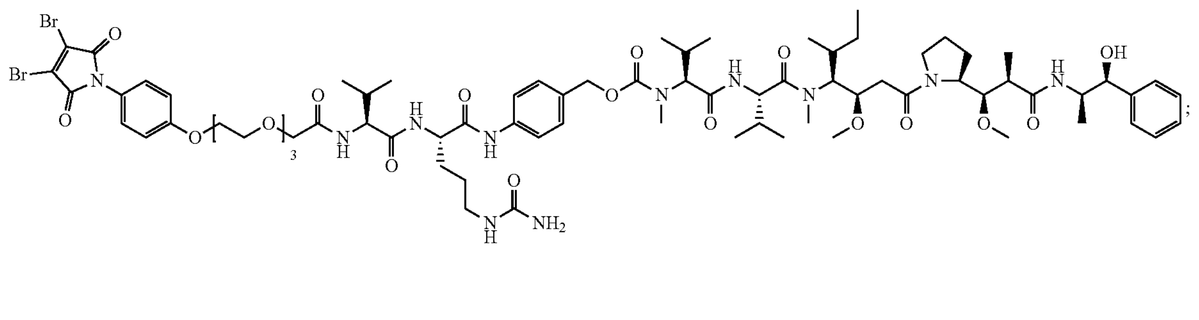
Formula 46
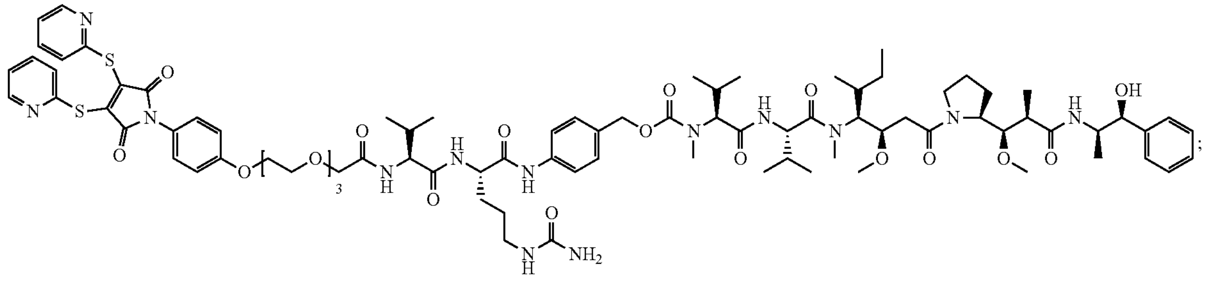

-continued
Formula 47
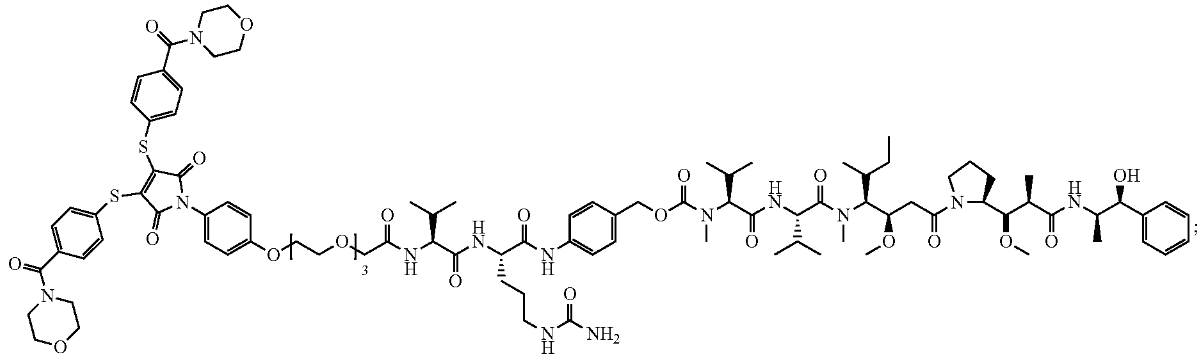
Formula 48
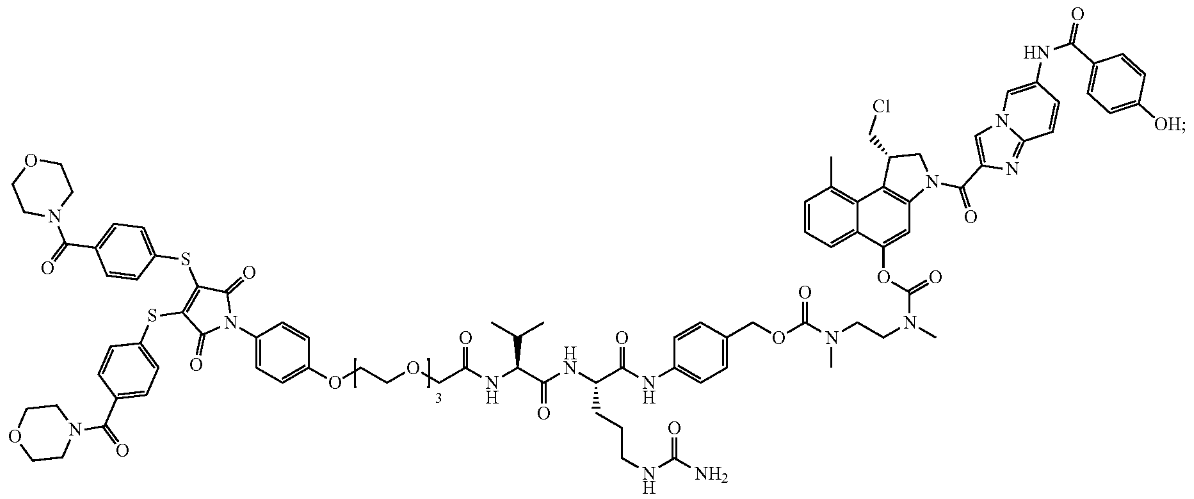
Formula 49
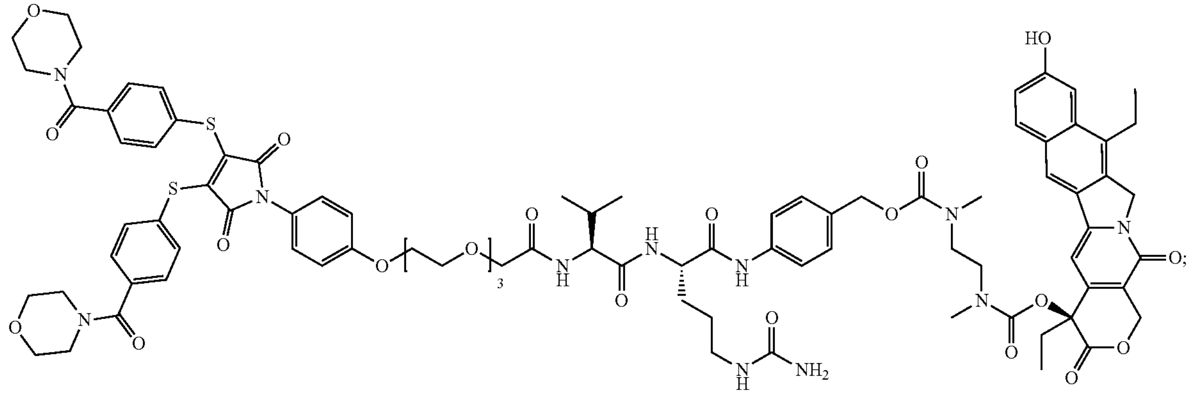

-continued
Ib-1
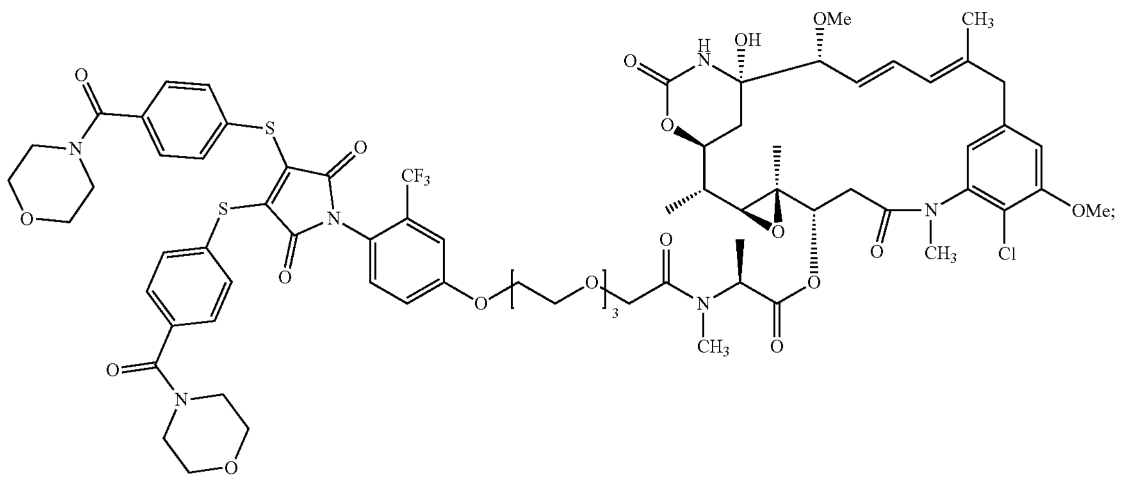
Ib-2
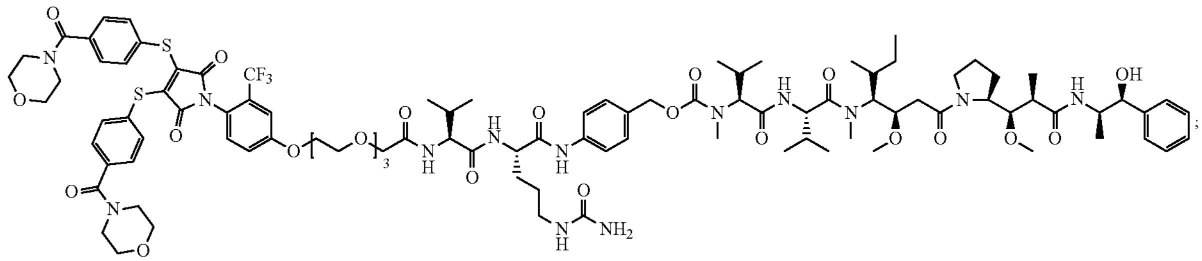
Ib-3
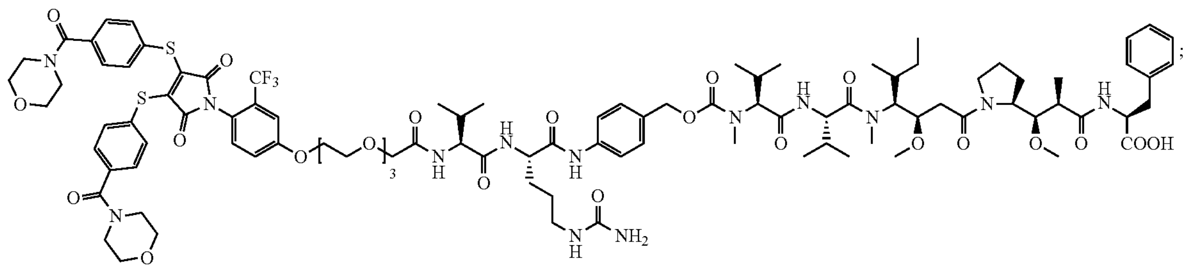
Ib-4
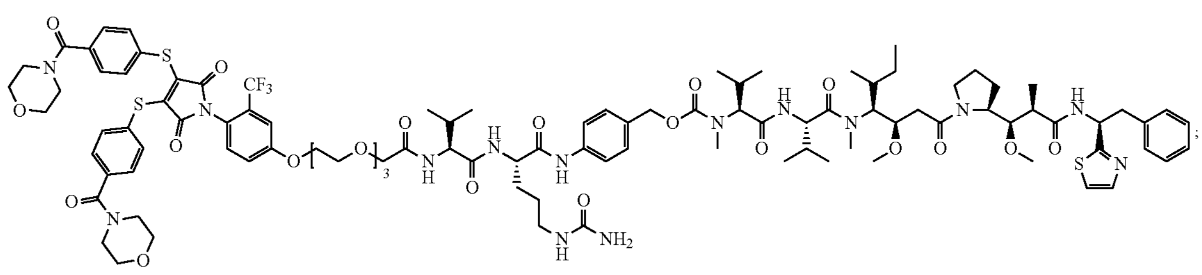

-continued
Ib-5
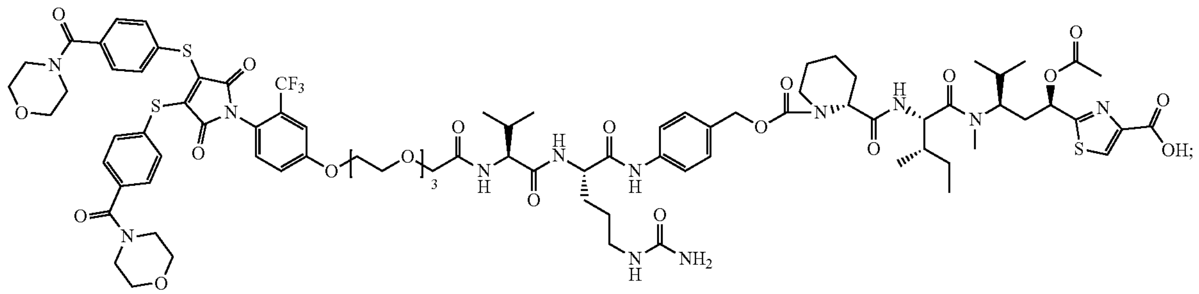
Ib-6
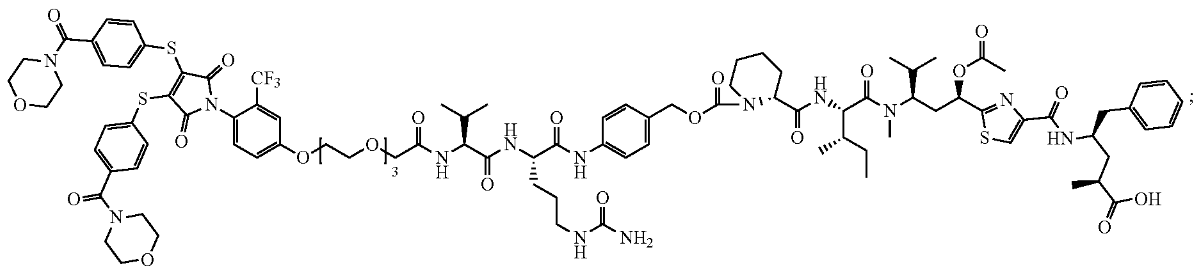
Ib-7
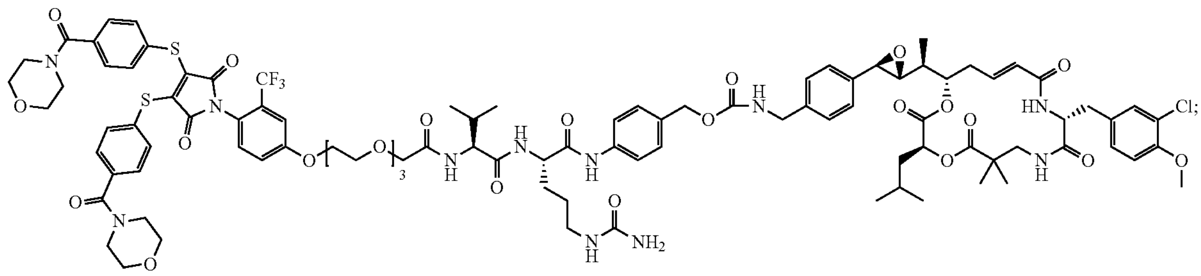
Ib-8
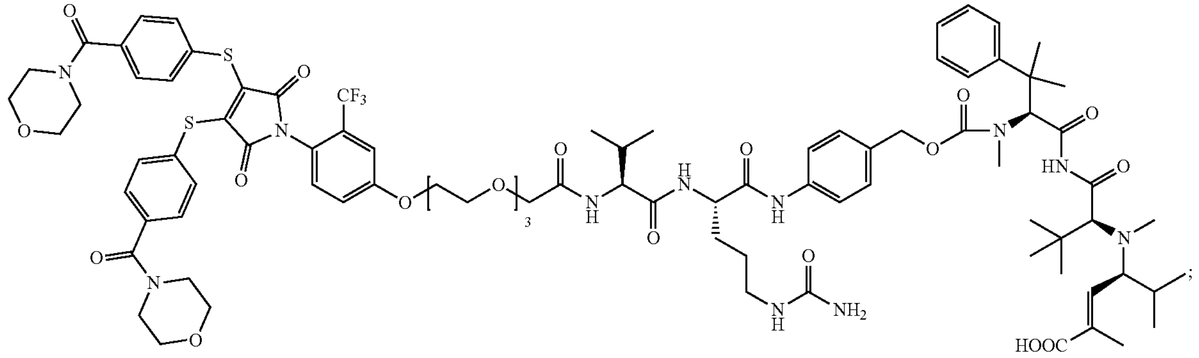
Ib-9
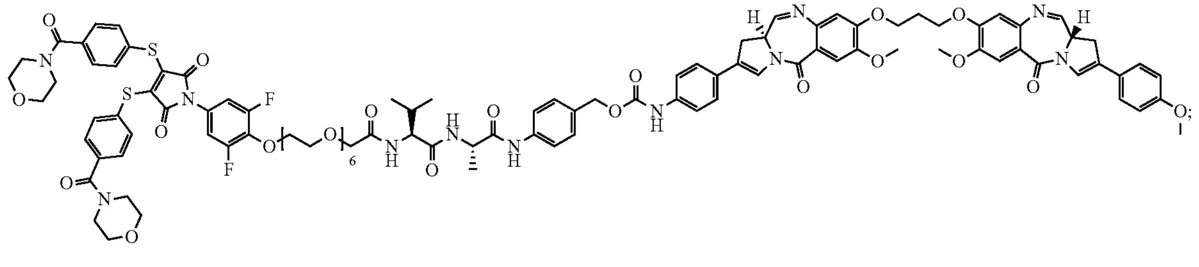

-continued
Ib-10
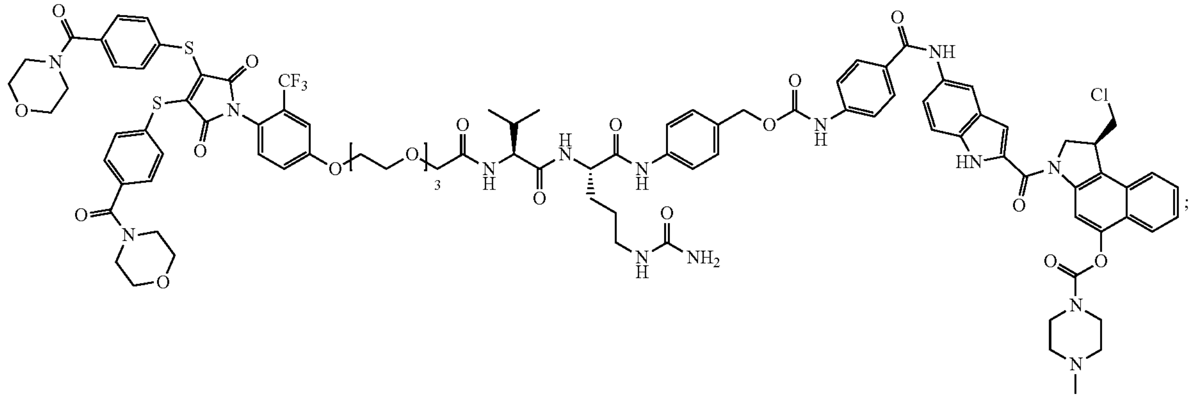
Ib-11
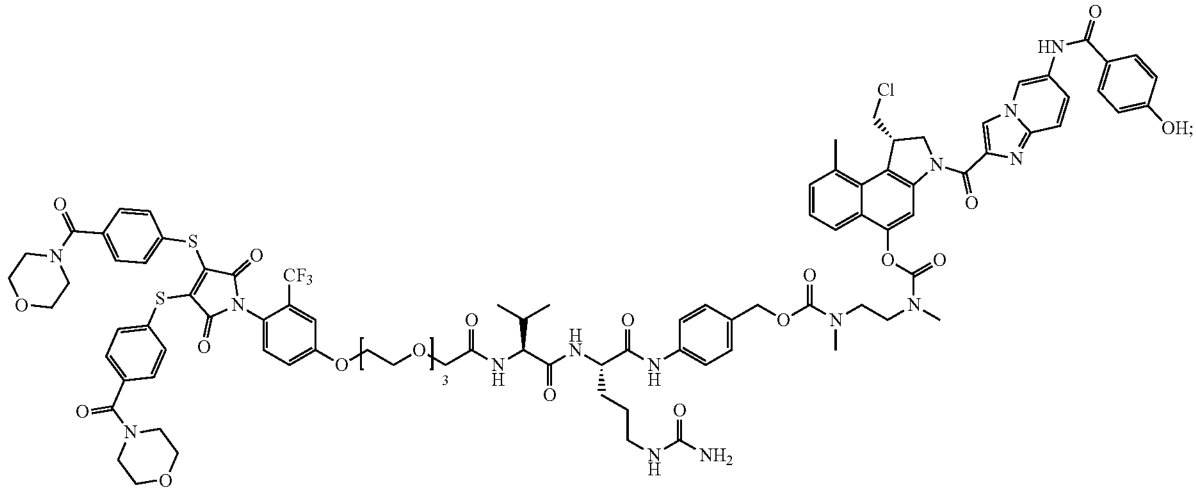
Ib-12
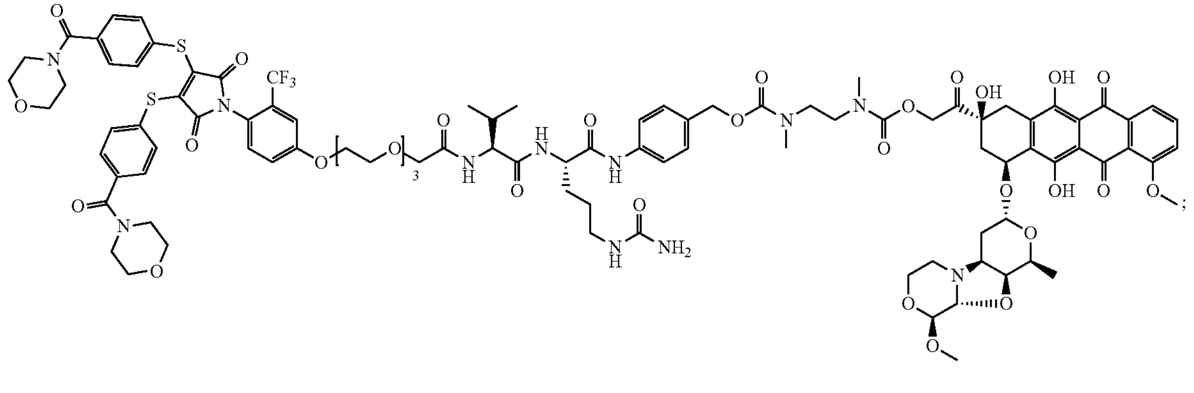

-continued
Ib-13
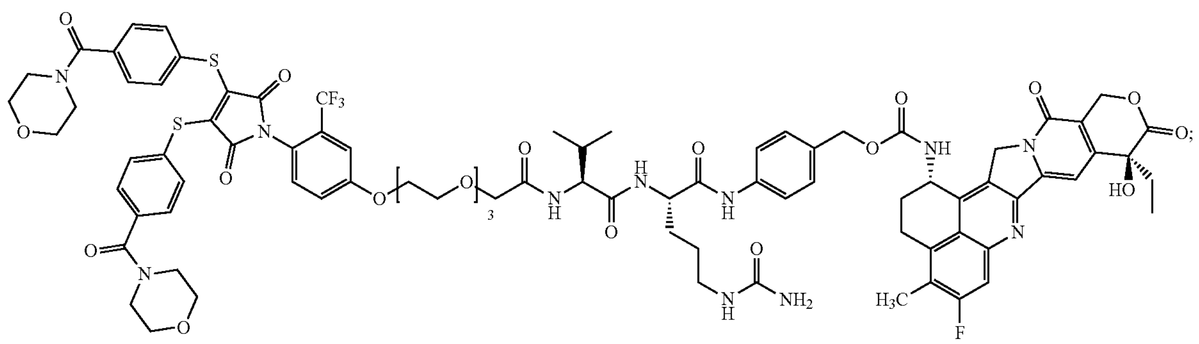
Ib-14
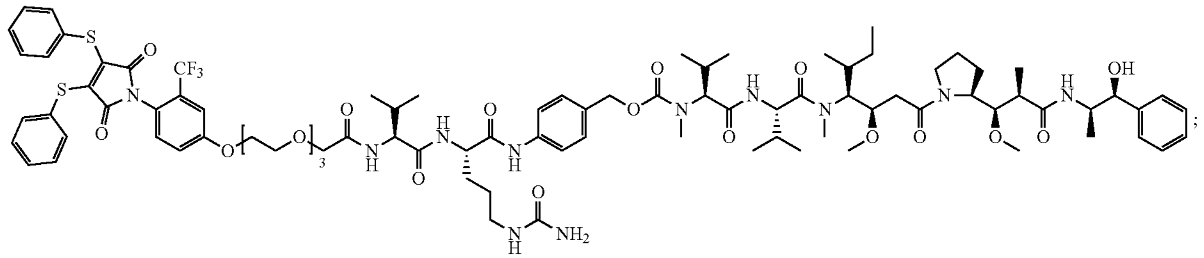
Ib-15
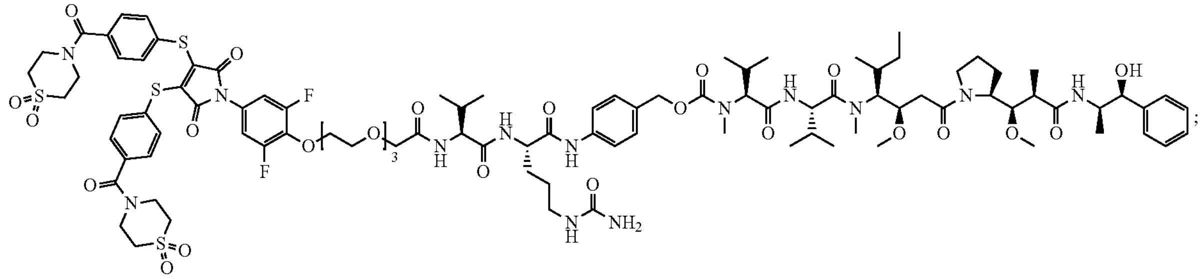
Ib-16
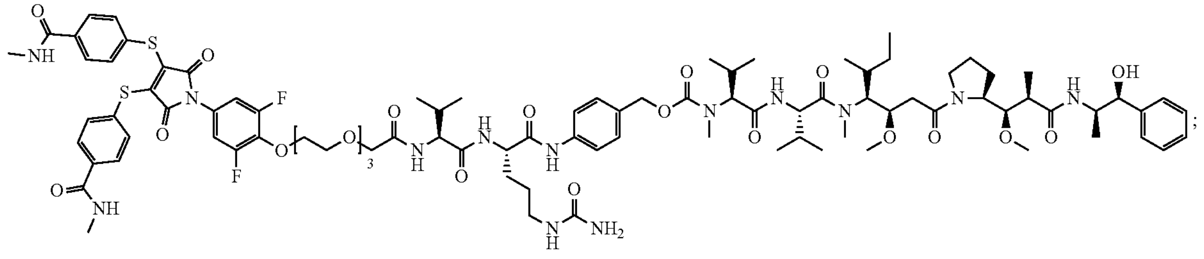
Ib-17
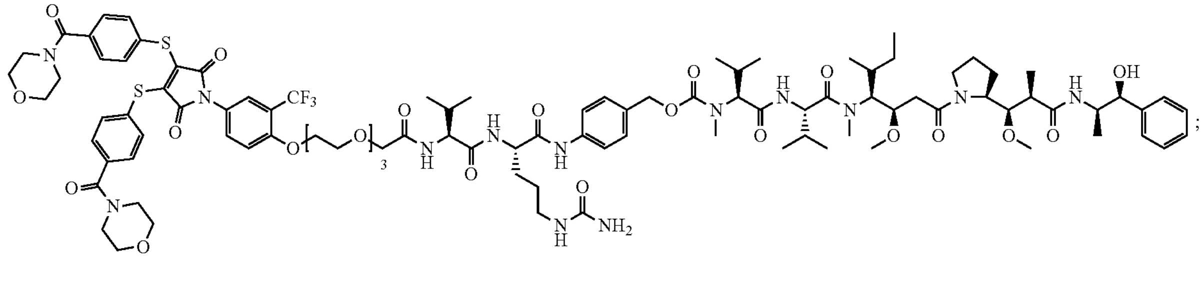

-continued
Ib-18
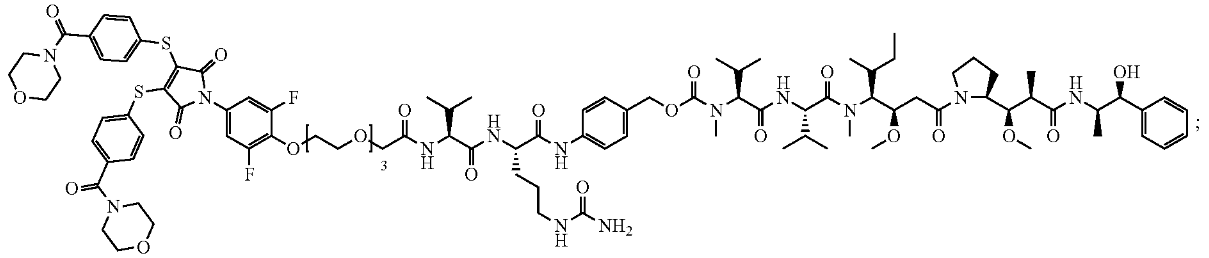
Ib-19
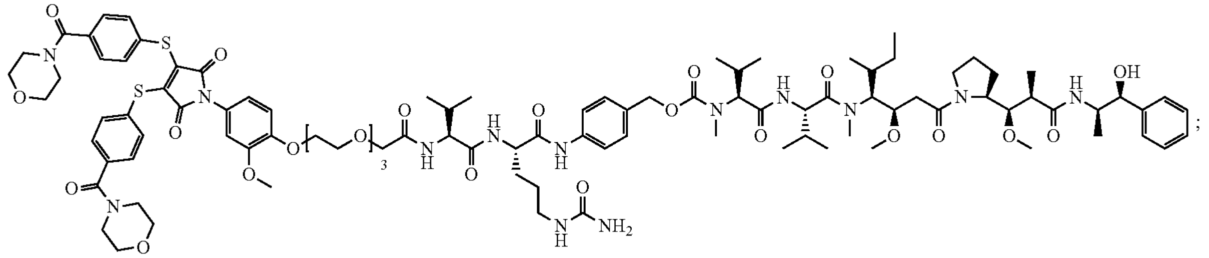
Ib-20
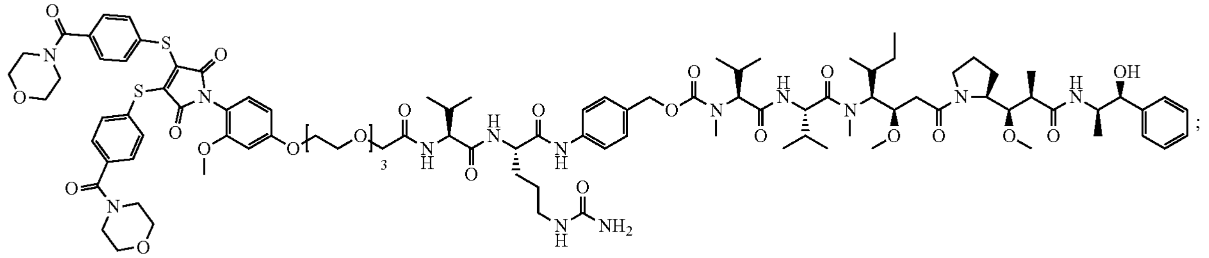
Ib-21
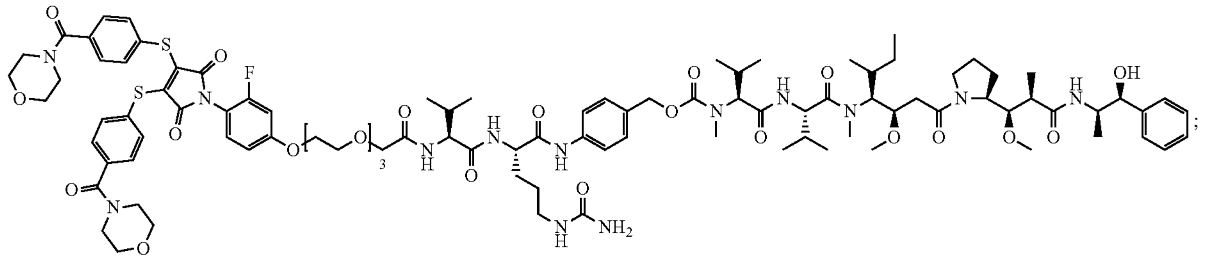
Ib-22
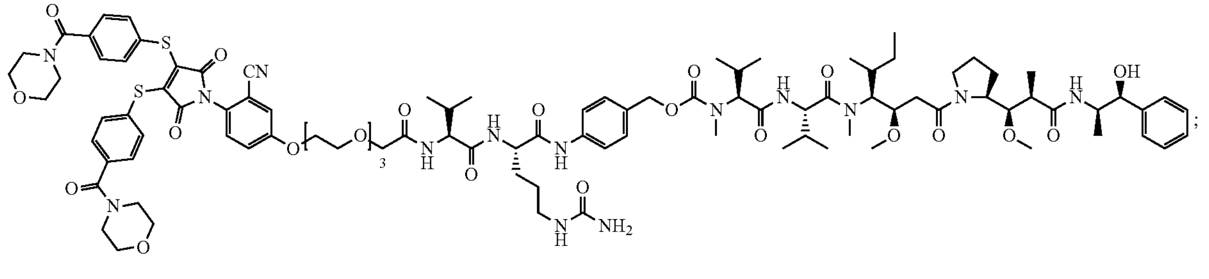

-continued

Ib-23

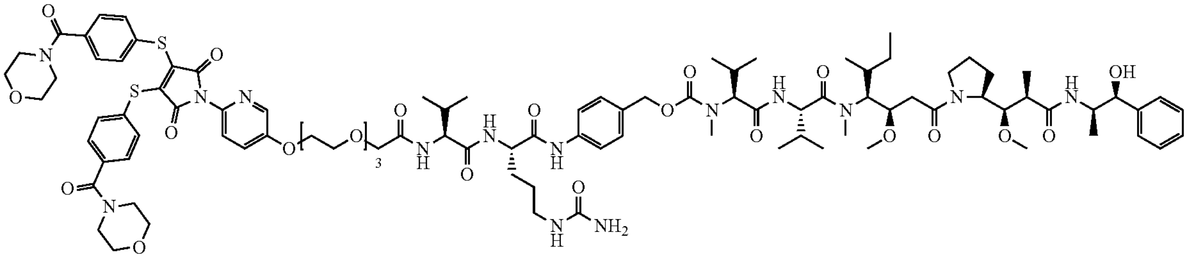

;

Ib-24

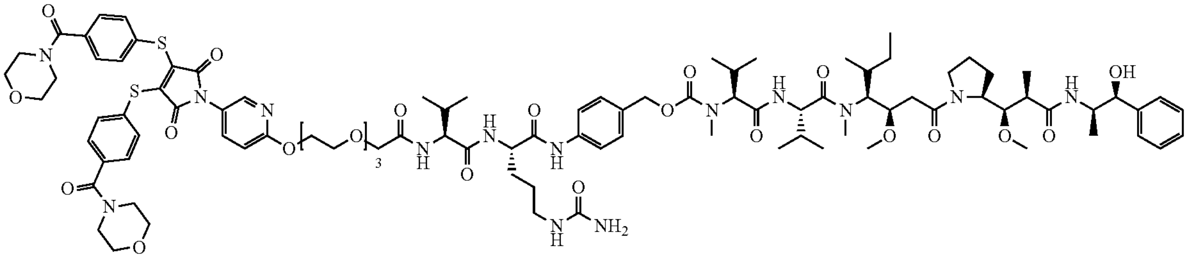

.

In the third aspect, the present invention provides an antibody drug conjugate, formed by coupling an antibody with the substituted maleamide linker-drug conjugate as shown in Formula Ib provided in the second aspect.

In another preferred embodiment, the conjugate has one or more drug components covalently linked.

In another preferred embodiment, the antibody and drug in the conjugate are covalently conjugated (e.g., they are covalently linked to the linker respectively).

In another aspect, the present invention provides an antibody drug conjugate, having a structure as shown in Formula Ic and/or Formula Id:

(Ic)

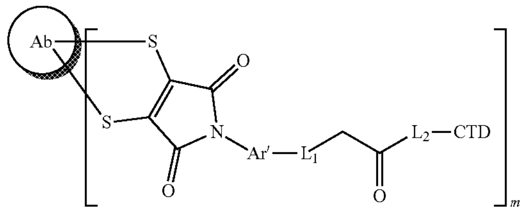

(Id)

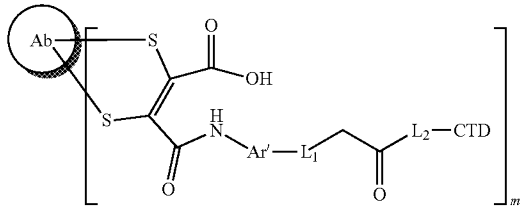

wherein Ar', $L_1$, $L_2$, and CTD are defined as above;
m=1.0-5.0, preferably m=3.0-4.2;
Ab is selected from the group consisting of protein, enzyme, antibody, antibody fragment, and peptide.

In another preferred embodiment, the conjugate as shown in Formula Id is a product upon ring-opening of N-phenyl maleamide in Formula Ic.

In another preferred embodiment, the antibody or Ab is selected from the group consisting of monoclonal antibody, bispecific antibody, chimeric antibody, humanized antibody and antibody fragment (preferably Fab fragment of an antibody).

In another preferred embodiment, the antibody-drug conjugate is obtained as follows: a disulfide bond in the hinge region of the antibody or antibody fragment is reduced to a pair of cysteine residues, and the sulfhydryl groups in the cysteine residues react with the aryl sulfide in Formula Ib through substitution, thereby linking the linker-drug conjugate as shown in Formula Ib to the antibody or antibody fragment.

In another preferred embodiment, the CTD is a cytotoxic small molecule drug, preferably, is a tubulin inhibitor, topoisomerase inhibitor and DNA binding agent.

In another further preferred embodiment, the tubulin inhibitor is selected from the group consisting of maytansine or its derivatives, Monomethyl auristatin E (MMAE), Monomethylauristatin F (MMAF), Monomethyl Dolastatin 10, Tubulysin or its derivatives, Cryptophycin or its derivatives, and Taltobulin.

In another further preferred embodiment, the DNA binding agent is selected from the group consisting of PBD or its derivatives and duocarmycin or its derivatives.

In another further preferred embodiment, the topoisomerase inhibitor is selected from the group consisting of metabolite PNU-159682 of Doxorubicin or its derivatives, and metabolite SN38 of irinotecan (CPT-11) or its derivatives.

In another preferred embodiment, the antibody is one capable of binding to a tumor-associated antigen selected from the group consisting of:

| | | | |
|---|---|---|---|
| HER2 | HER3 | CD19 | CD20 |
| CD22 | CD30 | CD33 | CD37 |
| CD45 | CD56 | CD66e | CD70 |
| CD74 | CD79b | CD138 | CD147 |
| CD223 | EpCAM | Mucin 1 | STEAP1 |
| GPNMB | FGF2 | FOLR1 | EGFR |

-continued

| | | | |
|---|---|---|---|
| EGFRvIII | Tissue factor (TF) | c-MET | Nectin 4 |
| AGS-16 | Guanylyl cyclase C | Mesothelin | SLC44A4 |
| PSMA | EphA2 | AGS-5 | GPC-3 |
| c-KIT | RoR1 | PD-L1 | CD27L |
| 5T4 | Mucin 16 | NaPi2b | STEAP |
| SLITRK6 | ETBR | BCMA | Trop-2 |
| CEACAM5 | SC-16 | SLC39A6 | Delta-like protein3(DLL3) |
| Claudin 18.2 | | | |

In another preferred embodiment, the antibody is a HER2 antibody, further preferably Trastuzumab or Pertuzumab.

In another preferred embodiment, the antibody is an EGFR antibody, further preferably Erbitux or Vectibix.

In another preferred embodiment, the antibody is a Tissue factor (TF) antibody.

In the fourth aspect, the present invention provides a pharmaceutical composition, comprising: (a) the antibody-drug conjugate according to the third aspect of the present invention; and (b) a pharmaceutically acceptable diluent, carrier or excipient.

In the fifth aspect, the present invention provides a use of the antibody-drug conjugate according to any one of the third aspect of the present invention for manufacturing a medicament for the treatment of a tumor.

In another preferred embodiment, the tumor is selected from the group consisting of breast cancer, ovarian cancer, non-Hodgkin's lymphoma, Hodgkin's lymphoma, acute lymphocytic leukemia, anaplastic large cell lymphoma, multiple myeloma, prostate cancer, non-small cell lung cancer, small cell lung cancer, malignant melanoma, squamous cell carcinoma, glioblastoma, renal cell carcinoma, gastrointestinal tumor, pancreatic cancer, prostate cancer, colorectal cancer, stomach cancer, neurospongioma, and mesothelioma.

In another aspect, the present invention provides a method for treating a tumor, the method including a following step: administering to a subject in need thereof a therapeutically effective amount of the antibody-drug conjugate as described in the third aspect of the present invention.

In another preferred embodiment, the subject is a mammal, preferably a human.

In the sixth aspect, the present invention provides a method for preparing the antibody-drug conjugate as described in the third aspect of the present invention, the method including the following steps:

(1) reacting an antibody with a reducing reagent in a buffer solution to obtain a reduced antibody;

(2) cross-linking a linker-drug conjugate with the reduced antibody obtained in step (1) in a mixture solution of a buffer solution and a certain amount of an organic solvent to obtain the antibody-drug conjugate.

In step (1), the inter-chain disulfide bonds in the antibody are reduced by the reducing reagent to produce sulfhydryl groups.

In another preferred embodiment, the reducing reagent is selected from the group consisting of tris(2-carboxyethyl) phosphine hydrochloride (TCEP), beta-mercaptoethanol, beta-mercaptoethylamine hydrochloride, and dithiothreitol (DTT).

In another preferred embodiment, the buffer solution is selected from the group consisting of potassium dihydrogen phosphate-sodium hydroxide ($KH_2PO_4$—NaOH)/sodium chloride (NaCl)/diethylene triamine pentacetate acid (DTPA) buffer solution; disodium hydrogen phosphate-citric acid/sodium chloride (NaCl)/diethylene triamine pentacetate acid (DTPA) buffer solution; boric acid-borax/sodium chloride (NaCl)/diethylene triamine pentacetate acid (DTPA) buffer solution; histidine-sodium hydroxide/sodium chloride (NaCl)/diethylene triamine pentacetate acid (DTPA) buffer solution; and PBS/diethylene triamine pentacetate acid (DTPA) buffer solution.

In another preferred embodiment, in step (2), the organic solvent in the reaction solution is no more than 15% by volume.

In another preferred embodiment, the organic solvent in step (2) is selected from the group consisting of acetonitrile (ACN), dimethylformamide (DMF), dimethylacetamide (DMA), and dimethyl sulfoxide (DMSO).

In another preferred embodiment, in step (2), the cross-linking is conducted at a temperature of 0-37° C.

In another preferred embodiment, if the reducing reagent used in step (1) is selected from beta-mercaptoethanol, beta-mercaptoethylamine hydrochloride, or dithiothreitol (DTT), a further step is included after step (1) and before step (2): passing the product through a desalting column or subjecting the product to ultrafiltration after the reduction reaction is completed to remove excessive reducing reagent.

In another preferred embodiments, synthesis scheme of the method is as follows:

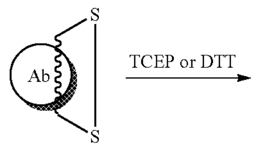

Inter-chain
Disulfide Bond

-continued

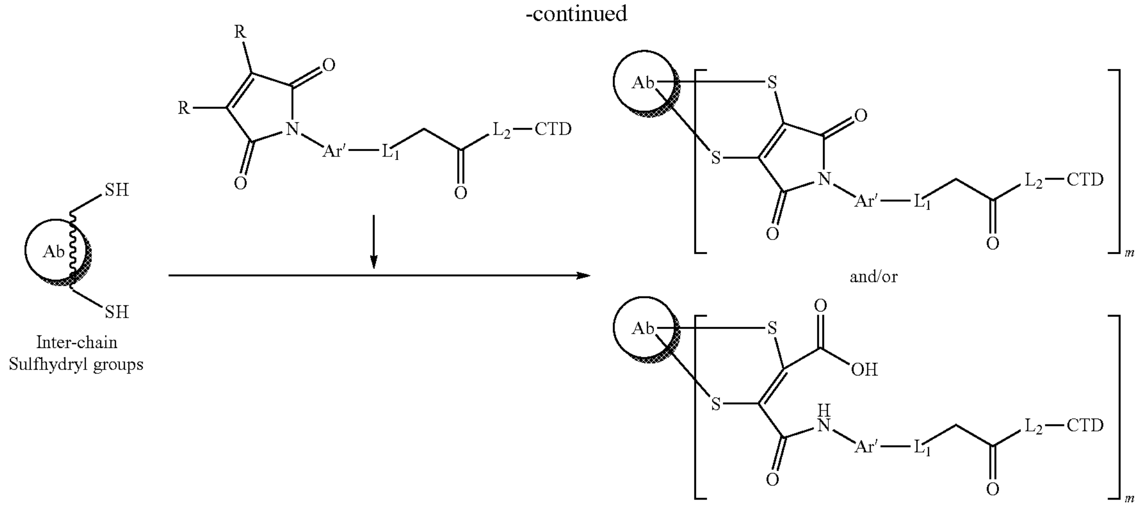

wherein R, Ab, Ar', $L_1$, $L_2$, CTD, and m are defined as above.

In another preferred embodiment, the method includes following steps:

1) Reduction: diluting an antibody stock solution to 2-10 mg/mL with a buffer solution, adding 140-200× excess molar ratio of dithiothreitol (DTT), or 6.0-20× excess molar ratio of tris(2-carboxyethyl)phosphine hydrochloride (TCEP) thereto, and stirring the obtained reaction solution at 10-35° C. for 2-48 hours;

2) Coupling: cooling the reaction solution obtained from step 1) to 0-10° C., adding a substituted maleimide compound thereto, and stirring at 0-37° C. for 2-5 hours.

In another further preferred embodiment, the method, after the reduction reaction of step 1) is completed, further includes a following step: passing the product through a desalting column or subjecting the product to ultrafiltration to remove the excessive DTT, if DTT is used as the reducing reagent in step 1).

In another further preferred embodiment, the substituted maleimide compound can be pre-dissolved in an organic solvent, and the organic solvent is selected from the group consisting of acetonitrile (ACN), dimethyl sulfoxide (DMSO), dimethylformamide (DMF), and dimethylacetamide (DMA); further preferably, the substituted maleimide compound is dissolved with the organic solvent to 10 mg/ml therein, meantime the organic solvent in the reaction solution is ensured to be no more than 15% by volume.

In another further preferred embodiment, the method, after the coupling of step 2) is completed, further includes a following step: purifying the reaction solution by filtration with sodium succinate/NaCl buffer solution or histidine-acetic acid/sucrose gel, and collecting sample at absorption peak according to UV280 ultraviolet absorption value.

In another further preferred embodiment, the method, after the coupling of step 2) is completed, further includes a following step: subjecting the reaction solution to ultrafiltration, and sterilizing by filtering, before the obtained product is stored at low temperature; further preferably, the storage temperature is −100 to −60° C.; more further preferably, a device used for the ultrafiltration has a pore size of 0.15 to 0.3 μm.

In another preferred embodiment, step 1) is carried out by using TCEP for reducing, without the need of removing the excessive TCEP.

In another preferred embodiment, the buffer solution in step 1) can be: 50 mM potassium dihydrogen phosphate-sodium hydroxide ($KH_2PO_4$—NaOH)/150 mM sodium chloride (NaCl)/1 mM diethylene triamine pentacetate acid (DTPA), pH 6-9; 50 mM disodium hydrogen phosphate-citric acid/150 mM sodium chloride (NaCl)/1 mM diethylene triamine pentacetate acid (DTPA), pH 6-9; 50 mM boric acid-borax/150 mM sodium chloride (NaCl)/1 mM diethylene triamine pentacetate acid (DTPA), pH 6-9; 50 mM histidine-sodium hydroxide/150 mM sodium chloride (NaCl)/1 mM diethylene triamine pentacetate acid (DTPA), pH 6-9; and PBS/1 mM diethylene triamine pentacetate acid (DTPA), pH 6-9.

The obtained antibody-drug conjugates have a homogeneous drug to antibody ratio (DAR). While, antibody-drug conjugates with certain difference in homogeneity can also be obtained by being prepared with different substituted maleimide linkers of the present invention. If conjugates with much better homogeneity are desired, the obtained antibody-drug conjugates can be further isolated and purified by a method selected from, but not limited to, the following methods: hydrophobic interaction chromatography (HIC), size exclusion chromatography (SEC), and ion exchange chromatography (IEC).

In the seventh aspect, the present invention provides a method for preparing the substituted maleimide linker (Formula E, which is a preferred example of Formula Ia) provided in the first aspect: performing a cyclization reaction of intermediate C and maleic anhydride dihalide to generate intermediate D, and performing a substitution reaction of intermediate D with aryl thiophenol to generate a linker as shown in Formula E. Synthesis scheme is as follows:

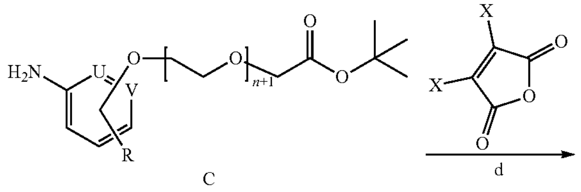

-continued

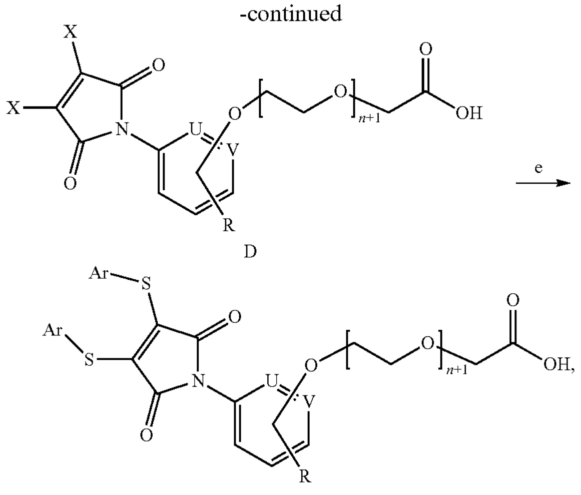

D

E wherein R and n are defined as above; X represents halogen, preferably Br or Cl; and U and V are independently N or C.

In another preferred embodiment, intermediate C can be obtained by reducing intermediate B, and synthesis scheme is as follows:

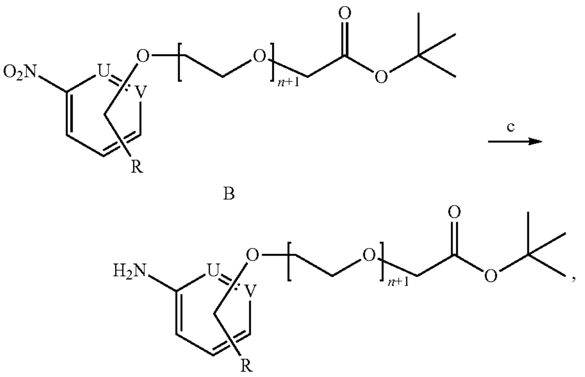

B

C wherein R, n, U, and V are defined as above.

In another further preferred embodiment, intermediate B can be obtained by a substitution reaction of compound A with fluoronitrobenzene, and synthesis scheme is as follows:

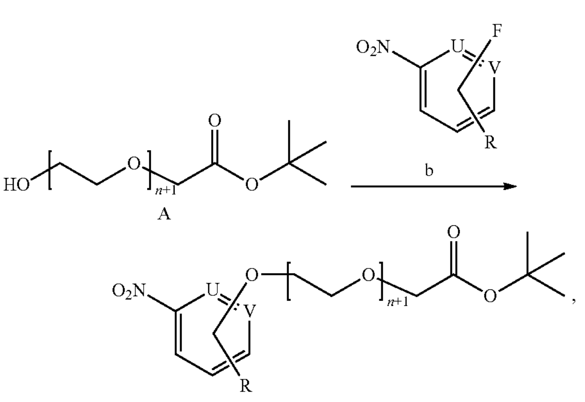

A

B wherein R, n, U, and V are defined as above.

In another further preferred embodiment, intermediate B can be prepared by following synthesis scheme:

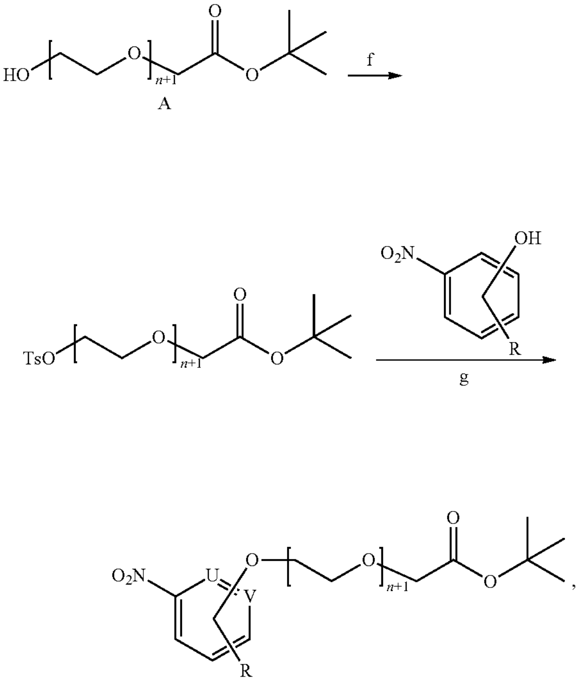

A

B wherein R, n, U, and V are defined as above.

In another more further preferred embodiment, compound A is obtained by reacting n-ethylene glycol with tert-butyl haloacetate, and synthesis scheme is as follows:

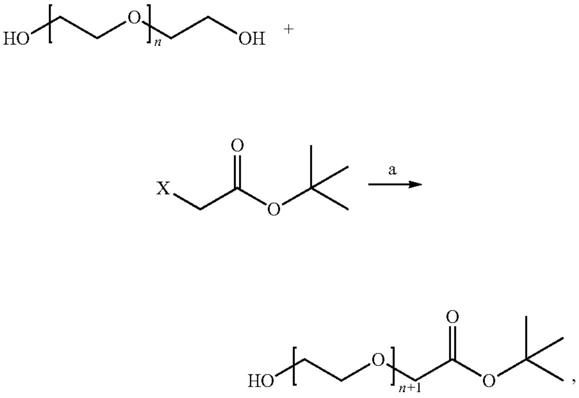

A wherein n and X are defined as above.

In the eighth aspect, the present invention provides a method for preparing the substituted maleimide linker-drug conjugate (Formula F1 or F'1, which is a preferred example of Formula Ib) provided in the second aspect, the method including: performing a condensation reaction of a substituted maleimide linker (Formula Ea, which is a preferred example of Formula Ia) and CTD (a cytotoxic drug) containing a dipeptide or tripeptide-PAB to generate F1 or F'1 respectively.

Synthesis schemes are as follows:

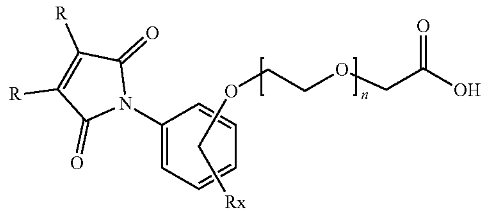

Ea

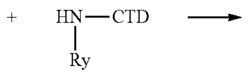

D1

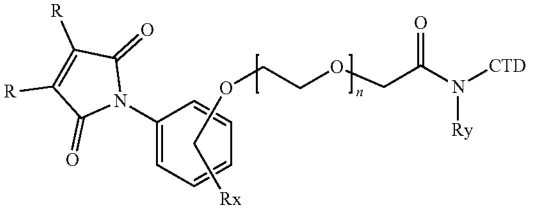

F1

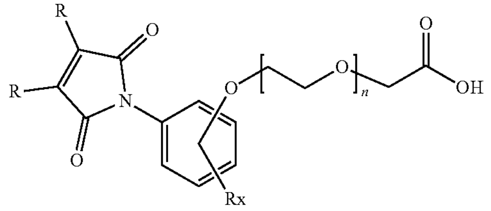

Ea

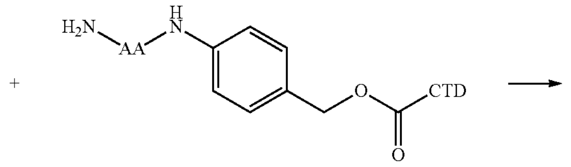

D'1

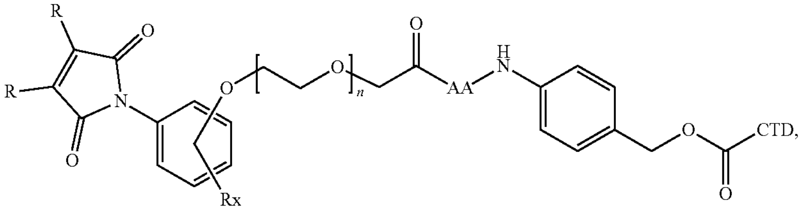

F'1 wherein R is defined as Formula a, Rx represents halogen, $C_1$-$C_4$ alkyl, $C_1$-$C_4$ alkoxy, trifluoromethyl, cyano or amide group, and Ry represents H or alkyl.

After having conducted extensive and intensive researches, the inventors found a class of linkers which can cross-couple with light chain-heavy chain and heavy chain-heavy chain of an antibody in whole or in part. Moreover, compared with traditional antibody-drug conjugates, the antibody-drug conjugates obtained by the above conjugation method have a narrower drug to antibody ratio (DAR) distribution. Based on the above findings, the inventors completed the present invention.

It should be understood that, within the scope of the present invention, the above-described technical features of the present invention and the technical features specifically described in the following (e.g., in Examples) can be combined with each other to form new or preferred technical solutions, which are not necessary to be listed one by one due to the limited space.

Definition

As used herein, unless otherwise specified, the term "$C_1$-$C_4$ alkyl" refers to a linear or branched alkyl containing 1-4 carbon atoms, such as methyl, ethyl, propyl, isopropyl, butyl, isobutyl, sec-butyl, tert-butyl, and the like.

The term "$C_1$-$C_4$ alkoxy" refers to a linear or branched alkoxy containing 1-4 carbon atoms, such as methoxy, ethoxy, propoxy, isopropoxy, butoxy, isobutoxy, sec-butoxy, tert-butoxy, and the like.

The term "halogen" refers to F, Cl, Br or I.

The term "$C_6$-$C_{10}$ aryl" refers to an aryl containing 6-10 carbon atoms, such as phenyl, naphthyl, and the like; and the aryl can be substituted or unsubstituted.

The term "5-12 membered heteroaryl" or "5-12 membered heteroarylene" refers to a heteroaryl or heteroarylene containing 5-12 carbon atoms and one or more (preferably 1-3) heteroatoms selected from the group consisting of O, S and/or N, and 5-8 membered heteroaryl or heteroarylene is preferred. The heteroaryl or heteroarylene can be substituted or unsubstituted.

In the invention, the term "pharmaceutically acceptable" ingredient refers to a substance that is suitable for use in human and/or animal without undue adverse side effects (such as toxicity, irritation, and allergic reaction), i.e. a substance having a reasonable benefit/risk ratio.

In the invention, the term "effective amount" refers to an amount of a therapeutic agent to treat, ameliorate, or prevent a target disease or condition, or to exhibit a detectable therapeutic or preventive effect. The precise effective amount for a subject will depend upon the subject's size and health, the nature and extent of the condition, and the therapeutic or combination of therapeutics selected for administration. Thus, it is not useful to specify an exact effective amount in advance. However, the effective amount for a given situation can be determined by routine experimentation and is within the judgment of the clinician.

Unless otherwise specified, all compounds in the invention are intended to include all possible optical isomers, such as single chiral compounds, or mixtures of various chiral compounds (i.e., racemates). In the compounds of the present invention, each chiral carbon atom may optionally be in R configuration or S configuration, or the mixture of R configuration and S configuration.

As used herein, the term "compound of the invention" refers to a compound as shown in Formula I. The term also comprises various crystal forms, pharmaceutically acceptable salts, hydrates or solvates of the compound of Formula I.

As used herein, the term "pharmaceutically acceptable salt" refers to salts suitable for use as pharmaceuticals which are formed by the compound of the present invention with acids or bases. The pharmaceutically acceptable salts include inorganic and organic salts. One preferred type of salts is salts formed by the compounds of the present invention with acid. Suitable acids for forming salts include, but are not limited to: inorganic acids such as hydrochloric acid, hydrobromic acid, hydrofluoric acid, sulfuric acid, nitric acid, phosphoric acid and the like: organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like; and acidic amino acids such as aspartic acid, glutamic acid and the like.

Unless otherwise specified, the term "amino acids" as used herein is intended to include any conventional amino acid, such as aspartic acid, glutamic acid, cysteine, asparagine, phenylalanine, glutamine, tyrosine, serine, methionine, tryptophan, glycine, valine, leucine, alanine, isoleucine, proline, threonine, histidine, lysine, and arginine.

When a trade name is used herein, it is intended to independently include product formulation under the trade name, corresponding generic drug, and active pharmaceutical ingredient(s) of the product under the trade name.

The term "antibody" herein is used in its broadest meaning and specifically encompasses monoclonal antibody, polyclonal antibody, dimer, multimer, multispecific antibody (e.g., bispecific antibody), and antibody fragment, as long as they exhibit desired biological activity (Miller et al (2003) Jour. of Immunology 170: 4854-4861). Antibody may be murine antibody, human antibody, humanized antibody, chimeric antibody, or antibody derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Antibodies that specifically bind to different epitopes have different structures. Thus, one antigen may have more than one corresponding antibodies. An antibody may comprise a full-length immunoglobulin molecule or an immunologically active portion of a full-length immunoglobulin molecule, i.e., contains a molecule that immunospecifically binds an antigen or part thereof of a target of interest, which includes but not limited to cancer cells or cells that produce autoimmune antibodies associated with autoimmune diseases. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulin can be derived from any species. In one aspect, however, the immunoglobulin is derived from human, murine, or rabbit.

An "antibody fragment" comprises a portion of a full length antibody, generally the antigen binding or variable region thereof. Examples of an antibody fragment include Fab, Fab', F(ab')2, and Fv fragments; diabodies; linear antibodies; minibodies (Olafsen et al (2004) Protein Eng. Design & Sel. 17(4):315-323); fragments produced by a Fab expression library; anti-idiotypic (anti-Id) antibodies; CDRs (complementary determining regions); and epitope-binding fragments of any of the above which immunospecifically bind to cancer cell antigens, viral antigens or microbial antigens; single-chain antibody molecules; and multispecific antibodies formed by antibody fragments.

Antibody constituting the antibody drug conjugate of the invention preferably retains the antigen binding capability it has in native, wild type state. Thus, antibodies of the present invention are capable of binding, preferably specifically, to antigens. Such antigens include, for example, tumor-associated antigens (TAAs), cell surface receptor proteins and other cell surface molecules, cell survival regulatory factors, cell proliferation regulatory factors, molecules (e.g., known or suspected to be functional) associated with tissue development or differentiation, lymphokines, cytokines, molecules involved in cell cycle regulation, molecules involved in vasculogenesis, and molecules associated with vasculogenesis. For example, an antigen to which a known antibody is capable of binding may be one or a subset of the above-mentioned categories, and other subsets comprise other molecules/antigens that have distinct characteristics (as compared to the antigen of interest).

Antibodies used in antibody drug conjugates include, but not limited to, antibodies against cell surface receptors and tumor-associated antigens. Such tumor-associated antigens are well known in the art, and their antibodies can be prepared by well-known methods and information for antibody preparation in the industry. To discover effective cellular targets useful for cancer diagnosis and therapy, researchers have sought to identify transmembrane or otherwise tumor-associated polypeptides that are specifically expressed on the surface of one or more types of cancer cells, and less or not expressed on one or more types of non-cancerous cells. Often, such tumor-associated polypeptides are more abundantly expressed on the surface of cancer cells as compared to non-cancerous cells. The identification of such tumor-associated factors can greatly improve the specific targeting of antibody-based cancer therapies.

Tumor-associated antigens include, but are not limited to, tumor-associated antigens (1)-(53) listed below. For convenience, information relevant to these antigens, all of which are known in the industry, is listed below and includes name, alternative name, and Genbank accession number. Nucleic acid and protein sequences corresponding to the tumor-associated antigens are available in public databases such as GenBank. Tumor-associated antigens correspondingly targeted by antibodies include all amino acid sequence variants and isoforms having at least 70%, 80%, 85%, 90%, or 95% sequence identity relative to the sequences identified in the cited references, or exhibit substantially the same biological properties and characteristics as tumor-associated antigens having sequences found in the cited references.

(1) HER2 (Gene ID: 2064, human epidermal growth factor receptor 2, abbreviated as HER2, also known as Neu, ErbB-2, CD340 (differentiation group 340) or p185), a protein encoded by ERBB2 gene. HER2 is a member of the epidermal growth factor receptor (EGFR/ErbB) family; (2) HER3 (Gene ID: 2065, epidermal factor receptor 3 (ErbB3/HER3), a member of the epidermal growth factor transmembrane receptor family. It has been confirmed in recent years that ErbB3/HER3 is closely related to the onset, recurrence and metastasis, chemotherapy and endocrine therapy of breast cancer, and has become a promising candidate target for treatment; (3) CD19 (Gene ID: 930); (4) CD20 (Gene ID: 931); (5) CD22 (Gene ID: 933); (6) CD30 (Gene ID: 943); (7) CD33 (Gene ID: 945); (8) CD37 (Gene ID: 951); (9) CD45 (Gene ID: 5788); (10) CD56 (Gene ID: 4684); (11) CD66e (Gene ID: 1048); (12) CD70 (Gene ID: 970); (13) CD74 (Gene ID: 972); (14) CD79b (Gene ID: 974); (15) CD138 (Gene ID: 6382); (16) CD147 (Gene ID: 682); (17) CD223 (Gene ID: 3902); (18) EpCAM (Gene ID: 4072); (19) Mucin 1 (Gene ID: 4582); (20) STEAP1 (Gene ID: 26872); (21) GPNMB (Gene ID: 10457); (22) FGF2 (Gene ID: 2247); (23) FOLR1 (Gene ID: 2348); (24) EGFR (Gene ID: 1956); (25) EGFRvIII (GenBank: GM832119.1); (26) Tissue factor (TF) (Gene ID: 2152); (27) c-MET (Gene ID: 4233); (28) Nectin 4 (Gene ID: 81607); (29) AGS-16; (30) Guanylyl cyclase C (Gene ID: 2984); (31) Mesothelin (Gene ID: 10232); (32) SLC44A4 (Gene ID: 80736): (33) PSMA (Gene ID: 2346); (34) EphA2 (Gene ID: 1969); (35) AGS-5; (36) GPC-3 (Gene ID: 2719); (37) c-KIT (Gene ID: 3815); (38) RoR1 (Gene ID: 4919); (39) PD-L1 (Gene ID: 29126); (40) CD27L (Gene ID: 970); (41) 5T4 (Gene ID: 7162); (42) Mucin 16 (Gene ID: 94025); (43) NaPi2b (Gene ID: 10568); (44) STEAP (Gene ID: 26872); (45) SLITRK6 (Gene ID: 84189); (46) ETBR (Gene ID: 1910); (47) BCMA (Gene ID: 608); (48) Trop-2 (Gene ID: 4070); (49) CEACAM5 (Gene ID: 1048); (50) SC-16; (51) SLC39A6 (Gene ID: 25800); (52) Delta-like protein3 (DLL3) (Gene ID: 10683); (53) Claudin 18.2 (Gene ID: 51208).

As used herein, the term "drug" refers to any compound possessing a desired biological activity and a reactive functional group available for preparing the conjugate of the invention. The desired biological activity includes activity useful in the diagnosis, cure, mitigation, treatment, or prevention of a disease in human or other animal. Thus, so long as it has the needed reactive functional group, the compound involved by the term "drug" include drugs identified in the official Chinese Pharmacopeia as well as e.g., official Homeopathic Pharmacopeia of the United States, or official National Formulary, or any supplements thereof. Exemplary drugs are set forth in the Physician's Desk Reference (PDR) and in the Orange Book maintained by the U.S. Food and Drug Administration (FDA). New drugs are continually being discovered and developed, and the present invention provides that those new drugs shall also be incorporated into the "drug" of the drug conjugates of the present invention.

Preferably, the drug is: a cytotoxic drug for cancer therapy; a protein or polypeptide possessing a desired biological activity, such as a toxin, e.g., abrin, ricin A, pseudomonas exotoxin, and diphtheria toxin; any other suitable protein, including tumor necrosis factor, α-interferon, β-interferon, neuronal growth factor, platelet derived growth factor, tissue plasminogen activator, and biological response modifier, for example, lymphokine, interleukin-1 (IL-1), interleukin-2 (IL-2), interleukin-6 (IL-6), granulocyte macrophage colony stimulating factor (GM-CSF), granulocyte colony stimulating factor, or any other growth factor.

One preferred drug that can be used in the present invention is maytansine or maytansinoids. Maytansine inhibits cell proliferation by inhibiting the formation of microtubules from tubulins. Maytansinoids are derivatives of maytansine. Both maytansine and maytansinoids are highly cytotoxic, but they have a greatly limited clinical use in cancer therapy due to poor selectivity for tumors. However, a high cytotoxicity enables them to be attractive drug moieties in ADCs. The structure shown below is deacetylmaytansine.

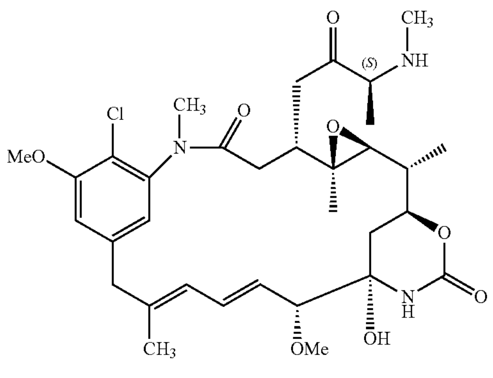

Deacetyl-maytansine

Another preferred drug that can be used in the present invention is auristatins. Auristatins are synthetic analogues of Dolastatin 10, which is a polypeptide isolated from marine mollusk Aplysia and found to have biological activity. Dolastatin 10 inhibits tubulin polymerization by binding to tubulin at the same domain as anticancer drug vincristine. Dolastitin 10, auristatin PE, and auristatin E are all linear peptides having four amino acids, three of which are unique to the dolastatin class compounds, and a C-terminal amide group. Two representative auristatins, monomethyl auristatin E (MMAE) and monomethyl auristatin F (MMAF), are preferred drug moiety candidates for ADCs.

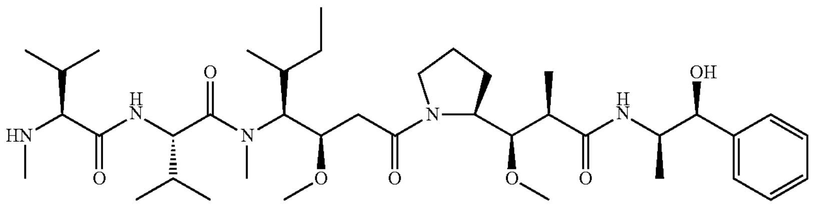

Monomethyl Auristatin E (MMAE)

-continued

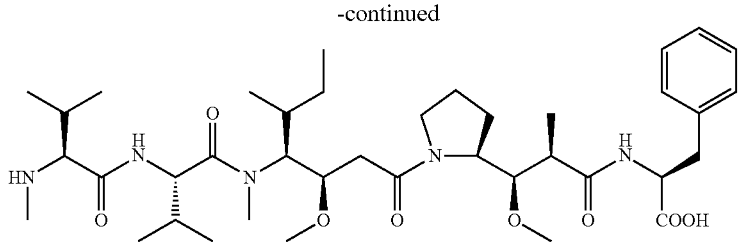

Monomethyl Auristatin F (MMAF)

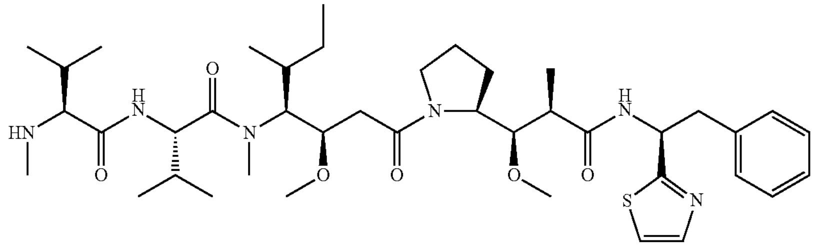

Monomethyl Dolastatin 10 (MMAD)

Yet another preferred drug that can be used in the present invention is tubulysins. Tubulysins, first isolated by researchers from myobacterial cultures, are exceptionally potent cell-growth inhibitors that act by inhibiting tubulin polymerization and thereby induce apoptosis. Tubulysin D is the most potent in the tubulysins, having an activity 10-1000 times larger than most other tubulin modifiers including, epothilone, vinblastine, and paclitaxel. Paclitaxel and vinblastine are current treatments for a variety of cancers, and epothilone derivatives are under activity evaluation in clinical trials. Synthetic derivatives of tubulysin D will provide essential information about inhibition mechanism and key binding interactions, and as anticancer agents, either as isolated entities or as chemical warheads on targeted antibodies or ligands, may have superior properties. Tubulysin D is a complex tetrapeptide that can be divided into four regions, Mep (D-N-methylpipecolinic acid), lie (isoleucine), Tuv (tubuvaline), and Tup (tubuphenylalanine), as shown in the formula:

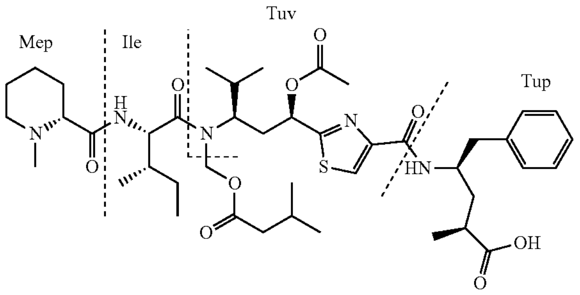 [SMILES: CC[C@H](C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccccc2)C[C@H](C)C(=O)O)cs1)C(C)C]

Still another preferred drug that can be used in the present invention is microbial-derived cryptophycin derivatives that inhibit tubulin polymerization. Cryptophycin is a novel anti-tumor active substance isolated from the culture of cyanobacteria, which can inhibit the formation of microtubule and is active against a variety of tumors. Cryptophycin is a fat-soluble compound containing 2 peptide bonds, 2 ester bonds, 5 optically active centers and an epoxy group. The two peptide and the two ester bonds are in one macrocyclic structure. The structures of Cryptophycin derivatives CP1 and CP2 are shown as follows:

CP1

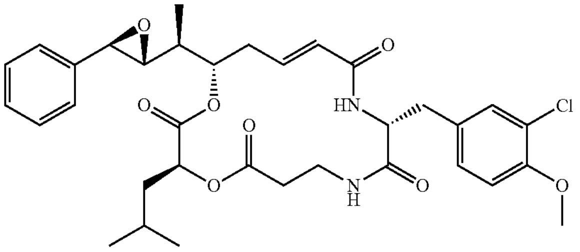

CP2

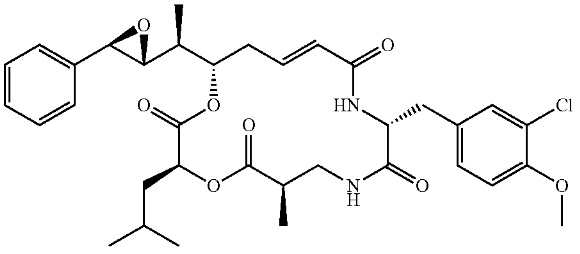

Another preferred drug that can be used in the present invention is a novel anti-microtubule agent Taltobulin (HTI-286, SPA-110). Taltobulin can inhibit multimerization of the purified microtubules, interfere with intracellular microtubule tissue, and induce mitosis blockade and cell apoptosis. Taltobulin is a potent inhibitor of cell proliferation and has an average IC50 of 2.5 nM for 18 human tumor cell lines. Taltobulin is not a suitable substrate for p-glycoprotein compared to anti-microtubule agents traditionally used. The structure of Taltobulin is shown as follow:

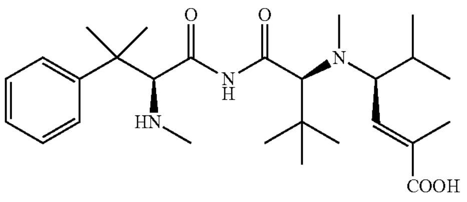 [SMILES: CN[C@H](C(=O)NC(=O)[C@@H](N(C)[C@H](/C=C(\C)C(=O)O)C(C)C)C(C)(C)C)C(C)(C)c1ccccc1]

In one aspect, the drug can be used is SN-38, a derivative of camptothecins. SN-38 is a biologically active metabolite of irinotecan hydrochloride (CPT-11), which belongs to an inhibitor against topoisomerase. SN-38 shows strongest inhibitory activity against type I DNA topoisomerase, inhibiting DNA synthesis dose-dependently and time-dependently, and causing frequent DNA single-strand breaks. The structure of SN-38 is shown as follow:

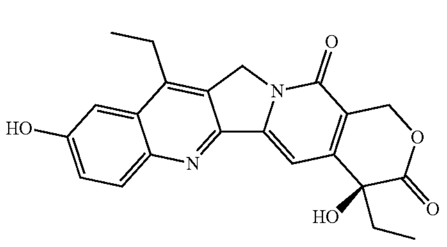 [SMILES: CCc1c2c(nc3ccc(O)cc13)-c1cc3c(c(=O)n1C2)COC(=O)[C@]3(O)CC]

In another aspect, the drug can be used is Exatecan, a derivative of camptothecins. Exatecan is a synthesized analogue of camptothecin, a type I topoisomerase inhibitor, with a stronger activity than SN-38. Exatecan shows strongest inhibitory activity against type I DNA topoisomerase, inhibiting DNA synthesis dose-dependently and time-dependently, and causing frequent DNA single-strand breaks. The structure of Exatecan is shown as follow:

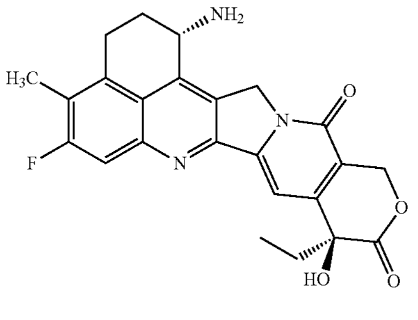 [SMILES: CC[C@@]1(O)C(=O)OCc2c1cc1n(c2=O)Cc2c-1nc1cc(F)c(C)c3c1c2[C@@H](N)CC3]

Yet another preferred drug that can be used in the present invention is amanitins (alpha-Amanitin) with a structure as follow. Alpha-Amanitin is a mycotoxin from *Amanita phalloides*, which is formed by two loops consisting of eight peptides and can inhibit eukaryotic RNA polymerase II and RNA polymerase III transcription.

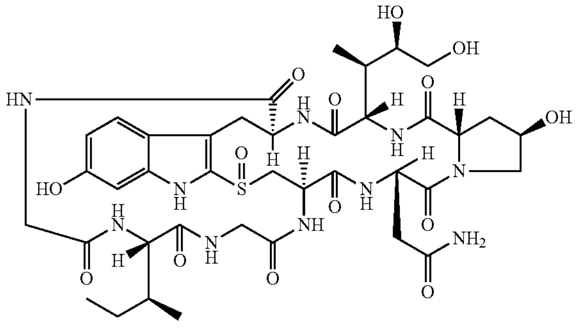 [SMILES: CC[C@H](C)[C@@H]1NC(=O)CNC(=O)[C@@H]2Cc3c([nH]c4cc(O)ccc34)S(=O)C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

Still another preferred drug that can be used in the present invention is benzodipyrrole antibiotics (duocarmycins, CC-1065 and the like) and other cyclopropapyrroloind-4-one (CPI) derivatives, both of which are potent DNA minor-groove binding alkylating agents. Cyclopropabenzindol-4-one (CBI) analogues are chemically more stable, biologically more potent, and synthetically easier than their parent compounds containing native CPI alkylating subunits. One representative CBI derivative is phenolic hydroxyl group-protected CBI derivative (see the formula below), which has decreased prodrug toxicity and improved water solubility (the formula below shows the general structure of seco-CBIs).

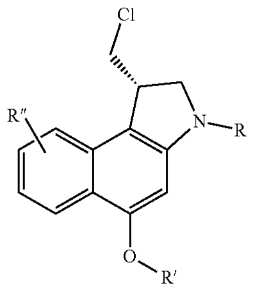

Yet still another preferred drug that can be used in the present invention is pyrrolo [2,1-c][1,4] benzodiazepines (PBDs) or PBD dimers. PBDs are a family of natural products produced by *Streptomyces* species with a unique characteristic of forming non-distortive covalent adducts in DNA minor groove, specifically at purine-guanine-purine sequences. There is a growing interest in using PBDs as part of a small-molecule strategy for targeting and locking DNA sequences and also as novel anticancer and antibacterial agents. The dimer, which is obtained by joining two PBD units together through their C8/C8'-hydroxyl functionalities via a flexible alkylene linker, has increased biological activity. PBD dimers are thought to lead to sequence-selective DNA lesions such as palindromic 5'-Pu-GATC-Py-3' interstrand crosslinks, which mainly accounts for their biological activity. These compounds have been shown to be highly useful cytotoxic agents and good drug candidates for ADCs.

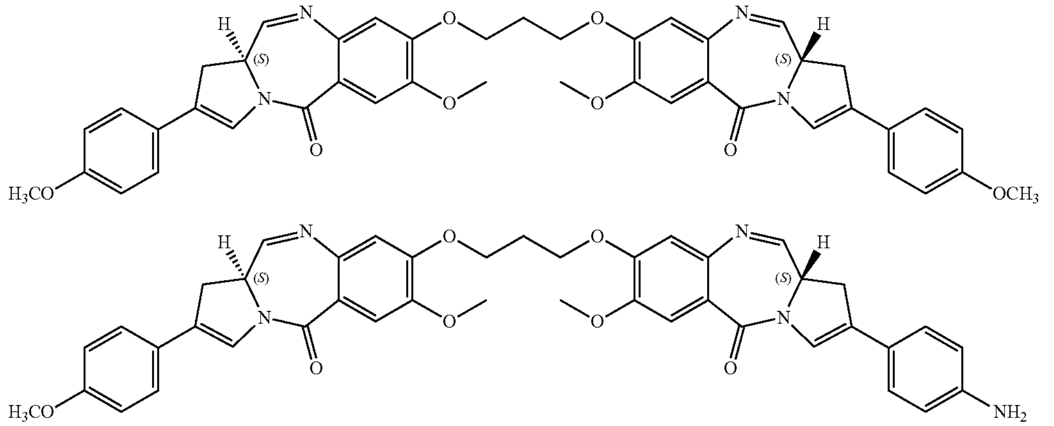

PBD dimers

Still yet another preferred drug that can be used in the present invention is PNU-159682 or derivatives thereof. PNU-159682 is a main active metabolite of Nemorubicin in human liver microsomes, with an activity 3000 times larger compared to MMDX and doxorubicin.

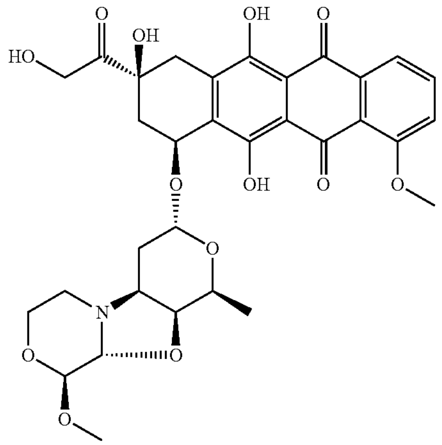

PNU-159682

In another aspect, the drugs are not limited to above-mentioned categories and include all those could be used in ADCs. Especially, the drugs may include cytotoxins that, like the cytotoxins having structures as shown in above D1-D12, are capable of coordinating with a linker through an amide bond of the linker, such as through a basic amine (primary or second amine) possessed.

According to drug release mechanism in cells, the terms "linker" or "ADC linker" can be divided into two types: noncleavable and cleavable linkers.

For ADCs with noncleavable linkers, the drug release mechanism is that: when a ADC is internalized into a cell after binding with an antigen, the Ab is enzymatically digested in lysosomes, resulting in the release of an active molecule composed with the small molecule drug, the linker, and amino acid residues of the antibody. This change in drug molecular structure will not diminish the cytotoxicity of the drug. Such an active molecule is, however, charged (duo to the amino acid residues) and not able to diffuse into neighboring cells. Hence, such active drugs cannot kill adjacent tumor cells not expressing the target antigen, i.e. antigen-negative cells (bystander effect).

Cleavable linkers, as the name implies, could be cleaved within the target cells and then the active drugs (small molecule drugs themselves) are released. Cleavable linkers can be categorized into two main groups: chemically labile and enzyme-labile linkers. Chemically labile linkers could be selectively cleaved upon differential properties between plasma and cytoplasm. Such properties include pH value, glutathione concentration, etc. PH sensitive linkers, are generally called acid-cleavable linkers. They are relatively stable in the neutral environment (pH 7.3-7.5) of blood, but will be hydrolyzed in mildly acidic endosomes (pH 5.0-6.5) and lysosomes (pH 4.5-5.0). First generation of ADCs mostly used these kinds of linkers, like hydrazone, carbonate, acetal, ketal, etc. However, due to the limited plasma stability of the acid-cleavable linkers, the ADCs based on these linkers have relatively short half-life (2-3 days). The shorter half-life, to some extent, precludes the application of pH-sensitive linkers in the new generations of ADCs.

Glutathione-sensitive linkers, are also called disulfide bond linkers. Drug release of such linkers-based ADCs is attributed to the difference between the high concentration of glutathione within a cell (millimolar range) and the relatively low concentration of glutathione in blood (micromolar range). This is especially true for tumor cells, where a hypoxia state results in enhanced activity of reductive enzymes and therefore even higher glutathione concentrations. Disulfide bonds are thermodynamically stable and thus exhibit good stability in plasma.

Enzyme-labile linkers, such as peptide linkers, are able to achieve better control of drug release. The peptide linkers can be effectively cleaved by lysosomal proteases, like Cathepsin B or plasmin, present at elevated levels in certain tumor tissues. This kind of peptide linkers are believed to be very stable in circulating plasma, as proteases are normally not active outside cells because of unfavorable pH and inhibition by serum protease inhibitors. Due to the high plasma stability and good intracellular cleaving selectivity and efficiency, enzyme-labile linkers are broadly selected as cleavable linker candidates in ADCs. Typical enzyme-labile linkers include Val-Cit (vc), Phe-Lys, etc.

A self-immolative linker is generally inserted between the cleavable linker and the active drug, or itself is part of the cleavable linker. Working mechanism for self-immolative linker is that it can undergo structure rearrangement spontaneously to release the active drug linked to it when the cleavable linker is cleaved under suitable condition. General self-immolative linkers include p-aminobenzyl alcohol (PAB) and $\beta$-glucuronides, etc.

Linker

The linker or coupling reagent of the present invention comprises a diarylthio maleamide unit and a coupling group. The diarylthio maleamide unit is used for crosslinking with the sulfhydryl in inter-chain of the antibody (upon reduction), while the coupling group is used to couple with the small molecule drug or a drug-linker unit. Compared to traditional ADCs with mono-dentate linker, the ADCs of the present invention are homogeneous and have stronger stability due to the bidentate binding between the diarylthio maleamide unit and the two sulfur atoms of the opened cysteine-cysteine disulfide bond in the antibody. In this regard, the ADCs of the present invention will have increased in vivo half-life, reduced amount of systemically released cytotoxins, and have safer drug properties than ADCs with mono-dentate linker.

In another aspect, the drug-linker units could be coupled to antibody via the linkers, producing partially inter-chain crosslinked conjugates. Compared to traditional ones, the antibody drug conjugates prepared by the method of the present invention have much narrower DAR distribution, and thus have greatly improved structural and pharmacological homogeneities.

The ADCs thus made can be used in targeted delivery of drugs to cell populations of interest, for example, tumor cells. The antibody drug conjugates will bind specifically to cell surface proteins, and the binding complex will be internalized rapidly into the cells. Once internalized, the drug will be released in an active form and produce effects. The antibody includes chimeric, humanized, or human antibody; antibody fragment that can bind to antigen; or Fc fused protein; or protein. The "drug" is a highly potent drug (see Definition), and could be polyethylene glycol in some case.

Antibody-Drug Conjugate

The antibody drug conjugate provided in this invention is composed by antibody, linker, and drug. The linker can be a cleavable linker or a non-cleavable linker.

Antibody is a globular protein which has a series of amino acids available for drug-linker conjugation. Due to tertiary and quaternary structures of the antibody, only solvent-accessible amino acids will be conjugatable. In fact, high-yielding conjugation to antibody often occurs at the $\varepsilon$-amino group of lysine residue or at the sulfhydryl group of cysteine residue.

The large number of lysine side-chains at the protein surface of an antibody give multiple linkage sites for drug conjugation, which leads to a mixture of ADCs containing different amounts of drugs conjugated (drug to antibody ratio, DAR) and conjugation sites.

The conjugation product provided by the invention, albeit still a mixture, has a much narrower DAR-distribution, as compared to antibody drug conjugates produced traditionally. The average DAR obtained is close to 4, within an optimized DAR range of 2-4 of ADCs. In addition, the conjugation product does not contain or contain minimal naked antibodies (DAR=0), which are ineffective for cell killing. Also, the conjugation product does not contain heavily conjugated antibodies (DAR=8), which will be cleared more rapidly than those with low DAR values. As a result, the ADC product provided in the invention shows much improved homogeneity.

Method for Preparing the Antibody-Drug Conjugate

Following shown is synthesis scheme of the antibody drug conjugate, from which it can be seen the inter-chain disulfide bonds in the antibody are reduced to generate 8 sulfhydryl groups, and then the substituted maleamide linker drug conjugate is cross-linked with the sulfhydryl groups of the reduced antibody to form the corresponding antibody drug conjugate. The antibody drug conjugate obtained is present in one or both of the forms as shown follows.

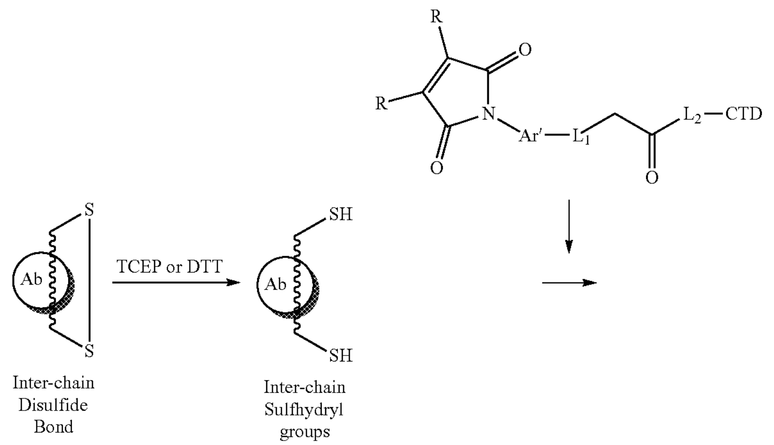

-continued

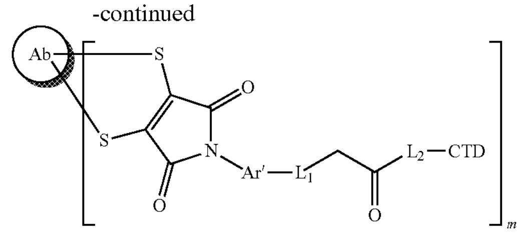

and/or

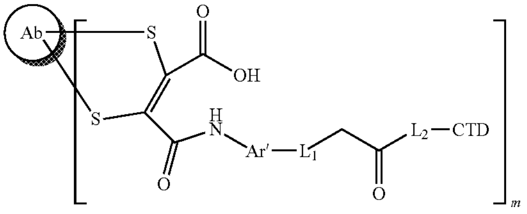

An antibody stock solution is diluted to 2-10 mg/mL with a buffer solution, and then 140-200× excess molar ratio of dithiothreitol (DTT), or 6.0-20× excess molar ratio of tris (2-carboxyethyl)phosphine hydrochloride (TCEP) is added thereto, and the obtained reaction solution is stirred at 10-35° C. for 2-48 hours; herein, the buffer solution used can be a buffer solution prepared in the following proportions: 50 mM potassium dihydrogen phosphate-sodium hydroxide ($KH_2PO_4$—NaOH)/150 mM sodium chloride (NaCl)/1 mM diethylene triamine pentacetate acid (DTPA), pH 6-9; 50 mM disodium hydrogen phosphate-citric acid/150 mM sodium chloride (NaCl)/1 mM diethylene triamine pentacetate acid (DTPA), pH 6-9; 50 mM boric acid-borax/150 mM sodium chloride (NaCl)/1 mM diethylene triamine pentacetate acid (DTPA), pH 6-9; 50 mM histidine-sodium hydroxide/150 mM sodium chloride (NaCl)/1 mM diethylene triamine pentacetate acid (DTPA), pH 6-9; and PBS/1 mM diethylene triamine pentacetate acid (DTPA), pH 6-9.

The reaction solution obtained from above is cooled down to 0-10° C.; and if dithiothreitol (DTT) is used as the reducing reagent, the excessive DTT is removed by passing the product through a desalting column or subjecting the product to ultrafiltration, and then a substituted maleamide compound (10 mg/ml, pre-dissolved in acetonitrile (ACN), dimethyl sulfoxide (DMSO), dimethylformamide (DMF) or dimethylacetamide (DMA)) is added thereto. The organic solvent in the reaction solution is ensured to be no more than 15% by volume. The obtained reaction solution is stirred at 0-37° C. for 2-4 hours for coupling. Further, if TCEP is used as for reducing, the coupling reaction can be carried out by adding the substituted maleamide compound directly without the need of removing the excessive TCEP.

The reaction solution after coupling reaction is purified by filtration with sodium succinate/NaCl buffer solution or histidine-acetic acid/sucrose gel, and then sample at absorption peak is collected according to UV280 ultraviolet absorption value. Or, the reaction solution is subjected to ultrafiltration for several times, and then is sterilized by filtering, before the obtained product is stored at low temperature. Preferably, the storage temperature is −100 to −60° C.; more preferably, a device used for filtration has a pore size of 0.15 to 0.3 μm.

The obtained antibody drug conjugates have a homogeneous drug to antibody ratio (DAR). While, antibody drug conjugates with certain difference in homogeneity can also be obtained by being prepared with different substituted maleamide linkers of the present invention. If conjugates with much better homogeneity are desired, the obtained antibody drug conjugates can be further isolated and purified by a method selected from, but not limited to the following methods: hydrophobic interaction chromatography (HIC), size exclusion chromatography (SEC), and ion exchange chromatography (IEC).

Pharmaceutical Composition and Administration Method Therefor

The antibody-drug conjugate provided by the present invention can target a specific cell population and bind to a cell surface specific protein (antigen), thereby releasing the drug into the cell in an active form through endocytosis or drug infiltration of the conjugate. Thus, the antibody-drug conjugate of the invention can be used to treat diseases of interest, and the antibody-drug conjugate mentioned above can be administered to a subject (e.g., a human) by a suitable route in a therapeutically effective amount. A subject in need of treatment can be a patient at risk of having or suspected of having a condition associated with the activity or amount of expression of a particular antigen. Such patients can be identified by routine physical examination.

Conventional methods, known to those of ordinary skill in the art of medicine, can be used to administer the pharmaceutical composition to the subject, depending upon the type of disease to be treated or where the disease is located. Such a composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by dripping method, by which a pharmaceutical formulation containing an antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of an antibody, can be dissolved and administered in a pharmaceutical excipient such as Water-for-Injection, 0.9% saline, or 5% glucose solution.

When the antibody drug conjugate as described herein is used as the therapeutic agent, it can be delivered by methods conventional in the art. For example, it can be introduced into cells using liposomes, hydrogels, cyclodextrins, biodegradable nanocapsules, or bioadhesive microspheres. Alternatively, nucleic acids or vectors can be locally delivered by direct injection or by use of an infusion pump. Other approaches include employing various transport and carrier systems, through the use of conjugates and biodegradable polymers.

The pharmaceutical composition of the present invention contains a safe and effective amount of the antibody-drug conjugate of the present invention and a pharmaceutically acceptable carrier. Such carriers include, but are not limited to, saline, buffer, glucose, water, glycerol, ethanol, and combinations thereof. In general, a pharmaceutical preparation should match with administration method, and the pharmaceutical composition of the present invention can be prepared as an injection, for example, prepared by a conventional method using a physiological saline or an aqueous solution containing glucose and other adjuvants. The pharmaceutical composition is preferably manufactured under aseptic conditions. The administration dosage of active ingredient is a therapeutically effective amount.

The effective amount of the antibody-drug conjugate of the present invention may vary depending on the mode of administration and the severity of the disease to be treated. The choice of preferred effective amount can be determined by one of ordinary skill in the art based on various factors (e.g., by clinical trials). Such factors include, but are not limited to, pharmacokinetic parameters of the bifunctional antibody conjugate of the present invention such as bioavailability, metabolism, half-life, etc.; severity of the disease to be treated in the patient, weight of the patient, and immunity status of the patient, route of administration, etc. In general, when the antibody-drug conjugate of the present invention is administered at a dose of about 0.0001 mg to 50 mg/kg animal body weight (preferably 0.001 mg to 10 mg/kg animal body weight) per day, a satisfactory result can be obtained. For example, as urgently required by therapeutic situation, several separate doses may be administered daily, or the dose may be proportionally reduced.

The dosage forms of the compound of the invention for topical administration include ointment, powder, patch, aerosol, and inhalant. The active ingredient is mixed with physiologically acceptable carriers and any preservatives, buffers, or propellants if necessary, under sterile conditions.

The compound of the invention can be administered alone, or in combination with other pharmaceutically acceptable therapeutics.

When the pharmaceutical composition is used, a safe and effective amount of compound of the present invention is applied to a mammal in need thereof (such as human), in which the applied amount is the pharmaceutically effective amount. For a person weighted 60 kg, the daily dose is usually 1-2000 mg, preferably 5-500 mg. Of course, the particular dose should also depend on other factors, such as the route of administration, patient healthy status etc, which are well within the skill of a skilled physician.

Experiments have Shown that the Main Advantages of the Present Invention are:

1. The novel linker provided by the present invention can couple with an antibody through a simple chemical method, and the DAR distribution of the conjugates obtained by using the linker is very narrow as compared with conventional ones. In this regard, the conjugates obtained by present invention have high homogeneity, in which conjugates with a single distribution (with a DAR of 4) account for more than 80%.

2. Among the conjugates provided by the present invention, naked antibodies or ADCs having low cross-linking degree account for almost zero percent (no components with a DAR of 0 or 1 are detected by mass spectrometry).

3. The applicant has demonstrated with a large number of experiments that the antibody-drug conjugates provided by the present invention are safe and effective in treating tumors. The hydrophilicity imparted by the conjugated ethylene glycol can be used to regulate biomolecular properties; and as compared to traditional mcVC-PAB conjugates, the inhibitory activity on tumor cell proliferation in vitro, biological activity, drug metabolism stability, safety and other druggabilities of the conjugates of the present invention, are improved or maintained.

4. The conjugation method provided by the present invention is suitable for most antibodies, which can avoid conducting tedious recombination and modification to each antibody for the purpose of introducing site-directed conjugation sites, and thus has a broad application prospect.

5. Compared with conjugation methods in the prior art, the conjugation method using maleamide-based crosslinking agent for disulfide bond bridging of the present invention has advantages including: crosslinking speed is fast and crosslinking reaction can be completed within 2-4 hours.

6. The maleamide-based disulfide bond bridging has a better stability, which is less prone to sulfhydryl-ether exchange in the body. What's more, compared with unsubstituted phenyl, the introduction of a substituent to Ar' can greatly slow down the secondary hydrolysis reaction occurred after the ring of the maleimide is opened, and thereby further enhance the stability of the antibody-drug conjugate in vitro and in vivo.

The present invention will be further illustrated below with reference to specific examples. It should be understood that these examples are only to illustrate the invention but not to limit the scope of the invention. If any experiment method in the following examples are not specified by detailed experiment conditions, it should conform to normal conditions, or those conditions suggested by manufacture(s). Unless indicated otherwise, parts and percentages are calculated by weight.

BRIEF DESCRIPTION OF THE DRAWINGS

FIG. 9-1 shows experiment results of proliferation inhibition of ADC-4 on human gastric cancer cells N87;

FIG. 9-2 shows experiment results of proliferation inhibition of ADC-2, ADC-3 and ADC-4 on Calu-3 human lung cancer cells;

FIG. 11-1 shows a chromatogram of hydrophobic interaction chromatography (HIC) of Pertuzumab;

FIG. 11-2 shows a chromatogram of hydrophobic interaction chromatography (HIC) of Pertuzumab-drug conjugate ADC-I;

FIG. 11-3 shows a chromatogram of hydrophobic interaction chromatography (HIC) of Pertuzumab-drug conjugate ADC-II;

FIG. 11-4 shows a chromatogram of hydrophobic interaction chromatography (HIC) of Pertuzumab-drug conjugate ADC-III;

FIG. 11-5 shows a chromatogram of hydrophobic interaction chromatography (HIC) of Pertuzumab-drug conjugate ADC-IV;

FIG. 11-6 shows a chromatogram of hydrophobic interaction chromatography (HIC) of Pertuzumab-drug conjugate ADC-V;

FIG. 11-7 shows a chromatogram of hydrophobic interaction chromatography (HIC) of Pertuzumab-drug conjugate ADC-VI;

FIG. 11-8 shows a chromatogram of hydrophobic interaction chromatography (HIC) of Pertuzumab-drug conjugate ADC-VI;

FIG. 12-1 shows a chromatogram of hydrophobic interaction chromatography (HIC) of Trastuzumab;

FIG. 12-2 shows a chromatogram of hydrophobic interaction chromatography (HIC) of Trastuzumab-drug conjugate ADC-VIII;

FIG. 13-1 shows a chromatogram of mass spectrum of Pertuzumab;

FIG. 13-2 shows a chromatogram of mass spectrum of Pertuzumab-drug conjugate ADC-I;

FIG. 13-3 shows a chromatogram of mass spectrum of Pertuzumab-drug conjugate ADC-II;

FIG. 13-4 shows a chromatogram of mass spectrum of Pertuzumab-drug conjugate ADC-III;

FIG. 13-5 shows a chromatogram of mass spectrum of Pertuzumab-drug conjugate ADC-IV;

FIG. 13-6 shows a chromatogram of mass spectrum of Pertuzumab-drug conjugate ADC-V;

FIG. 13-7 shows a chromatogram of mass spectrum of Pertuzumab-drug conjugate ADC-VI;

FIG. 13-8 shows a chromatogram of mass spectrum of Pertuzumab-drug conjugate ADC-VII;

FIG. 14-1 shows a chromatogram of mass spectrum of Trastuzumab;

FIG. 14-2 shows a chromatogram of mass spectrum of Trastuzumab-drug conjugate ADC-VIII;

FIG. 16-1 shows a HIC chromatogram of ADC control at day 0 at room temperature;

FIG. 16-2 shows a HIC chromatogram of ADC control at day 2 at room temperature;

FIG. 16-3 shows a HIC chromatogram of ADC control at day 4 at room temperature;

FIG. 16-4 shows a HIC chromatogram of ADC control at day 7 at room temperature;

FIG. 17-1 shows a HIC chromatogram of ADC-I at day 0 at room temperature;

FIG. 17-2 shows a HIC chromatogram of ADC-I at day 2 at room temperature;

FIG. 17-3 shows a HIC chromatogram of ADC-I at day 4 at room temperature;

FIG. 17-4 shows a HIC chromatogram of ADC-I at day 7 at room temperature;

FIG. 18-1 shows a HIC chromatogram of ADC-II at day 0 at room temperature;

FIG. 18-2 shows a HIC chromatogram of ADC-II at day 2 at room temperature;

FIG. 18-3 shows a HIC chromatogram of ADC-II at day 4 at room temperature;

FIG. 18-4 shows a HIC chromatogram of ADC-II at day 7 at room temperature;

FIG. 19-1 shows a HIC chromatogram of ADC-VII at day 0 at room temperature;

FIG. 19-2 shows a HIC chromatogram of ADC-VII at day 2 at room temperature;

FIG. 19-3 shows a HIC chromatogram of ADC-VII at day 4 at room temperature;

FIG. 19-4 shows a HIC chromatogram of ADC-VII at day 7 at room temperature;

DETAILED DESCRIPTION OF EMBODIMENTS

Figure 1:
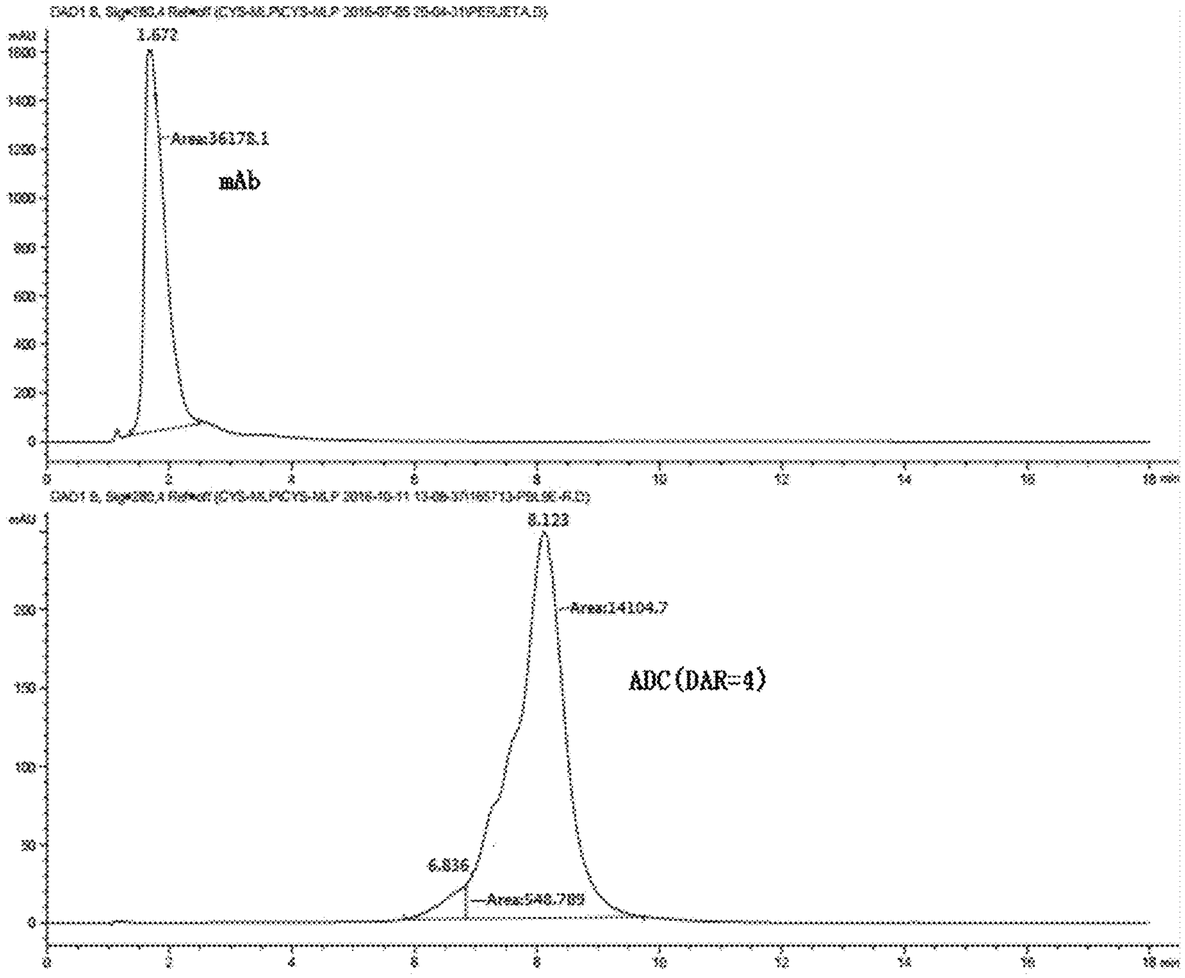
FIG. 1 shows chromatograms of hydrophobic interaction chromatography (HIC) of Pertuzumab and Pertuzumab drug conjugate for comparison.

After having conducted extensive and intensive researches, the inventors found a class of linkers which can cross-couple with light chain-heavy chain and heavy chain-heavy chain of an antibody in whole or in part. Moreover, compared with traditional antibody drug conjugates, the antibody drug conjugates obtained by the above conjugation method have a narrower drug to antibody ratio (DAR)

distribution. Based on the above findings, the inventors completed the present invention.

One of Specific Designs:

preparation and use of the substituted maleamide linker as shown in Formula Ia, wherein Ar' is selected from the group tively, the 2,3-dibromomaleimide can react with methyl chloroformate directly to generate intermediate E'; and intermediate C is reacted with intermediate E or intermediate E' to generate linker F. Synthesis scheme and specific examples are as follows:

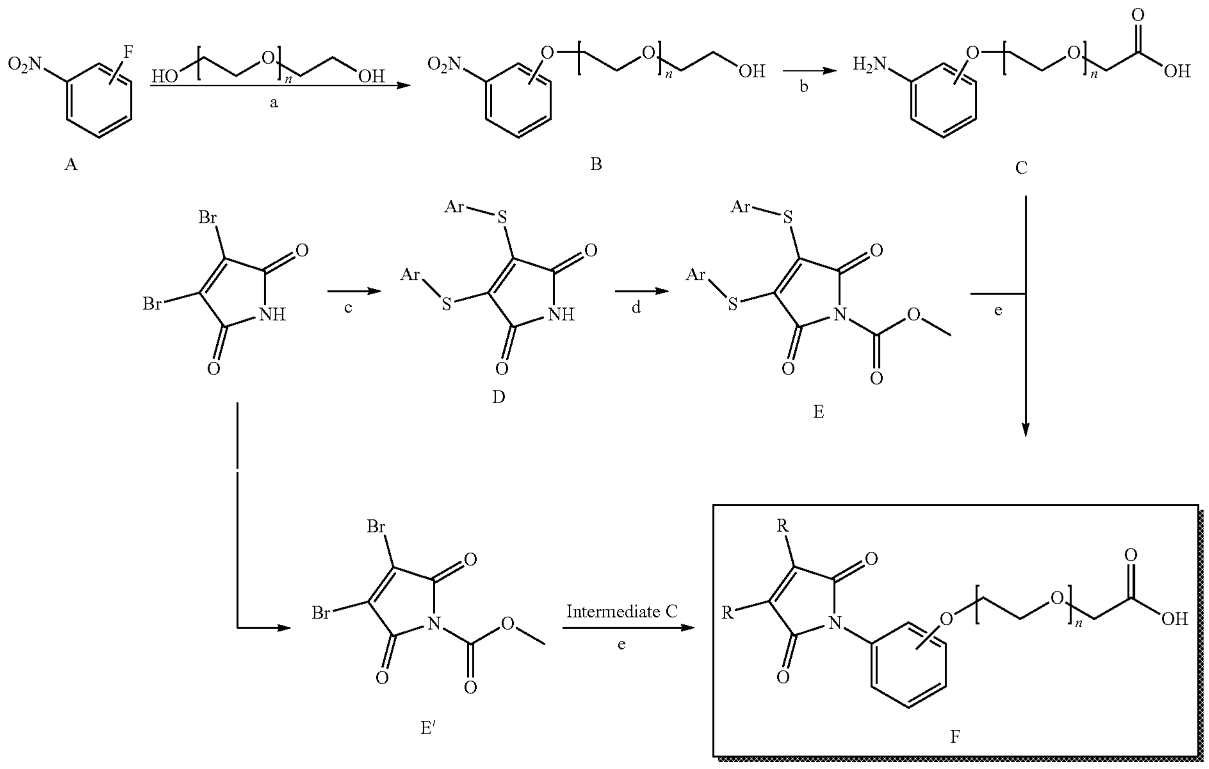

consisting of unsubstituted $C_6$-$C_{10}$ arylene and unsubstituted 5-12 membered heteroarylene.

(Ia)

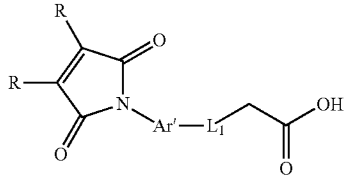

Section 1: Synthesis and Preparation Methods of the Linker Solution 1

The substituted maleamide linker as shown in Formula Ia, which is provided in the first aspect of the present invention, can be synthesized by the method listed in Solution 1. Specifically, intermediate B can be obtained through a substitution reaction between n-ethylene glycol and fluoronitrobenzene, in which the nitro subsequently is reduced to generate amino compound C; intermediate D can be obtained through a substitution reaction between 2,3-dibromomaleimide and aryl thiophenol, and is then reacted with methyl chloroformate to generate intermediate E; alterna- Example 1: Synthesis and Preparation of Compounds as Shown in Formulas 1-12

1.1 Synthesis of Compound F-1 (Formula 1)

1.1.1 Synthesis of Intermediate B-1 (Step a)

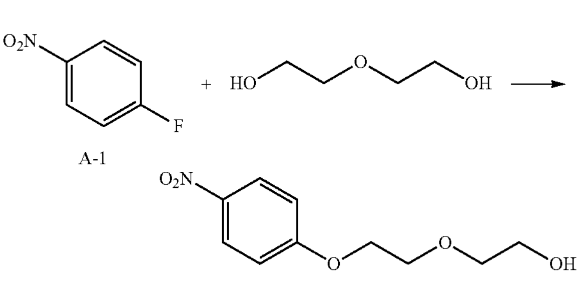

A-1

B-1

4-fluoronitrobenzene (10.0 g, 0.071 mol), diethylene glycol (75.2 g, 0.71 mol) and potassium carbonate (14.7 g, 0.11 mol) were weighted and placed in a 250 mL round-bottom flask, and were stirred for 22 hours at 80° C. under the protection of nitrogen. The obtained mixture was then cooled down to room temperature slowly, extracted with dichloromethane, washed successively with 1 mol/L diluted hydrochloric acid, water and saturated salt water, and dried with anhydrous sodium sulfate, and the solvent was rotary evaporated off. The residue was subjected to column chromatography (silica gel, 200-300 mesh, PE/EtOAC 10:1) to obtain a light yellow transparent liquid product (15.1 g, 94% yield). Theoretical value via LC-MS (M+): 227.08, and measured value via LC-MS (ESI, M+H+): 228.12.

1.1.2 Synthesis of Intermediate C-1 (Step b)

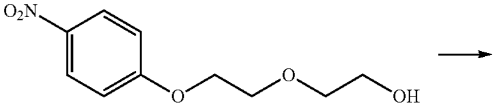

B-1

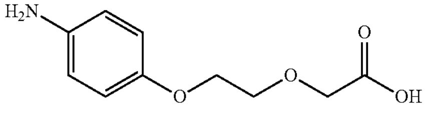

C-1

Intermediate B-1 (3.0 g, 9.52 mmol) was dissolved in acetone (30 mL), and cooled in ice cold water, and then a freshly prepared Jones reagent (15 mL) was dropped slowly therein. The obtained reaction mixture was stirred at room temperature for 3 hours, cooled in ice water followed by slowly dropping isopropanol therein, and then stirred for 15 minutes in an ice-water bath. Subsequently the organic solvent was rotary evaporated off. The aqueous phase was extracted with diethyl ether for three times, and then the organic phases was combined, washed with saturated salt water, and dried with anhydrous sodium sulfate, and the solvent therein was rotary evaporated off. The obtained yellow oily crude was used in the next step directly without being purified.

The crude obtained was dissolved in tetrahydrofuran (30 mL), and then 10% palladium-carbon (300 mg) was added thereto to allow a hydrogenation at 30° C. for 6 hours. After removing the catalyst by suction filtration, the solvent was rotary evaporated off to give a brownish yellow oily crude, which was used in the next step directly without being purified. Theoretical value via LC-MS (M+): 211.08, and measured value via LC-MS (ESI, M+H+): 212.05.

1.1.3 Synthesis of Intermediate D-1 (Step c)

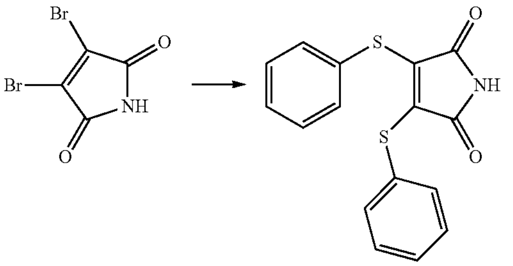

D-1

2,3-dibromomaleimide (7.0 g, 27.69 mmol) was dissolved in methanol (80 mL), and sodium acetate (4.5 g, 55.4 mmol) and thiophenol (11.3 mL, 110.7 mmol) were added thereto. The obtained reaction mixture was stirred at room temperature for 30 minutes, and then the organic solvent was rotary evaporated off. The residue was extracted with dichloromethane, washed successively with water and saturated salt water, and dried with anhydrous sodium sulfate, and then the solvent was rotary evaporated off. The obtained crude was co-crystallized with petroleum ether/ethyl acetate, suction filtrated and dried to obtain a bright yellow solid D-1 (6.5 g, 75% yield).

1.4.4 Synthesis of Intermediate E-1 (Step d)

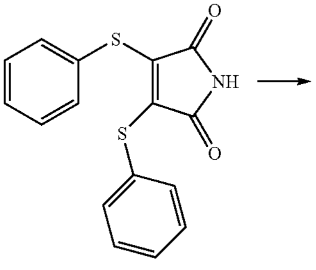

D-1

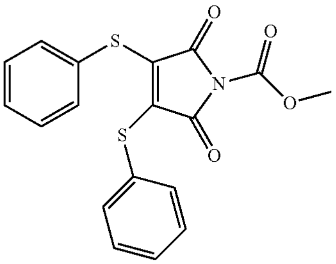

E-1

Intermediate D-1 (3.0 g, 9.6 mmol) and N-methylmorpholine (1.37 mL, 12.5 mmol) were dissolved in ethyl acetate (40 mL), and cooled in ice water followed by slowly dropping methyl chloroformate (1.11 mL, 14.4 mmol) thereto. The reaction mixture was diluted with ethyl acetate after being stirred at room temperature for 30 minutes, extracted with water added, washed successively with water and saturated salt water, and dried with anhydrous sodium sulfate, and then the solvent was rotary evaporated off. The obtained crude was co-crystallized with petroleum ether/ethyl acetate, suction filtrated and dried to obtain a bright yellow solid E-1 (3.5 g, 98% yield).

1.1.5 Synthesis of Intermediate F-1 (Step e)

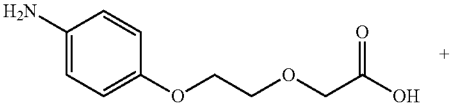

C-1

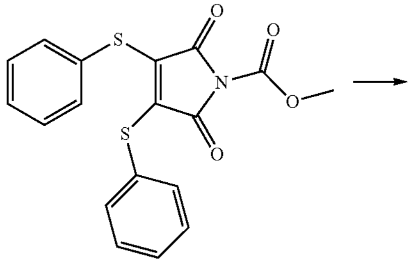

E-1

-continued

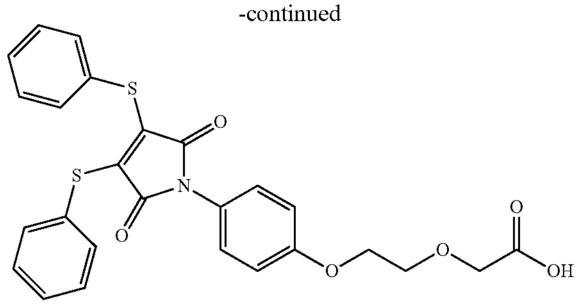

F-1

Intermediate C-1 (2.0 g, 9.5 mmol) was dissolved in anhydrous dichloromethane (40 ml), and then intermediate E-1 (3.5 g, 9.5 mmol) was added thereto. The obtained reaction mixture was stirred at room temperature for 24 hours under the protection of nitrogen. The reaction mixture was stirred at room temperature overnight after addition of silica gel (12 g, 200-300 mesh). Then the solvent was rotary evaporated off and the residue was subjected to dry column chromatography (silica gel, 200-300 mesh, dichloromethane/methanol 10:1) to obtain F-1, which was an orange oily product (4.1 g, 85% yield). Theoretical value via LC-MS (M+): 507.08, and measured value via LC-MS (ESI, M+H+): 508.11.

1.2 Synthesis of Compound F-2 (Formula 2)

F-2

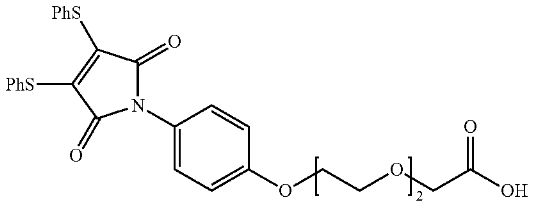

Compound F-2 was synthetized by the same steps for synthesizing compound F-1 of Example 1.1, with the exception that diethylene glycol in step a was changed to triethylene glycol. Product F-2 obtained after 5 steps of reaction was orange oily product. Theoretical value via LC-MS (M+): 551.11, and measured value via LC-MS (ESI, M+H+): 552.13.

1.3 Synthesis of Compound F-3 (Formula 3)

F-3

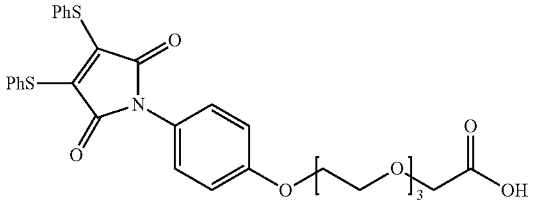

Compound F-3 was synthetized by the same steps for synthesizing compound F-1 of Example 1.1, with the exception that diethylene glycol in step a was changed to tetraethylene glycol. Product F-3 obtained after 5 steps of reaction was an orange oily product. Theoretical value via LC-MS (M+): 595.13, and measured value via LC-MS (ESI, M+H+): 596.14.

1.4 Synthesis of Compound F-4 (Formula 4)

F-4

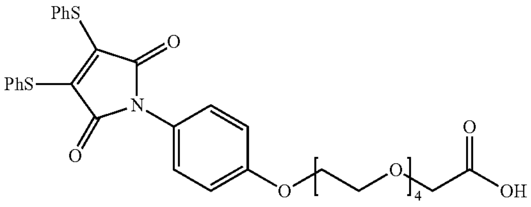

Compound F-4 was synthetized by the same steps for synthesizing compound F-1 of Example 1.1, with the exception that diethylene glycol in step a was changed to pentaethylene glycol. Product F-4 obtained after 5 steps of reaction was an orange oily product. Theoretical value via LC-MS (M+): 639.16, and measured value via LC-MS (ESI, M+H+): 640.18.

1.5 Synthesis of Compound F-5 (Formula 5)

F-5

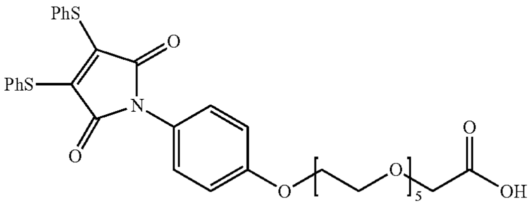

Compound F-5 was synthetized by the same steps for synthesizing compound F-1 of Example 1.1, with the exception that diethylene glycol in step a was changed to hexaethylene glycol. Product F-5 obtained after 5 steps of reaction was an orange oily product. Theoretical value via LC-MS (M+): 683.19, and measured value via LC-MS (ESI, M+H+): 684.21.

1.6 Synthesis of Compound F-6 (Formula 6)

F-6

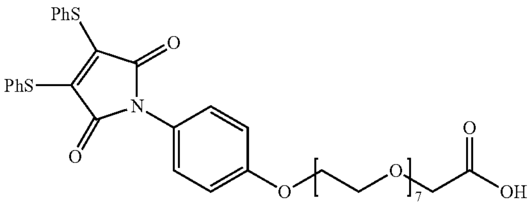

Compound F-6 was synthetized by the same steps for synthesizing compound F-1 of Example 1.1, with the exception that diethylene glycol in step a was changed to octaethylene glycol. Product F-6 obtained after 5 steps of reaction was an orange yellow oily product. Theoretical value via LC-MS (M+): 771.24, and measured value via LC-MS (ESI, M+H+): 772.26.

1.7 Synthesis of Compound F-7 (Formula 7)

F-7

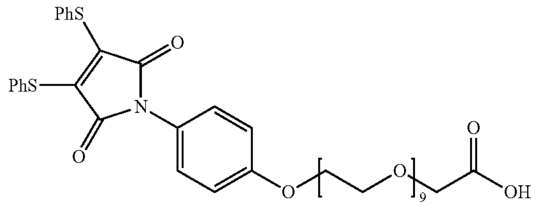

Compound F-7 was synthetized by the same steps for synthesizing compound F-1 of Example 1.1, with the exception that diethylene glycol in step a was changed to decaethylene glycol. Product F-7 obtained after 5 steps of reaction was an orange oily product. Theoretical value via LC-MS (M+): 895.29, and measured value via LC-MS (ESI, M+H+): 896.31.

1.8 Synthesis of Compound F-8 (Formula 8)

F-8

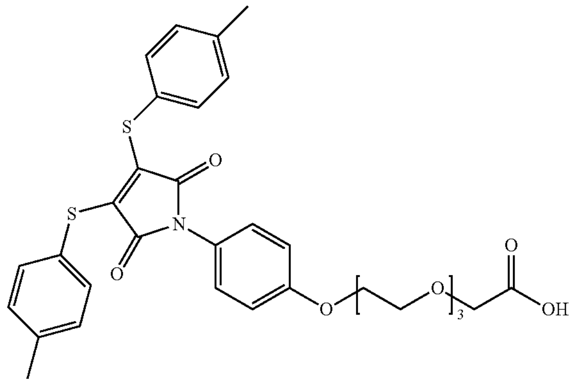

Compound F-8 was synthetized by the same steps for synthesizing compound F-3 of Example 1.3, with the exception that thiophenol in step c was changed to p-methylthiophenol. Product F-8 obtained after 5 steps of reaction was an orange oily product. Theoretical value via LC-MS (M+): 623.16, and measured value via LC-MS (ESI, M+H+): 624.18.

1.9 Synthesis of Compound F-9 (Formula 9)

F-9

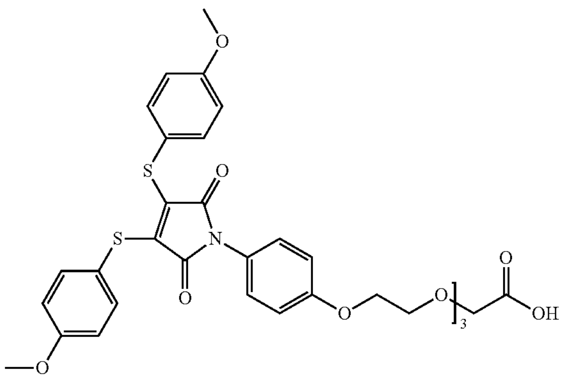

Compound F-9 was synthetized by the same steps for synthesizing compound F-3 of Example 1.3, with the exception that thiophenol in step c was changed to p-methoxythiophenol. Product F-9 obtained after 5 steps of reaction was an orange oily product. Theoretical value via LC-MS (M+): 655.15, and measured value via LC-MS (ESI, M+H+): 656.17.

1.10 Synthesis of Compound F-10 (Formula 10)

F-10

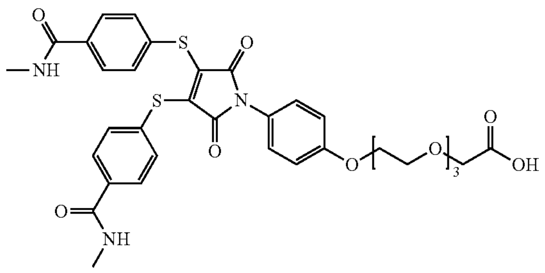

Compound F-10 was synthetized by the same steps for synthesizing compound F-3 of Example 1.3, with the exception that thiophenol in step c was changed to 4-(N-methylformamide) thiophenol. Product F-10 obtained after 5 steps of reaction was an orange oily product. Theoretical value via LC-MS (M+): 709.18, and measured value via LC-MS (ESI, M+H+): 710.23.

1.11 Synthesis of Compound F-11 (Formula 11)

F-11

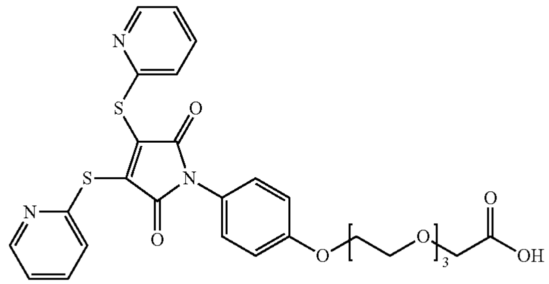

Compound F-11 was synthetized by the same steps for synthesizing compound F-3 of Example 1.3, with the exception that thiophenol in step c was changed to 2-mercaptopyridine. Product F-11 obtained after 5 steps of reaction was an orange oily product. Theoretical value via LC-MS (M+): 597.12, and measured value via LC-MS (ESI, M+H+): 598.13.

1.12 Synthesis of Compound F-12 (Formula 12)

F-12

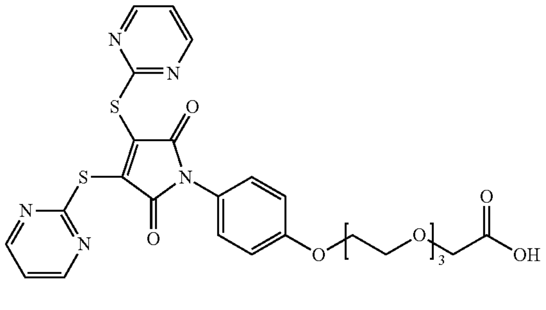

Compound F-12 was synthetized by the same steps for synthesizing compound F-3 of Example 1.3, with the exception that thiophenol in step c was changed to 2-mercaptopyrimidine. Product F-12 obtained after 5 steps of reaction was an orange oily product. Theoretical value via LC-MS (M+): 599.11, and measured value via LC-MS (ESL, M+H+): 600.13.

1.13 Synthesis of Compound F-13 (Formula 13)

F-13

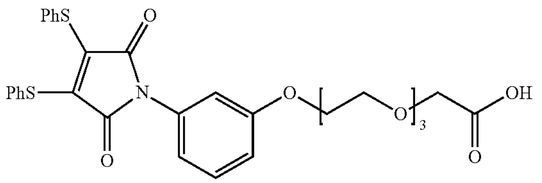

Compound F-13 was synthetized by the same steps for synthesizing compound F-3 of Example 1.3, with the exception that 4-fluoronitrobenzene in step a was changed to 3-fluoronitrobenzene. Product F-13 obtained after 5 steps of reaction was an orange oily product. Theoretical value via LC-MS (M+): 595.13, and measured value via LC-MS (ESI, M+H+): 596.15.

1.14 Synthesis of Compound F-14 (Formula 14)

F-14

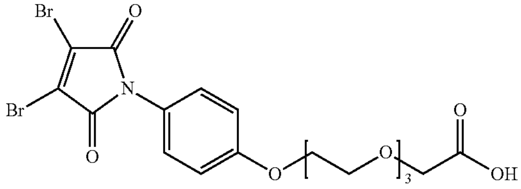

Compound F-14 was synthetized by the same steps for synthesizing compound F-3 of Example 1.3, with the exception that intermediate E-1 in step e was changed to intermediate E' (substituted with bromine). Product F-14 obtained after 4 steps of reaction was a colorless oily product. Theoretical value via LC-MS (M+): 534.95, and measured value via LC-MS (ESI, M+H+): 536.01.

1.15 Synthesis of Compound F-15 (Formula 15)

F-15

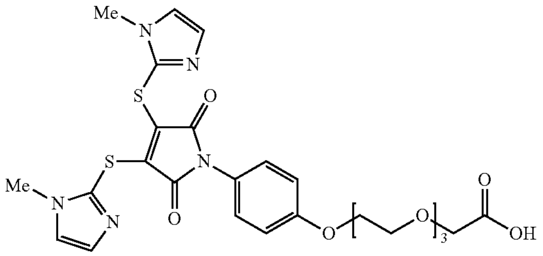

Compound F-15 was synthetized by the same steps for synthesizing compound F-3 of Example 1.3, with the exception that thiophenol in step c was changed to 2-mercapto-1-methylimidazole. Product F-15 obtained after 5 steps of reaction was an orange oily product. Theoretical value via LC-MS (M+): 603.15, and measured value via LC-MS (ESI, M+H+): 604.14.

1.16 Synthesis of Compound F-16 (Formula 16)

F-16

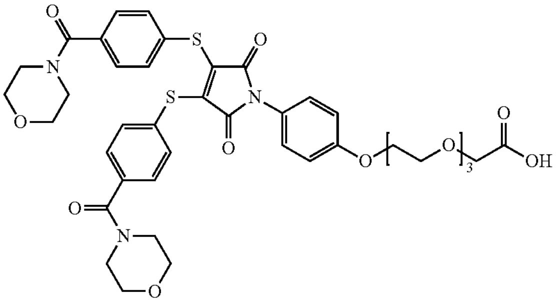

Compound F-16 was synthetized by the same steps for synthesizing compound F-3 of Example 1.3, with the exception that thiophenol in step c was changed to 4-(N-morpholineformamide) thiophenol. Product F-16 obtained after 5 steps of reaction was an orange oily product. Theoretical value via LC-MS (M+): 821.23, and measured value via LC-MS (ESI, M+H+): 822.21.

1.17 Synthesis of Compound F-17 (Formula 17)

F-17

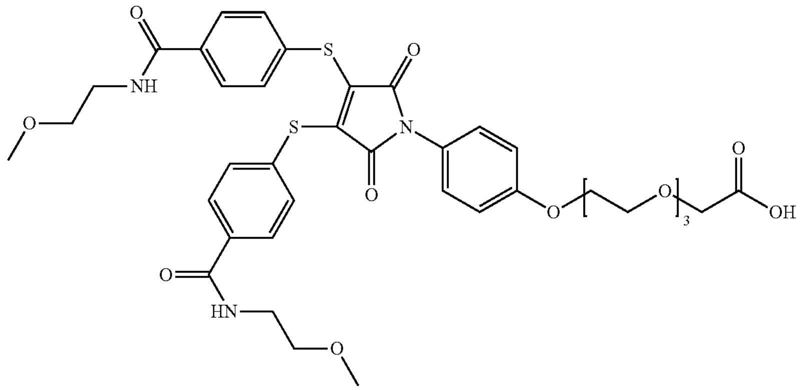

Compound F-17 was synthetized by the same steps for synthesizing compound F-3 of Example 1.3, with the exception that thiophenol in step c was changed to 4-(N-2-methoxyethylformamide) thiophenol. Product F-17 obtained after 5 steps of reaction was an orange oily product. Theoretical value via LC-MS (M+): 797.23, and measured value via LC-MS (ESI, M+H+): 798.31.

1.18 Synthesis of Compound F-18 (Formula 18)

F-18

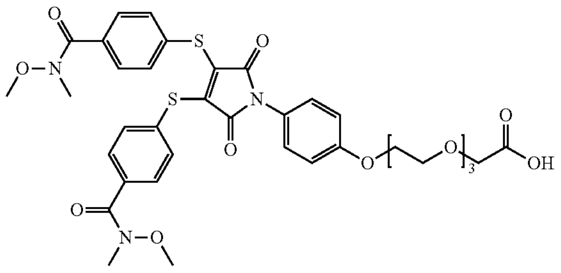

Compound F-18 was synthetized by the same steps for synthesizing compound F-3 of Example 1.3, with the exception that thiophenol in step c was changed to 4-(N-methoxy-N-methylformamide) thiophenol. Product F-18 obtained after 5 steps of reaction was an orange oily product. Theoretical value via LC-MS (M+): 769.20, and measured value via LC-MS (ESI, M+H+): 770.28.

The substituted maleamide linker represented by Formula Ia can also be synthesized by the method shown in the following scheme. Specifically, intermediate B can be obtained through a substitution reaction between n-ethylene glycol and fluoronitrobenzene, and is then reacted with tert-butyl bromoacetate to generate intermediate Z; alternatively, intermediate Z can also be obtained by reacting n-ethylene glycol with tert-butyl bromoacetate following by another substitution reaction with fluoronitrobenzene; intermediate Z was then reduced to generate intermediate Y; intermediate D can be obtained through a substitution reaction between 2,3-dibromomaleimide and aryl thiophenol, and is then reacted with methyl chloroformate to generate intermediate E; Intermediate E is reacted with intermediate Y to obtain intermediate X; and the tert-butyl ester in intermediate X is removed under acidic condition to obtain linker W. An example of synthesis scheme is as follows:

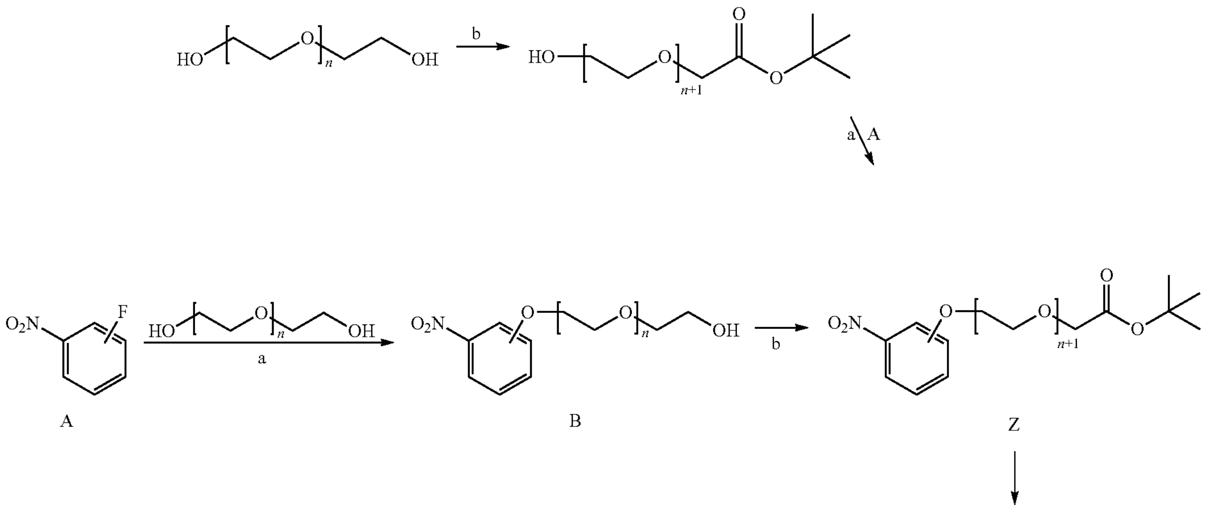

A B Z

-continued

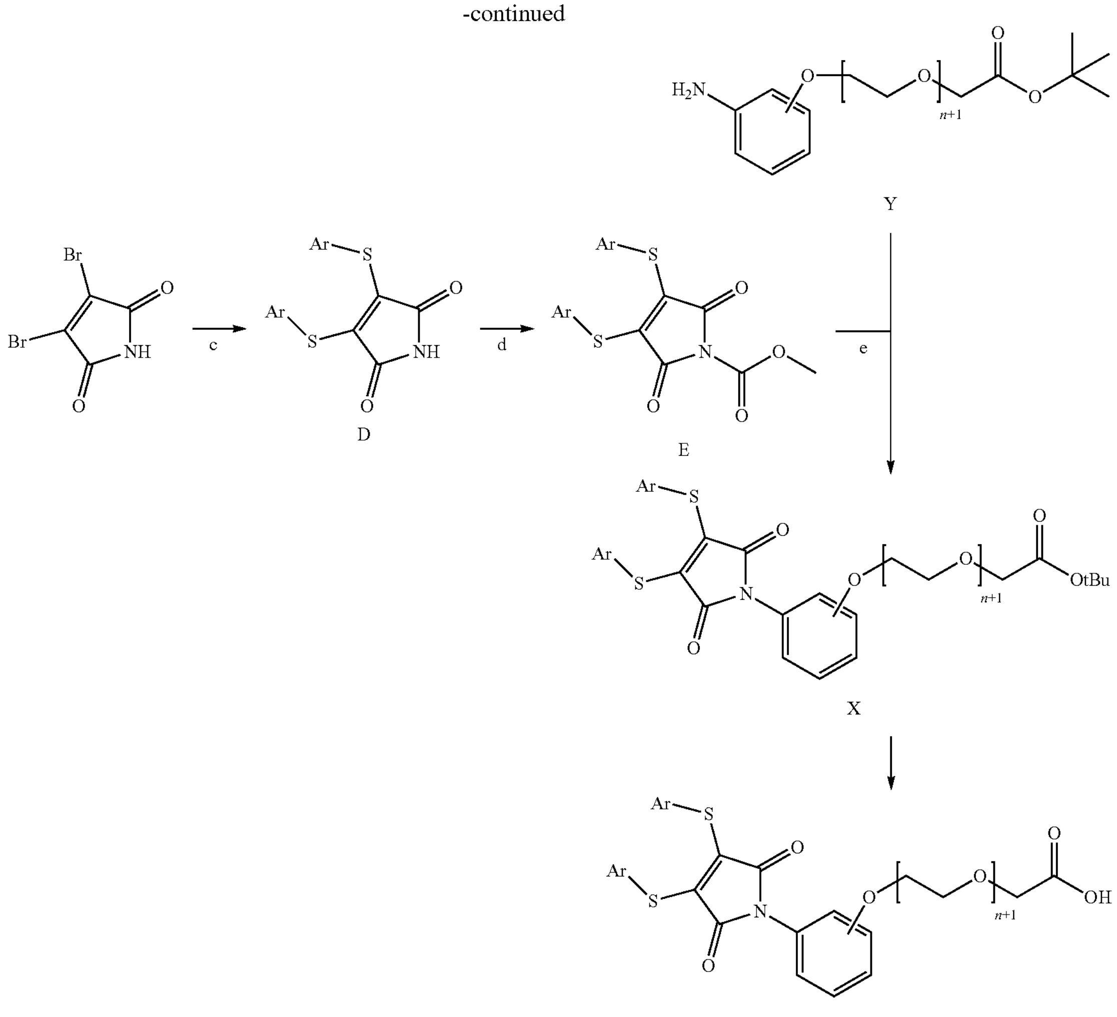

Y D E X W

Solution 2:

The substituted maleamide linker-drug conjugate (Formula 19-Formula 25) as shown in Formula Ib, which is provided in the second aspect of the present invention, can be synthesized by the synthesis scheme listed in Solution 2. Specifically, compound F is condensed and coupled with a cytotoxic drug CTD (D1-D11, which are commercially available) to obtain a series of molecules represented by Formula G. Synthesis scheme and specific examples are as follows:

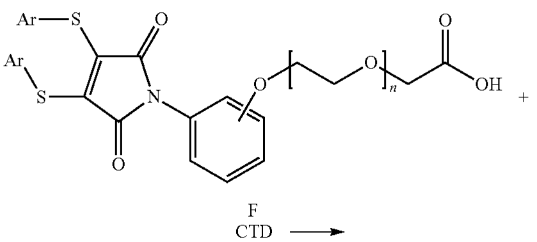

F

CTD

-continued

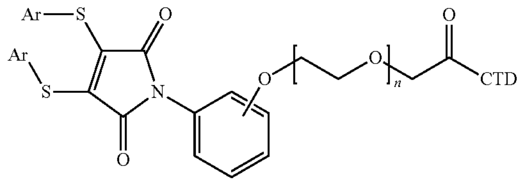

G

Example 2: Synthesis and Preparation of Compounds as Shown in Formulas 19-25

2.1 Synthesis of Compound G-1 (Formula 19)

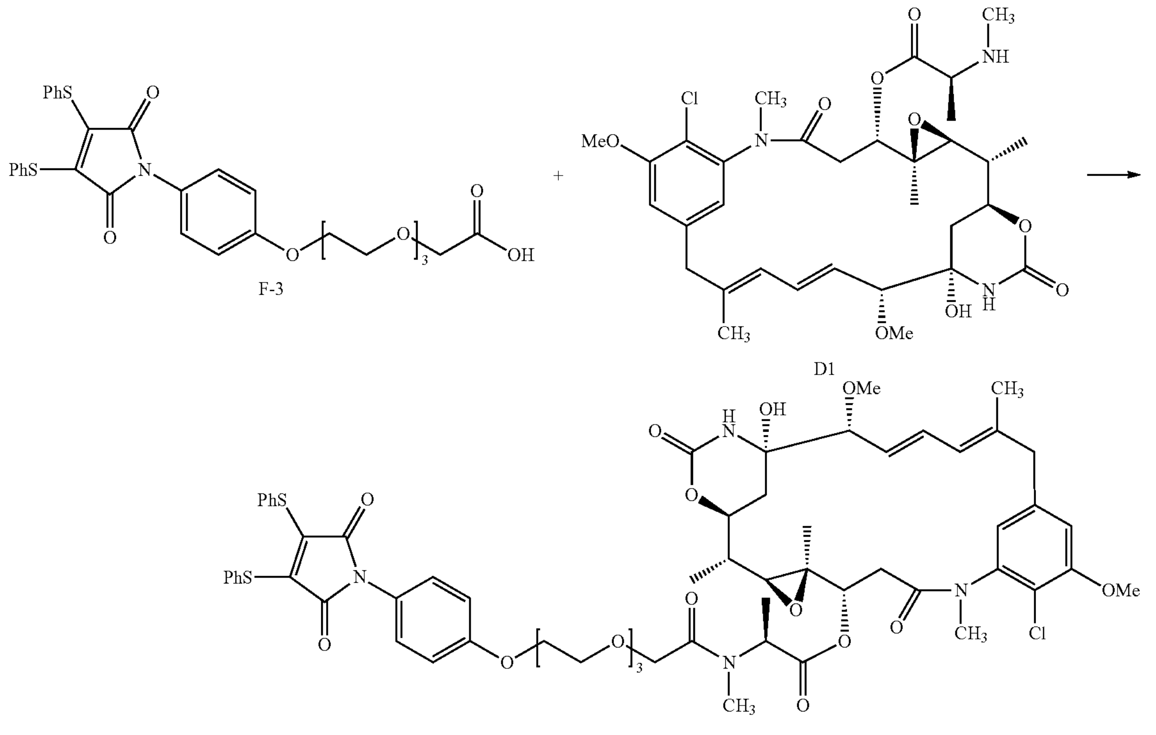

F-3 D1 G-1

Compound F-3 (200 mg, 0.34 mmol) and compound D1 (220 mg, 0.34 mmol) were dissolved in N,N-dimethylformamide (10 mL) and then 1-ethyl-(3-dimethylaminopropyl) carbodiimide hydrochloride (EDCl) (77 mg, 0.40 mmol) and 1-hydroxybenzotriazole (HOBT) (54 mg, 0.40 mmol) were added thereto. The reaction mixture was stirred overnight at room temperature, and then diluted with ethyl acetate, extracted with addition of water, washed successively with water and saturated salt water, and dried with anhydrous sodium sulfate, and then the solvent was rotary evaporated off. The obtained crude was isolated and purified by using a silica gel chromatographic column (dichloromethane/methanol), suction filtrated and dried to obtain a yellow amorphous solid G-1 (3.5 g, 98% yield). Theoretical value via LC-MS (M+): 1226.40, and measured value via LC-MS (ESI, M+H+): 1227.42.

2.2 Synthesis of Compound G-2 (Formula 20)

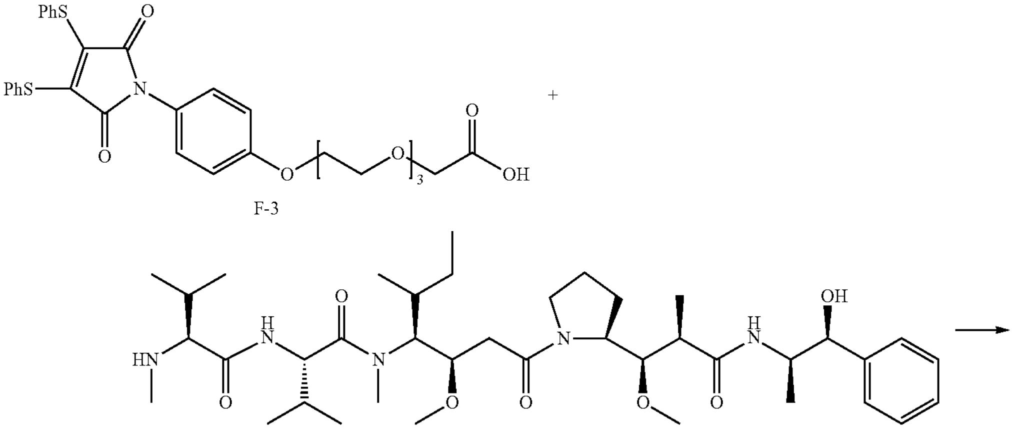

F-3 D2

-continued

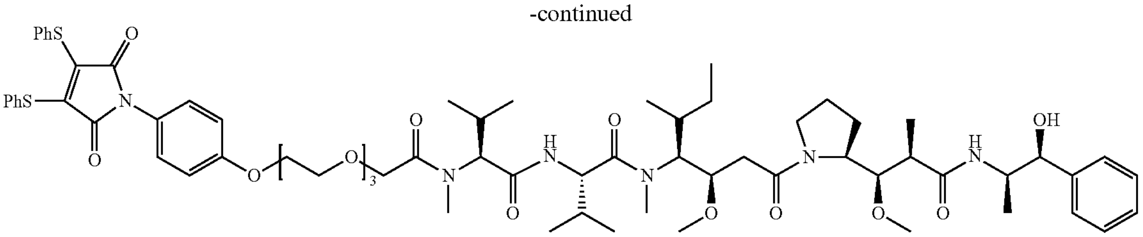

G-3

Compound G-2 was synthetized by the same steps for synthesizing compound G-1 of Example 2.1, with the exception that compound D1 was changed to compound D2. Product G-2 obtained was yellow amorphous solid. Theoretical value via LC-MS (M+): 1294.63, and measured value via LC-MS (ESI, M+H+): 1295.64.

2.3 Synthesis of Compound G-3 (Formula 21)

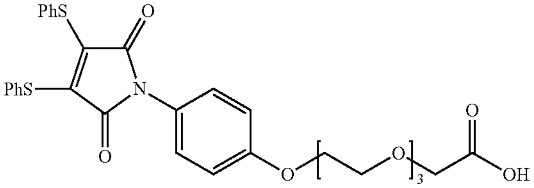

F-3

+

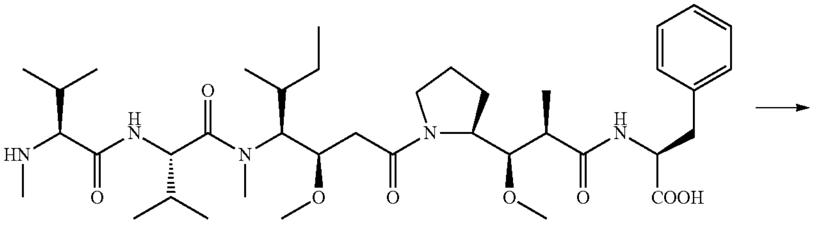

D3

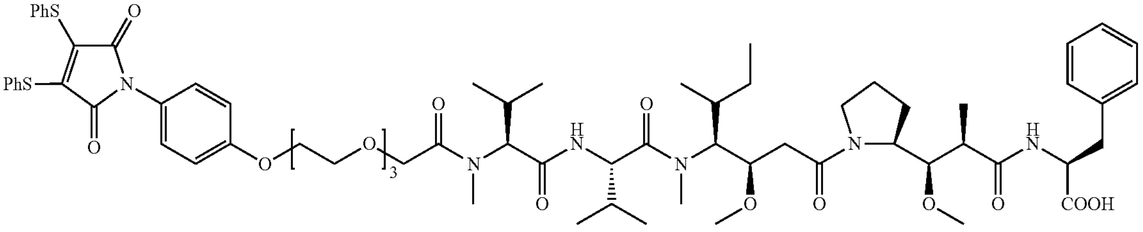

G-3

Compound G-3 was synthetized by the same steps for synthesizing compound G-1 of Example 2.1, with the exception that compound D1 was changed to compound D3. Product G-3 obtained was yellow amorphous solid. Theoretical value via LC-MS (M+): 1308.61, and measured value via LC-MS (ESI, M+H+): 1309.63.

2.4 Synthesis of Compound G-4 (Formula 22)
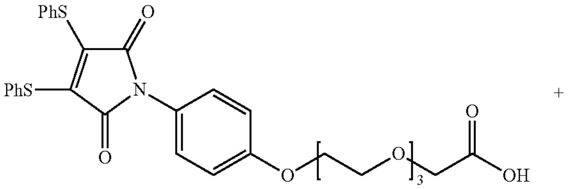
F-3
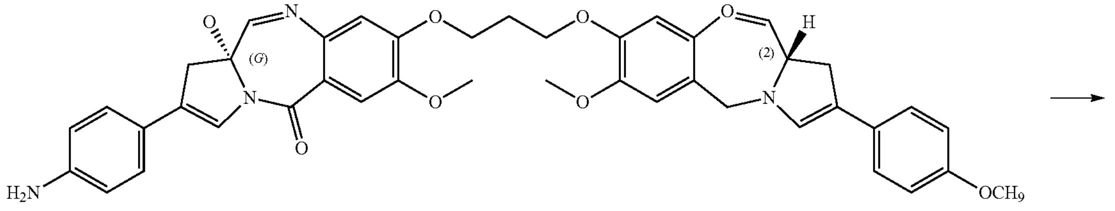
D5
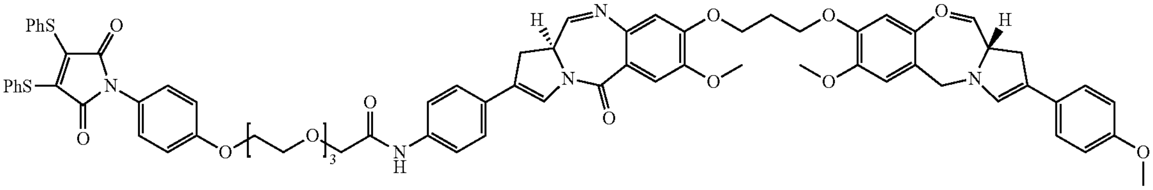
G-4
Compound G-4 was synthetized by the same steps for synthesizing compound G-1 of Example 2.1, with the exception that compound D1 was changed to compound D9. Product G-4 obtained was yellow amorphous solid. Theoretical value via LC-MS (M+): 1302.41, and measured value via LC-MS (ESI, M+H+): 1303.43.
2.5 Synthesis of Compound G-5 (Formula 23)
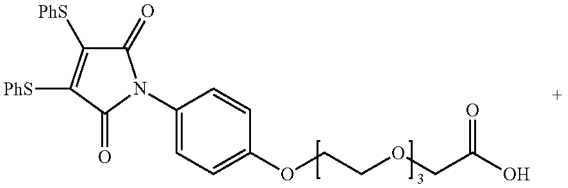
F-3
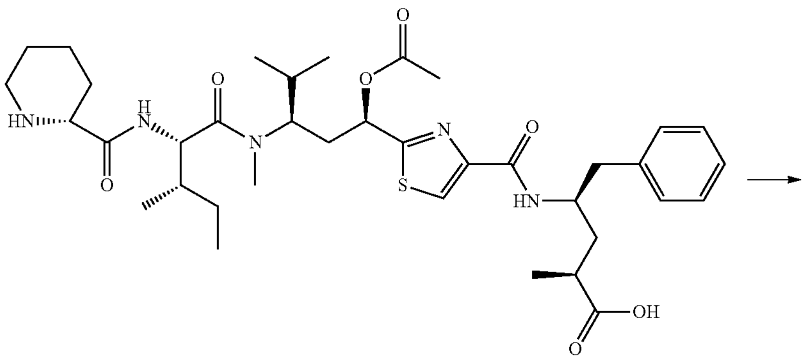
D6

-continued

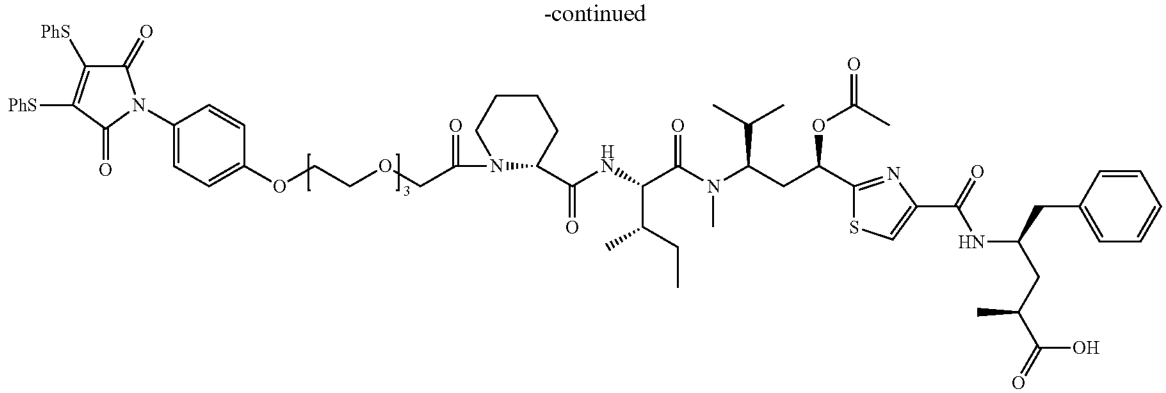

G-3

Compound G-5 was synthetized by the same steps for synthesizing compound G-1 of Example 2.1, with the exception that compound D1 was changed to compound D6. Product G-5 obtained was yellow amorphous solid. Theoretical value via LC-MS (M+): 1290.51, and measured value via LC-MS (ESI, M+H+): 1291.53.

2.6 Synthesis of Compound G-6 (Formula 24)

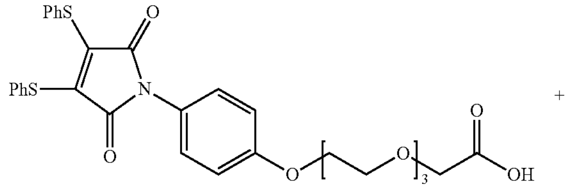

F-3

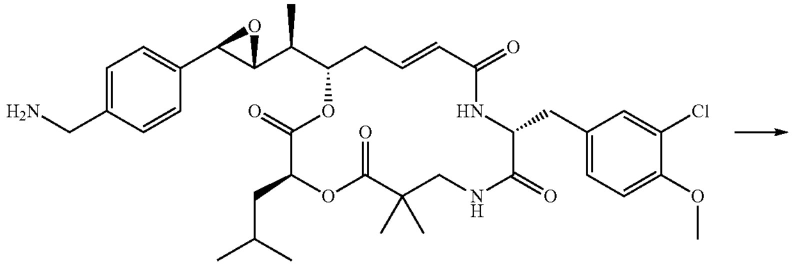

D7

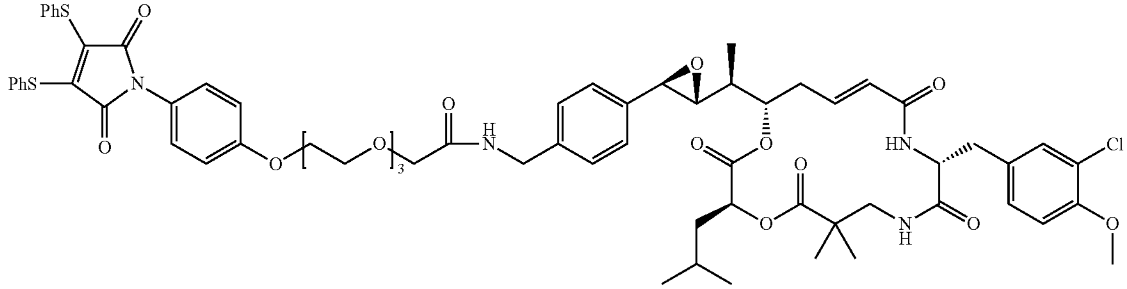

G-5

Compound G-6 was synthetized by the same steps for synthesizing compound G-1 of Example 2.1, with the exception that compound D1 was changed to compound D7. Product G-6 obtained was yellow amorphous solid. Theoretical value via LC-MS (M+): 1274.44, and measured value via LC-MS (ESI, M+H+): 127545.

2.7 Synthesis of Compound G-7 (Formula 25)

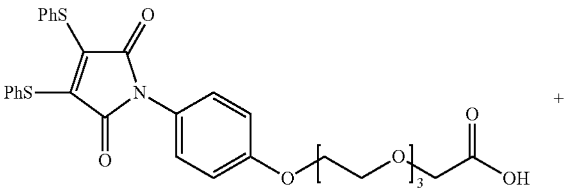

F-3

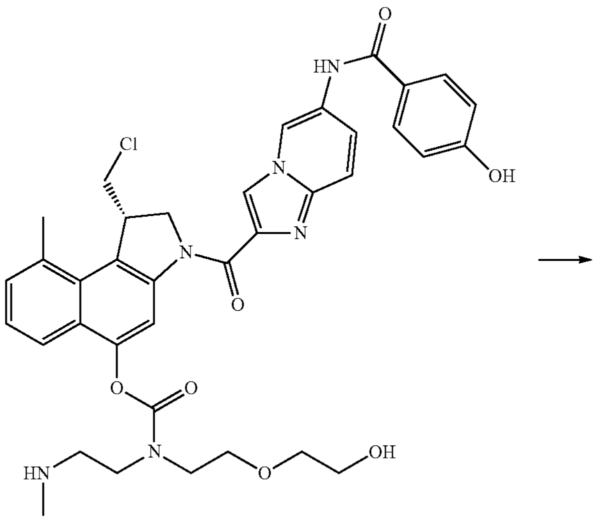

D11

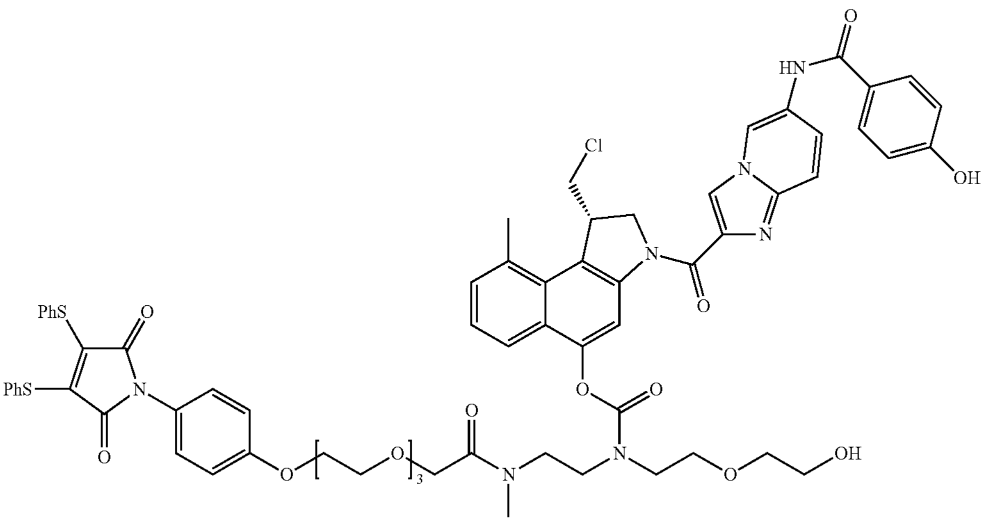

G-7

Compound G-7 was synthetized by the same steps for synthesizing compound G-1 of Example 2.1, with the exception that compound D1 was changed to compound D11. Product G-7 obtained was yellow amorphous solid. Theoretical value via LC-MS (M+): 1291.38, and measured value via LC-MS (ESI, M+H+): 1292.40.

Solution 3:

The substituted maleamide linker-drug conjugate (Formula 26-Formula 49) as shown in Formula Ib, which is provided in the second aspect of the present invention, can be synthesized by the synthesis scheme listed in Solution 3. Specifically, compound F is condensed with an amino in dipeptide/tripeptide-PAB linker (commercially available), and then the PAB group is condensed and coupled with a cytotoxic drug CTD (D1-D11) after being activated by bis(p-nitrophenyl) carbonate, thus a series of molecules represented by Formula K are obtained. Synthesis scheme and specific examples are as follows:

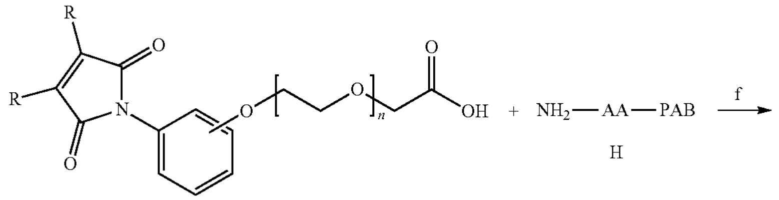
H
F
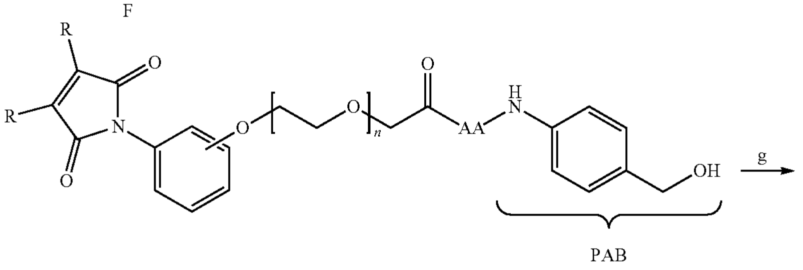
I
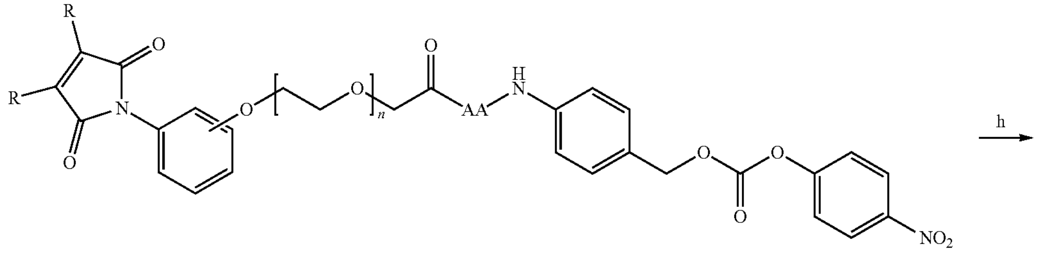
J
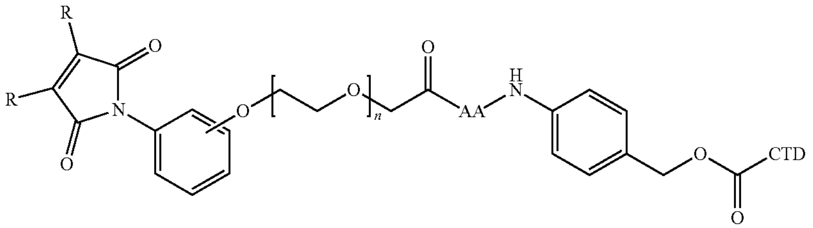
K
3.1 Synthesis of Compound K-1 (Formula 26)
3.1.1 Synthesis of Intermediate I-1 (Step f)
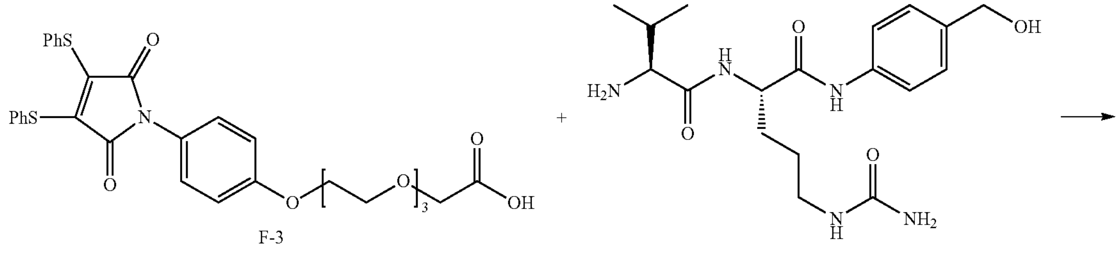
F-3
H-1

-continued

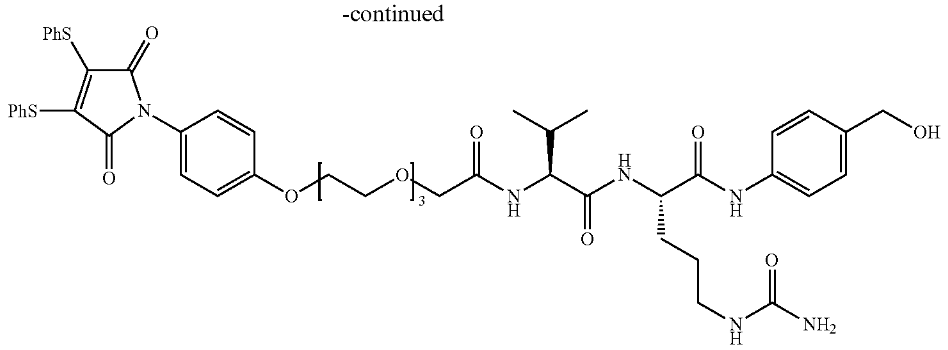

I-1

Compound F-3 (2.0 g, 3.36 mmol) was dissolved in anhydrous N,N-dimethylformamide (25 mL) and then EDCl (963 mg, 5.04 mmol), HOBt (681 mg, 5.04 mmol) and N-methylmorpholine (1.11 ml, 10.08 mmol) were successively added thereto under the protection of nitrogen. The reaction mixture was stirred under the protection of nitrogen at room temperature for 20 minutes, and then compound H-1 (Val-Cit-PAB, 1.91 g, 5.04 mmol) was added thereto. The reaction mixture was stirred under the protection of nitrogen overnight at room temperature. The solvent was rotary evaporated off and the residue was subjected to dry column chromatography (silica gel, 200-300 mesh, DCM/MeOH 10:1) to obtain 1-1, which was an orange oily product (2.0 g, 62.2% yield). Theoretical value via LC-MS (M+): 956.34, and measured value via LC-MS (ESI, M+H+): 957.37.

3.1.2 Synthesis of Intermediate J-1 (Step g)

Compound I-1 (1.5 g, 1.57 mmol) was dissolved in anhydrous N,N-dimethylformamide (10 mL) and then N,N-diisopropylethylamine (0.52 mL, 3.14 mmol) and bis(p-nitrophenyl) carbonate (717 mg, 2.335 mmol) were successively added thereto under the protection of nitrogen. The reaction mixture was stirred at room temperature for 15 hours and then the solvent was rotary evaporated off. The residue was subjected to dry column chromatography (silica gel, 200-300 mesh, DCM/MeOH 20:1) to obtain J-1, which was an orange oily product (1.4 g, 79.9% yield). Theoretical value via LC-MS (M+): 1121.35, and measured value via LC-MS (ESI, M+H+): 1122.37.

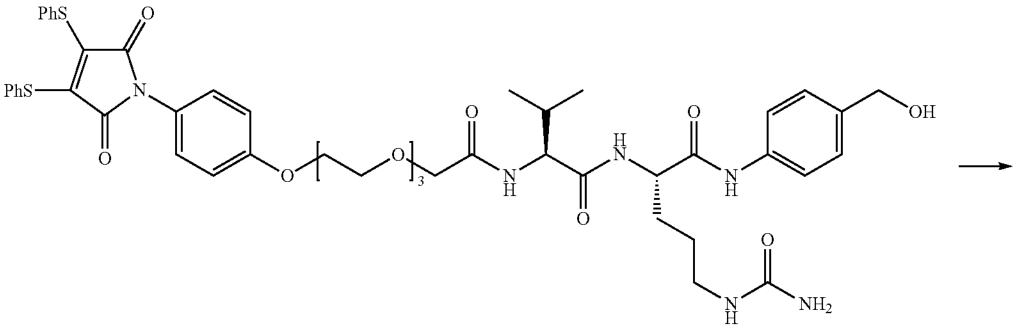

I-1

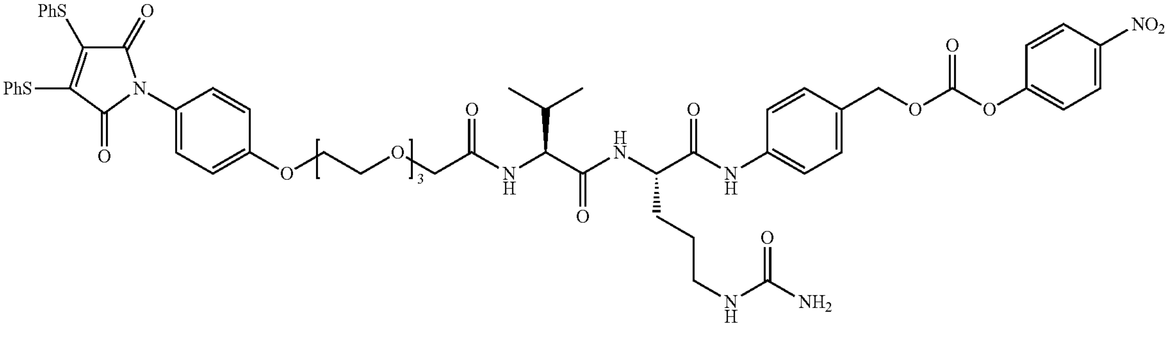

J-1

3.1.3 Synthesis of Intermediate K-1 (Step h)

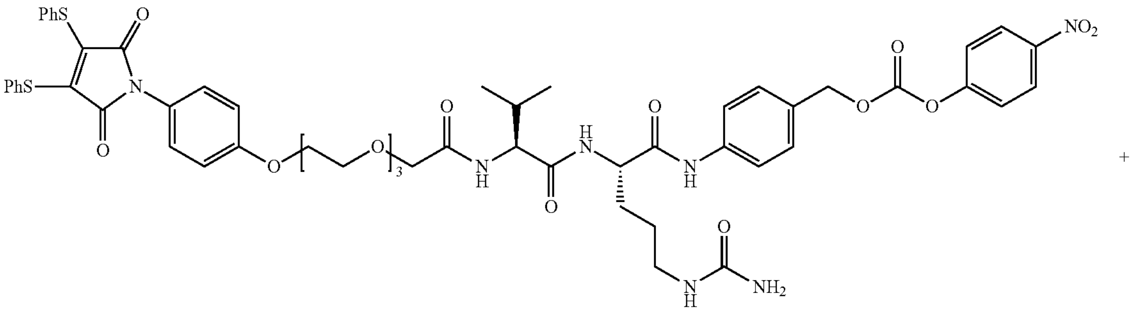

J-1

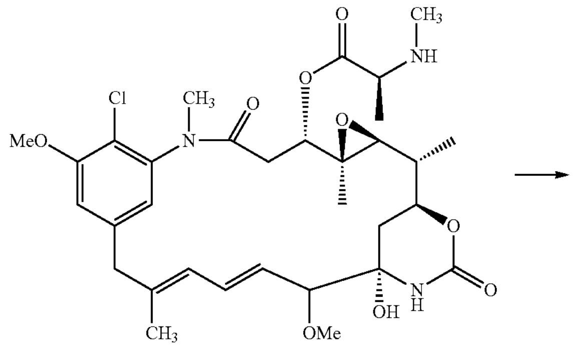

D-1

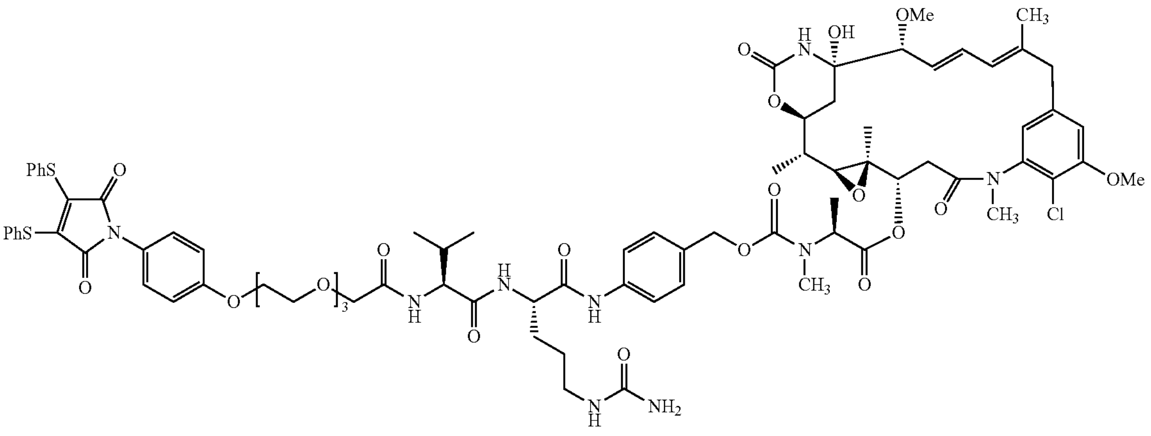

K-1

Compound J-1 (0.5 g, 0.52 mmol) was dissolved in anhydrous N,N-dimethylformamide (5 mL) and then N,N-diisopropylethylamine (0.172 mL, 1.04), HOBt (70 mg, 0.52 mmol) and compound D1 (340 mg, 0.52 mmol) were successively added thereto under the protection of nitrogen. The reaction mixture was stirred under the protection of nitrogen overnight at room temperature, and then the solvent was rotary evaporated off. The residue was subjected to dry column chromatography (silica gel, 200-300 mesh, DCM/MeOH 10:1) to obtain K-1, which was yellow amorphous solid (310 mg, 36.33% yield). Theoretical value via LC-MS (M+): 1631.60, and measured value via LC-MS (ESI, M+H+): 1632.62.

3.2 Synthesis of Compound K-2 (Formula 27)

K-2

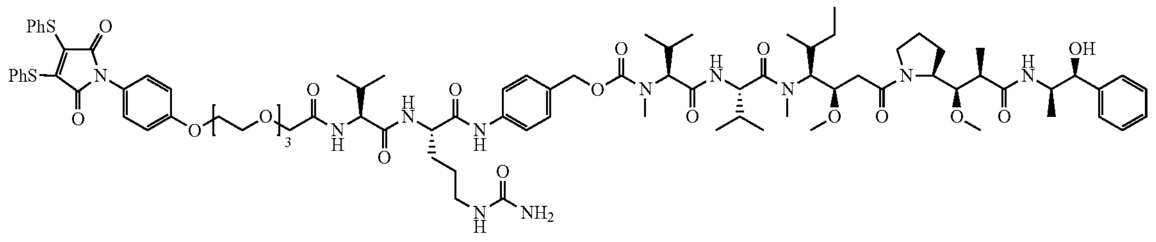

Compound K-2 was synthetized by the same steps for synthesizing compound K-1 of Example 3.1, with the exception that compound D1 in step h was changed to compound D2 (Monomethylauristatin E). Product K-2 obtained after 3 steps of reaction was yellow amorphous solid. Theoretical value via LC-MS (M+): 1699.83, and measured value via LC-MS (ESI, M+H+): 1610.85.

3.3 Synthesis of Compound K-3 (Formula 28)

K-3

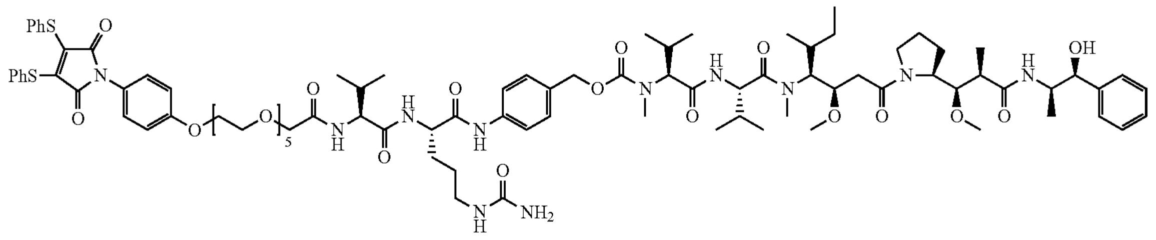

Compound K-3 was synthetized by the same steps for synthesizing compound K-1 of Example 3.1, with the exception that compound F-3 in step f was changed to F-5 and compound D1 in step h was changed to D2 (Monomethylauristatin E). Product K-3 obtained after 3 steps of reaction was yellow amorphous solid. Theoretical value via LC-MS (M+): 1787.88, and measured value via LC-MS (ESI, M+H+): 1788.90.

3.4 Synthesis of Compound K-4 (Formula 29)

K-4

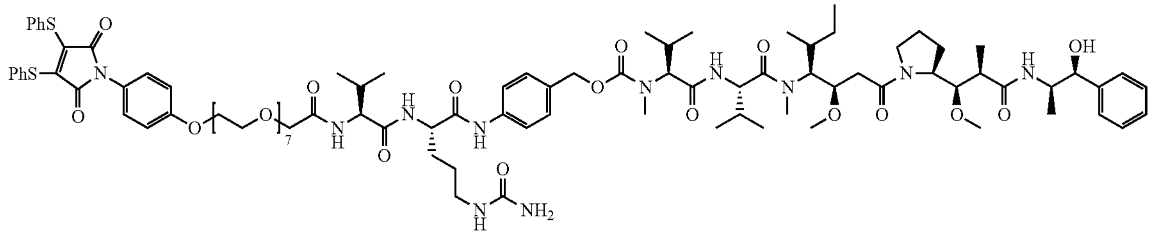

Compound K-4 was synthetized by the same steps for synthesizing compounds K-1 of Example 3.1, with the exception that compound F-3 in step f was changed to F-6 and compound D1 in step h was changed to D2 (Monomethylauristatin E). Product K-4 obtained after 3 steps of reaction was yellow amorphous solid. Theoretical value via LC-MS (M+): 1875.93, and measured value via LC-MS (ESI, M+H+): 1876.95.

3.5 Synthesis of Compound K-5 (Formula 30)

K-5

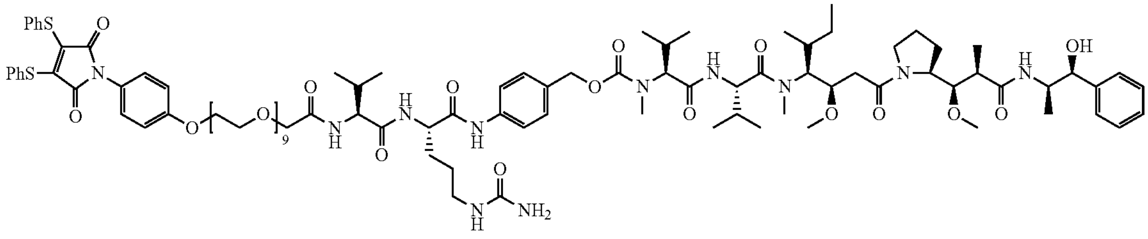

Compound K-4 was synthetized by the same steps for synthesizing compound K-1 of Example 3.1, with the exception that compound F-3 in step f was changed to F-7 and compound D1 in step h was changed to D2 (Monomethylauristatin E). Product K-4 obtained after 3 steps of reaction was yellow amorphous solid. Theoretical value via LC-MS (M+): 1963.99, and measured value via LC-MS (ESI, M+H+): 18765.01.

3.6 Synthesis of Compound K-6 (Formula 31)

K-6

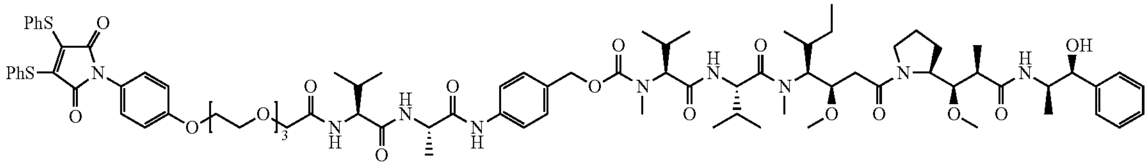

Compound K-6 was synthetized by the same steps for synthesizing compound K-1 of Example 3.1, with the exception that compound H-1 in step f was changed to H-2 (Val-Ala-PAB) and compound D1 in step h was changed to D2 (Monomethylauristatin E). Product K-6 obtained after 3 steps of reaction was yellow amorphous solid. Theoretical value via LC-MS (M+): 1613.78, and measured value via LC-MS (ESI, M+H+): 1614.80.

3.7 Synthesis of Compound K-7 (Formula 32)

K-7

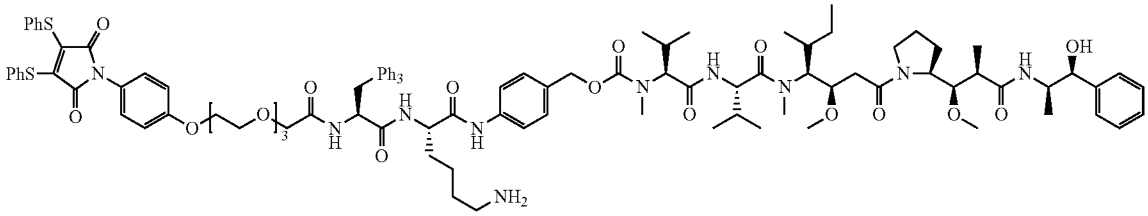

Compound K-7 was synthetized by the same steps for synthesizing compound K-1 of Example 3.1, with the exception that compound H-1 in step f was changed to H-3 (Phe-Lys-PAB) and compound D1 in step h was changed to D2 (Monomethylauristatin E). Product K-7 obtained after 3 steps of reaction was yellow amorphous solid. Theoretical value via LC-MS (M+): 1718.84, and measured value via LC-MS (ESI, M+H+): 1719.86.

3.8 Synthesis of Compound K-8 (Formula 33)

K-8

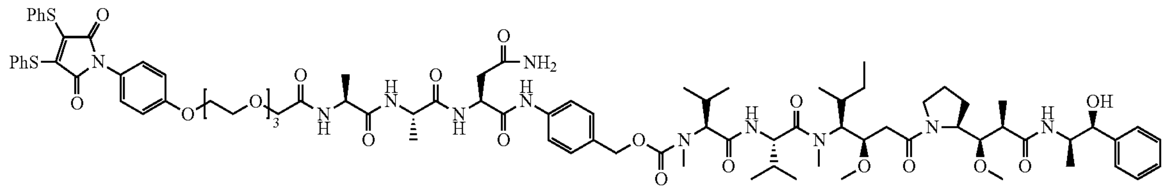

Compound K-8 was synthetized by the same steps for synthesizing compound K-1 of Example 3.1, with the exception that compound H-1 in step f was changed to H-4 (Ala-Ala-Asn-PAB) and compound D1 in step h was changed to D2 (Monomethylauristatin E). Product K-8 obtained after 3 steps of reaction was yellow amorphous solid. Theoretical value via LC-MS (M+): 1699.79, and measured value via LC-MS (ESI, M+H+): 1700.80.

3.9 Synthesis of Compound K-9 (Formula 34)

K-9

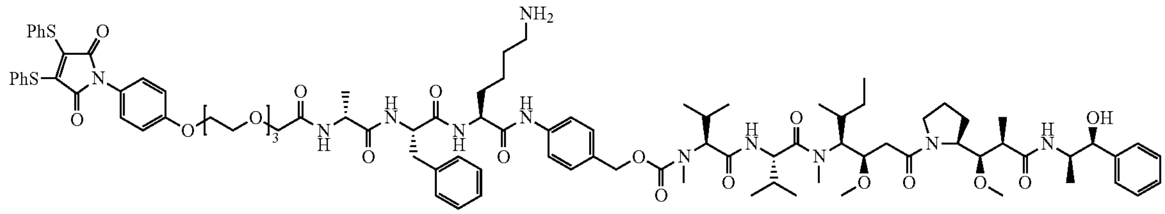

Compound K-9 was synthetized by the same steps for synthesizing compound K-1 of Example 3.1, with the exception that compound H-1 in step f was changed to H-5 (D-Ala-Phe-Lys-PAB) and compound D1 in step h was changed to D2 (Monomethylauristatin E). Product K-9 obtained after 3 steps of reaction was yellow amorphous solid. Theoretical value via LC-MS (M+): 1789.88, and measured value via LC-MS (ESI, M+H+): 179090.

3.10 Synthesis of Compound K-10 (Formula 35)

K-10

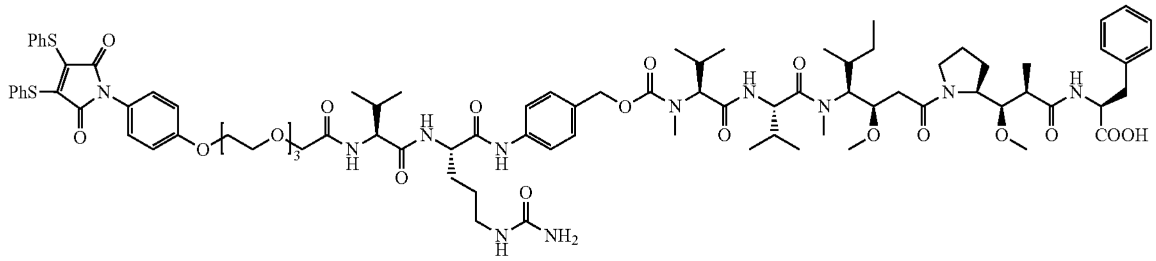

Compound K-10 was synthetized by the same steps for synthesizing compound K-1 of Example 3.1, with the exception that compound D in step h was changed to D3 (Monomethylauristatin F). Product K-10 obtained after 3 steps of reaction was yellow amorphous solid. Theoretical value via LC-MS (M+): 1713.81, and measured value via LC-MS (ESI, M+H+): 1714.83.

3.11 Synthesis of Compound K-11 (Formula 36)

K-11

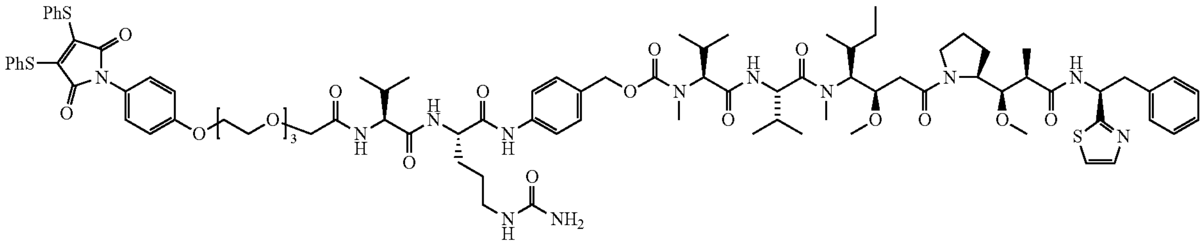

Compound K-12 was synthetized by the same steps for synthesizing compound K-1 of Example 3.1, with the exception that compound D1 in step h was changed to D4 (Monomethyl Dolestatin 10, MMAD). Product K-12 obtained after 3 steps of reaction was yellow amorphous solid. Theoretical value via LC-MS (M+): 1752.80, 125 and measured value via LC-MS (ESI, M+H+): 1753.82.

3.12 Synthesis of Compound K-12 (Formula 37)

K-12

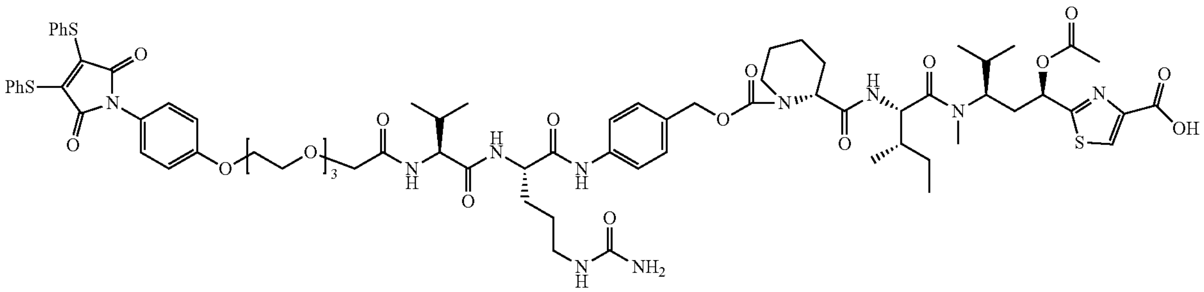

Compound K-12 was synthetized by the same steps for synthesizing compound K-1 of Example 3.1, with the exception that compound D1 in step h was changed to D5 (Tubulysin derivative 1). Product K-12 obtained after 3 steps of reaction was yellow amorphous solid. Theoretical value via LC-MS (M+): 1506.59, and measured value via LC-MS (ESI, M+H+): 1507.61.

3.13 Synthesis of Compound K-13 (Formula 38)

K-13

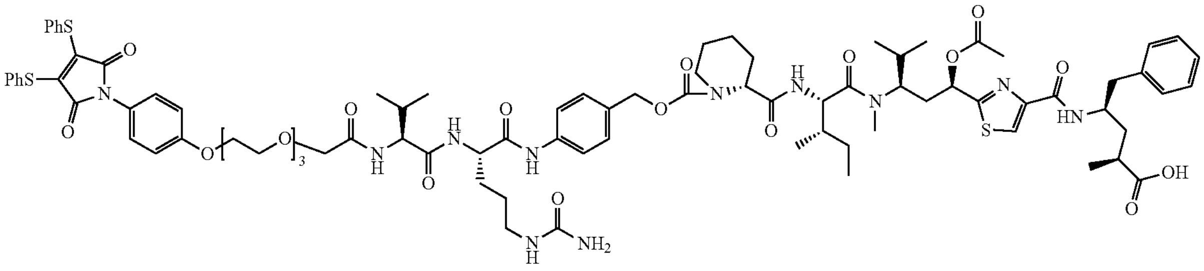

Compound K-13 was synthetized by the same steps for synthesizing compound K-1 of Example 3.1, with the exception that compound D1 in step h was changed to D6 (Tubulysin derivative 2). Product K-13 obtained after 3 steps of reaction was yellow amorphous solid. Theoretical value via LC-MS (M+): 1695.71, and measured value via LC-MS (ESI, M+H+): 1696.73.

3.14 Synthesis of Compound K-14 (Formula 39)

K-14

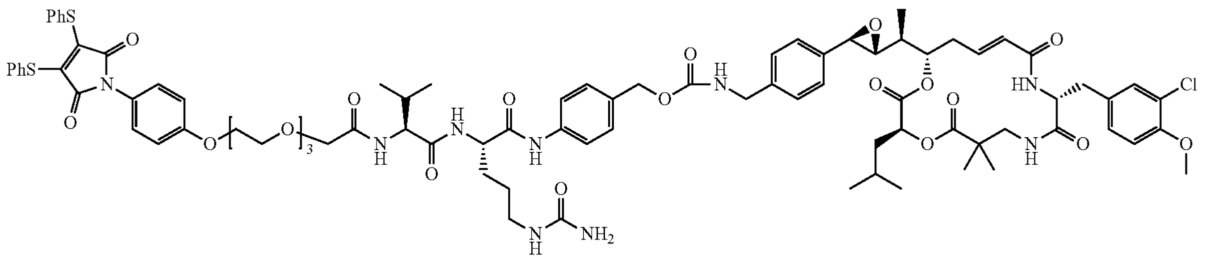

Compound K-14 was synthetized by the same steps for synthesizing compound K-1 of Example 3.1, with the exception that compound D1 in step h was changed to D6 (Cryptophycin derivative). The product K-14 obtained after 3 steps of reaction was yellow amorphous solid. Theoretical value via LC-MS (M+): 1679.64, and measured value via LC-MS (ESI, M+H+): 1680.66.

3.15 Synthesis of Compound K-15 (Formula 40)

K-15

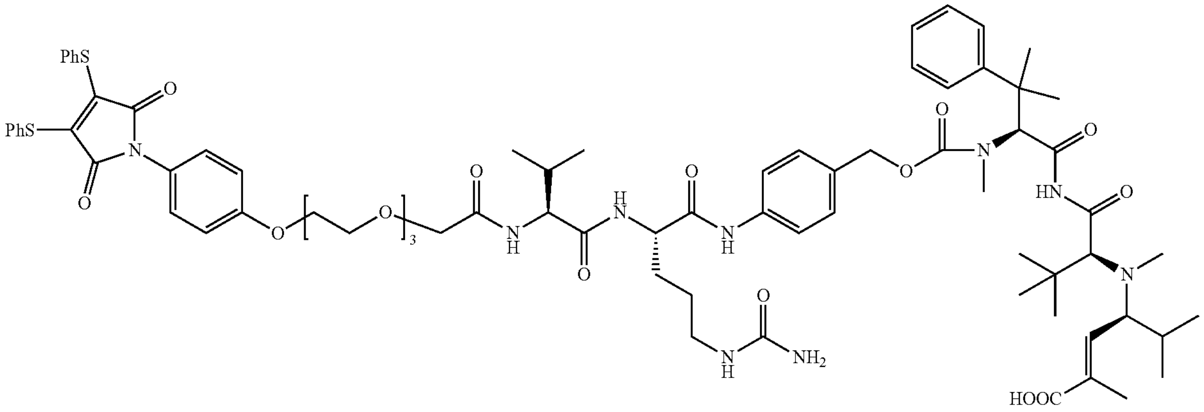

Compound K-15 was synthetized by the same steps for synthesizing compound K-1 of Example 3.1, with the exception that compound D in step h was changed to D8 (Taltobulin). Product K-15 obtained after 3 steps of reaction was brownish yellow amorphous solid. Theoretical value via LC-MS (M+): 1455.65, and measured value via LC-MS (ESI, M+H+): 1456.6.

3.16 Synthesis of Compound K-16 (Formula 41)

K-16

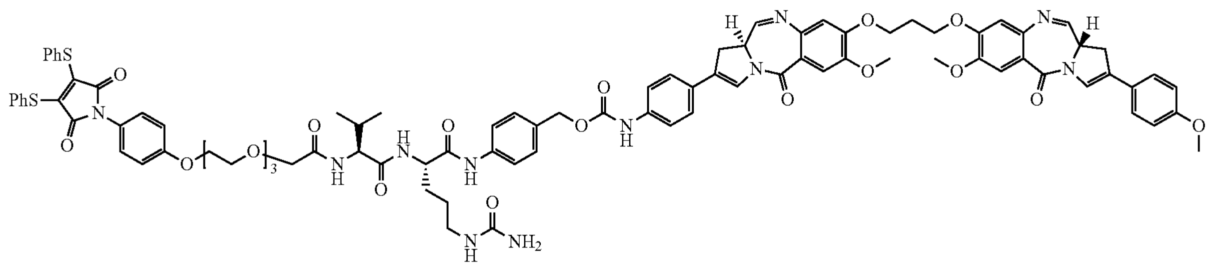

Compound K-16 was synthetized by the same steps for synthesizing compound K-1 of Example 3.1, with the exception that compound D1 in step h was changed to D9 PB dimer) duct K-16 obtained ater 3 steps of reaction was brownish yellow amorphous solid. Theoretical value via LC-MS (M+): 1455.61, and measured value via LC-MS (ESI, M+H+): 145708.63.

3.17 Synthesis of Compound K-17 (Formula 42)

K-17

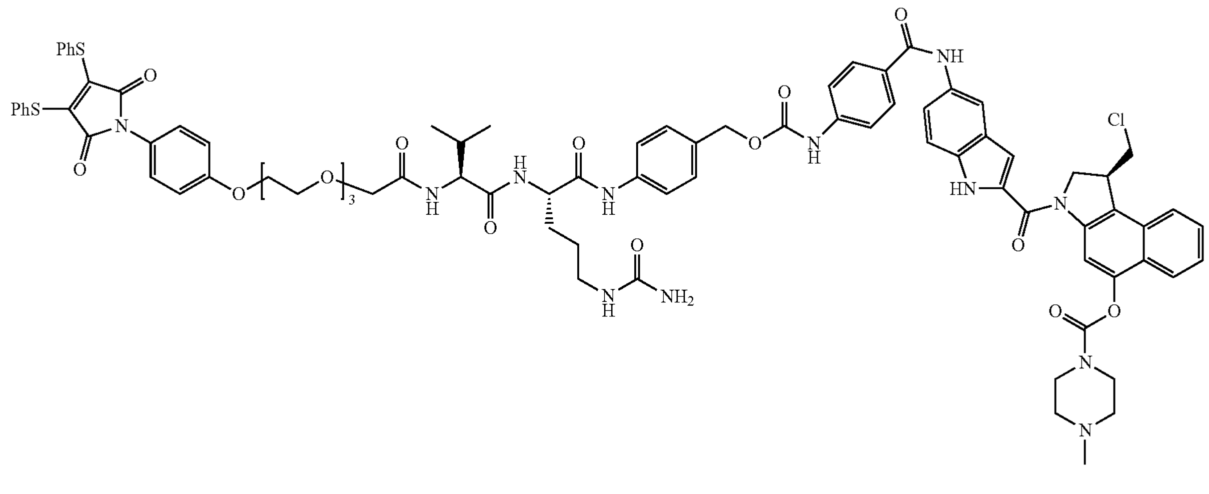

Compound K-17 was synthetized by the same steps for synthesizing compound K-1 of Example 3.1, with the exception that compound D1 in step h was changed to D10 (Duocarmycin derivative 1). Product K-17 obtained after 3 steps of reaction was brownish yellow amorphous solid. Theoretical value via LC-MS (M+): 1618.55, and measured value via LC-MS (ESI, M+H+): 1619.57.

3.18 Synthesis of Compound K-18 (Formula 43)

K-18

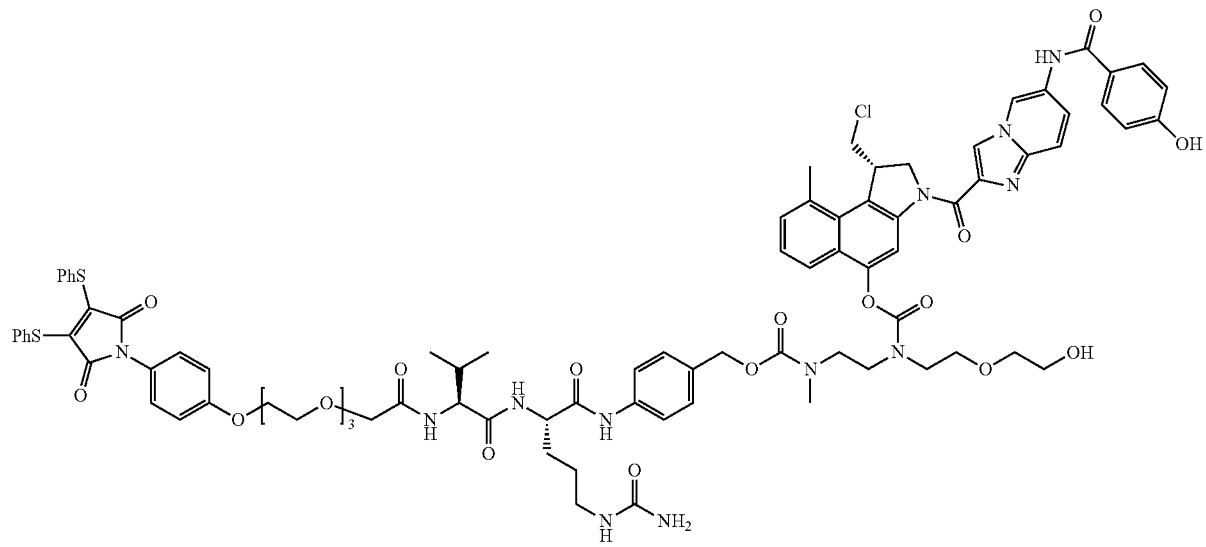

Compound K-18 was synthetized by the same steps for synthesizing compound K-1 of Example 3.1, with the exception that compound D1 in step h was changed to D11 (Duocarmycin derivative 2). Product K-18 obtained after 3 steps of reaction was brownish yellow amorphous solid. Theoretical value via LC-MS (M+): 1696.58, and measured value via LC-MS (ESI, M+H+): 1697.60.

3.19 Synthesis of Compound K-19 (Formula 44)

K-19

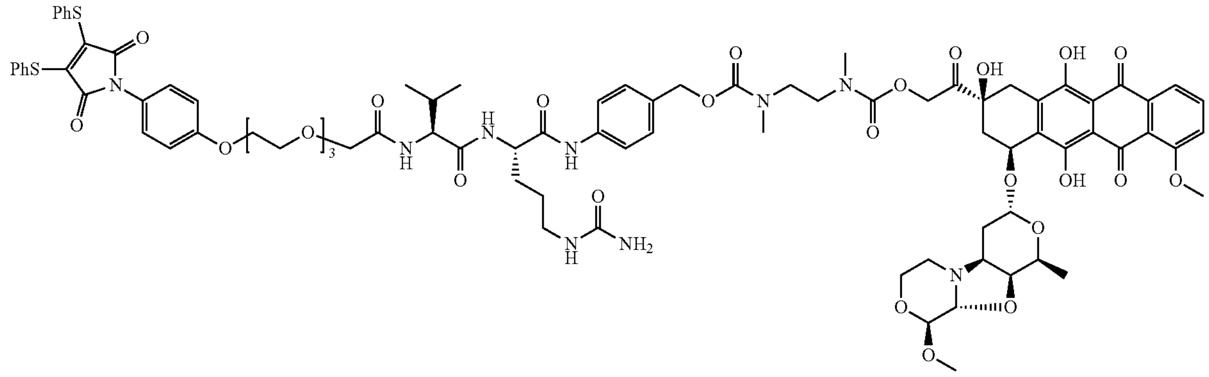

Compound K-19 was synthetized by the same steps for synthesizing compound K-1 of Example 3.1, with the exception that compound D1 in step h was changed to D12 (PNU-159682 derivative). Product K-19 obtained after 3 steps of reaction was brownish yellow amorphous solid. Theoretical value via LC-MS (M+): 1737.61, and measured value via LC-MS (ESI, M+H+): 173868.

3.20 Synthesis of Compound K-20 (Formula 45)

K-20

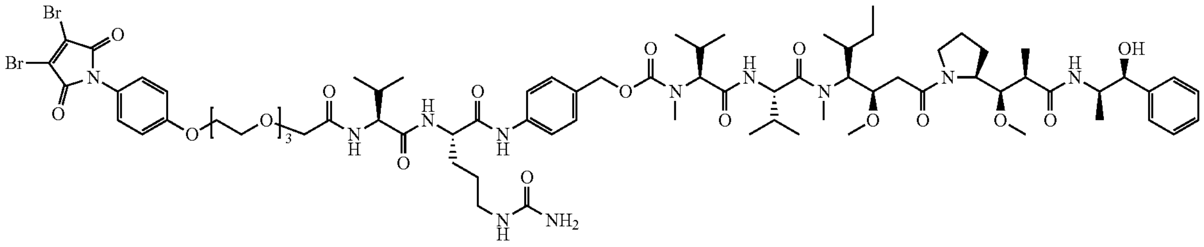

Compound K-20 was synthetized by the same steps for synthesizing compound K-1 of Example 3.1, with the exception that intermediate F-3 in step f was changed to intermediate F-14. Product K-20 obtained after 3 steps of reaction was yellow amorphous solid. Theoretical value via LC-MS (M+): 1639.64, and measured value via LC-MS (ESI, M+H+): 1640.61.

3.21 Synthesis of Compound K-21 (Formula 46)

K-21

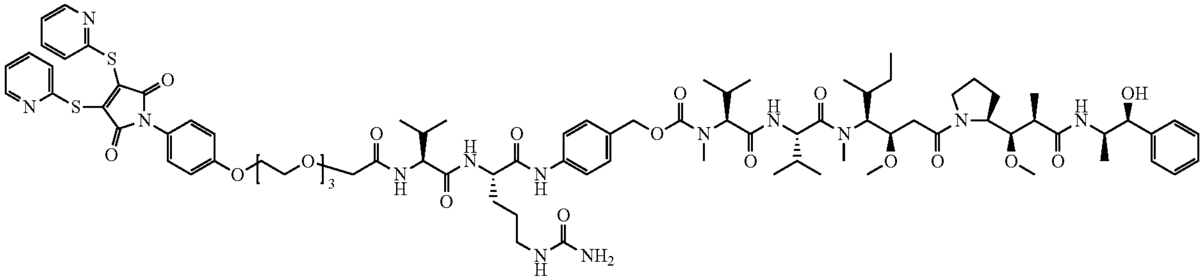

Compound K-21 was synthetized by the same steps for synthesizing compound K-1 of Example 3.1, with the exception that intermediate F-3 in step f was changed to intermediate F-11. Product K-21 obtained after 3 steps of reaction was yellow amorphous solid. Theoretical value via LC-MS (M+): 1701.82, and measured value via LC-MS (ESI, M+H+): 1702.86.

3.22 Synthesis of Compound K-22 (Formula 47)

K-22

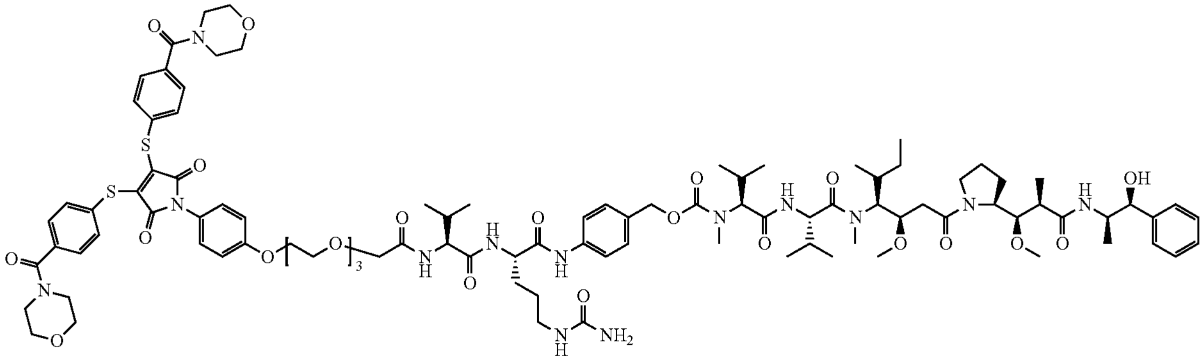

Compound K-22 was synthetized by the same steps for synthesizing compound K-1 of Example 3.1, with the exception that intermediate F-3 in step f was changed to intermediate F-16. Product K-22 obtained after 3 steps of reaction was yellow amorphous solid. Theoretical value via LC-MS (M+): 1925.92, and measured value via LC-MS (ESI, M+H+): 1926.88.

3.23 Synthesis of Compound K-23 (Formula 48)

Compound K-24 was synthetized by the same steps for synthesizing compound K-1 of Example 3.1, with the exception that intermediate F-3 in step f was changed to intermediate F-16 and compound D1 in step h was changed to D13 (SN38 derivative). Product K-24 obtained after 3 steps of reaction was yellow amorphous solid. Theoretical value via LC-MS (M+): 1714.64, and measured value via LC-MS (ESI, M+H+): 1715.61.

K-23

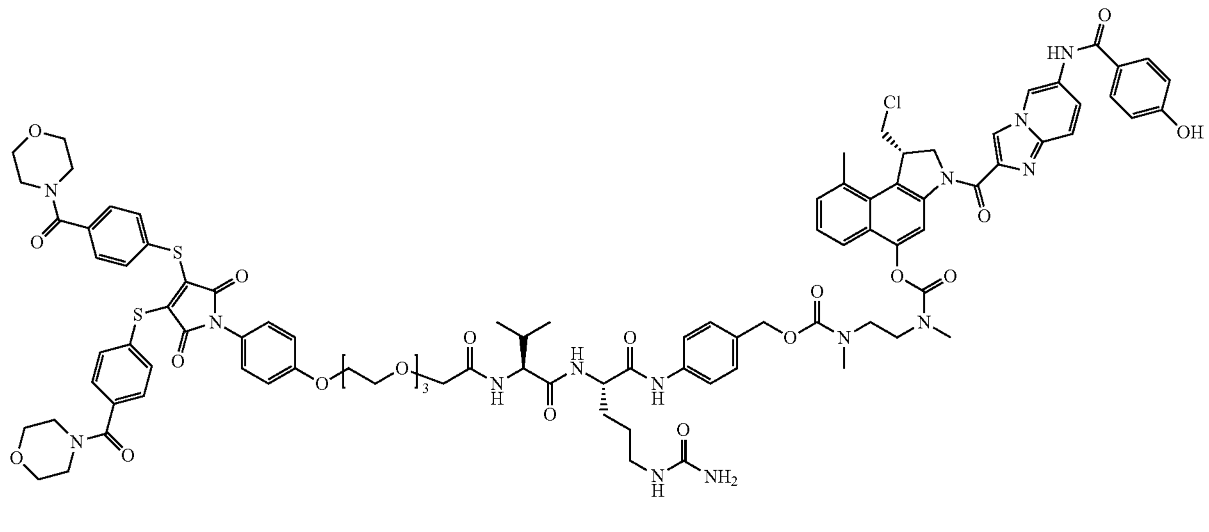

Compound K-23 was synthetized by the same steps for synthesizing compound K-1 of Example 3.1, with the exception that intermediate F-3 in step f was changed to intermediate F-16 and compound D1 in step h was changed to D11 (Duocarmycin derivative 2). Product K-23 obtained after 3 steps of reaction was yellow amorphous solid. Theoretical value via LC-MS (M+): 1848.64, and measured value via LC-MS (ESI, M+H+): 1849.58.

3.24 Synthesis of Compound K-24 (Formula 49)

Section 2: Preparation and Detection of the Antibody Drug Conjugate

Example 1: Preparation of ADC-1

A pertuzumab stock solution was diluted to 5 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer

K-24

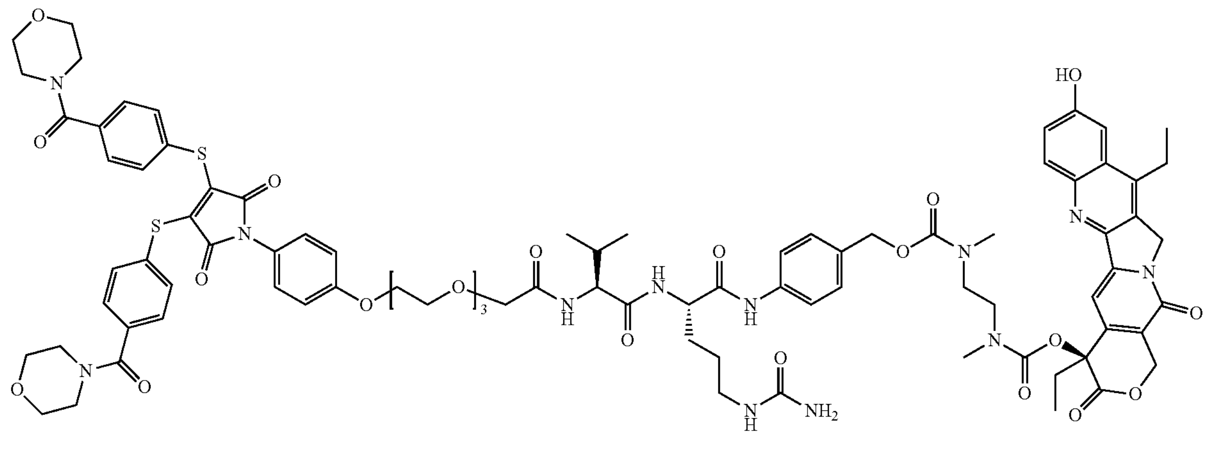

solution with a pH of 7.4, and then 6.0× excess molar ratio of tris(2-carboxyethyl)phosphine hydrochloride (TCEP) was added thereto. The obtained reaction solution was stirred at 35° C. for 10 hours.

Subsequently, without being purified, the reaction solution was cooled down to 8° C. and an appropriate amount of dimethyl sulfoxide (DMSO) and 6× excess molar ratio of compound G-2 (10 mg/ml, pre-dissolved in DMSO) were added thereto, and DMSO in the reaction system was ensured to be no more than 15% by volume. The obtained reaction solution was stirred at 37° C. for 3 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.15 μm, and the obtained product was stored at −60° C.

Example 2: Preparation of ADC-2

A pertuzumab stock solution was diluted to 5 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 7.4, and then 10× excess molar ratio of tris(2-carboxyethyl)phosphine hydrochloride (TCEP) was added thereto. The obtained reaction solution was stirred at 10° C. for 4 hours.

Subsequently, without being purified, the reaction solution was cooled down to 5° C. and an appropriate amount of dimethylacetamide (DMA) and 6× excess molar ratio of compound K-2 (10 mg/ml, pre-dissolved in DMA) were added thereto, and DMA in the reaction system was ensured to be no more than 10% by volume. The obtained reaction solution was stirred at 25° C. for 2.5 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.22 μm, and the obtained product was stored at −80° C.

Example 3: Preparation of ADC-3

A pertuzumab stock solution was diluted to 5 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 7.4, and then 20× excess molar ratio of tris(2-carboxyethyl)phosphine hydrochloride (TCEP) was added thereto. The obtained reaction solution was stirred at 15° C. for 2 hours.

Subsequently, without being purified, the reaction solution was cooled down to 10° C. and an appropriate amount of acetonitrile (ACN) and 6× excess molar ratio of compound K-3 (10 mg/ml, pre-dissolved in ACN) were added thereto, and ACN in the reaction system was ensured to be no more than 10% by volume. The obtained reaction solution was stirred at 10° C. for 4 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized by filtrating and the obtained product was stored at low temperature. For example, the collected samples were sterilized through a filtration device with a pore size of 0.20 μm, and the obtained product was stored at −90° C.

Example 4: Preparation of ADC-4

A pertuzumab stock solution was diluted to 5 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 7.4, and then 8× excess molar ratio of tris(2-carboxyethyl)phosphine hydrochloride (TCEP) was added thereto. The obtained reaction solution was stirred at 25° C. for 48 hours.

Subsequently, without being purified, the reaction solution was cooled down to 0° C. and an appropriate amount of dimethylformamide (DMF) and 6× excess molar ratio of compound K-4 (10 mg/ml, pre-dissolved in DMF) were added thereto, and DMF in the reaction system was ensured to be no more than 8% by volume. The obtained reaction solution was stirred at 0° C. for 2 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.3 μm, and the obtained product was stored at −100° C.

Figure 2:
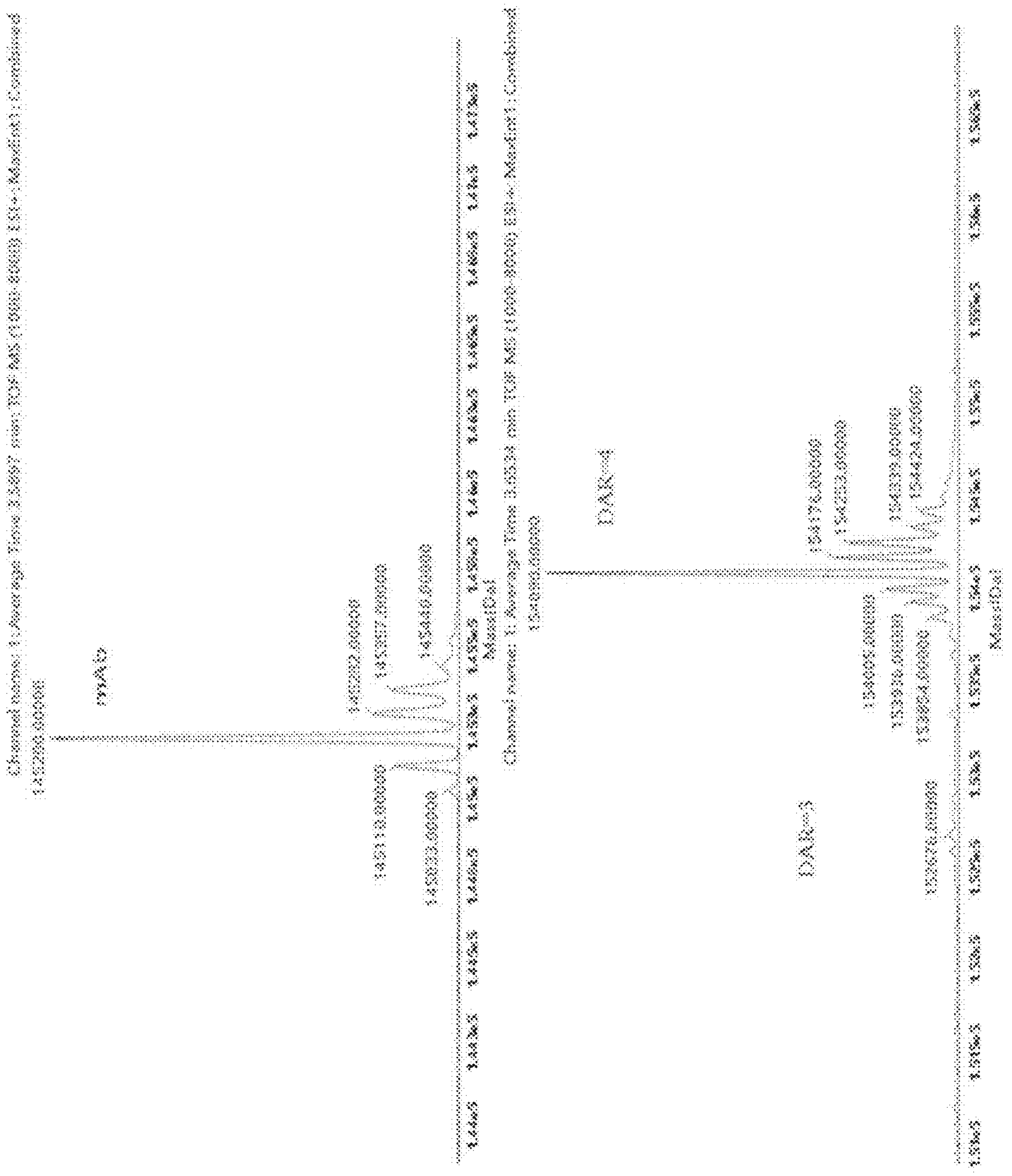
FIG. 2 shows chromatograms of mass spectrum of Pertuzumab and Pertuzumab drug conjugate for comparison.

The product obtained from Example 1 and pertuzumab were compared by hydrophobic interaction chromatography (HIC) (FIG. 1) and mass spectrometry (FIG. 2). Results showed that, the conjugates obtained by using the linker provided by the present invention had a very narrow distribution of DAR values, average of which was close to 4. In this regard, the conjugates obtained by present invention have high homogeneity, in which conjugates with a single distribution (with a DAR of 4) account for more than 80%. The value of m was identified to be between 3.0 and 4.2. The same results were obtained when the products obtained from Examples 2-4 were analyzed with the same methods, in which m was between 1.0 and 5.0.

Section 3: Biological Detections of the Antibody Drug Conjugate

1. Molecular Binding Assay

The principle of Biacore instrument for detecting the intermolecular affinity of proteins is based on Surface Plasmon Resonance (SPR) technology. SPR is an optical physical phenomenon. A surface plasma wave is generated at the interface between a prism and a metal film (Au) when a P-polarized beam is incident on one facet of the prism in a certain angle range. Resonance of free electrons in the metal film is caused when the propagation constant of the incident beam matches the propagation constant of the surface plasma wave. So for analysis, a biomolecular recognition film is firstly fixed on the surface of a sensor chip, and then a sample to be tested is allowed to flow through the surface of the sensor chip. If there is a molecule in the sample that can interact with the biomolecular recognition film on the surface of the sensor chip, refractive index of the surface of the Au film changes accordingly, thereby resulting in changes in SPR angle finally. Information such as concentration, affinity, kinetic constant, and specificity of an analyte can be obtained by detecting the changes in SPR angle.

Binding affinities of three monoclonal antibody samples comprising Pertuzumab, ADC-2 and ADC-4 to Human ErbB2 were detected through binding experiment using Biacore.

TABLE 1 affinity and kinetic parameters of the three monoclonal antibody samples with Human ErbB2

| Sample | ka (1/Ms) | kd (1/s) | $K_D$ (M) |
|---|---|---|---|
| Pertuzumab | 1.902E+05 | 1.239E−03 | 6.517E−10 |
| ADC-2 | 2.232E+05 | 1.294E−04 | 5.799E−10 |
| ADC-4 | 1.956E+05 | 1.310E−04 | 6.969E−10 |

In this experiment, the binding activities of three monoclonal antibody samples Pertuzumab, ADC-2 and ADC-4 to Human ErbB2 were characterized by using surface plasmon resonance technology, and all the three samples showed binding to Human ErbB2. The experiment results showed that the above three monoclonal antibody samples had similar affinity to Human ErbB2, all in a range of 0.5-0.7 nM.

2. Cellular Binding Assay of ADC-2 to Her2

Experimental materials used in the following experiment: RPMI1640 medium, 0.25% trypsin-EDTA, fetal bovine serum, 100× sodium pyruvate and 100× penicillin-streptomycin were purchased from Gibco; Secondary antibody labeled with fluorescein isothiocyanate (FITC) was purchased from Invitrogen; and NCI-N87 gastric cancer cells were obtained from Kunming Cell Bank of Chinese Academy of Sciences. All other reagents used were analytical grade. FACSCalibur flow cytometer (BD) was used.

In this Example, binding affinities of ADC-2, P-mcVC-MMAE and Pertuzumab to Her2 highly expressing cells were investigated.

Her2 highly expressing human gastric cancer NCI-N87 cells were used in this Example. The NCI-N87 cells were incubated in RPMI1640 medium containing 10% fetal bovine serum in a 5% CO2 incubator at 37° C. The cells that subcultured for 4 to 5 days were counted and then collected into a 15 mL centrifuge tube, washed twice with cold PBS, and centrifuged at 1000 rpm for 5 min at 4° C. The obtained cells were resuspended in PBS containing 5% fetal bovine serum, incubated at 37° C. for 30 min, then centrifuged at 1000° C. for 5 min at 4° C., and the supernatant was removed. The obtained cells were resuspended in cold PBS, dispensed into EP tubes at $1\times10^6$ cells/1.5 mL, centrifuged at 1000 rpm for 5 min at 4° C., and the supernatant was removed. Subsequently, 0.5 mL of ADC-2, P-mcVC-MMAE, Pertuzumab and human IgG in different concentrations were added to the EP tubes, which were then centrifuged at 1000 rpm for 5 min at 4° C. after being placed on ice for 40 min. The obtained residues were washed twice with 1 ml cold PBS, and then 200 μL of FITC-labeled secondary antibody was added to each tube. The EP tubes were placed on ice for 40 minutes in the dark, centrifuged at 1000 rpm for 5 min at 4° C. and the supernatant was removed. The obtained cells were washed twice with 1 ml cold PBS, and then resuspended by addition of 0.5 ml cold PBS, placed on ice in the dark. Mean fluorescence intensity (MFI) of the binding of each of ADC-2, P-mcVC-MMAE and Pertuzumab in different concentrations to the cells was detected using FACSCalibur flow cytometer. The fluorescence intensity of the human IgG binding was of non-specific binding.

Figure 3:
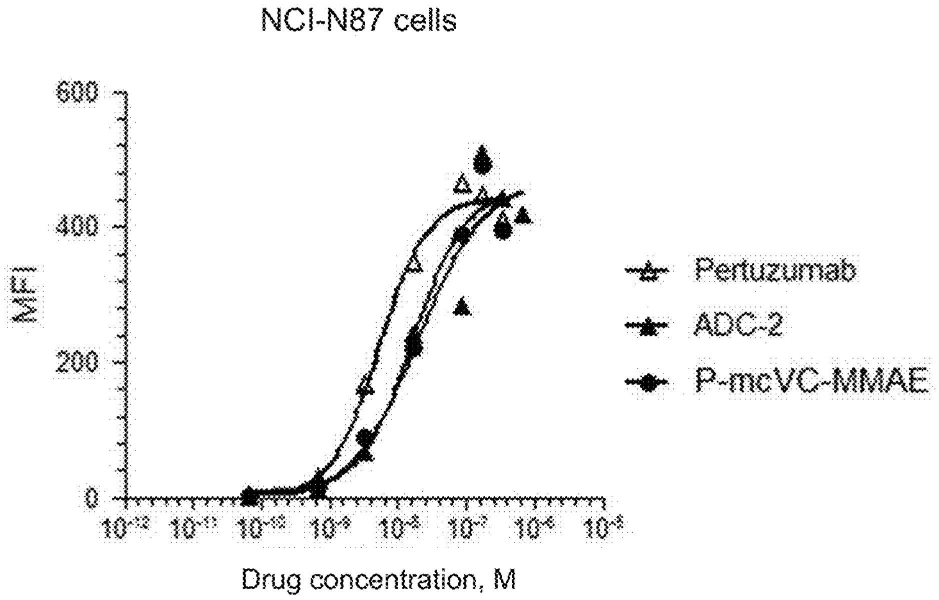
FIG. 3 shows experiment results of binding of ADC-2, P-mcVC-MMAE and Pertuzumab to antigen Her 2 on the surface of NCI-N87 cells.

As shown in FIG. 3, ADC-2, P-mcVC-MMAE, and Pertuzumab all bound to antigen Her2 on the surface of the NCI-N87 cells, and with the increasing of concentration, the bindings of ADC-2, P-mcVC-MMAE and Pertuzumab to Her2 were increased. What's more, the binding affinities of the monoclonal antibodies to Her2 of NCI-N87 cells were comparable and no significant difference was observed.

3. Biological Activity Assay of Cell Proliferation In Vitro

Experimental materials used in the following experiment: DMEM, RPMI1640 medium, DMEM/F12K, 0.25% trypsin-EDTA, fetal bovine serum, 100× sodium pyruvate and 100× penicillin-streptomycin were purchased from Gibco; sulforhodamine B (SRB) was purchased from Sigma; BT-474 human breast cancer cells, SK-RB-3 human breast cancer cells, MDA-MB-231 human breast cancer cells and NCI-N87 human gastric cancer cells were obtained from Kunming Cell Bank of Chinese Academy of Sciences; Panc-1 human pancreatic cancer cells, MDA-MB-468 human breast cancer cells and MCF-7 human breast cancer cells were obtained from Cell Bank in Shanghai Institutes for Biological Sciences; and SKOV-3 human ovarian cancer cells and Du-145 human prostate cancer cells were obtained from American Type Culture Collection (ATCC). All other reagents used were analytical grade. 96-well Flat Bottom Polystyrene (Corning, catalog No. 3599) and Synergy 2 Microplate Reader (Bio-Tek) were used.

In this Example, effects of ADC-2, ADC-4, P-mcVC-MMAE, Kadcyla, and Pertuzumab on the proliferation of tumor cell lines were investigated.

Sulforhodamine B (SRB)-based colorimetric method was used in this Example to evaluate the anti-proliferative effect of the drugs. SRB is a pink anionic dye which is easily soluble in water and can specifically bind to basic amino acids making up proteins in cells under an acidic condition. It provides an absorption peak at 510 nm, and the absorbance is linearly and positively correlated with the amount of cells. In this regard, the method can be used in a quantitative detection of cell number.

Cell lines used in this Example were: BT-474, SK-RB-3, MDA-MB-231, MDA-MB-468, MCF-7 human breast cancer cells, NCI-N87 human gastric cancer cells, SKOV-3 human ovarian cancer cells, Du-145 human prostate cancer cells, and Panc-1 human pancreatic cancer.

BT-474, SK-BR-3 and NCI-N87 cells in RPMI 1640 medium containing 10% fetal bovine serum, SKOV-3, Du-145, Panc-1, MCF-7 and MDA-MB-231 cells in DMEM containing 10% fetal bovine serum, and MDA-MB-468 cells in DMEM/F12 containing 10% fetal bovine serum were incubated to logarithmic growth phase in a 5% CO2 incubator at 37° C. The above cells in the logarithmic growth phase were inoculated into 96-well plates at a density of $2\times10^3$ to $9\times10^3$ cells per well, 100 μL per well, cultured for 24 hours and then different concentrations of drugs were added thereto for 5 days. Specifically, each drug was prepared into nine concentrations by diluting in 3, 4 or 5-fold, each concentration was set in duplicate wells, and corresponding concentration of vehicle control wells and medium control wells without cells were set too. At the end of drug action, culture solutions were decanted, and 100 μl of a pre-cooled trichloroacetic acid solution (30%, w/v) at 4° C. was added to each well and the cells were fixed at 4° C. for 1 hour. Subsequently, the cells were washed with deionized water for 5 times, and dried at room temperature, and then 100 μL of 0.4% (w/v) SRB dye (Sigma, prepared with 1% glacial acetic acid) was added to each well. After being incubated and stained at room temperature for 30 minutes, the cells were washed with 1% glacial acetic acid for 4 times to remove unbound dyes, and then dried at room temperature. Afterwards, 100 μL of 10 mM Tris solution was added per well. After being incubated and stained at room temperature for 15 minutes, the cells was washed with 1% glacial acetic acid for 5 times to remove unbound SRB, and then dried at room temperature. Dyes bound to the proteins in cells were dissolved by addition of 10 mM Tris buffer (pH=10.5) per well, and the absorbance (OD value) was measured at wavelengths of 510 nm and 690 nm using Synergy 2 Microplate Reader (Bio-Tek). $A=OD_{510}-OD_{690}$.

$$\text{Inhibition rate }(\%)=(A_{control}-A_{drug})/A_{control}\times 100\%$$

Figure 4:
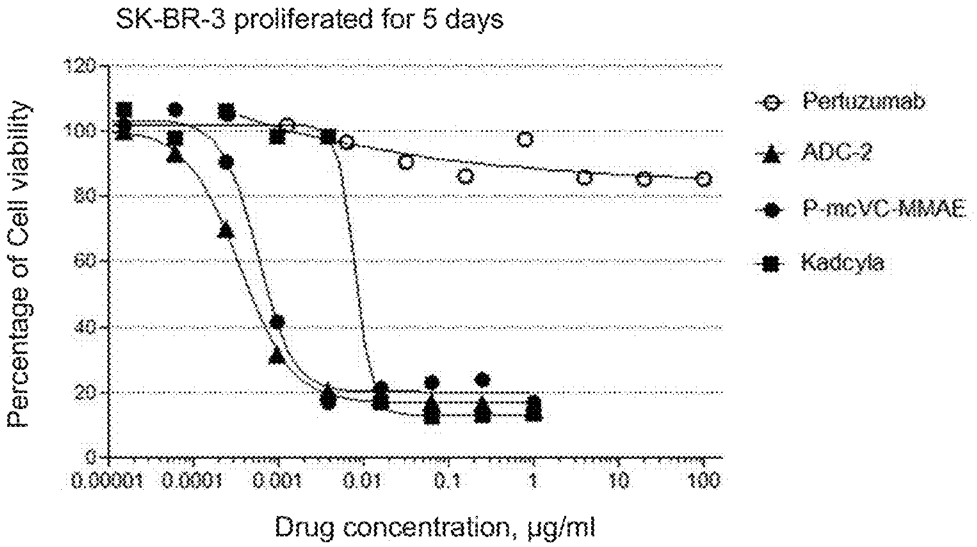
FIG. 4 shows experiment results of proliferation inhibition of ADC-2, P-mcVC-MMAE, Kadcyla and Pertuzumab on human breast cancer cells SK-BR-3.
Figure 5:
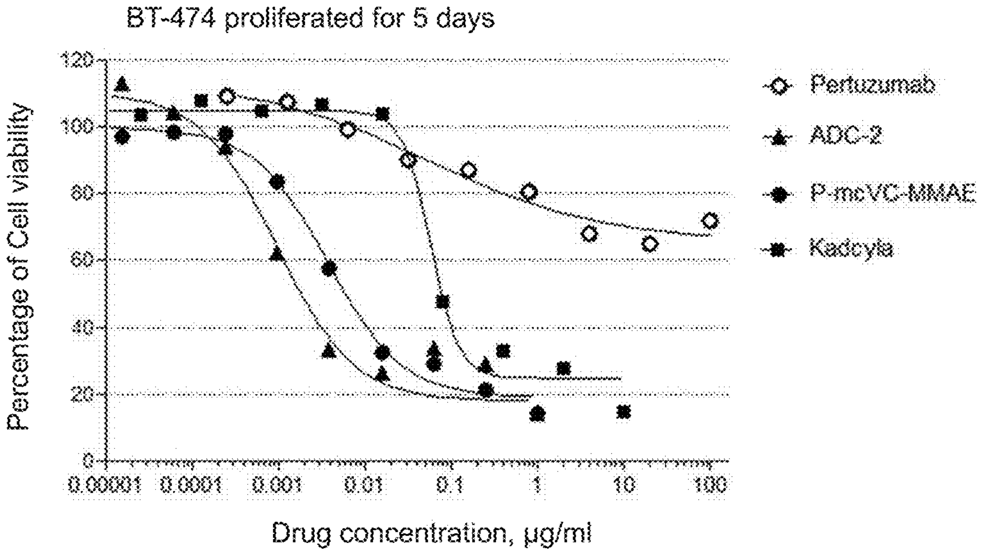
FIG. 5 shows experiment results of proliferation inhibition of ADC-2, P-mcVC-MMAE, Kadcyla and Pertuzumab on human breast cancer cells BT-474.
Figure 6:
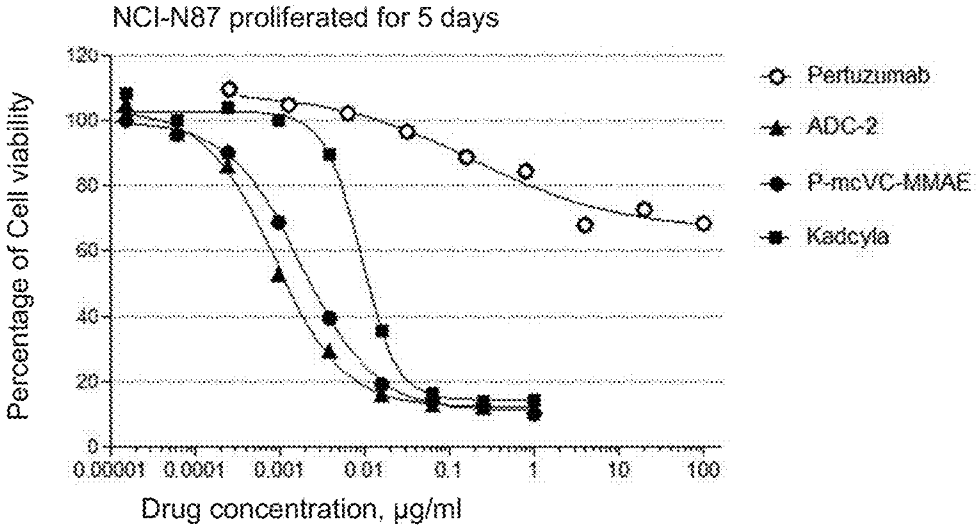
FIG. 6 shows experiment results of proliferation inhibition of ADC-2, P-mcVC-MMAE, Kadcyla and Pertuzumab on human gastric cancer cells N87.
Figure 7:
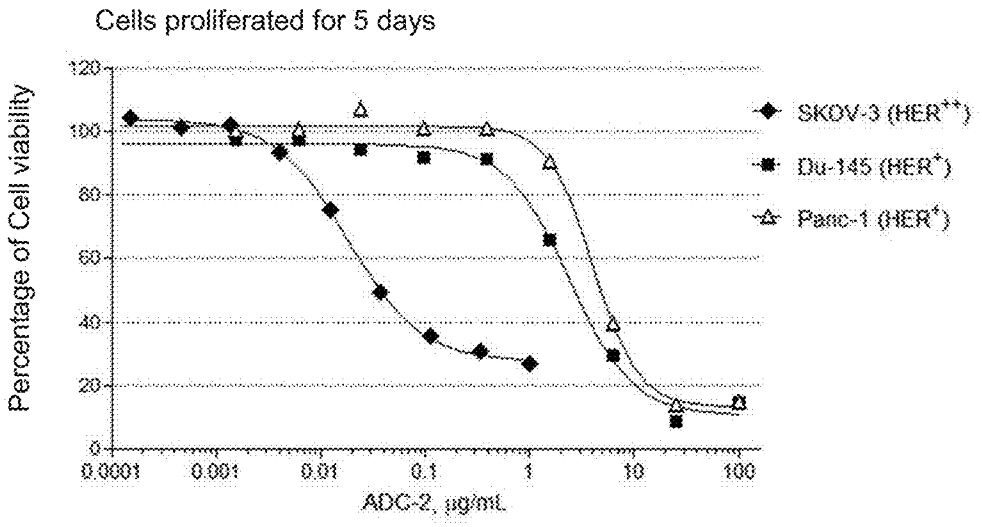
FIG. 7 shows experiment results of proliferation inhibition of ADC-2 on SKOV-3 human ovarian cancer cells, Du-145 human prostate cancer cells and Panc-1 human pancreatic cancer cells.
Figure 8:
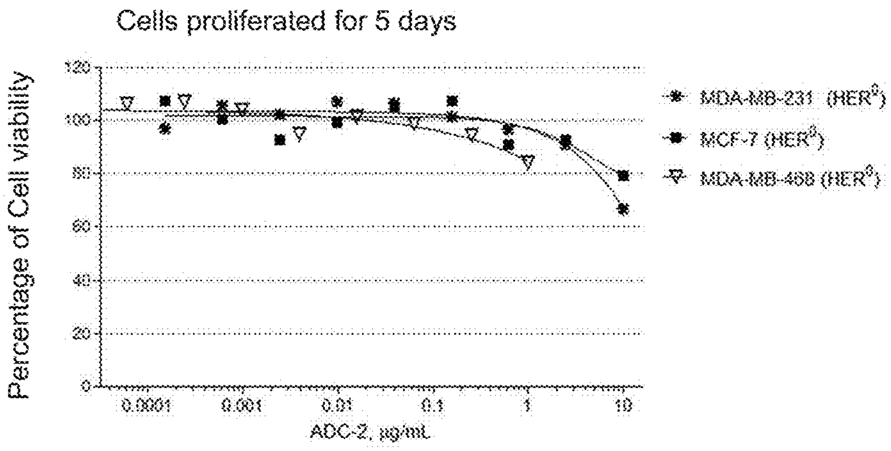
FIG. 8 shows experiment results of proliferation inhibition of ADC-2 on human breast cancer cells MCF-7, MDA-MB-231 and MDA-MB-468.
Figures 1, 9:
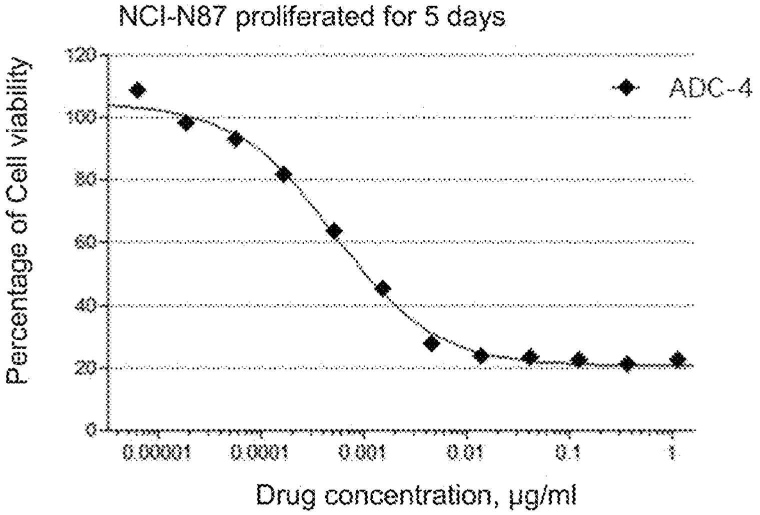
Figures 2, 9:
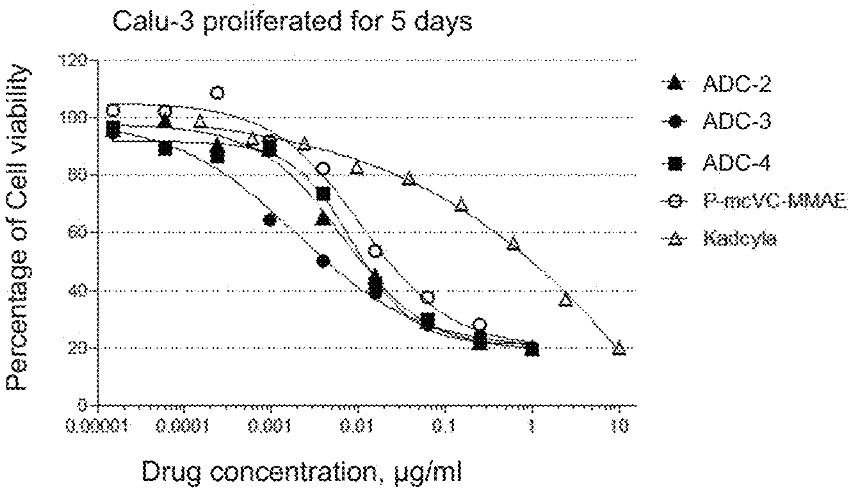

In this experiment, effects of ADC-2, ADC-4, P-mcVC-MMAE, Kadcyla, and Pertuzumab on the proliferation of various Her2 highly expressing tumor cell lines in vitro cultured were investigated. Meanwhile, effects of ADC-2 on the proliferation of various tumor cell lines which do not highly express Her2 in vitro cultured were also studied. As shown in FIGS. 4-6, significant inhibition of tumor cell proliferation could be observed with Her2 highly expressing SK-BR-3, BT-474 human breast cancer cells and NCI-N87 human gastric cancer cells which were treated with ADC-2, P-mcVC-MMAE and Kadcyla. Specifically, the inhibitory activity of ADC-2 and P-mcVC-MMAE on tumor cell proliferation was significantly higher than that of Kadcyla and the inhibitory activity of ADC-2 on tumor cell proliferation was essentially comparable to that of P-mcVC-MMAE. However, ADC-2 had a slightly higher inhibitory activity on the proliferation of BT-474 tumor cells than P-mcVC-MMAE. In addition, compared to Pertuzumab which was naked, the antibody drug conjugates, including ADC-2, P-mcVC-MMAE and Kadcyla had significantly higher inhibitory activity on the proliferation of tumor cells. As shown in FIG. 7, ADC-2 also showed good inhibitory effects on the proliferation of SKOV-3 human ovarian cancer cells, Du-145 human prostate cancer cells and Panc-1 human pancreatic cancer cells which did not highly express Her2. In contrast, the inhibitory activities of ADC-2 on the proliferation of human breast cancer MCF-7, MDA-MB-231 and MDA-MB-468 cells which did not express Her2 were significantly lower (FIG. 8). The above results indicate that antibody drug conjugate ADC-2 essentially has no effects on cells not expressing the target antigen, and thus, the toxic and side effects of ADC-2 will be significantly lesser. As shown in FIG. 9-1, ADC-4 showed a potent proliferation inhibition effect on NCI-N87 human gastric cancer cells which highly expressed Her2. And as shown in FIG. 9-1, ADC-2, ADC-3 and ADC-4 showed potent proliferation inhibition effects on Calu-3 human lung cancer cells which expressed Her2 moderately.

4. In Vivo Anti-Tumor Efficacy Assay

Efficacy of the conjugates of the present invention can be detected in vivo. In brief, an allograft or xenograft of cancer cells can be implanted into rodents and then the implanted tumors are treated with the conjugates. Tested mice can be administered drug treatment or control treatment, monitored for weeks or longer to observe tumor doubling time, log-killing, and tumor suppression.

1) Experimental Animals 6-7 weeks BALB/cA-nude mice (♀) were purchased from Shanghai Lingchang Biotechnology Co., Ltd. Production license number: SCXK (Shanghai) 2013-0018; animal certificate number: 2013001815683; and feeding environment: SPF level.

2) Experimental Steps

Those nude mice were subcutaneously inoculated with human gastric cancer NCI-N87 cells, and then randomly divided into groups (D0) when tumors grew to 100-250 $mm^3$. Doses and regimen of administration are provided in FIG. 10. Tumor volume was measured 2-3 times a week, the mice were weighed, and corresponding data were recorded. The tumor volume (V) was calculated as: $V=\frac{1}{2}\times a\times b^2$; in which a and b represent length and width respectively. T/C $(\%)=(T-T0)/(C-C0)\times 100$, in which T and C represent the tumor volumes at the end of the experiment; T0 and C0 represent the tumor volumes at the beginning of the experiment.

3) Experiment Results

Figure 10:
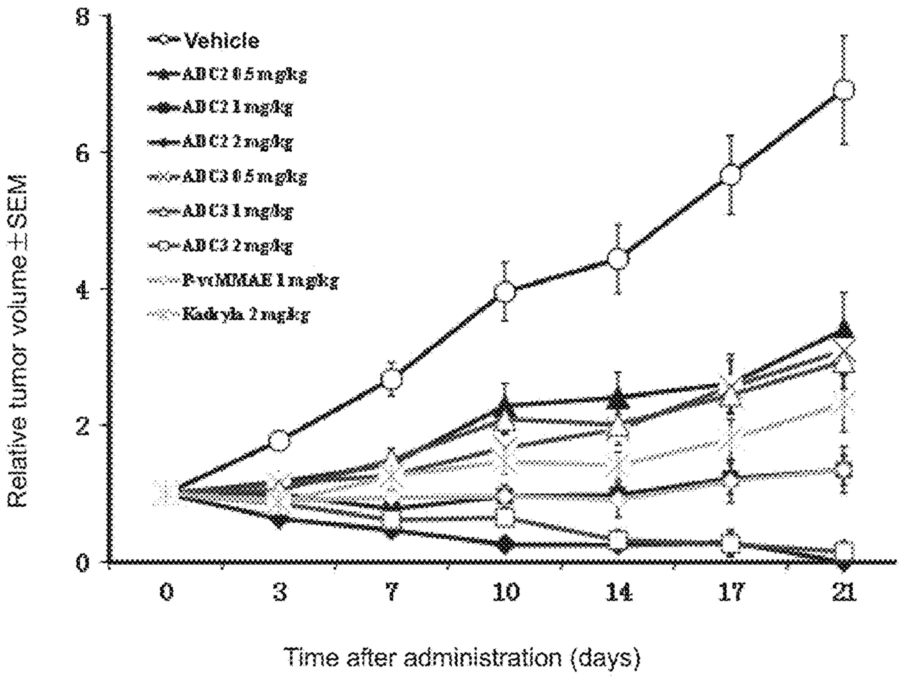
FIG. 10 shows results of study on inhibition activity of ADC-2, ADC-3, P-mcVC-MMAE and Kadcyla on human gastric cancer NCI-N87 subcutaneous xenograft tumor in nude mice.
Figures 1, 11:
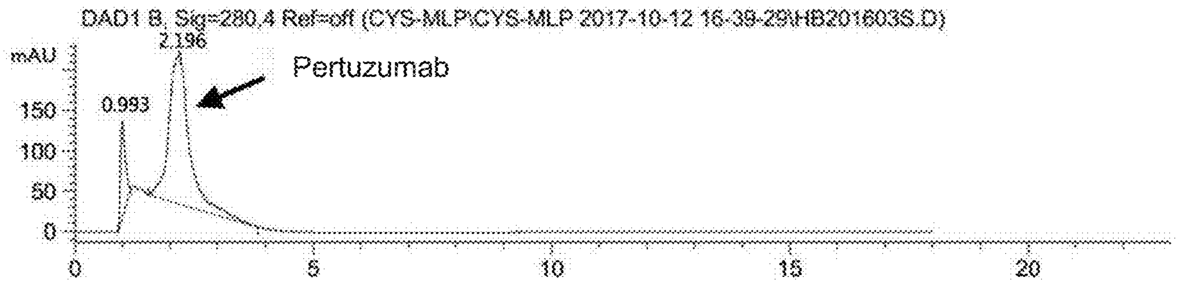
Figures 2, 11:
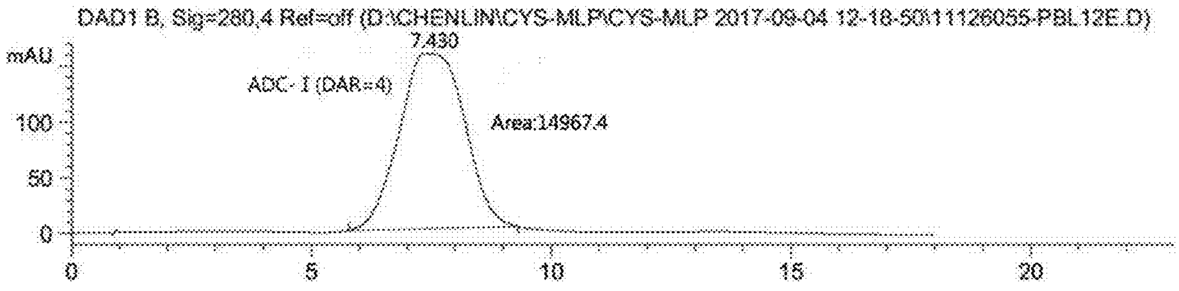
Figures 3, 11:
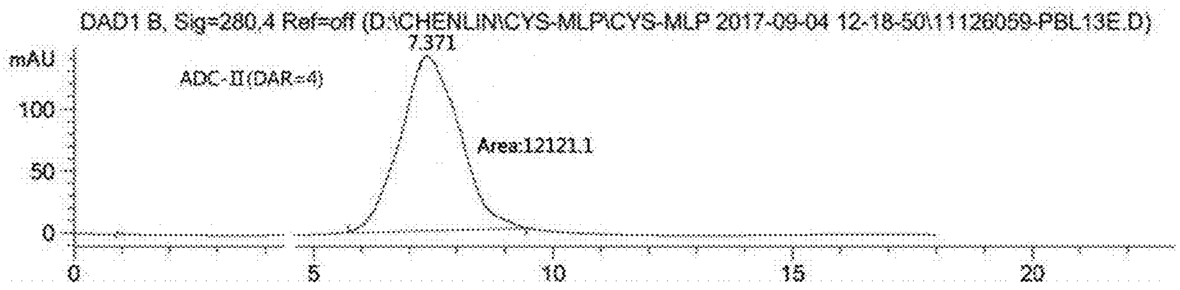
Figures 4, 11:
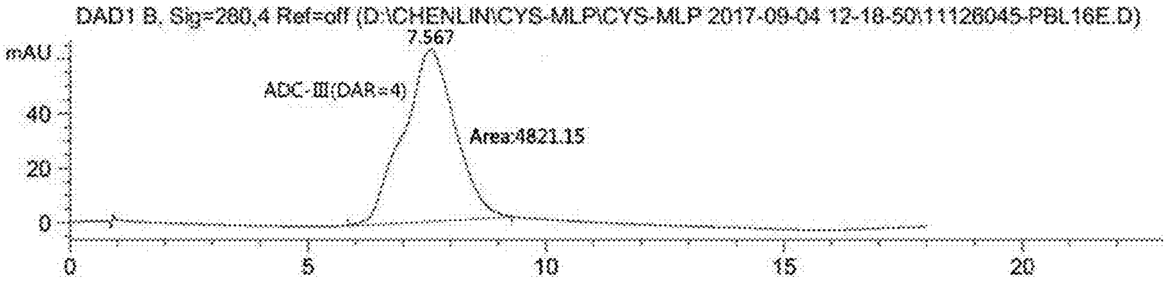
Figures 5, 11:
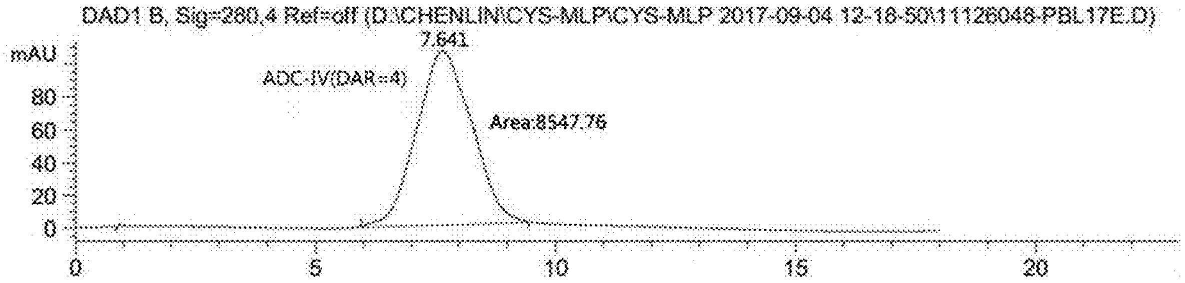
Figures 6, 11:
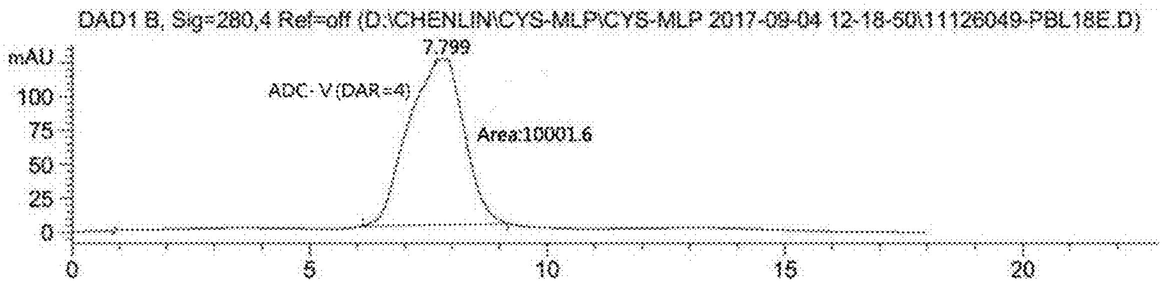
Figures 7, 11:
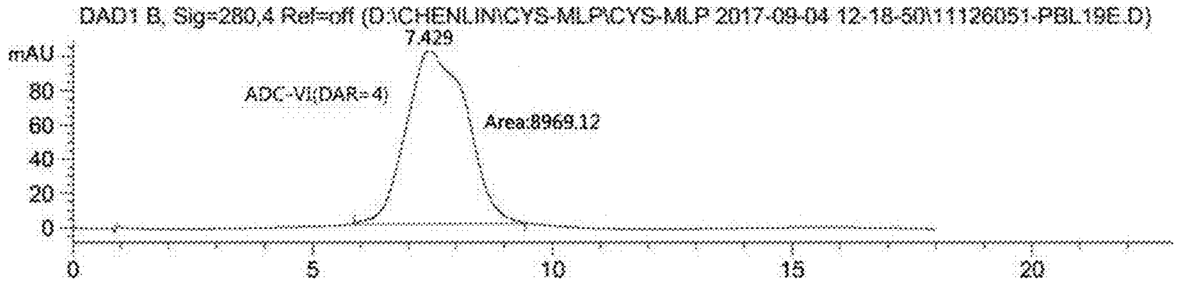
Figures 8, 11:
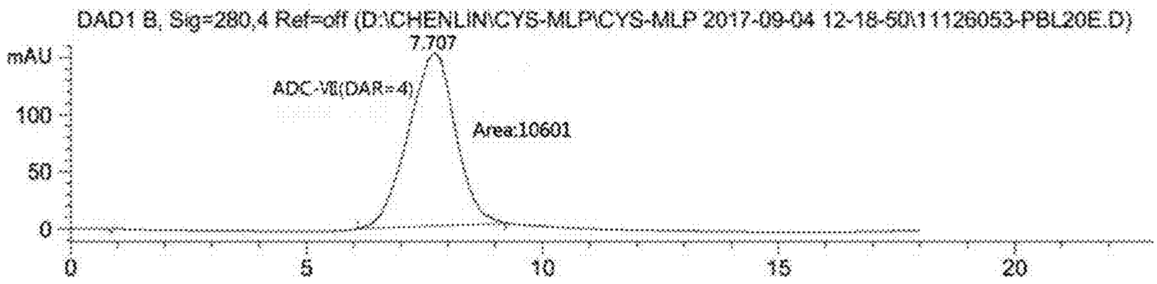
Figures 1, 12:
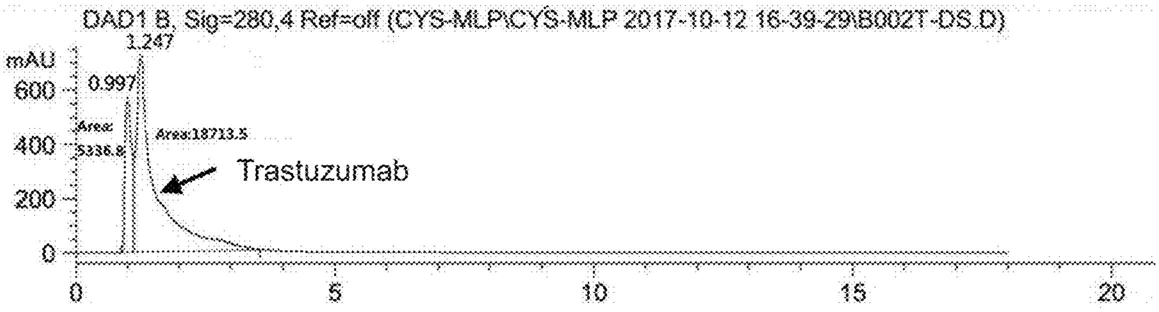
Figures 2, 12:
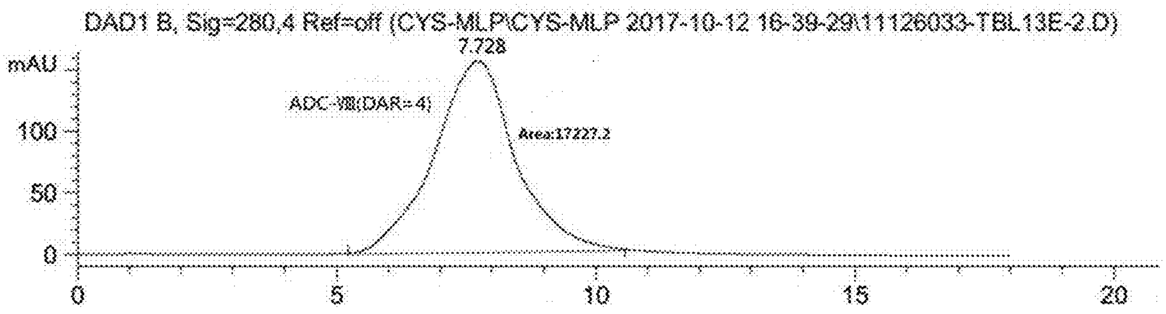
Figures 1, 13:
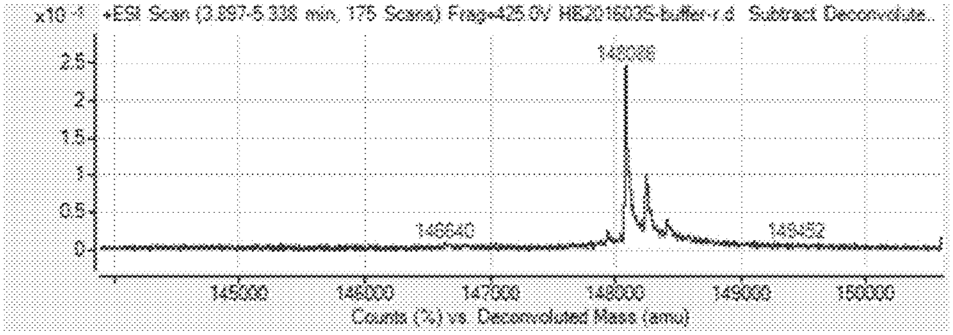
Figures 2, 13:
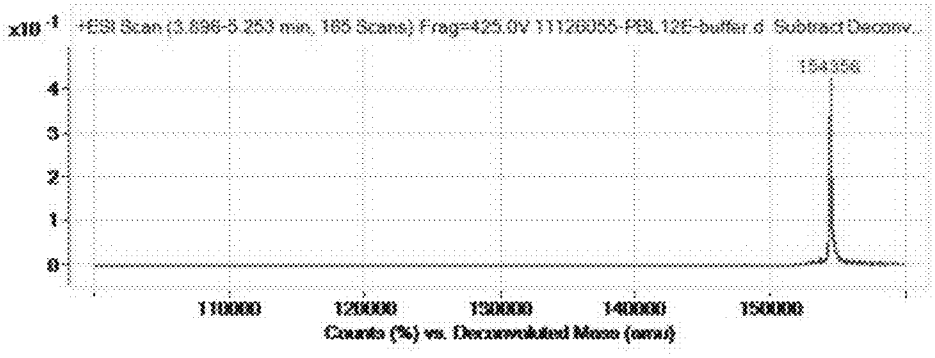
Figures 3, 13:
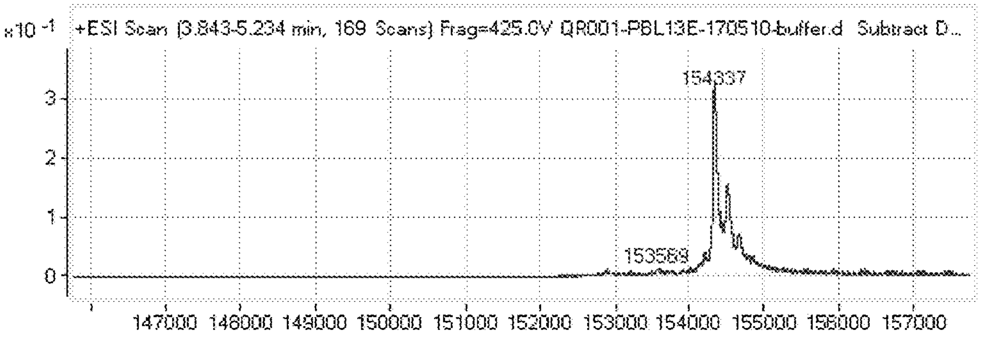
Figures 4, 13:
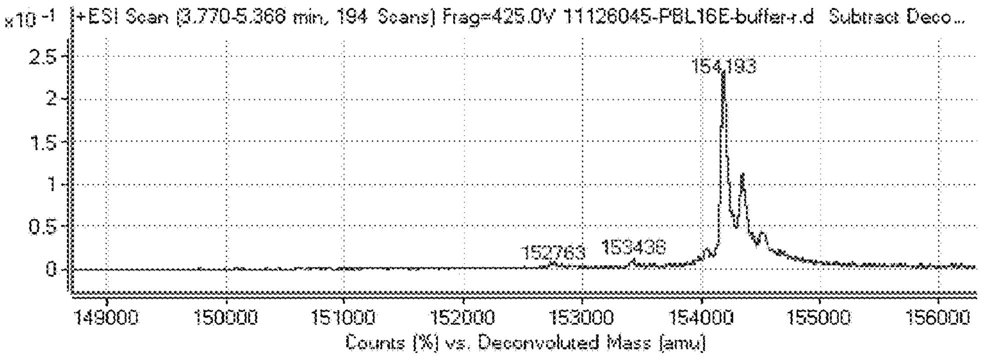
Figures 5, 13:
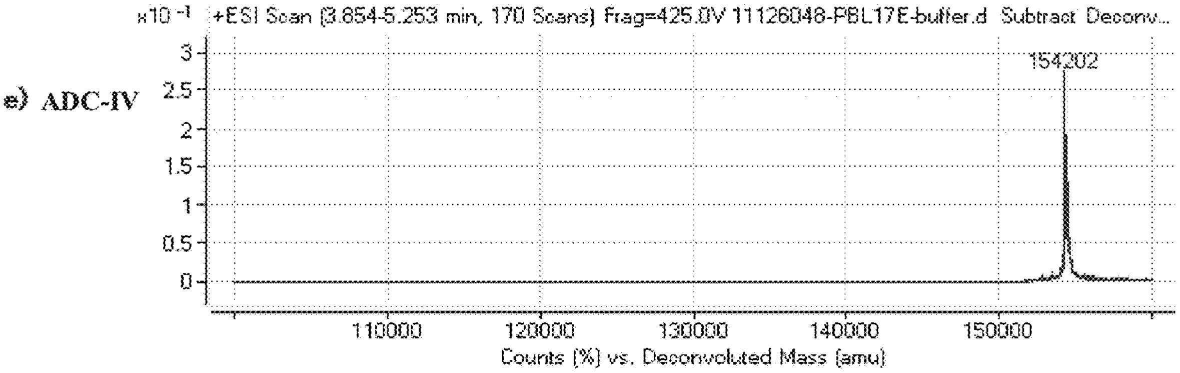
Figures 6, 13:
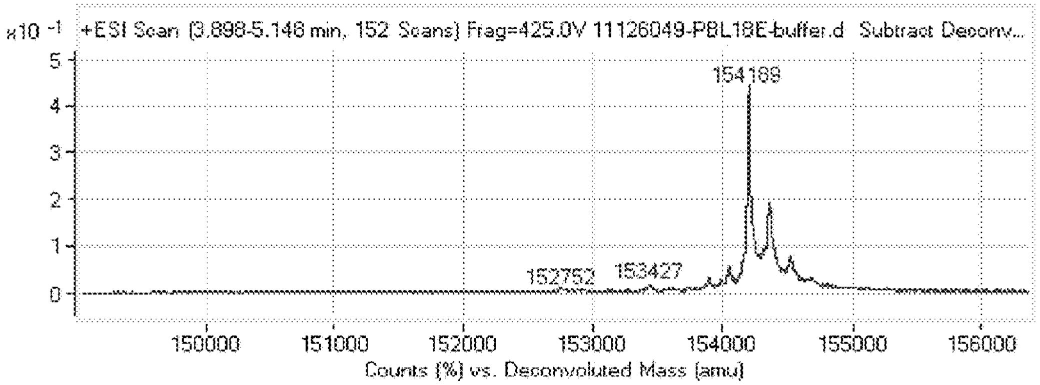
Figures 7, 13:
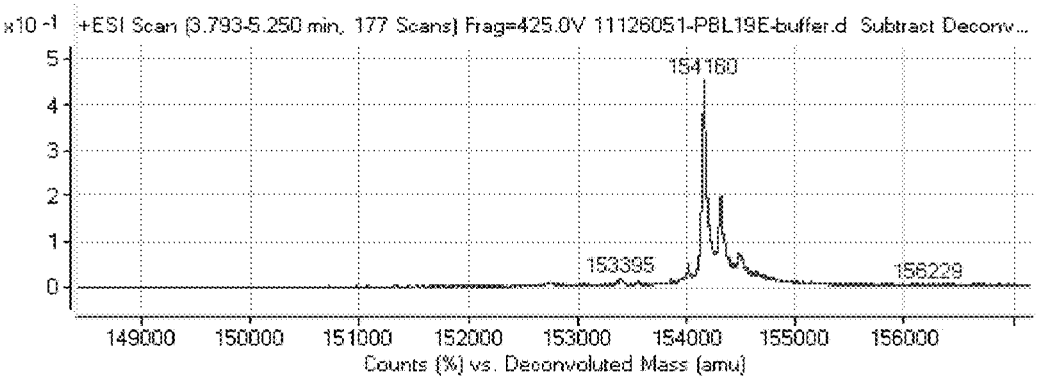
Figures 8, 13:
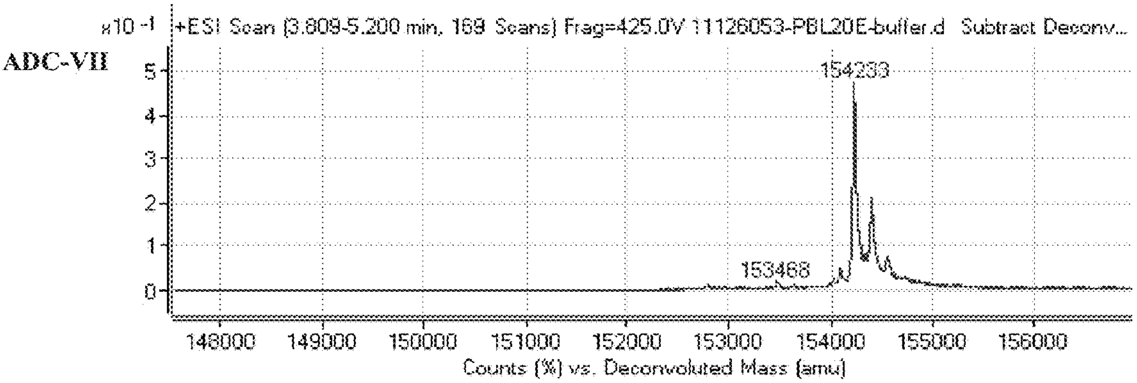
Figures 1, 14:
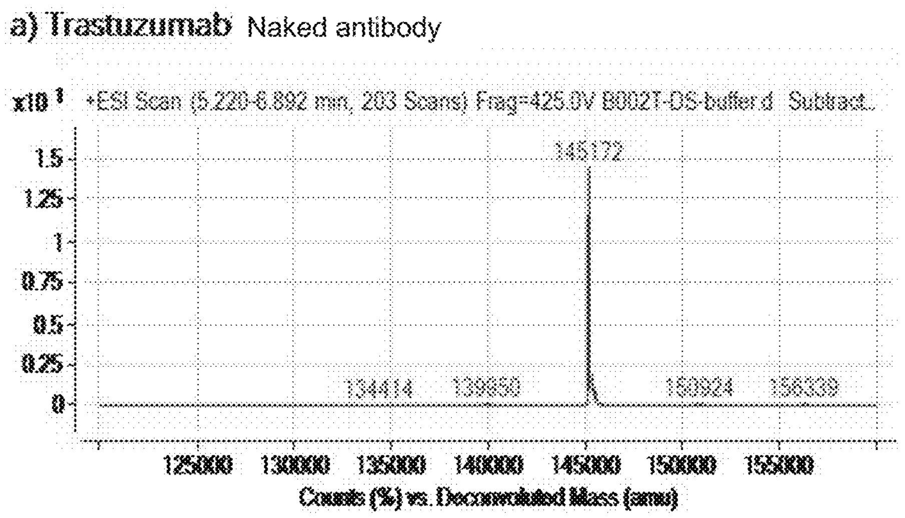
Figures 2, 14:
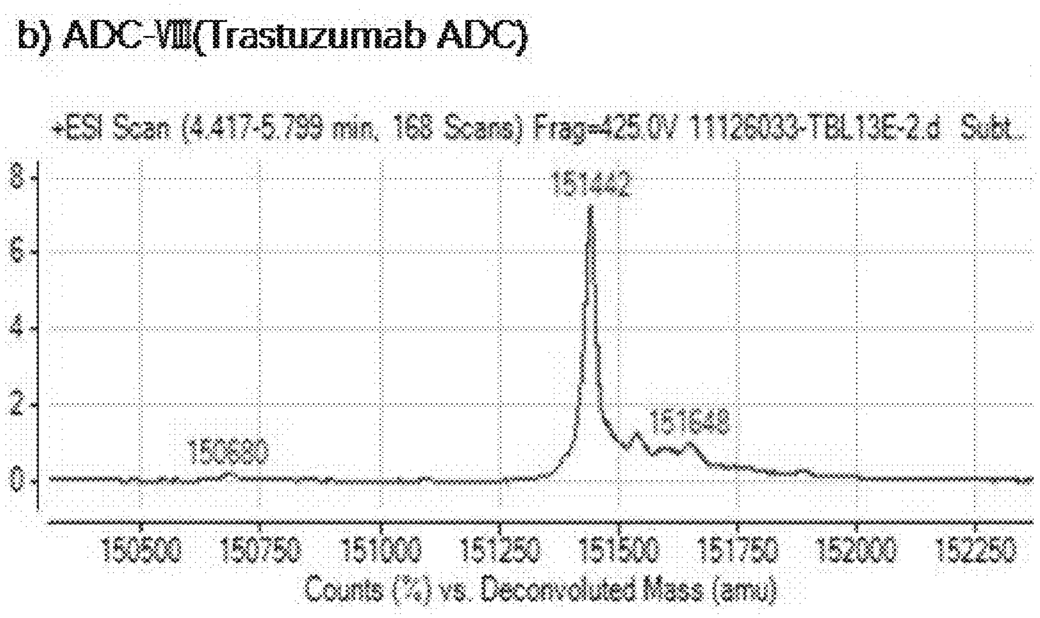

FIG. 10 shows that ADC-2 (0.5, 1, 2 mg/kg, IV, once a week, 2 times in total) can inhibit the growth of human gastric cancer NCI-N87 subcutaneous xenografts in nude mice dose-dependently and significantly, and the tumor inhibition rates are 59%, 94%, and 200% respectively. Specifically, in the group treated with 1 mg/kg, the tumors of 3/6 mice were partially regressed; and in the group treated with 2 mg/kg, the tumors of 6/6 mice were completely regressed. Inhibition rates of ADC3 (0.5, 1, 2 mg/kg, IV, once a week, 2 times in total) on NCI-N87 are 65%, 69% and 185% respectively. Specifically, in the group treated with 2 mg/kg, the tumor of 1/6 mouse was partially regressed and the tumors of 5/6 mice were completely regressed. Inhibition rate of P-vcMMAE (1 mg/kg, IV, once a week, 2 times in total) on NCI-N87 is 94%. Specifically, the tumors of 2/6 mice were partially regressed. Inhibition rates of reference drug Kadcyla (2 mg/kg, IV, once a week, 2 times in total) is 77%. What's more, those tumor-bearing mice had good tolerance to the drugs, and no symptom such as weight loss occurred.

Another One of Specific Designs:

preparation and use of the substituted maleamide linker as shown in Formula Ia, wherein Ar' is selected from the group consisting of substituted $C_6$-$C_{10}$ arylene and substituted 5-12 membered heteroarylene.

The First Group of Examples: Synthesis and Preparation Methods of the Compound 1.1 Synthesis of Compound E-1 (Formula Ia-1)

1.1.1 Synthesis of Intermediate A-1 (Step a)

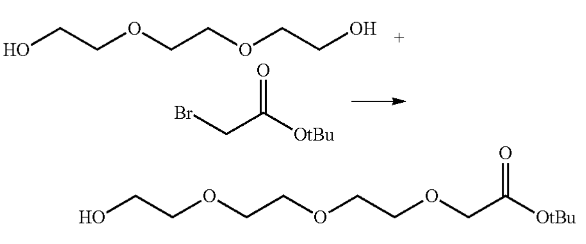

Triethylene glycol (92 g, 613 mmol) was dissolved in tBuOH (200 ml). The obtained solution was placed in ice bath, KOtBu (22.91 g, 204 mmol) was added thereto, and stirred for 30 minutes. Subsequently, tert-butyl bromoacetate (39.8 g, 204 mmol) dissolved in tBuOH (40 ml) was added dropwise under the protection of argon, and the obtained mixture was stirred overnight at room temperature. TLC on the next day indicated that the reaction was completed. Tert-butanol was rotary evaporated off. The residue was added to 400 ml of dichloromethane, and the organic phase was washed with 400 ml of water. The obtained aqueous phase was extracted once with 300 ml of dichloromethane. The organic phases were combined and washed once with saturated salt water, and dried over anhydrous sodium sulfate and then the solvent was rotary evaporated off. The obtained crude was subjected to column chromatography (petroleum ether: ethyl acetate=3:1->1:1) to obtain intermediate A-1 (24 g, 44.5% yield), which was a yellow oily product.

1.1.2 Synthesis of Intermediate B-1 (Step b)

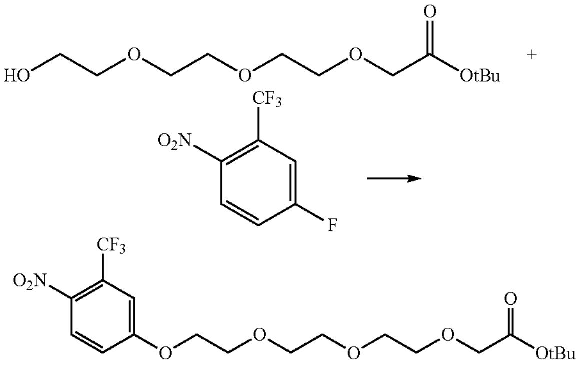

Intermediate A-1 (7.8 g, 29.5 mmol), 5-fluoro-2-nitrobenzotrifluoride (9.26 g, 44.3 mmol), and $K_2CO_3$ powder (6.12 g, 44.3 mmol) were placed in a 250 mL round bottom reaction flask. Under the protection of nitrogen, the obtained mixture was heated to 80° C. and stirred for 48 hours. TLC indicated that only a small amount of starting materials was remained.

It was then cooled down to room temperature, extracted with 500 ml dichloromethane. The organic phase was washed once with 400 ml of 1 N diluted hydrochloric acid, once with 400 ml water and once with 400 ml saturated salt water, and dried with anhydrous sodium sulfate, and the solvent was rotary evaporated off. The residue was purified by column chromatography (silica gel, 200-300 mesh), rinsed with petroleum ether: ethyl acetate 30:1-10:1, to obtain intermediate B-1 (7.5 g, 56.1% yield), which was a yellow oily product.

1.1.3 Intermediate C-1

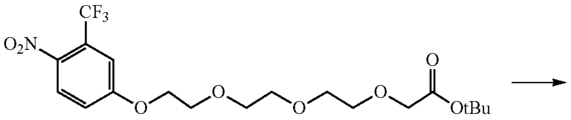

-continued

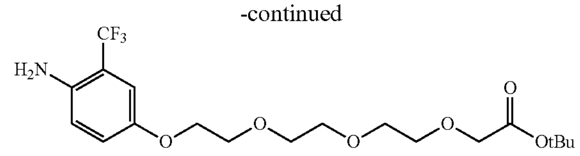

Intermediate B-1 (6 g, 13.23 mmol) was dissolved in 100 mL of anhydrous ethanol and then the obtained solution was added to a reaction flask containing 1.2 g of 10% Pd—C. A hydrogenation reaction was carried out for 6 hours (1 atm, 38° C.), and TLC indicated that the reaction was completed. The reaction mixture was filtered through diatomaceous earth, and the filter cake was rinsed with ethanol, and the filtrate was rotary evaporated off to obtain intermediate C-1 (5 g, 89% yield), which was a yellow oily product.

1.1.4 Compound E-1

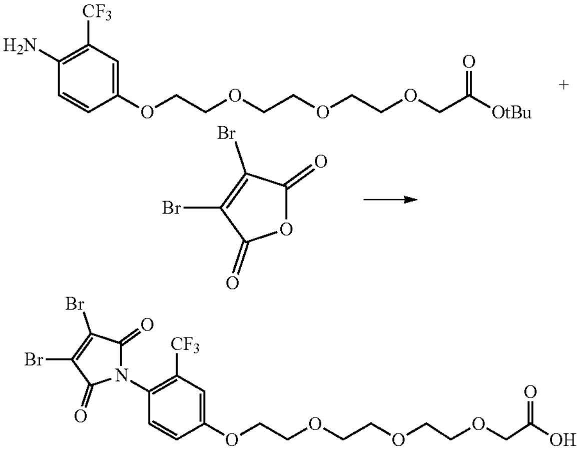

Intermediate C-1 (0.8 g, 1.889 mmol) was weighed and placed into a parallel reaction tube, then AcOH (3 ml) was added thereto under the protection of nitrogen, and stirred to dissolve. Then, 3,4-dibromomaleic anhydride (0.483 g, 1.889 mmol) was added to the tube, and the obtained reaction mixture was heated to 110° C. and stirred overnight under the protection of nitrogen. The reaction was detected by TLC. Afterwards, the reaction mixture was cooled to room temperature and the solvent was rotary evaporated off. The residue was further rotary evaporated twice by addition of toluene, thereby obtaining compound E-1, which was a brown oily product and was used in the next step directly without being purified.

1.2 Synthesis of Compound E-2 (Formula Ia-2) (Step e)

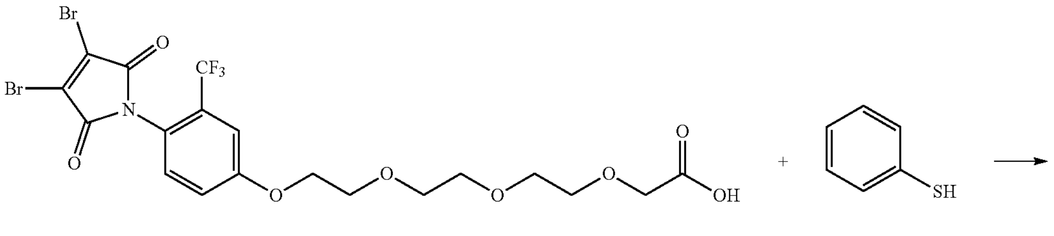

-continued

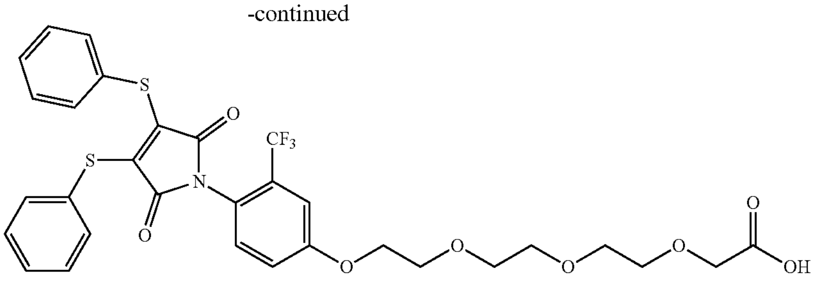

Compound E-1 (2.0 g, 1.35 mmol) was weighed and placed into a 100 ml round bottom flask, then 30 ml of anhydrous dichloromethane was added thereto under the protection of nitrogen and stirred to dissolve. Then, 297 mg of thiophenol was weighed and added thereto under the protection of nitrogen. After thiophenol dissolved, DIPEA (0.44 ml, 2.70 mmol) was slowly added dropwise to the flask which was in an ice bath. Afterwards, the reaction mixture was stirred for 5 minutes, and then the ice bath was removed. After stirring at room temperature for 2 hours under the protection of nitrogen, TLC indicated that the reaction was completed.

The solvent was evaporated under reduced pressure, the residue was isolated and purified by column chromatography (200-300 mesh silica gel). The column was loaded and rinsed with dichloromethane, and then rinsed with methanol which polarity slowly increased from 2% to 10%. The eluent was collected and the solvent was evaporated to obtain E-2 (0.92 g, 79% yield), which was an orange oily product. Theoretical value via LC-MS (M+): 595.13, and measured value: 596.15 (ESI, M+H+).

1.3 Synthesis of Compound E-3 (Formula Ia-3)

Compound E-3 was synthetized by the same steps for synthesizing compound E-2 of Example 1.2, with the exception that thiophenol in step e was changed to 2-mercaptopyridine. Product E-3 obtained was an orange oily product.

1.4 Synthesis of Compound E-4 (Formula Ia-4)

Compound E-4 was synthetized by the same steps for synthesizing compound E-2 of Example 1.2, with the exception that 5-fluoro-2-nitrobenzotrifluoride in step b was changed to 4-fluoro-2-methoxy-1-nitrobenzene and thiophenol in step e was changed to 4-(N-morpholineformamide) thiophenol. Product E-4 obtained was an orange oily product.

1.5 Synthesis of Compound E-5 (Formula Ia-5)

Compound E-5 was synthetized by the same steps for synthesizing compound E-2 of Example 1.2, with the exception that 5-fluoro-2-nitrobenzotrifluoride in step b was changed to 1-fluoro-2-methoxy-4-nitrobenzene and thiophenol in step e was changed to 4-(N-morpholineformamide) thiophenol. Product E-5 obtained was an orange oily product.

1.6 Synthesis of Compound E-6 (Formula Ia-6)

Compound E-6 was synthetized by the same steps for synthesizing compound E-2 of Example 1.2, with the exception that 5-fluoro-2-nitrobenzotrifluoride in step b was changed to 5-fluoro-2-nitrobenzonitrile and thiophenol in step e was changed to 4-(N-morpholineformamide) thiophenol. Product E-6 obtained was an orange oily product.

1.7 Synthesis of Compound E-7 (Formula Ia-7)

Compound E-7 was synthetized by the same steps for synthesizing compound E-2 of Example 1.2, with the exception that 5-fluoro-2-nitrobenzotrifluoride in step b was changed to 2-fluoro-5-nitrobenzonitrile and thiophenol in step e was changed to 4-(N-morpholineformamide) thiophenol. Product E-7 obtained was an orange oily product.

1.8 Synthesis of Compound E-8 (Formula Ia-8)

Compound E-8 was synthetized by the same steps for synthesizing compound E-2 of Example 1.2, with the exception that 5-fluoro-2-nitrobenzotrifluoride in step b was changed to 5-fluoro-2-nitrobenzamide and thiophenol in step e was changed to 4-(N-morpholineformamide) thiophenol. Product E-8 obtained was an orange oily product.

1.9 Synthesis of Compound E-9 (Formula Ia-9)

Compound E-9 was synthetized by the same steps for synthesizing compound E-2 of Example 1.2, with the exception that 5-fluoro-2-nitrobenzotrifluoride in step b was changed to 4-fluoro-1-nitro-2-(trifluoromethyl)benzene and thiophenol in step e was changed to 4-(N-morpholineformamide) thiophenol. Product E-9 obtained was an orange oily product.

1.10 Synthesis of Compound E-10 (Formula Ia-10)

Compound E-10 was synthetized by the same steps for synthesizing compound E-2 of Example 1.2, with the exception that 5-fluoro-2-nitrobenzotrifluoride in step b was changed to 1-fluoro-4-nitro-2-(trifluoromethyl)benzene and the thiophenol in step e was changed to 4-(N-morpholineformamide) thiophenol. Product E-10 obtained was an orange oily product.

1.11 Synthesis of Compound E-11 (Formula Ia-11)

1.11.1 Intermediate F-11 (Step f)

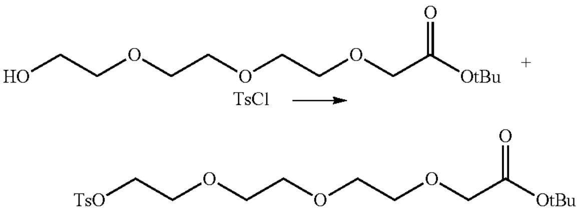

In a 250 ml round bottom flask, intermediate A-1 (4 g, 15.13 mmol), triethylamine (2.53 ml, 18.16 mmol) and dimethylaminopyridine (0.370 g, 3.03 mmol) were dissolved in 100 ml dichloromethane dried with molecular sieve and then stirred. Subsequently, 4-toluene sulfonyl chloride (3.17 g, 16.65 mmol) was added in batches in an ice bath, and the obtained reaction system was stirred under the protection of argon at room temperature overnight.

To the reaction system, 100 ml of dichloromethane was added for extraction, and then the organic phase was washed once with 200 ml of 1 N diluted hydrochloric acid, twice with 200 ml water and once with 200 ml saturated brine, and dried with anhydrous sodium sulfate, and the solvent was rotary evaporated off. The residue was isolated by column chromatography, in which the column was packed with 200-300 mesh silica gel and eluted with PE:EA=5:1-2:1. The collected eluent was rotary evaporated off to obtain intermediate F-11 (2.8 g, 44.2% yield).

1.11.2 Intermediate B-11 (Step g)

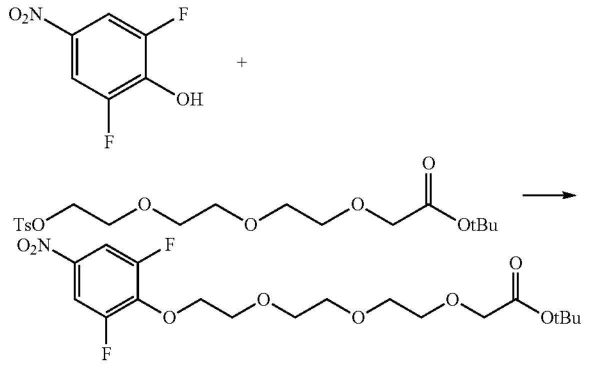

Intermediate F-11 (1 g, 2.389 mmol) and 2,6-difluoro-4-nitrophenol (0.315 g, 1.797 mmol) were dissolved in 20 ml DMF, and then $K_2CO_3$ (0.497 g, 3.59 mmol) was added thereto. The obtained mixture was heated to 100° C. and stirred for 5 hours. The solvent was rotary evaporated off and then the residue was dissolved in 200 ml dichloromethane for extraction. The organic phase was then washed once with 200 ml of 1 N diluted hydrochloric acid, once with 200 ml water and once with 200 ml saturated salt water, and dried with anhydrous sodium sulfate, and the solvent was rotary evaporated off. The residue was purified by column chromatography, in which the column was packed with 200-300 mesh silica gel and eluted with PE:EA=5:1-3:1. The collected eluent was rotary evaporated off to obtain intermediate B-11 (600 mg, 79% yield).

1.11.3 Intermediate C-11

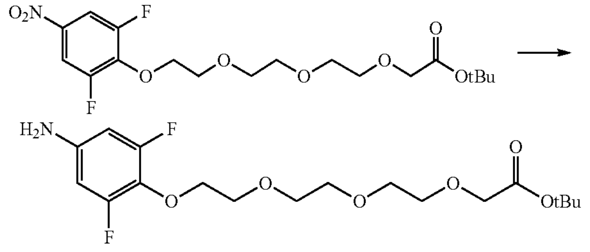

Intermediate B-11 (600 mg, 1.42 mmol) was dissolved in 100 mL of anhydrous ethanol and then the obtained solution was added to a reaction flask containing 120 mg of 10% Pd—C. A hydrogenation reaction was carried out for 6 hours (1 atm, 38° C.), and TLC indicated that the reaction was completed. The reaction mixture was filtered through diatomaceous earth, and the filter cake was rinsed with ethanol, and the filtrate was rotary evaporated off to obtain intermediate C-11 (450 mg, 81% yield), which was a yellow oily product.

1.11.4 Intermediate D-11

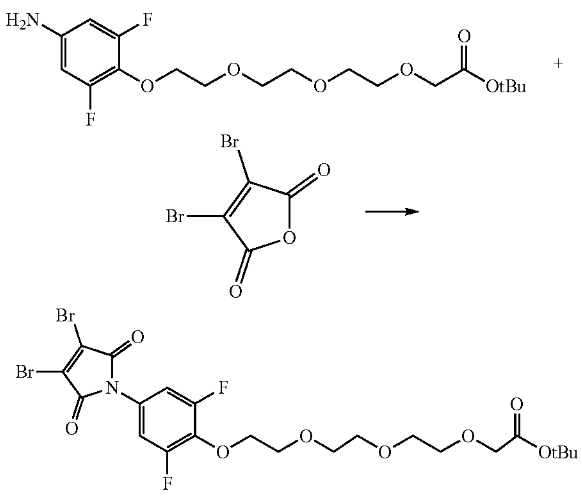

Intermediate C-11 (0.40 g, 1.02 mmol) was weighed and placed into a parallel reaction tube, then AcOH (3 ml) was added thereto under the protection of nitrogen, and stirred to dissolve. Then, 3,4-dibromomaleic anhydride (0.261 g, 1.02 mmol) was added to the tube, and the obtained reaction mixture was heated to 110° C. and stirred overnight under the protection of nitrogen. The reaction was detected by TLC. Afterwards, the reaction mixture was cooled to room temperature and the solvent was rotary evaporated off. The residue was further rotary evaporated twice by addition of toluene, thereby obtaining intermediate D-11, which was a brown oily product and was used in the next step directly without being purified.

1.11.5 Intermediate E-11

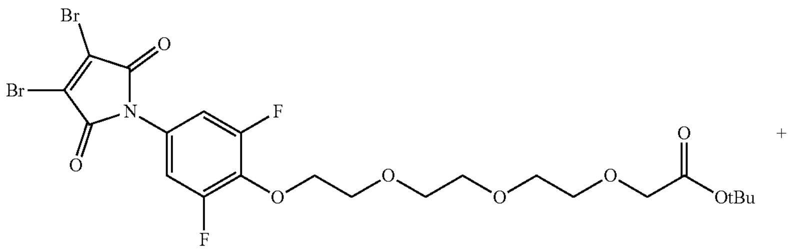

-continued

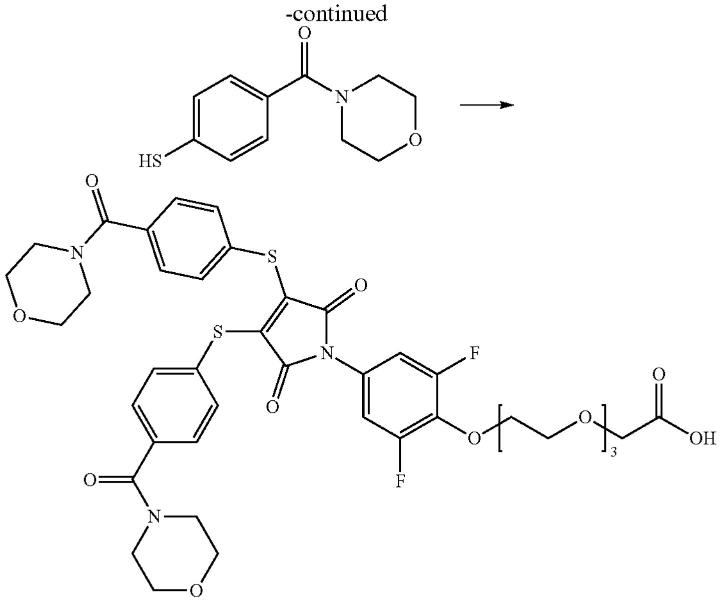

Compound D-11 (600 mg, 0.95 mmol) was weighed and placed into a 100 ml round bottom flask, then 30 ml of anhydrous dichloromethane was added thereto under the protection of nitrogen and stirred to dissolve. Then, 425 mg (1.91 mmol) of 4-(N-morpholineformamide) thiophenol was weighed and added thereto under the protection of nitrogen. After 4-(N-morpholineformamide) thiophenol dissolved, DIPEA (0.36 ml, 1.91 mmol) was slowly added dropwise to the flask which was in an ice bath. Afterwards, the reaction mixture was stirred for 5 minutes, and then the ice bath was removed. After stirring at room temperature for 2 hours under the protection of nitrogen, TLC indicated that the reaction was completed.

The solvent was evaporated under reduced pressure, the residue was isolated and purified by column chromatography (200-300 mesh silica gel). The column was loaded and rinsed with dichloromethane, and then rinsed with methanol which polarity slowly increased from 2% to 10%. The eluent was collected and the solvent was evaporated to obtain E-11 (0.62 g, 76% yield), which was an orange oily product. Theoretical value via LC-MS (M+): 857.21, and measured value: 858.23 (ESL, M+H+).

1.12 Synthesis of Compound E-12 (Formula Ia-12)

Compound E-12 was synthetized by the same steps for synthesizing compound E-11 of Example 1.11, with the exception that 2,6-difluoro-4-nitrophenol in step g was changed to 3-fluoro-4-nitrophenol. Product E-12 obtained was an orange oily product.

1.13 Synthesis of Compound E-13 (Formula Ia-13)

Compound E-13 was synthetized by the same steps for synthesizing compound E-11 of Example 1.11, with the exception that 2,6-difluoro-4-nitrophenol in step g was changed to 2,5-difluoro-4-nitrophenol. Product E-13 obtained was an orange oily product.

1.14 Synthesis of Compound E-14 (Formula Ia-14)

Compound E-14 was synthetized by the same steps for synthesizing compound E-11 of Example 1.11, with the exception that triethylene glycol in step a was changed to diethylene glycol. Product E-14 obtained was an orange oily product.

1.15 Synthesis of Compound E-15 (Formula Ia-15)

Compound E-15 was synthetized by the same steps for synthesizing compound E-11 of Example 1.11, with the exception that triethylene glycol in step a was changed to tetraethylene glycol. Product E-15 obtained was an orange oily product.

1.16 Synthesis of Compound E-16 (Formula Ia-16)

Compound E-16 was synthetized by the same steps for synthesizing compound E-11 of Example 1.11, with the exception that triethylene glycol in step a was changed to pentaethylene glycol. Product E-16 obtained was an orange oily product.

1.17 Synthesis of Compound E-17 (Formula Ia-17)

Compound E-17 was synthetized by the same steps for synthesizing compound E-11 of Example 1.11, with the exception that triethylene glycol in step a was changed to hexaethylene glycol. Product E-17 obtained was an orange oily product.

1.18 Synthesis of Compound E-18 (Formula Ia-18)

Compound E-18 was synthetized by the same steps for synthesizing compound E-11 of Example 1.11, with the exception that triethylene glycol in step a was changed to dodecaethylene glycol. Product E-18 obtained was an orange oily product.

1.19 Synthesis of Compound E-19 (Formula Ia-19)

Compound E-19 was synthetized by the same steps for synthesizing compound E-11 of Example 1.11, with the exception that 4-(N-morpholineformamide) thiophenol in step e was changed to thiomorpholine-1,1-dioxide. Product E-19 obtained was an orange oily product.

1.20 Synthesis of Compound E-20 (Formula Ia-20)

Compound E-20 was synthetized by the same steps for synthesizing compound E-11 of Example 1.11, with the exception that 4-(N-morpholineformamide) thiophenol in step e was changed to 4-(N-methylformamide) thiophenol. Product E-20 obtained was an orange oily product.

1.21 Synthesis of Compound E-21 (Formula Ia-21)

Compound E-21 was synthetized by the same steps for synthesizing compound E-2 of Example 1.2, with the exception that 5-fluoro-2-nitrobenzotrifluoride in step b was changed to 5-fluoro-2-nitropyridine and thiophenol in step e was changed to 4-(N-morpholineformamide) thiophenol. Product E-21 obtained was an orange oily product.

1.22 Synthesis of Compound E-22 (Formula Ia-22)

Compound E-22 was synthetized by the same steps for synthesizing compound E-2 of Example 1.2, with the exception that 5-fluoro-2-nitrobenzotrifluoride in step b was changed to 2-fluoro-5-nitropyridine and thiophenol in step e was changed to 4-(N-morpholineformamide) thiophenol. Product E-21 obtained was an orange oily product.

The Second Group of Examples: Synthesis and Preparation of Compounds as Shown in Formulas Ib-1-Ib-24

2.1 Synthesis of Compound F1-1 (Formula Ib-1)

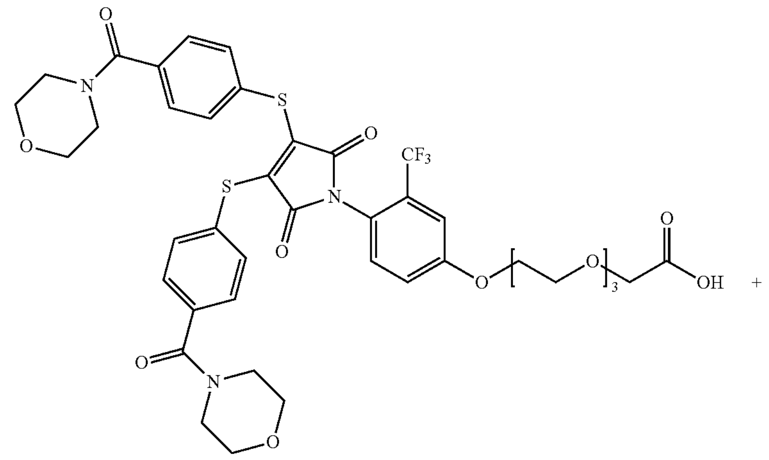

E1-9

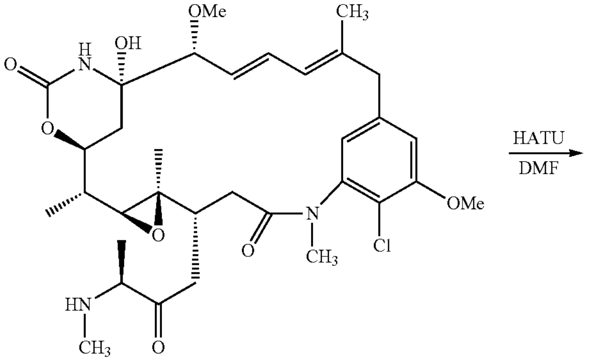

D1-1

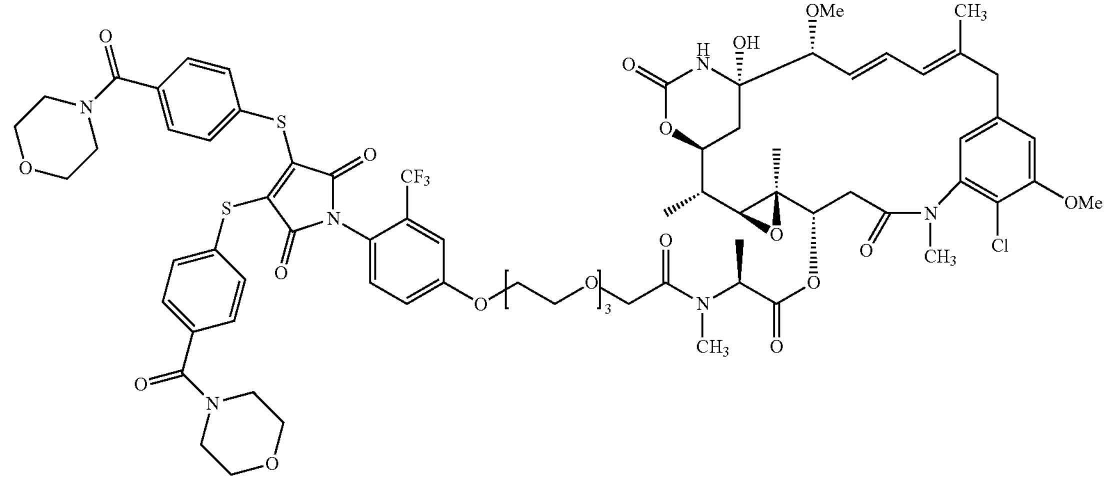

F1-1

Compound E1-9 (300 mg, 0.337 mmol) was weighted and placed into a 100 ml round-bottom flask, and stirred to dissolve by addition of anhydrous DMF (20 mL) under the protection of nitrogen. Afterwards, HATU (154 mg, 0.404 mmol) and DIEA (0.11 ml, 0.674 mmol) were weighted and added into the flask successively. The obtained mixture was stirred for 15 minutes at room temperature followed by adding compound D1-1 (219 mg, 0.337 mmol) thereto. The obtained reaction mixture was stirred overnight at room temperature at the protection of nitrogen. TLC and HPLC indicated that raw material E9 disappeared with overnight reaction. The solvent was evaporated off under reduced pressure and the residue was quantitatively analyzed, and then isolated and purified by reverse-phase HPLC to obtain a yellow amorphous powder product F1-1 (0.350 g, 0.230 mmol, 68.2% yield). Theoretical value via LC-MS (M+): 1520.48, and measured value: 1521.51 (ESI, M+H+).

2.2 Synthesis of Compound F1-2 (Formula Ib-2)

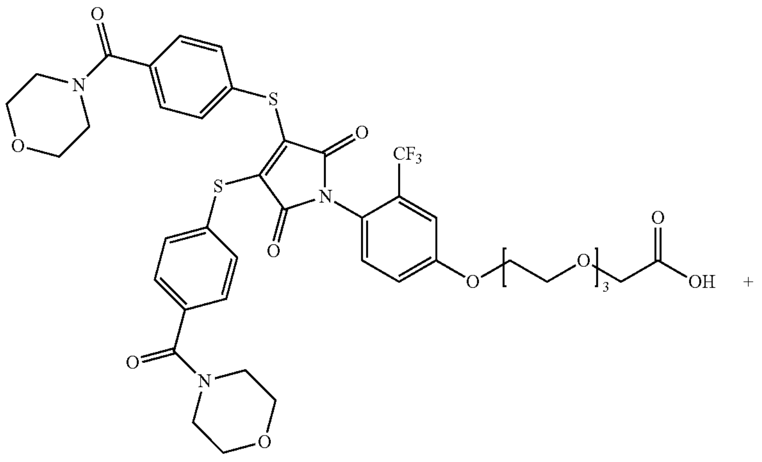

E1-9

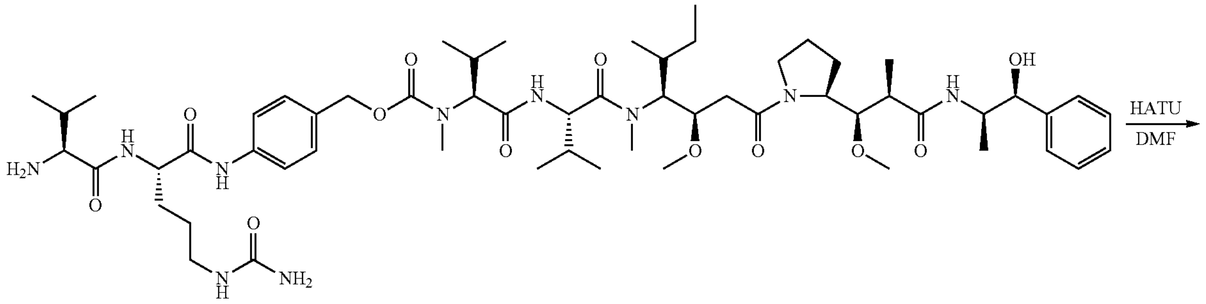

D1-2

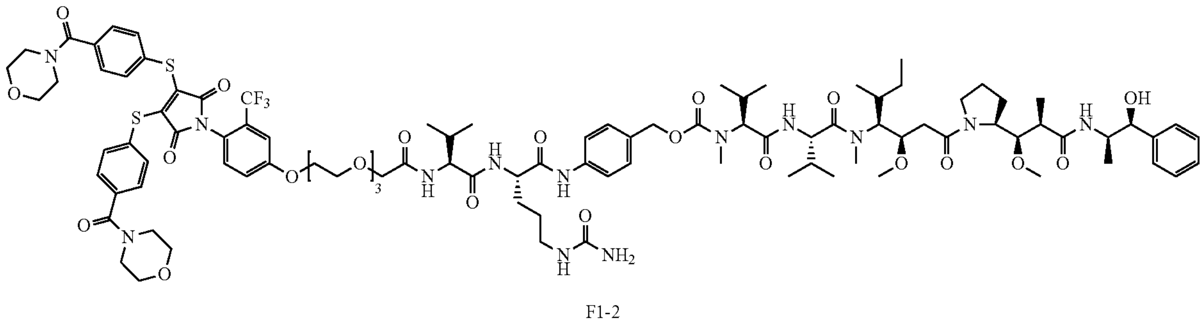

F1-2

Compound F1-2 was synthetized by the same steps for synthesizing compound F1-1 of Example 2.1, with the exception that compound D1-1 was changed to compound D1-2. Product F1-2 obtained was a yellow amorphous powder. Theoretical value via LC-MS (M+): 1993.91, and measured value: 1994.93 (ESI, M+H+).

2.3 Synthesis of Compound F1-3 (Formula Ib-3)
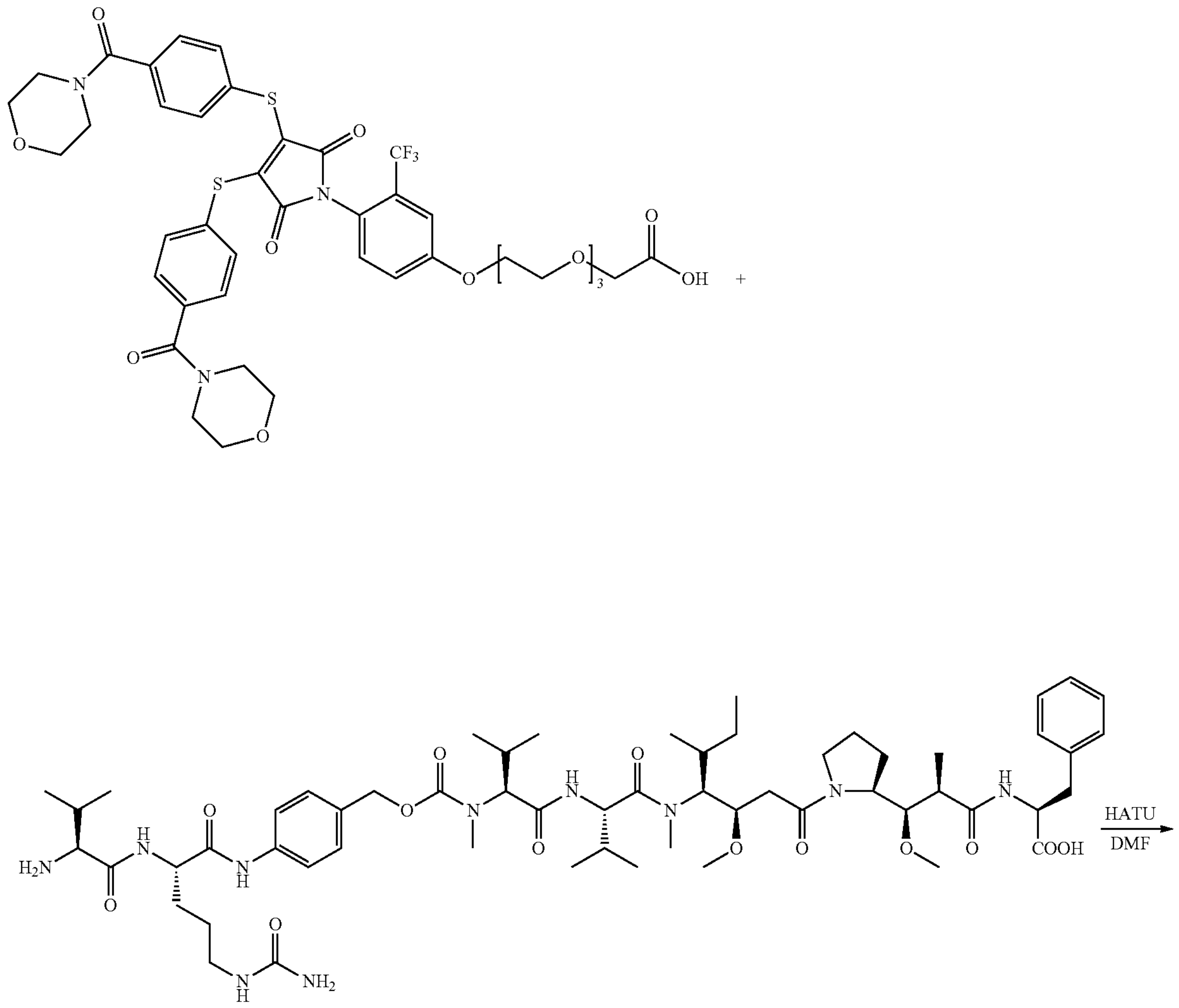
D1-3
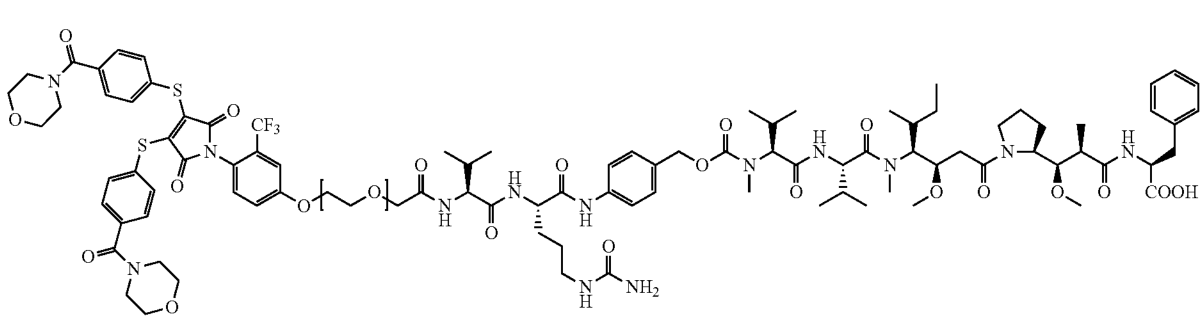
F1-3
Compound F1-3 was synthetized by the same steps for synthesizing compound F1-1 of Example 2.1, with the exception that compound D1-1 was changed to compound D1-3. Product F1-3 obtained was a yellow amorphous powder. Theoretical value via LC-MS (M+): 2007.89, and measured value: 2008.91 (ESI, M+H+).

2.4 Synthesis of Compound F1-4 (Formula Ib-4)
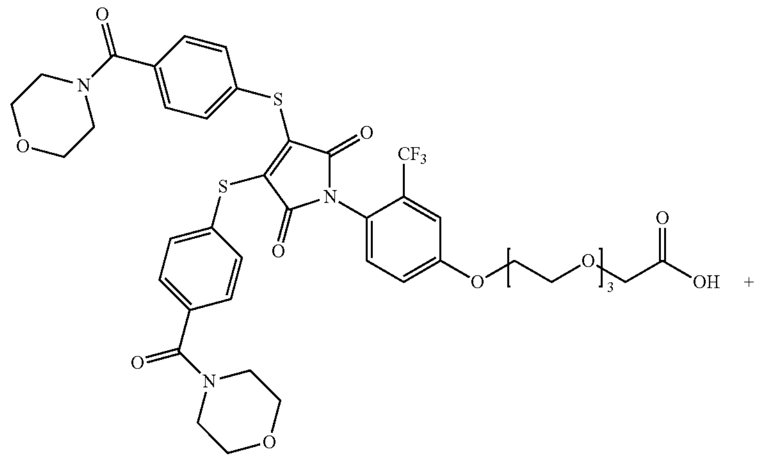
E1-9
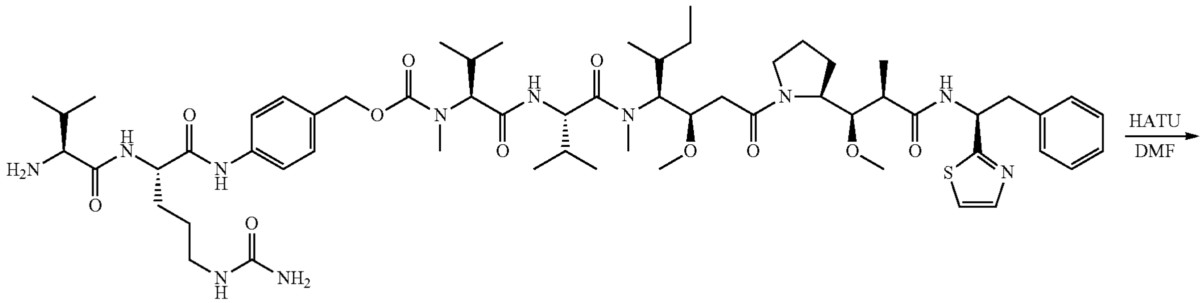
D1-4
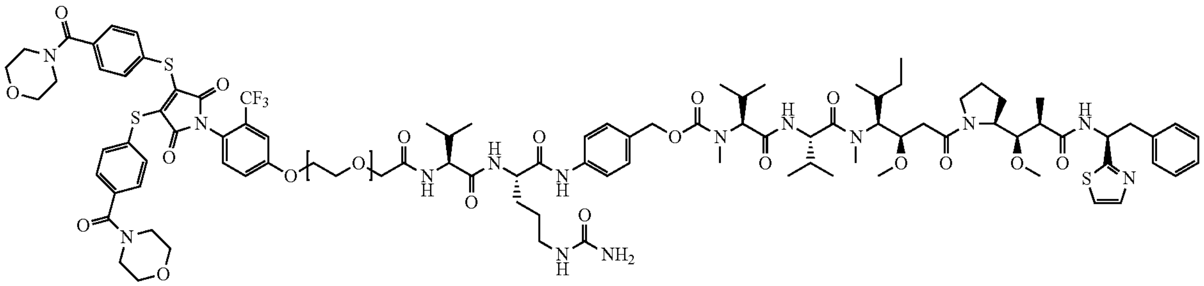
F1-4
Compound F1-4 was synthetized by the same steps for synthesizing compound F1-1 of Example 2.1, with the exception that compound D1-1 was changed to compound D1-4. Product F1-4 obtained was a yellow amorphous powder. Theoretical value via LC-MS (M+): 2046.88, and measured value: 2047.86 (ESI, M+H+).

2.5 Synthesis of Compound F1-5 (Formula Ib-5)
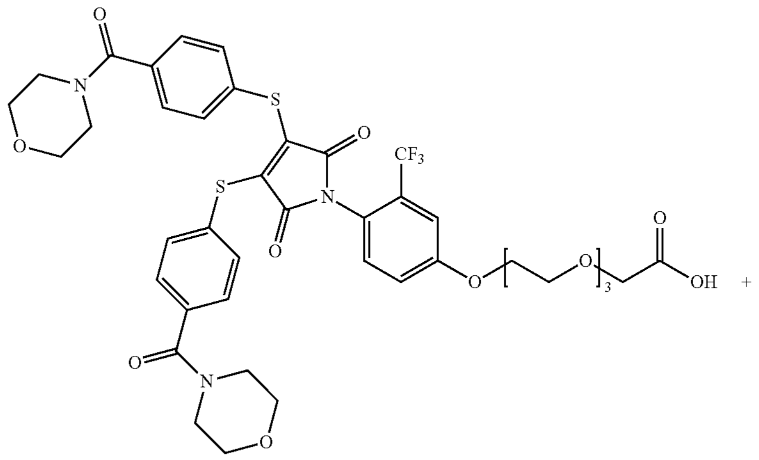
E1-9
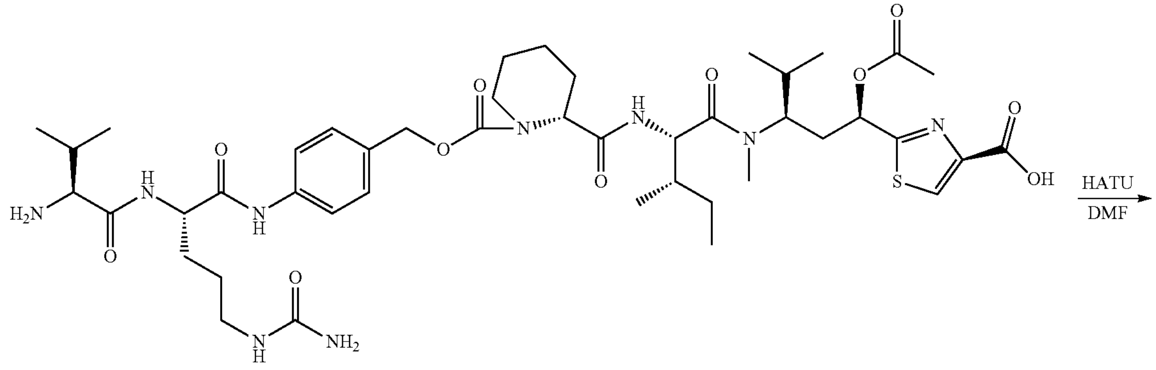
D1-5
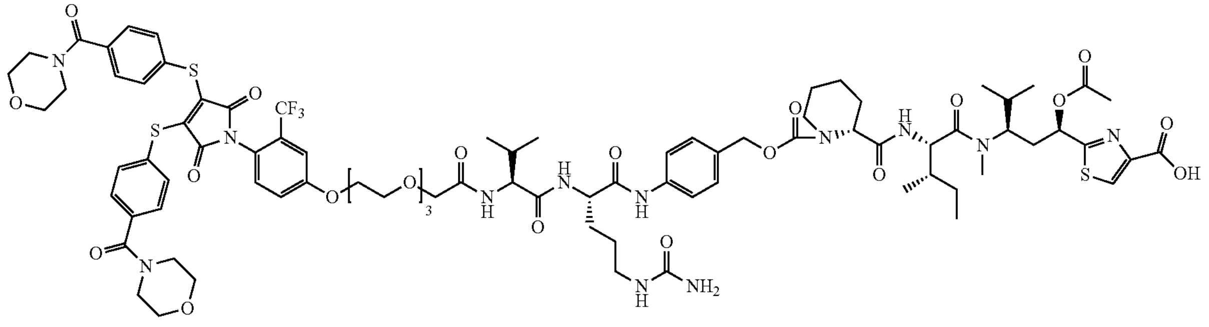
F1-5
Compound F1-5 was synthetized by the same steps for synthesizing compound F1-1 of Example 2.1, with the exception that compound D1-1 was changed to compound D1-5. Product F1-5 obtained was a yellow amorphous powder. Theoretical value via LC-MS (M+): 1800.67, and measured value: 1801.65 (ESI, M+H+).

2.6 Synthesis of Compound F1-6 (Formula Ib-6)
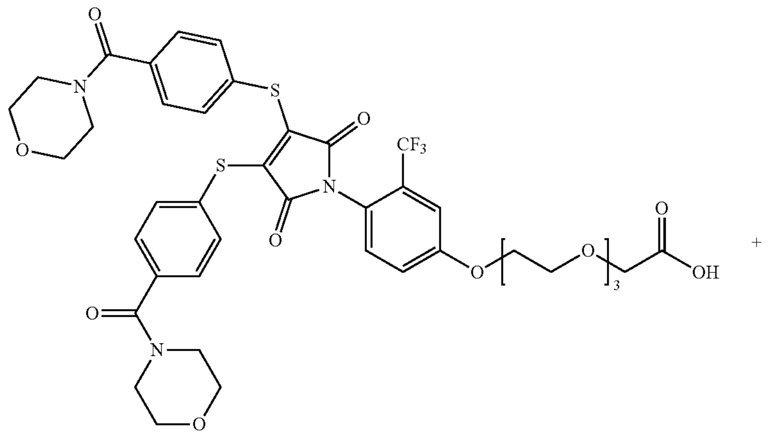
E1-9
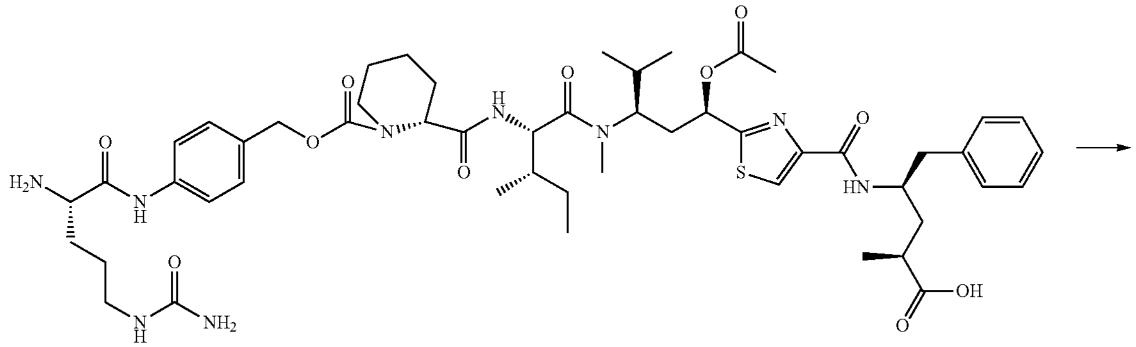
D1-6
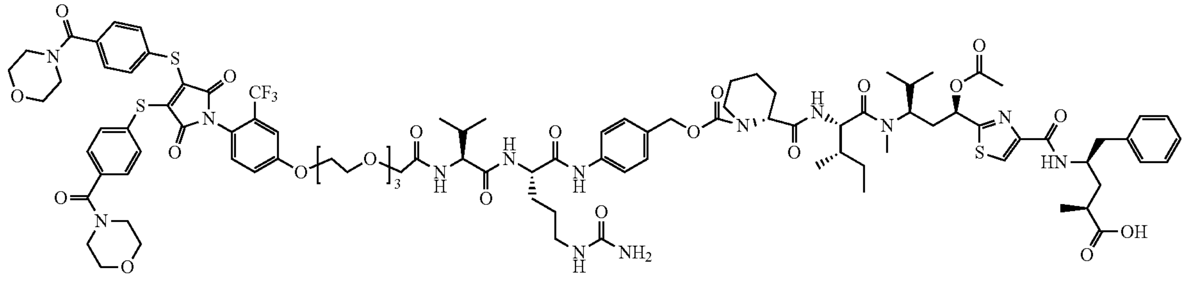
F1-6
Compound F1-6 was synthetized by the same steps for synthesizing compound F1-1 of Example 2.1, with the exception that compound D1-1 was changed to compound D1-6. Product F1-6 obtained was a yellow amorphous powder. Theoretical value via LC-MS (M+): 1989.79, and measured value: 1990.80 (ESI, M+H+).

2.7 Synthesis of Compound F1-7 (Formula Ib-7)
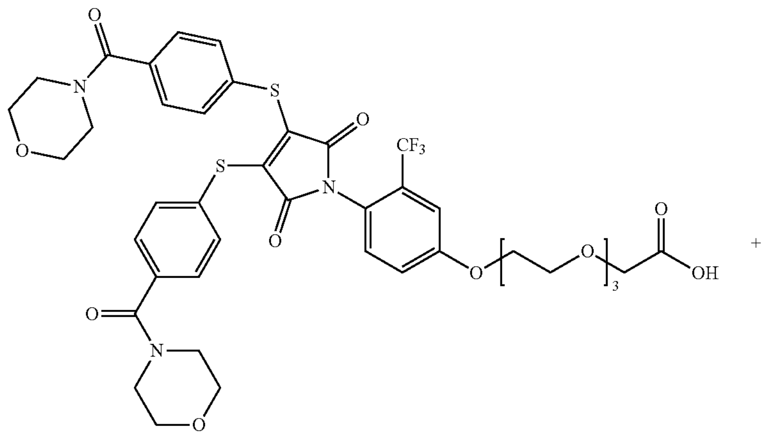
E1-9
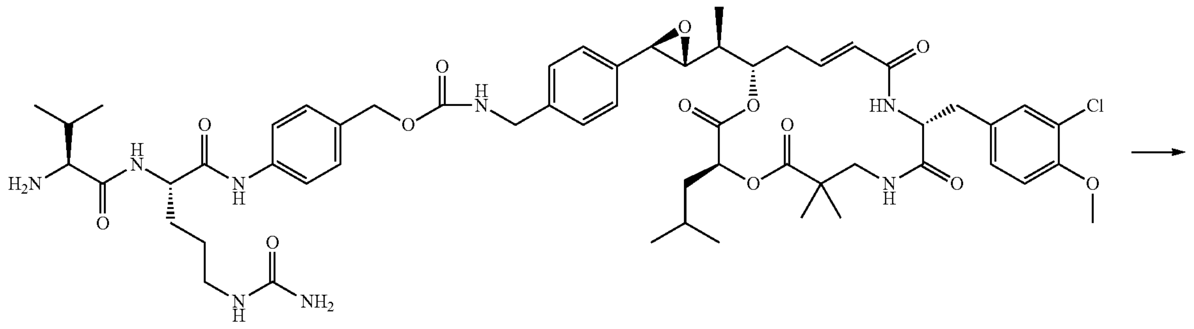
D1-7
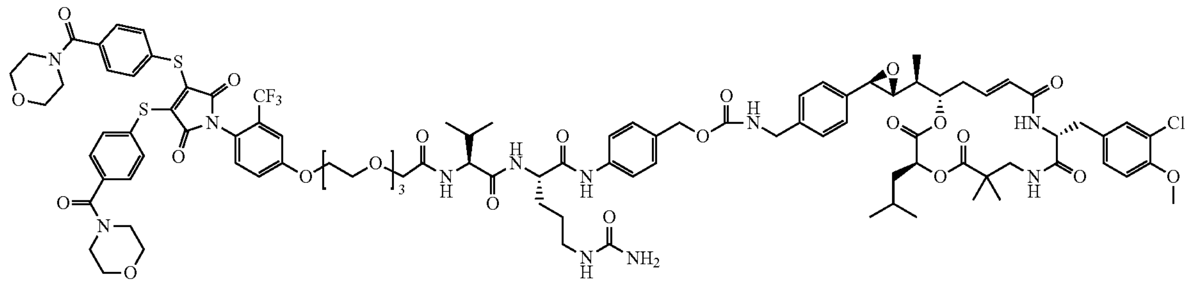
F1-7
Compound F1-7 was synthetized by the same steps for synthesizing compound F1-1 of Example 2.1, with the exception that compound D1-1 was changed to compound D1-7. Product F1-7 obtained was a yellow amorphous powder. Theoretical value via LC-MS (M+): 1973.72, and measured value: 1974.72 (ESI, M+H+).

2.8 Synthesis of Compound F1-8 (Formula Ib-8)
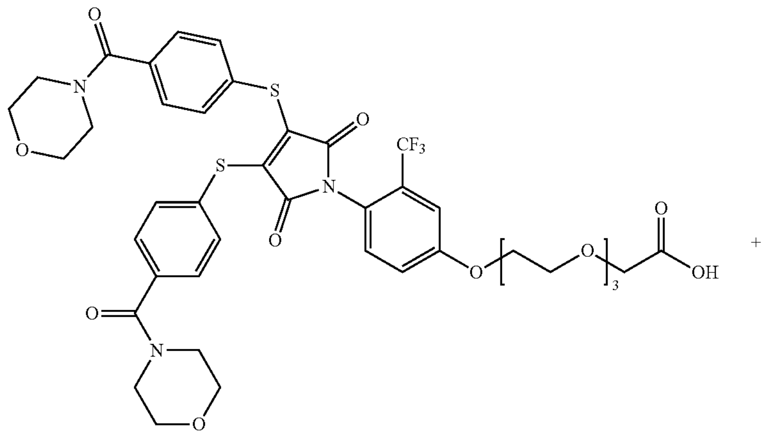
E1-9
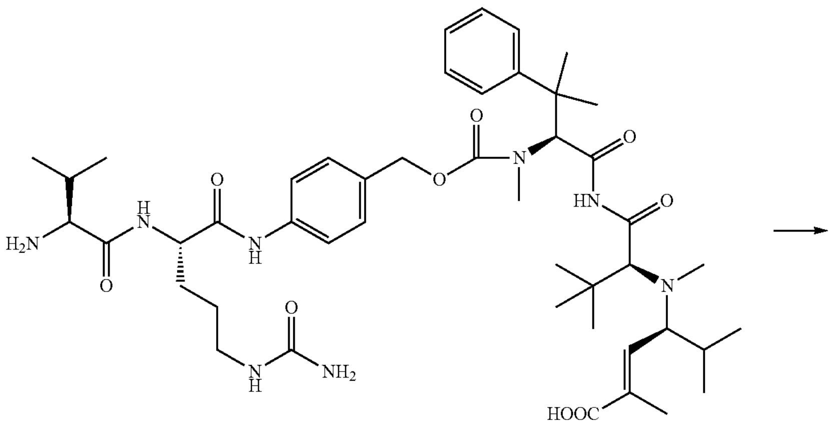
D1-8
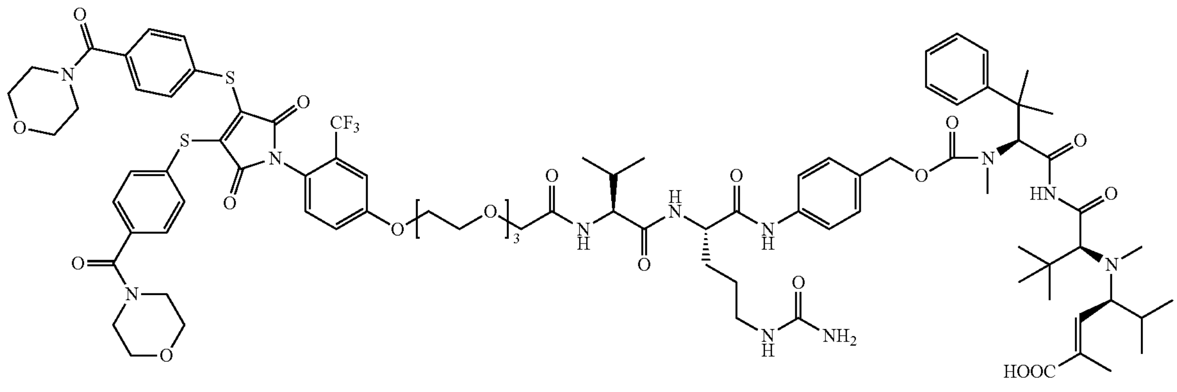
F1-8
Compound F1-8 was synthetized by the same steps for synthesizing compound F1-1 of Example 2.1, with the exception that compound D1-1 was changed to compound D1-8. Product F1-8 obtained was a yellow amorphous powder. Theoretical value via LC-MS (M+): 1749.73, and measured value: 1750.75 (ESI, M+H+).

2.9 Synthesis of Compound F1-9 (Formula Ib-9)
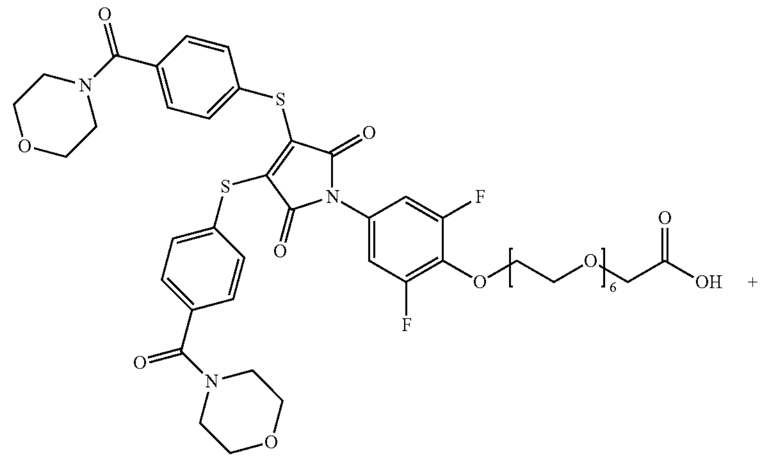
E1-17
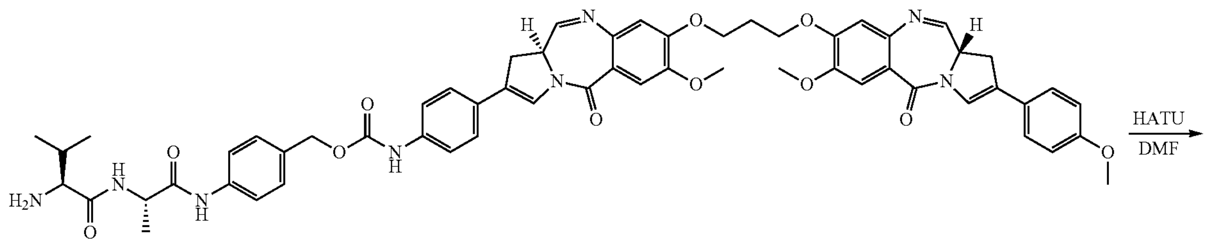
D1-9
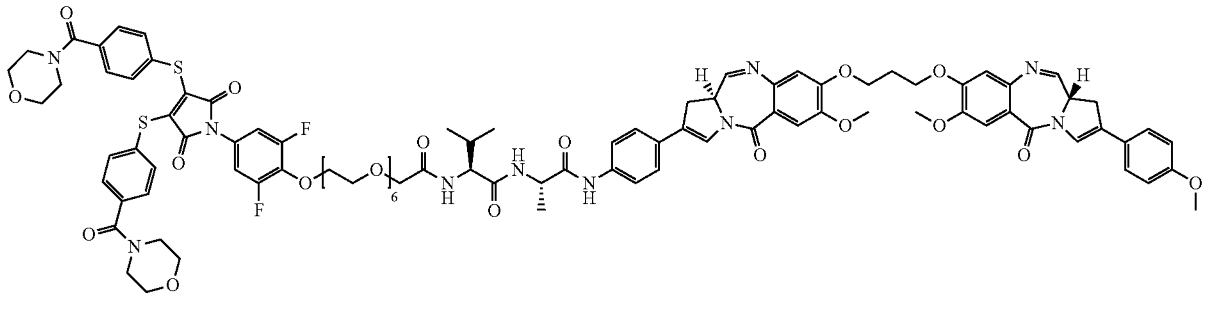
F1-9
Compound F1-9 was synthetized by the same steps for synthesizing compound F1-1 of Example 2.1, with the exception that compounds E1-9 and D1-1 were changed to compounds E1-17 and D1-9 respectively. Product F1-9 obtained was a yellow amorphous powder. Theoretical value via LC-MS (M+): 2015.72, and measured value: 2016.73 (ESI, M+H+).

2.10 Synthesis of Compound F-10 (Formula Ib-10)
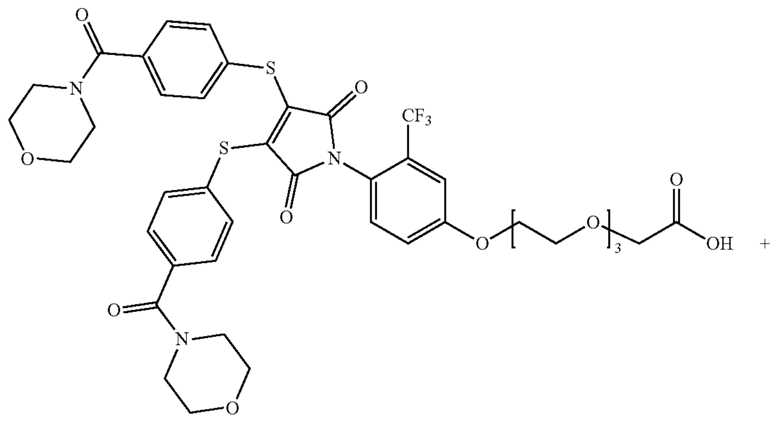
E1-9
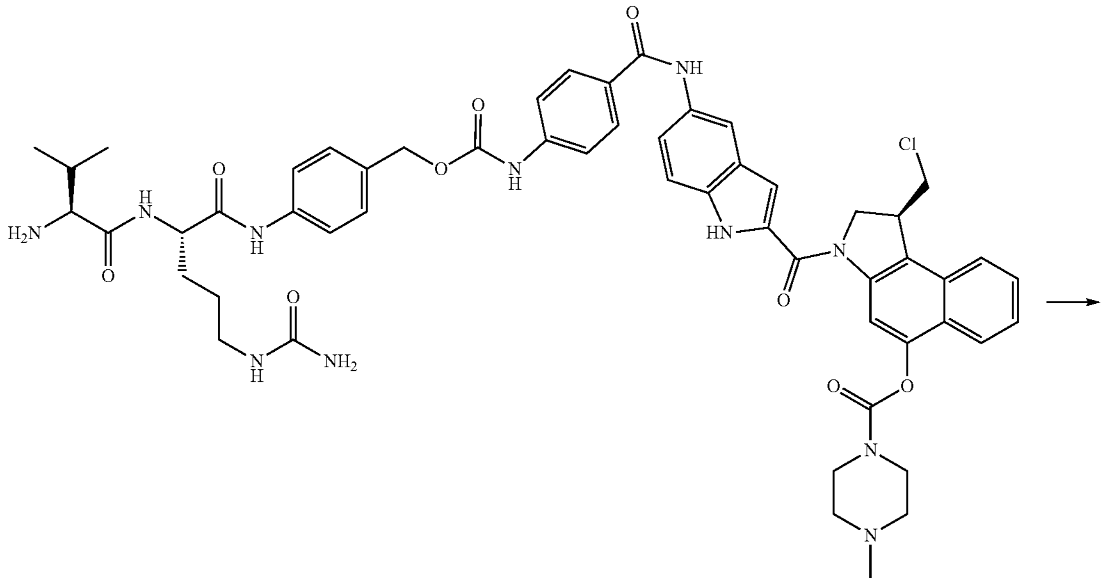
D1-10
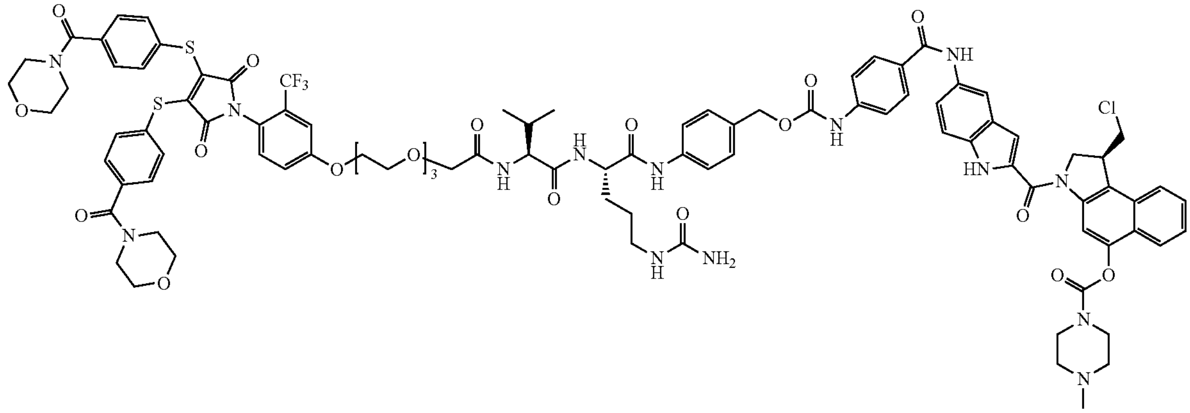
F1-10
Compound F1-10 was synthetized by the same steps for synthesizing compound F1-1 of Example 2.1, with the exception that compound D1-1 was changed to compound D1-10. Product F1-10 obtained was a yellow amorphous powder. Theoretical value via LC-MS (M+): 1912.63, and measured value: 1913.65 (ESI, M+H+).

2.11 Synthesis of Compound F1-11 (Formula Ib-11)
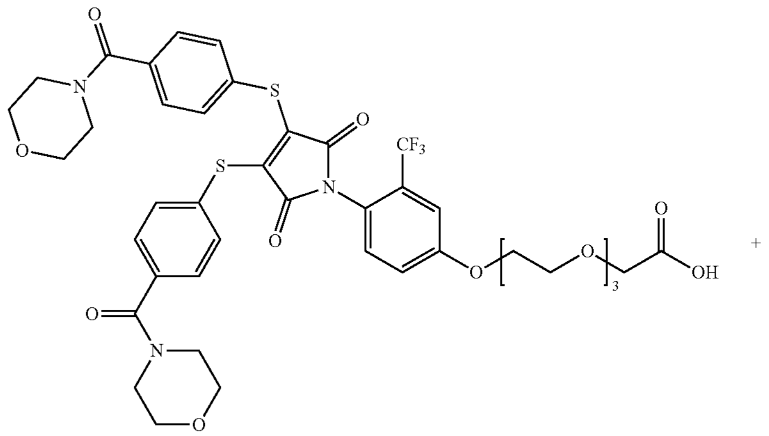
E1-9
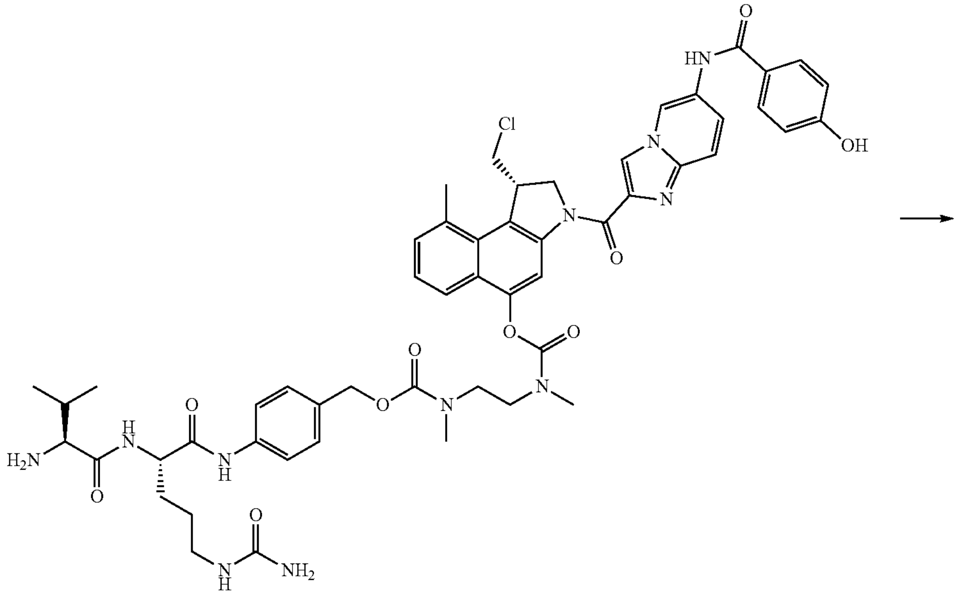
D1-11
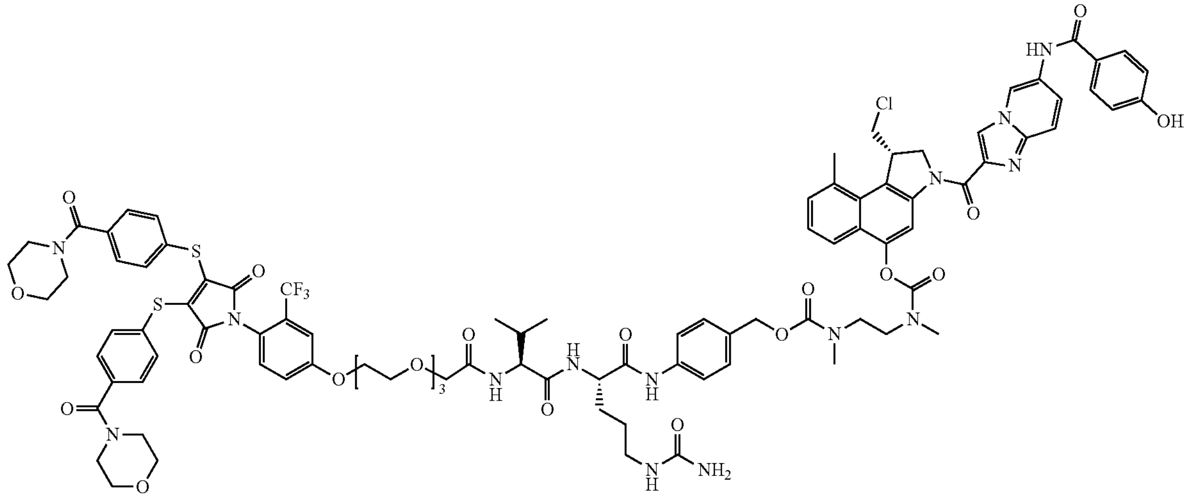
F1-11

Compound F1-1 was synthetized by the same steps for synthesizing compound F1-1 of Example 2.1, with the exception that compound D1-1 was changed to compound D1-11. Product F1-11 obtained was a yellow amorphous powder. Theoretical value via LC-MS (M+): 1916.63, and measured value: 1917.61 (ESI, M+H+).

2.12 Synthesis of Compound F1-12 (Formula Ib-12)

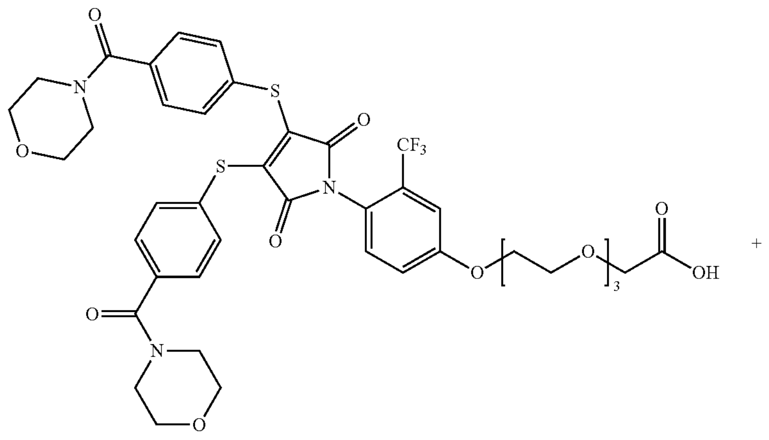

E1-9

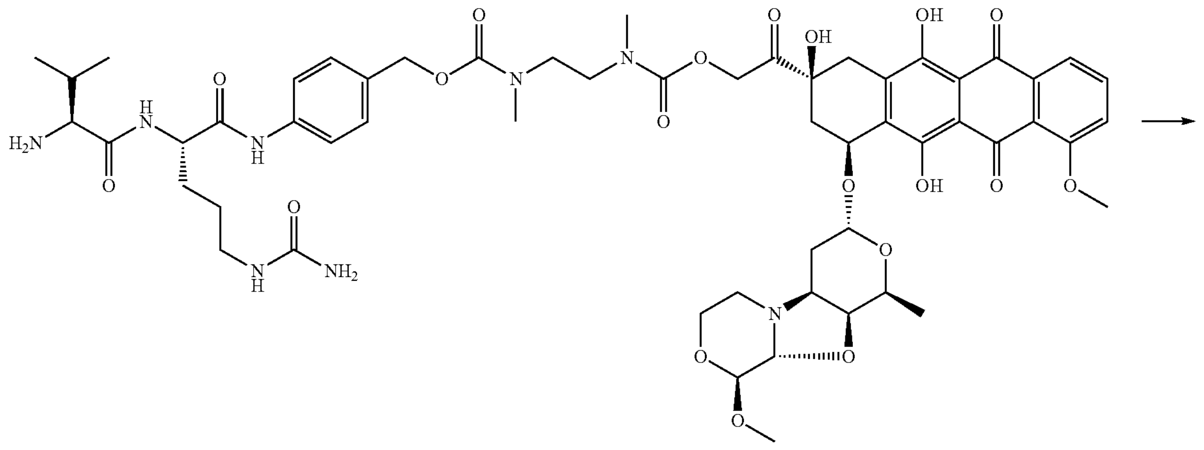

D1-12

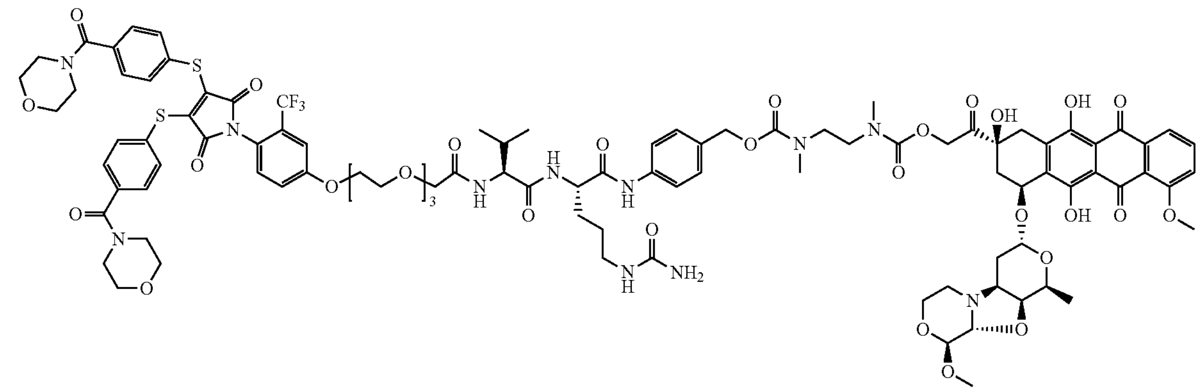

F1-12

Compound F1-12 was synthetized by the same steps for synthesizing compound F1-1 of Example 2.1, with the exception that compound D1-1 was changed to compound D1-12. Product F1-12 obtained was a yellow amorphous powder. Theoretical value via LC-MS (M+): 2031.70, and measured value: 2032.71 (ESI, M+H+).

2.13 Synthesis of Compound F1-13 (Formula Ib-13)
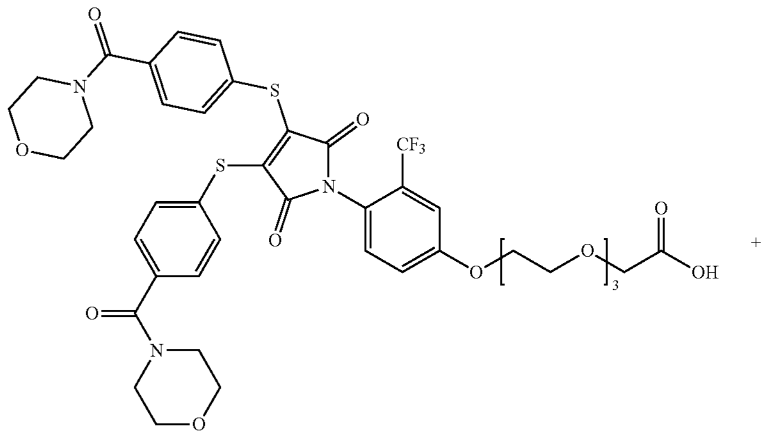
E1-9
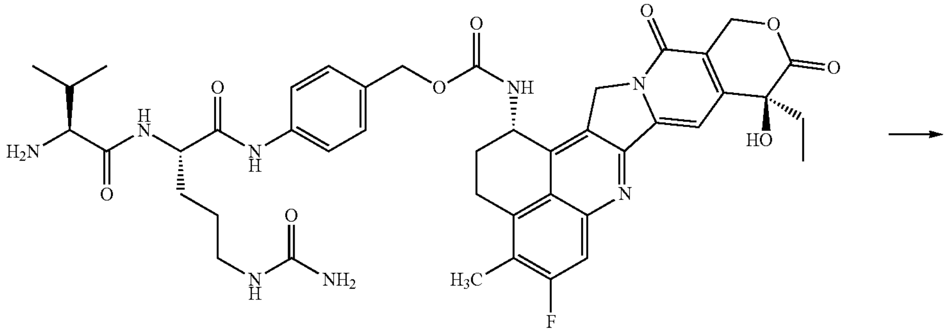
D1-13
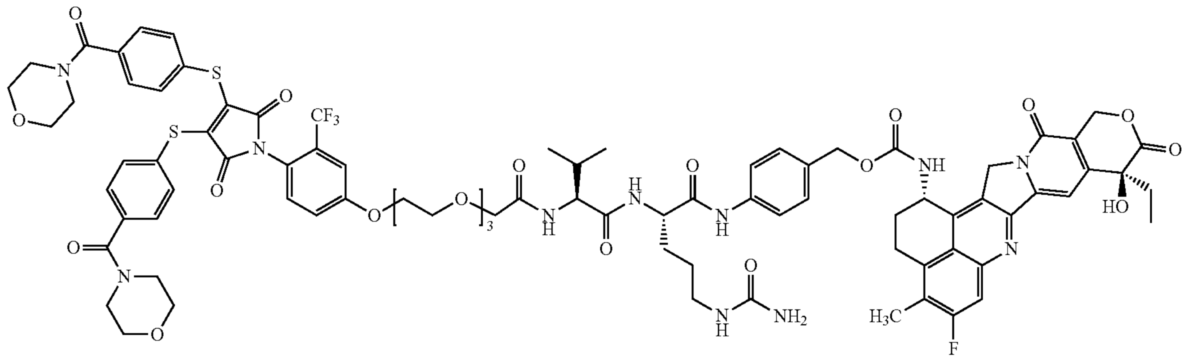
F1-13
Compound F1-13 was synthetized by the same steps for synthesizing compound F1-1 of Example 2.1, with the exception that compound D1-1 was changed to compound D1-13. Product F1-13 obtained was a yellow amorphous powder. Theoretical value via LC-MS (M+): 1711.57, and measured value: 1712.55 (ESI, M+H+).

2.14 Synthesis of Compound F1-14 (Formula Ib-14)
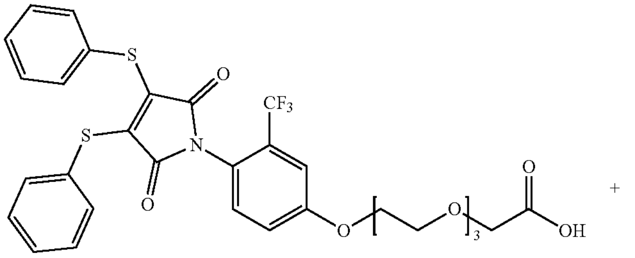
E1-2
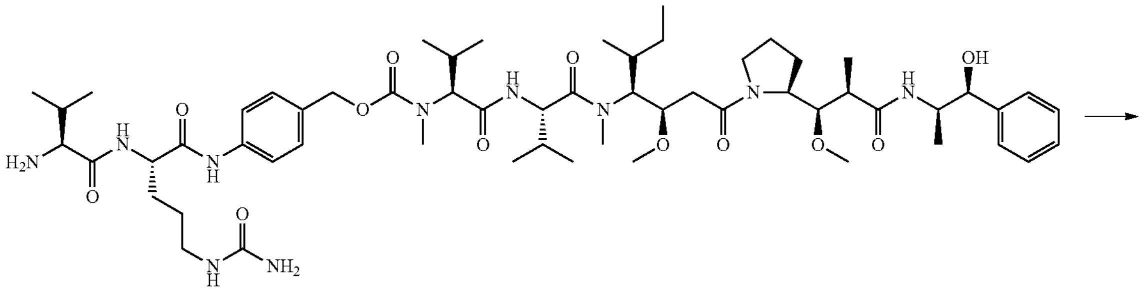
D1-2
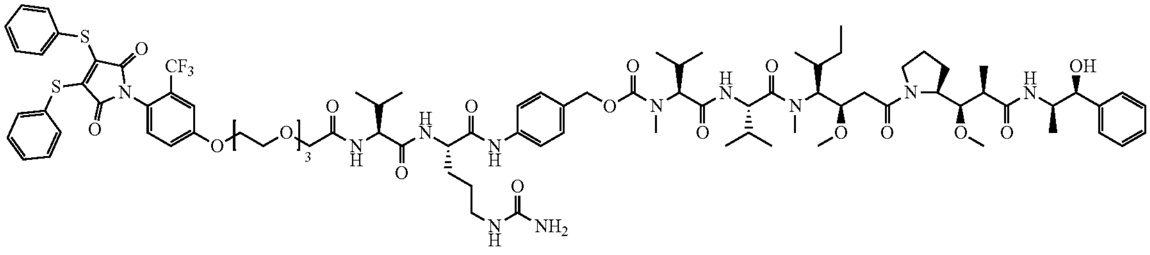
F1-14
Compound F1-14 was synthetized by the same steps for synthesizing compound F1-1 of Example 2.1, with the exception that compounds E1-9 and D1-1 were changed to compounds E1-2 and D1-2 respectively. Product F1-14 obtained was a yellow amorphous powder. Theoretical value via LC-MS (M+): 1767.82, and measured value: 1768.83 (ESI, M+H+).
2.15 Synthesis of Compound F1-15 (Formula Ib-15)
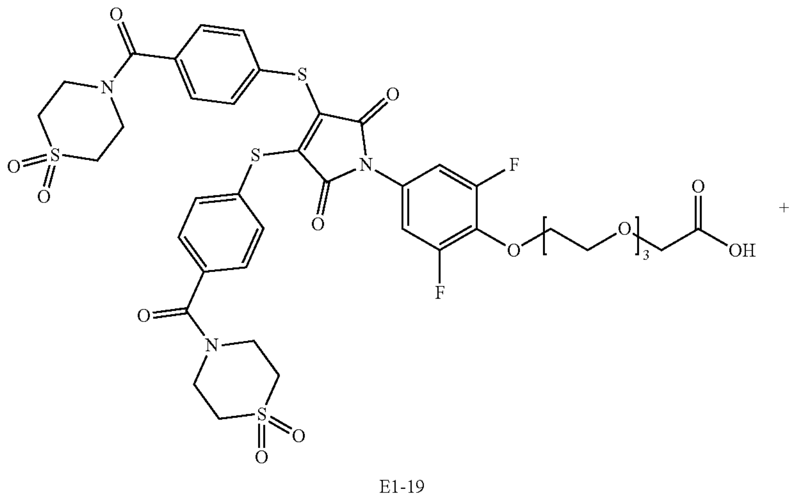
E1-19

-continued
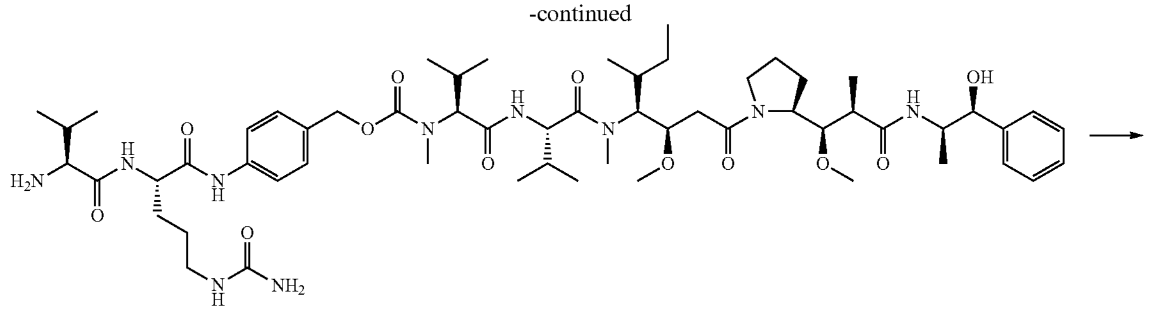
D1-2
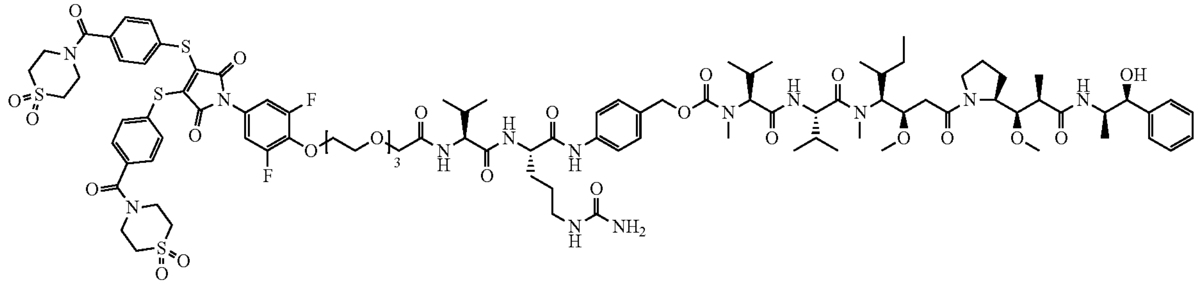
F1-15
Compound F1-15 was synthetized by the same steps for synthesizing compound F1-1 of Example 2.1, with the exception that compounds E1-9 and D1-1 were changed to compounds E1-19 and D1-2 respectively. Product F1-15 obtained was a yellow amorphous powder. Theoretical value via LC-MS (M+): 2057.84, and measured value: 2058.87 (ESI, M+H+).
2.16 Synthesis of Compound F1-16 (Formula Ib-16)
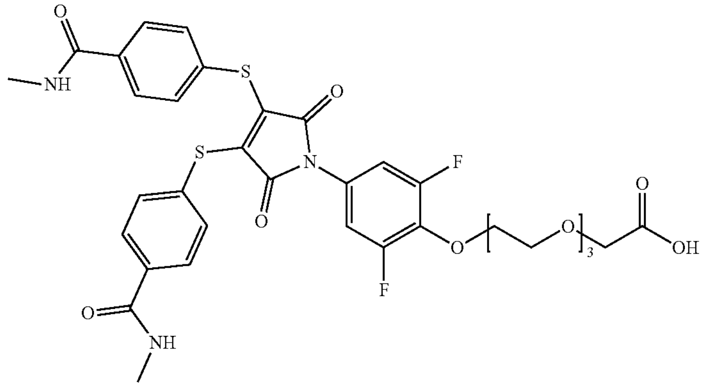
+
E1-20
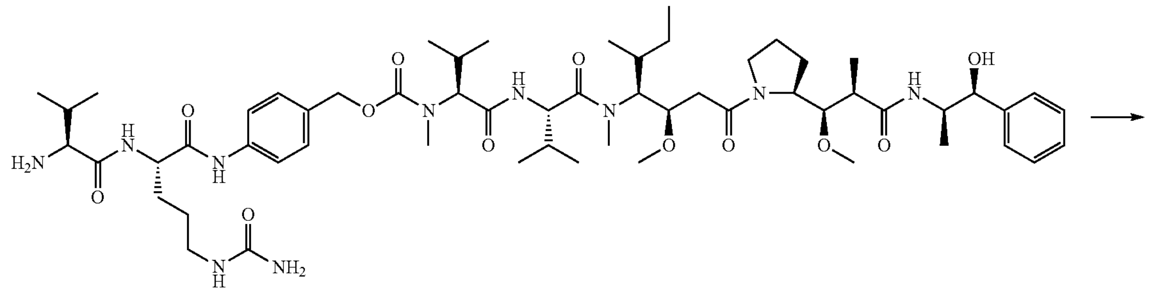
D1-2

-continued

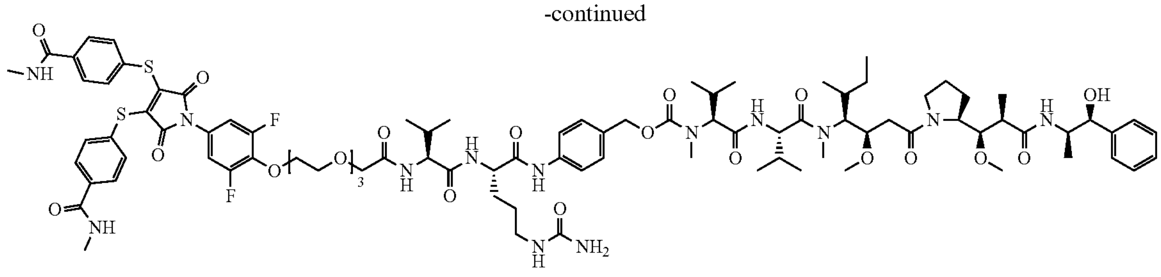

F1-16

Compound F1-16 was synthetized by the same steps for synthesizing compound F1-1 of Example 2.1, with the exception that compounds E1-9 and D1-1 were changed to compounds E1-20 and D1-2 respectively. Product F1-16 obtained was a yellow amorphous powder. Theoretical value via LC-MS (M+): 1849.85, and measured value: 1850.83 (ESI, M+H+).

2.17 Synthesis of Compound F1-17 (Formula Ib-17)

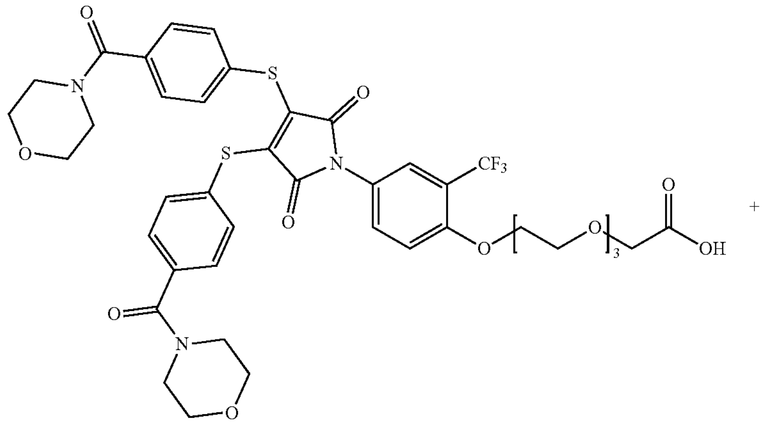

E1-10

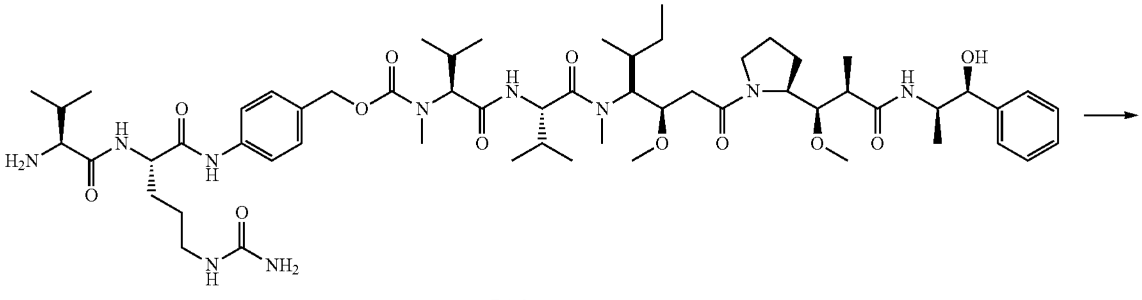

D1-2

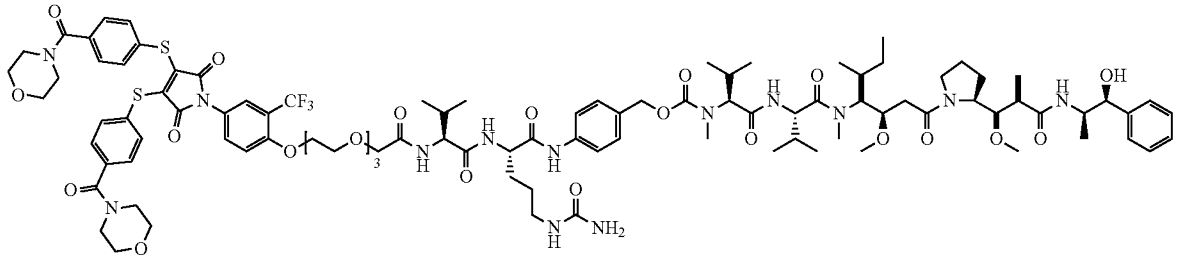

F1-17

Compound F1-17 was synthetized by the same steps for synthesizing compound F1-1 of Example 2.1, with the exception that compounds E1-9 and D1-1 were changed to compounds E1-10 and D1-2 respectively. Product F1-17 obtained was a yellow amorphous powder. Theoretical value via LC-MS (M+): 1993.91, and measured value: 1994.90 (ESI, M+H+).

2.18 Synthesis of Compound F1-18 (Formula Ib-18)
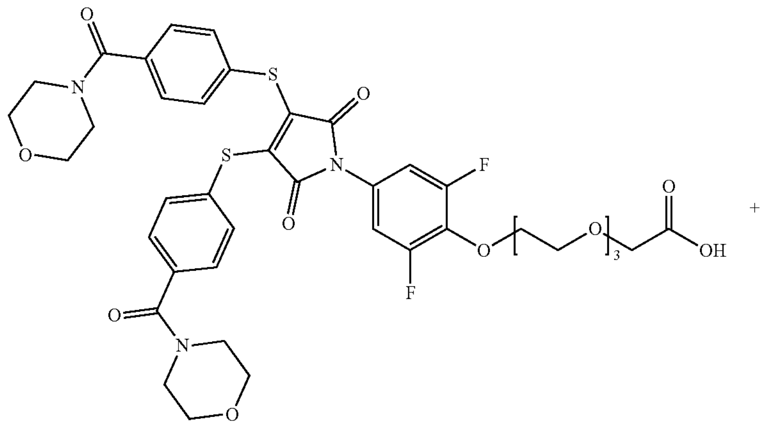
E1-11
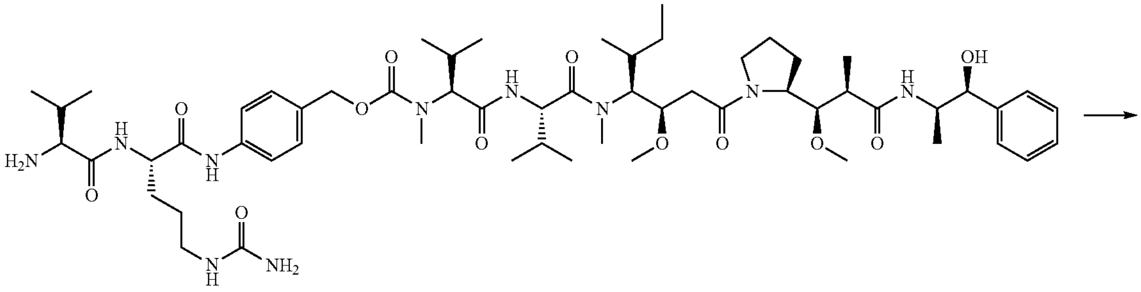
D1-2
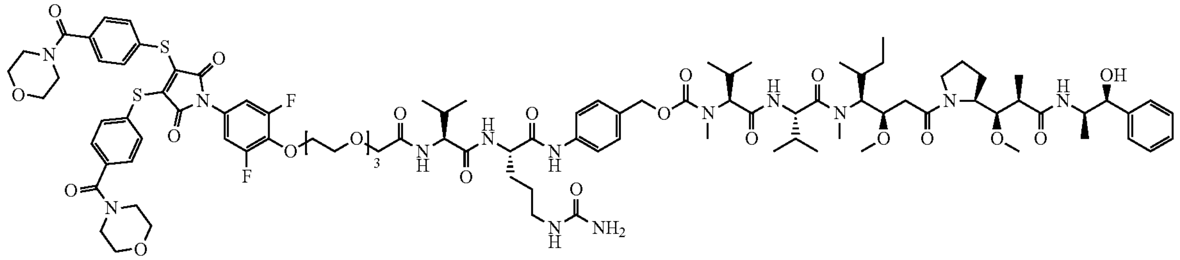
F1-18
Compound F1-18 was synthetized by the same steps for synthesizing compound F1-1 of Example 2.1, with the exception that compounds E1-9 and D1-1 were changed to compounds E1-11 and D1-2 respectively. Product F1-18 obtained was a yellow amorphous powder. Theoretical value via LC-MS (M+): 1961.90, and measured value: 1962.91 (ESI, M+H+).

2.19 Synthesis of Compound F1-19 (Formula Ib-19)
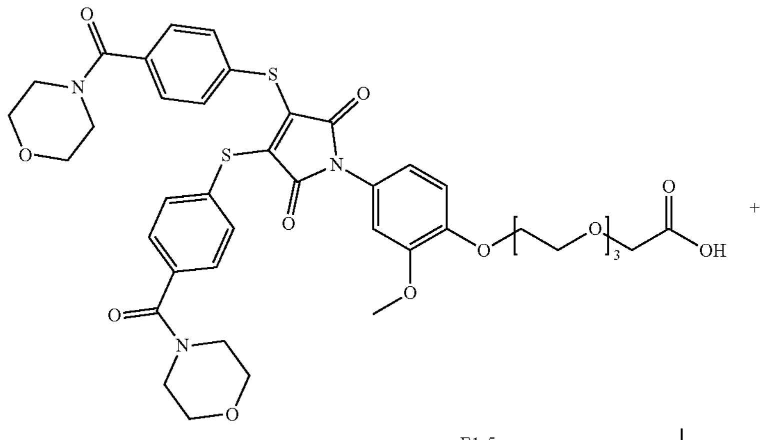
E1-5
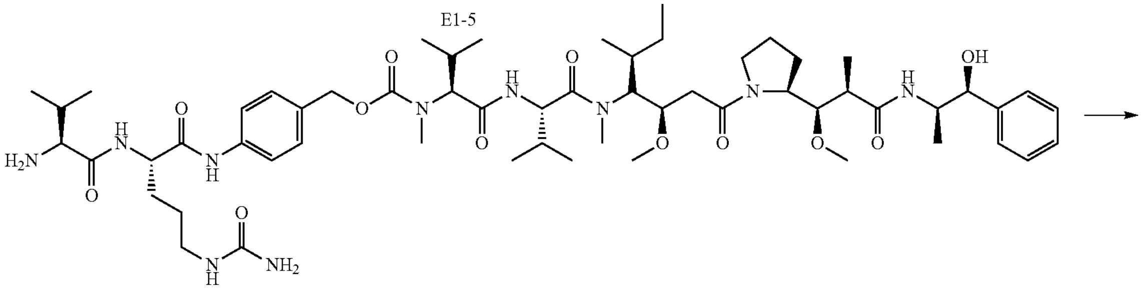
D1-2
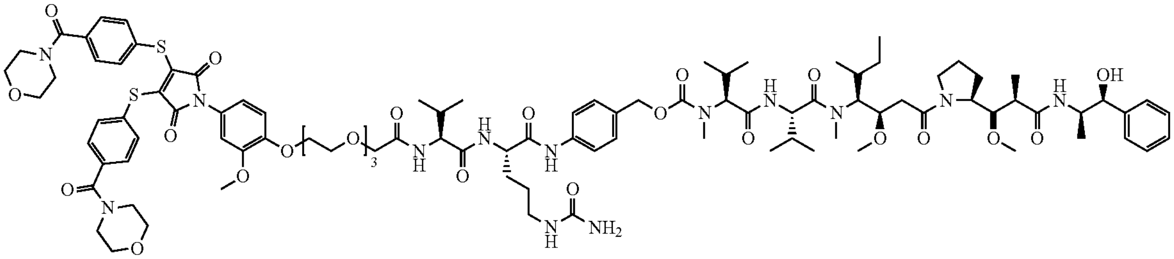
F1-19
Compound F1-19 was synthetized by the same steps for synthesizing compound F1-1 of Example 2.1, with the exception that compounds E1-9 and D1-1 were changed to compounds E1-5 and D1-2 respectively. Product F1-19 obtained was a yellow amorphous powder. Theoretical value via LC-MS (M+): 1955.93, and measured value: 1956.95 (ESI, M+H+).
2.20 Synthesis of Compound F1-20 (Formula Ib-20)
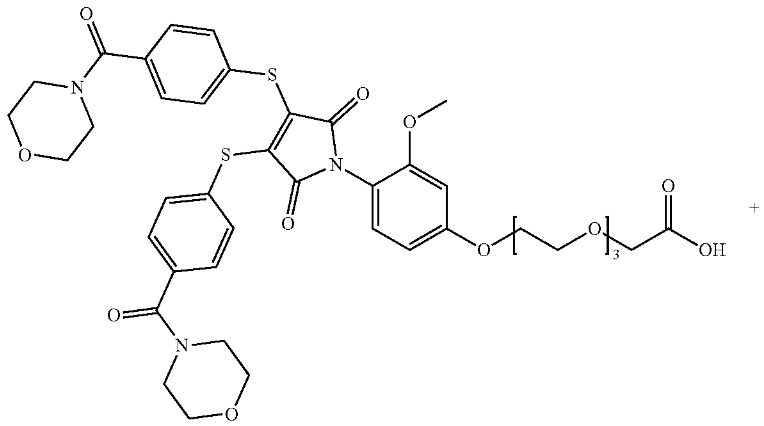
E1-4

-continued
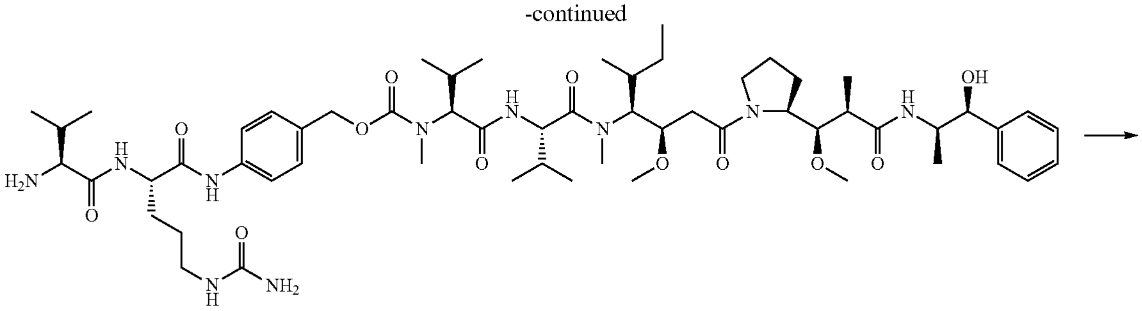
D1-2
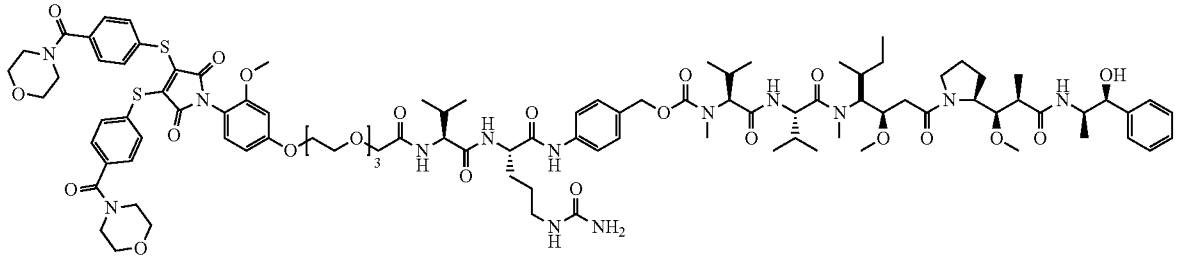
F1-20
Compound F1-20 was synthetized by the same steps for synthesizing compound F1-1 of Example 2.1, with the exception that compounds E1-9 and D1-1 were changed to compounds E1-4 and D1-2 respectively. Product F1-20 obtained was a yellow amorphous powder. Theoretical value via LC-MS (M+): 1955.93, and measured value: 1956.95 (ESI, M+H+).
2.21 Synthesis of Compound F1-21 (Formula Ib-21)
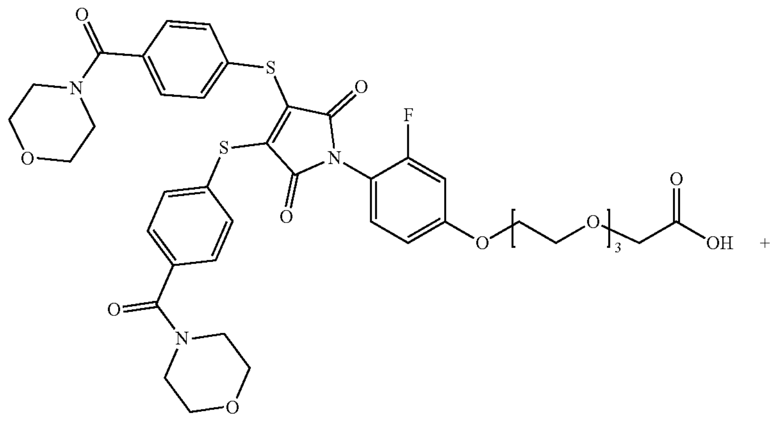
E1-12
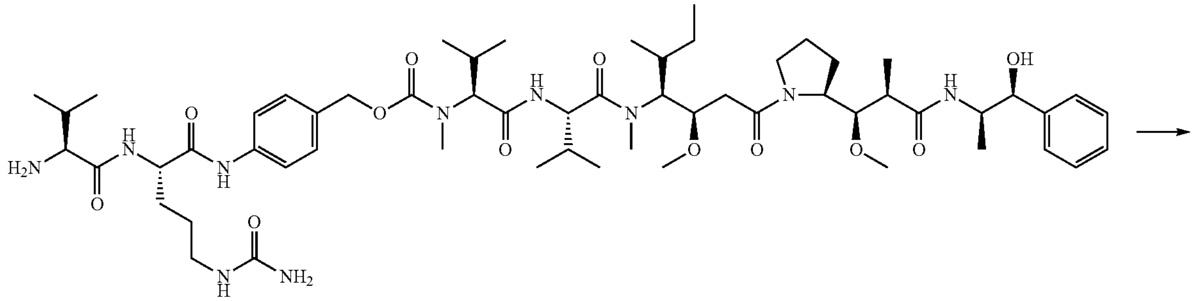
D1-2

-continued

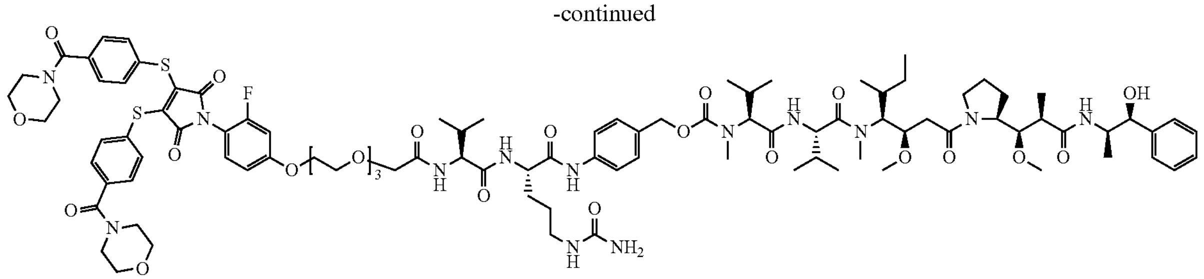

F1-21

Compound F1-21 was synthetized by the same steps for synthesizing compound F1-1 of Example 2.1, with the exception that compounds E1-9 and D1-1 were changed to compounds E1-12 and D1-2 respectively. Product F1-21 obtained was a yellow amorphous powder. Theoretical value via LC-MS (M+): 1943.91, and measured value: 1944.90 (ESI, M+H+).

2.22 Synthesis of Compound F1-22 (Formula Ib-22)

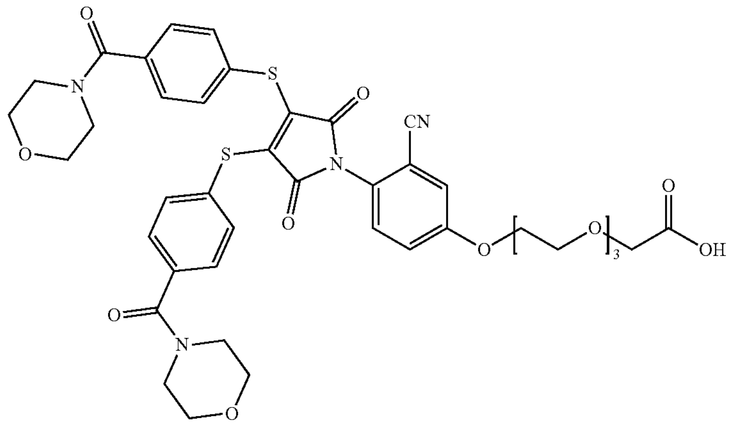

E1-6

+

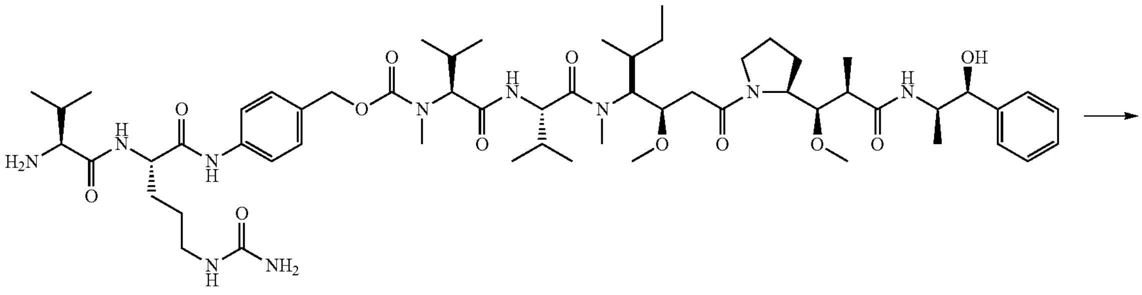

D1-2

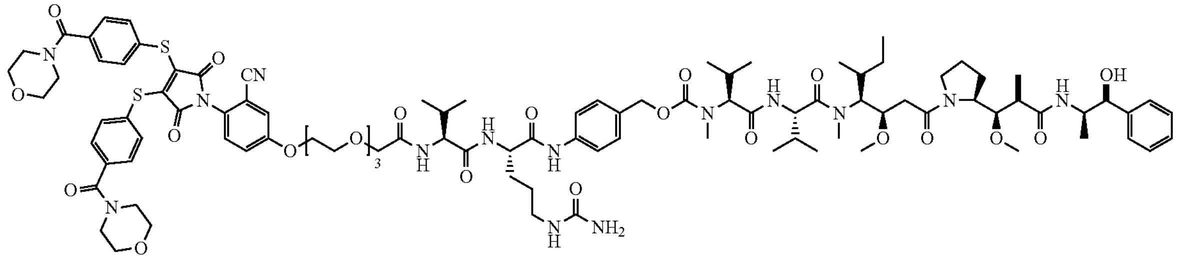

F1-22

Compound F1-22 was synthetized by the same steps for synthesizing compound F1-1 of Example 2.1, with the exception that compounds E1-9 and D1-1 were changed to compounds E1-6 and D1-2 respectively. Product F1-22 obtained was a yellow amorphous powder. Theoretical value via LC-MS (M+): 1950.92, and measured value: 1951.93 (ESI, M+H+).

2.23 Synthesis of Compound F1-23 (Formula Ib-23)
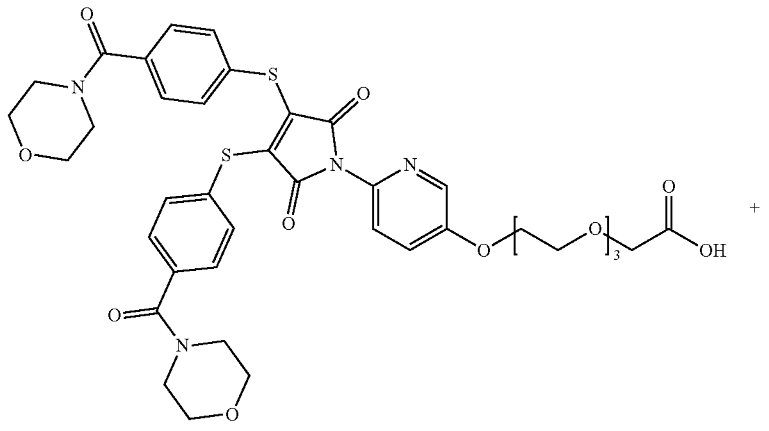
E1-21
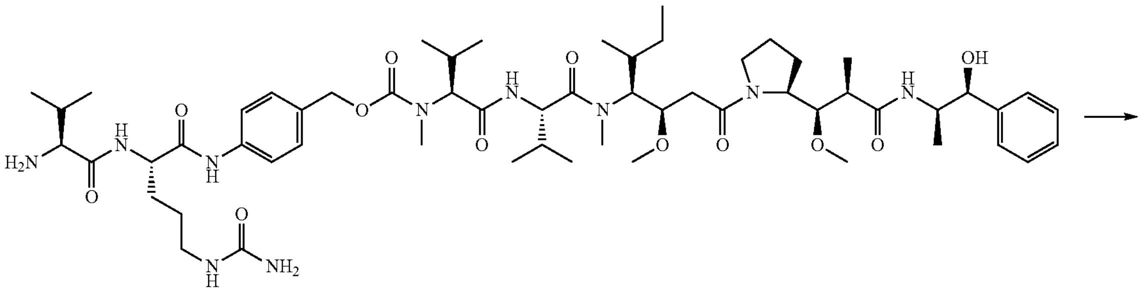
D1-2
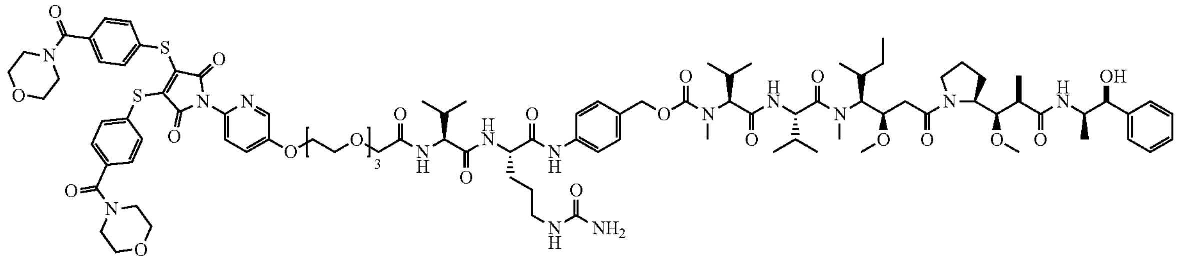
F1-23
Compound F1-23 was synthetized by the same steps for synthesizing compound F1-1 of Example 2.1, with the exception that compounds E1-9 and D1-1 were changed to compounds E1-21 and D1-2 respectively. Product F1-23 obtained was a yellow amorphous powder. Theoretical value via LC-MS (M+): 1926.92, and measured value: 1927.93 (ESI, M+H+).

2.24 Synthesis of Compound F1-24 (Formula Ib-24)

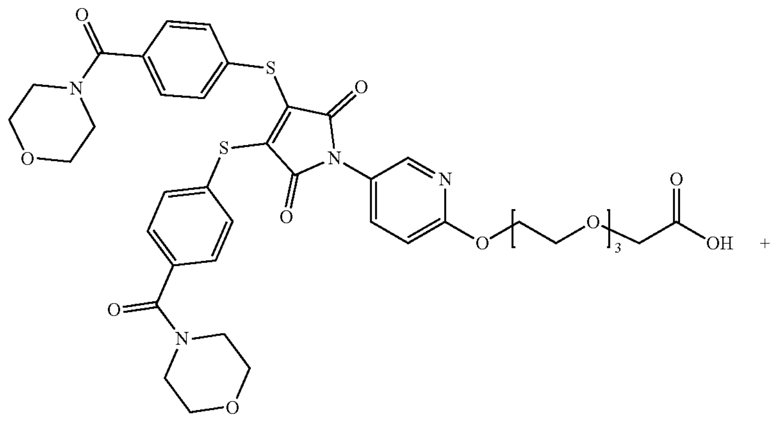

E1-22

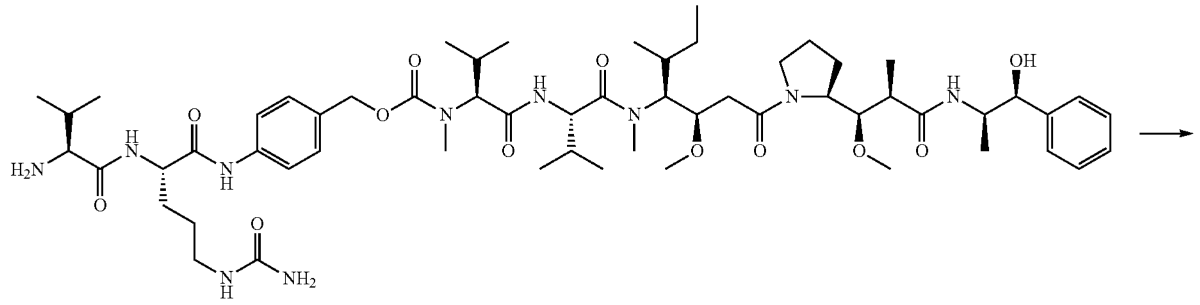

D1-2

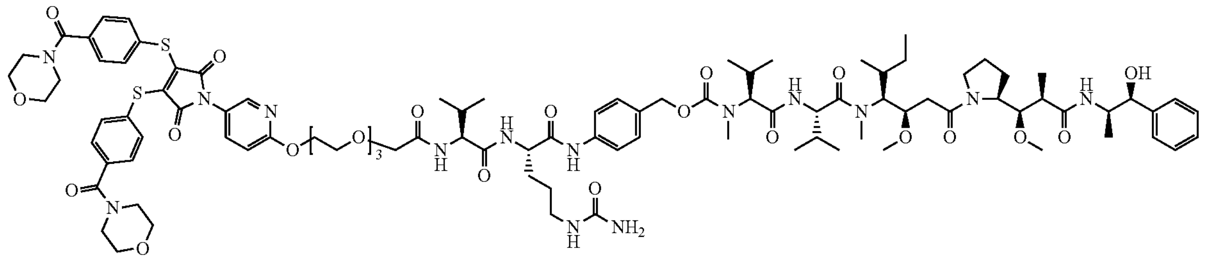

F1-24

Compound F1-24 was synthetized by the same steps for synthesizing compound F1-1 of Example 2.1, with the exception that compounds E1-9 and D1-1 were changed to compounds E1-22 and D1-2 respectively. Product F1-24 obtained was a yellow amorphous powder. Theoretical value via LC-MS (M+): 1926.92, and measured value: 1927.93 (ESI, M+H+).

The Third Group of Examples: Preparation of the Antibody Drug Conjugate

1. Preparation of ADC-I

A pertuzumab stock solution was diluted to 2 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 7, and then 6.0× excess molar ratio of tris(2-carboxyethyl)phosphine hydrochloride (TCEP) was added thereto. The obtained reaction solution was stirred at 35° C. for 2.5 hours.

Subsequently, without being purified, the reaction solution was cooled down to 8° C. and an appropriate amount of dimethyl sulfoxide (DMSO) and 6× excess molar ratio of compound F1-17 (10 mg/ml, pre-dissolved in DMSO) were added thereto, and DMSO in the reaction system was ensured to be no more than 15% by volume. The obtained reaction solution was stirred at 37° C. for 3 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.15 μm, and the obtained product was stored at −60° C.

2. Preparation of ADC-II

A pertuzumab stock solution was diluted to 5 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 6, and then 10× excess molar ratio of tris(2-carboxyethyl)phosphine hydrochloride (TCEP) was added thereto. The obtained reaction solution was stirred at 10° C. for 40 hours.

Subsequently, without being purified, the reaction solution was cooled down to 5° C. and an appropriate amount of dimethylacetamide (DMA) and 6× excess molar ratio of compound F1-2 (10 mg/ml, pre-dissolved in DMA) were added thereto, and DMA in the reaction system was ensured to be no more than 10% by volume. The obtained reaction solution was stirred at 25° C. for 2.5 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.22 μm, and the obtained product was stored at −80° C.

3. Preparation of ADC-III

A pertuzumab stock solution was diluted to 5 mg/mL with PBS//1 mM diethylene triamine pentacetate acid (DTPA) reaction buffer solution with a pH of 7.4, and then 20× excess molar ratio of tris(2-carboxyethyl)phosphine hydrochloride (TCEP) was added thereto. The obtained reaction solution was stirred at 15° C. for 2 hours.

Subsequently, without being purified, the reaction solution was cooled down to 10° C. and an appropriate amount of acetonitrile (ACN) and 6× excess molar ratio of compound F1-20 (10 mg/ml, pre-dissolved in ACN) were added thereto, and ACN in the reaction system was ensured to be no more than 10% by volume. The obtained reaction solution was stirred at 10° C. for 4 hours for coupling.

The reaction solution after coupling reaction was purified by filtration with a desalting column using histidine-acetic acid/sucrose gel (pH 8.0), and then sample at absorption peak was collected according to UV280 ultraviolet absorption value. The collected sample was sterilized through a filtration device with a pore size of 0.20 μm, and the obtained product was stored at −90° C.

4. Preparation of ADC-IV

A pertuzumab stock solution was diluted to 8 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 7, and then 8× excess molar ratio of tris(2-carboxyethyl)phosphine hydrochloride (TCEP) was added thereto. The obtained reaction solution was stirred at 25° C. for 25 hours.

Subsequently, without being purified, the reaction solution was cooled down to 5° C. and an appropriate amount of dimethylformamide (DMF) and 6× excess molar ratio of compound F1-19 (10 mg/ml, pre-dissolved in DMF) were added thereto, and DMF in the reaction system was ensured to be no more than 8% by volume. The obtained reaction solution was stirred at 0° C. for 2 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.3 μm, and the obtained product was stored at −80° C.

5. Preparation of ADC-V

A pertuzumab stock solution was diluted to 6 mg/mL with 50 mM histidine-sodium hydroxide/150 mM sodium chloride (NaCl)/1 mM diethylene triamine pentacetate acid (DTPA) reaction buffer solution with a pH of 7.4, and then 8× excess molar ratio of tris(2-carboxyethyl)phosphine hydrochloride (TCEP) was added thereto. The obtained reaction solution was stirred at 35° C. for 15 hours.

Subsequently, without being purified, the reaction solution was cooled down to 10° C. and an appropriate amount of dimethylformamide (DMF) and 6× excess molar ratio of compound F1-22 (10 mg/ml, pre-dissolved in DMF) were added thereto, and DMF in the reaction system was ensured to be no more than 8% by volume. The obtained reaction solution was stirred at 0° C. for 5 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.15 μm, and the obtained product was stored at −100° C.

6. Preparation of ADC-VI

A pertuzumab stock solution was diluted to 10 mg/mL with 50 mM boric acid-borax/150 mM sodium chloride (NaCl)/1 mM diethylene triamine pentacetate acid (DTPA) reaction buffer solution with a pH of 9; and then 8× excess molar ratio of tris(2-carboxyethyl)phosphine hydrochloride (TCEP) was added thereto. The obtained reaction solution was stirred at 25° C. for 10 hours.

Subsequently, without being purified, the reaction solution was cooled down to 10° C. and an appropriate amount of dimethylformamide (DMF) and 6× excess molar ratio of compound F1-21 (10 mg/ml, pre-dissolved in DMF) were added thereto, and DMF in the reaction system was ensured to be no more than 8% by volume. The obtained reaction solution was stirred at 0° C. for 4 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.2 μm, and the obtained product was stored at −60° C.

7. Preparation of ADC-VII

A pertuzumab stock solution was diluted to 3 mg/mL with 50 mM potassium dihydrogen phosphate-sodium hydroxide ($KH_2PO_4$—NaOH)/150 mM sodium chloride (NaCl)/1 mM diethylene triamine pentacetate acid (DTPA) reaction buffer solution with a pH of 8, and then 8× excess molar ratio of tris(2-carboxyethyl)phosphine hydrochloride (TCEP) was added thereto. The obtained reaction solution was stirred at 15° C. for 48 hours.

Subsequently, without being purified, the reaction solution was cooled down to 0° C. and an appropriate amount of dimethylformamide (DMF) and 6× excess molar ratio of compound F1-18 (10 mg/ml, pre-dissolved in DMF) were added thereto, and DMF in the reaction system was ensured to be no more than 8% by volume. The obtained reaction solution was stirred at 0° C. for 3 hours for coupling.

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.3 μm, and the obtained product was stored at −70° C.

8. Preparation of ADC-VIII

A trastuzumab stock solution was diluted to 5 mg/mL with 50 mM disodium hydrogen phosphate-citric acid/150 mM sodium chloride (NaCl)/1 mM diethylene triamine pentacetate acid (DTPA) reaction buffer solution with a pH of 7.4, and then 8× excess molar ratio of tris(2-carboxyethyl) phosphine hydrochloride (TCEP) was added thereto. The obtained reaction solution was stirred at 25° C. for 5 hours.

Subsequently, without being purified, the reaction solution was cooled down to 0° C. and an appropriate amount of dimethylformamide (DMF) and 6× excess molar ratio of compound F1-2 (10 mg/ml, pre-dissolved in DMF) were added thereto, and DMF in the reaction system was ensured to be no more than 8% by volume. The obtained reaction solution was stirred at 0° C. for 2 hours for coupling.

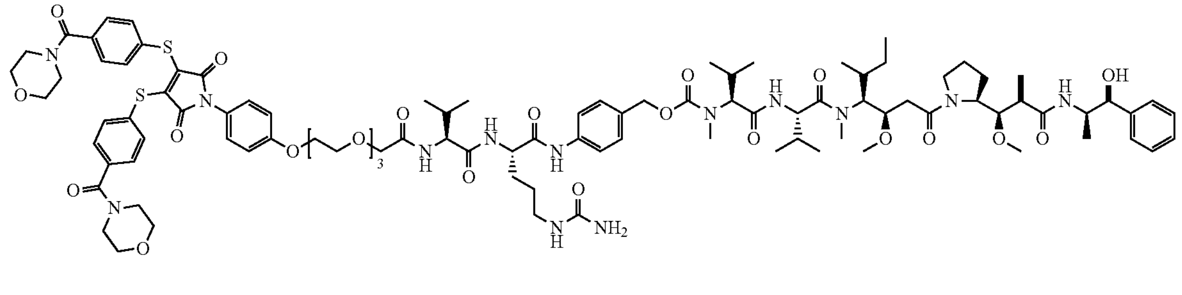

The reaction solution after coupling reaction was purified by filtration with a desalting column using histidine-acetic acid/sucrose gel (pH 6.0), and then sample at absorption peak was collected according to UV280 ultraviolet absorption value. The collected sample was sterilized through a filtration device with a pore size of 0.3 μm, and the obtained product was stored at −80° C.

The Fourth Group of Examples: Detection and Stability Study of the Antibody Drug Conjugate By hydrophobic interaction chromatography (HIC) analysis on antibody conjugated drugs, important information such as the number and position of coupling sites and the drug to antibody ratio (DAR) can be obtained. In this regard, the inventors performed HIC analysis on the above ADC products based on the following conditions, and the obtained chromatograms were shown in FIGS. 11-1 to 11-8 and FIGS. 12-1 to 12-2.

Agilent 1290 Infinity

Chromatographic column: Waters Protein-Pak Hi Res HIC (4.6*100 mm, 2.5 μm)

Mobile phase: 2.5 M ammonium sulfate (containing 125 mM phosphate buffer): 125 mM phosphate buffer: isopropanol;

Flow rate: 0.7 mL/min, column temperature: 25° C.

In addition, LC-MS technology has been used to analyze structure and composition of ADCs, evaluate stability of the linkers in the ADCs, and analyze and determine relative proportions between components having different DARs. In this regard, the inventors performed LC-MS analysis on the above ADC products based on the following conditions, and the obtained chromatograms were shown in FIGS. 13-1 to 13-8 and FIGS. 14-1 to 14-2.

Instrument: Agilent 6520 Q-TOF

Chromatographic column: Polyhydroxyethyl-A (PHEA) (PolyLC, Columbia, Md.) 2.1 mm*200 mm; 5 μm particles with 300 Å pores Mobile phase: 200 mM ammonium acetate Flow rate: 0.1 mL/min:

Column temperature: 25° C.

The maleamide-based disulfide bond bridging has a better stability, which is less prone to sulfhydryl-ether exchange in the body. In order to further prove that the introduction of a substituent to Ar' can greatly slow down the secondary hydrolysis reaction occurred after the ring of the maleamide is opened, and also enhance the stability of the antibody-drug conjugate compared to the unsubstituted phenyl, the inventors had prepared a control ADC in this experiment. The control ADC was obtained by coupling pertuzumab and a compound in which Ar' is just a 1,4-substituted phenyl (as shown in following formula) through the same coupling method as that for preparing ADC-I.

Antibody drug conjugates ADC-1, ADC-II and ADC-VII were selected to compare with the control ADC. Specifically, ADC samples which had the same antibody concentration and were stored in buffers, were placed at 25° C. and then sampled on day 0, 2, 4, and 7 respectively.

Figure 15:
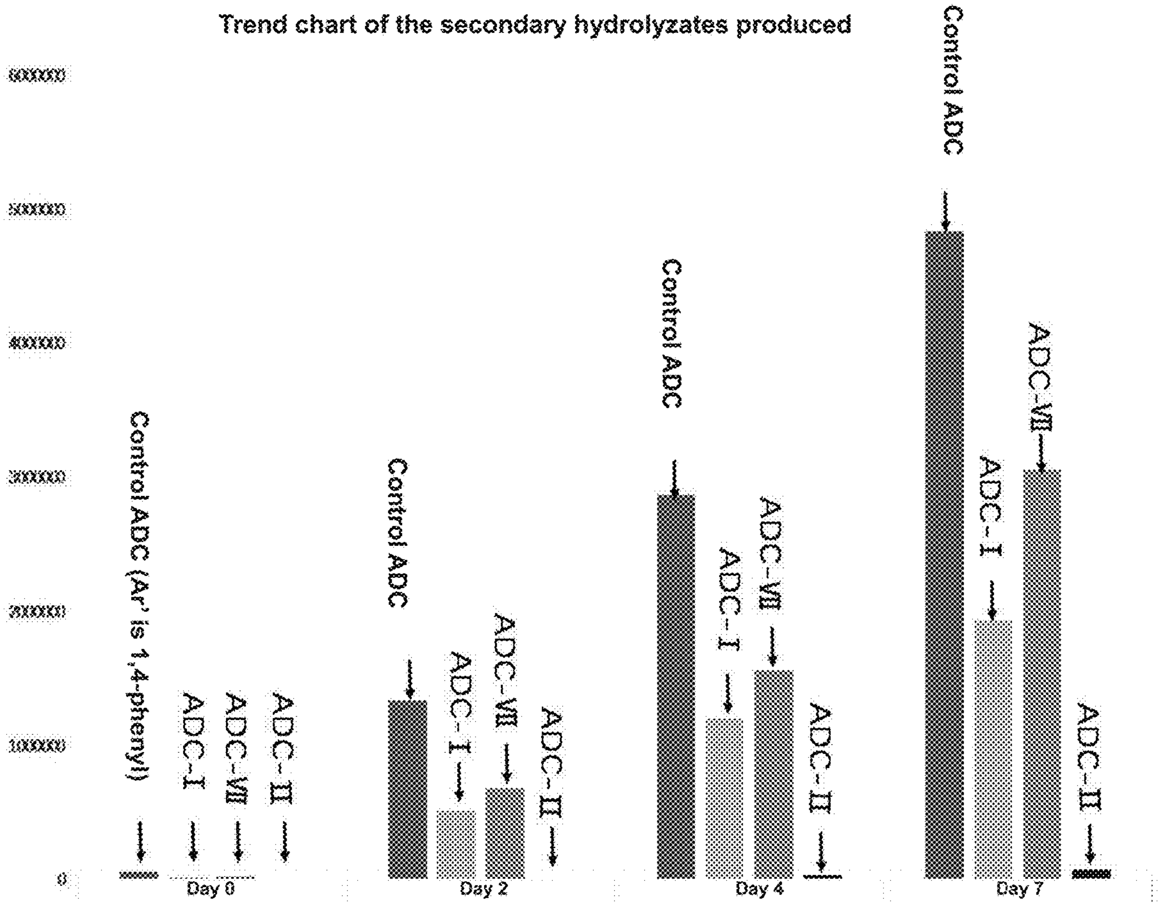
FIG. 15 shows a trend chart of secondary hydrolyzates produced by ADC control, ADC-I, ADC-II, and ADC-VII, which are detected using LC-MS (Q-TOF) at day 0-7 at room temperature.

Corresponding amount of secondary hydrolyzate formed in each antibody drug conjugate (ADC) sample was determined by LC-MS (Q-TOF), and characteristic peak in mass spectrum of the secondary hydrolyzate was extracted and the peak area was calculated. Changing trend in the amounts of the secondary hydrolyzates in each ADC sample were obtained by comparing the change in the peak areas from day 0 to 7, and see the following data and FIG. 15 for details. From the following data it can be seen that the amounts of the secondary hydrolyzates formed in the control ADC sample are significantly higher than those formed in the ADC-I, ADC-II, and ADC-VII samples.

| Days | Control ADC | ADC-I | ADC-VII | ADC-II |
|---|---|---|---|---|
| Day 0 | 61779.22 | 12978.85 | 24559.1 | 0 |
| Day 2 | 1335141 | 513786.8 | 679699.3 | 11842.82 |
| Day 4 | 2876314 | 1204614 | 1561592 | 34018.8 |
| Day 7 | 4835396 | 1933476 | 3061651 | 79192.73 |

Figures 1, 16:
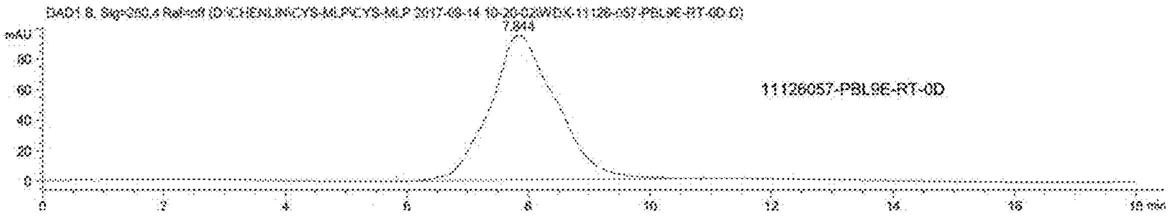
Figures 2, 16:
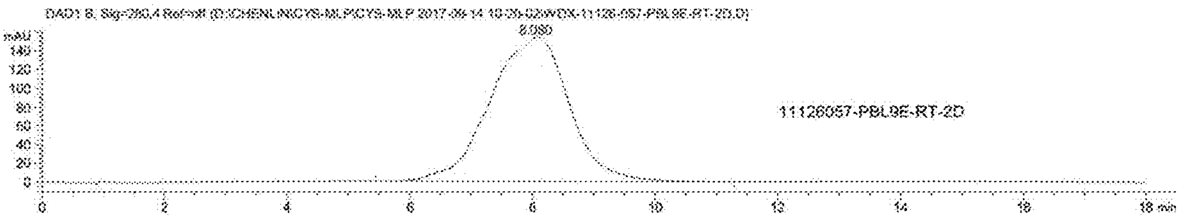
Figures 3, 16:
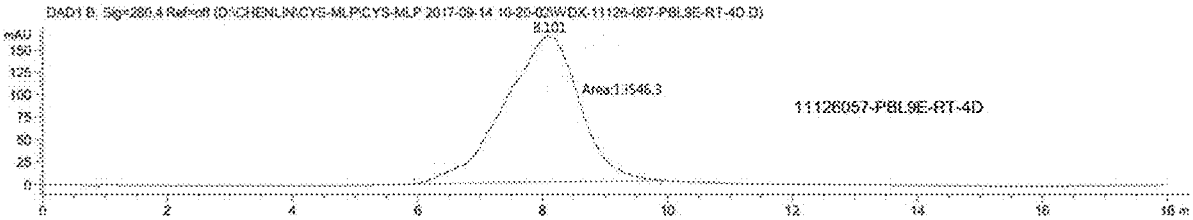
Figures 4, 16:
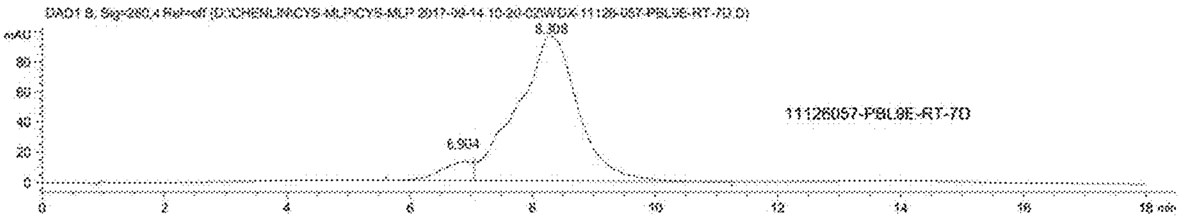
Figures 1, 17:
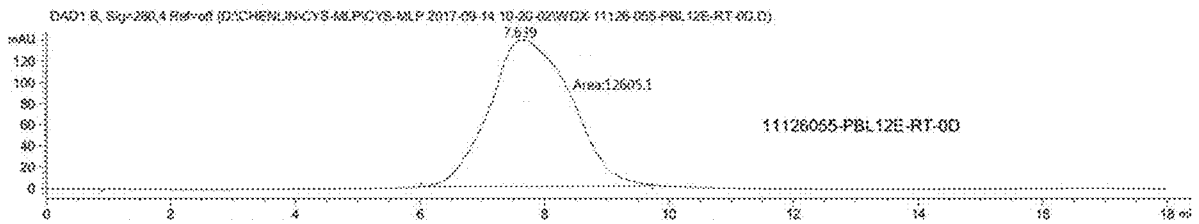
Figures 2, 17:
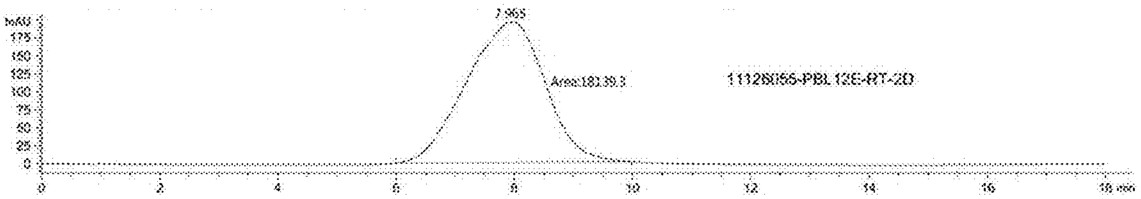
Figures 3, 17:
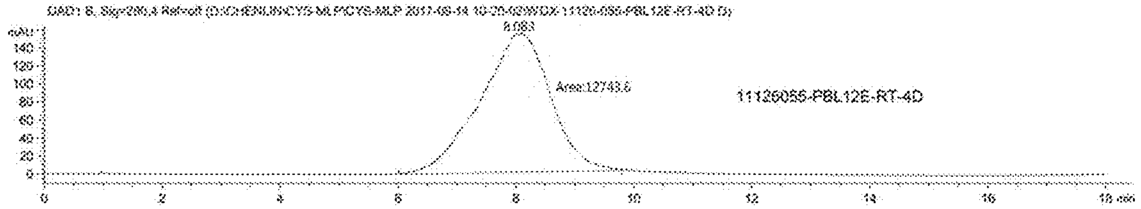
Figures 4, 17:
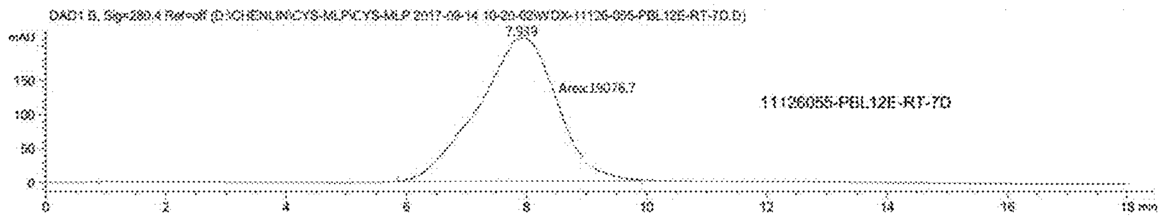
Figures 1, 18:
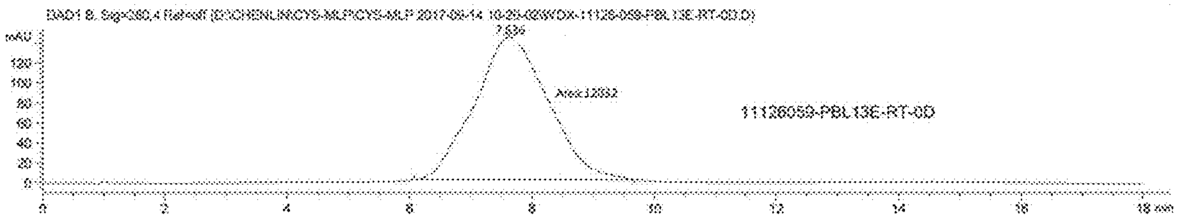
Figures 2, 18:
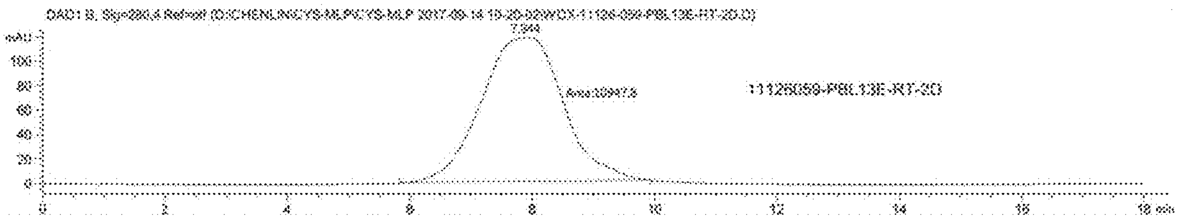
Figures 3, 18:
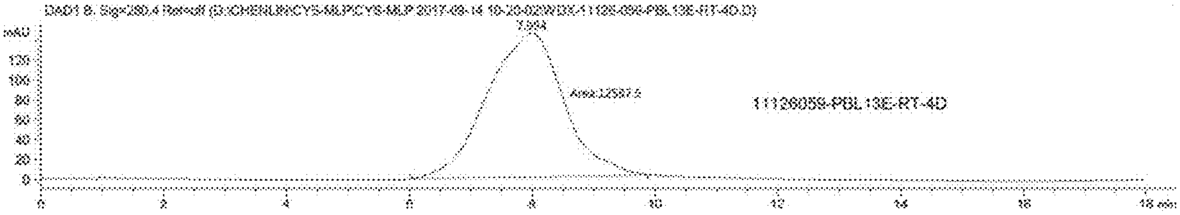
Figures 4, 18:
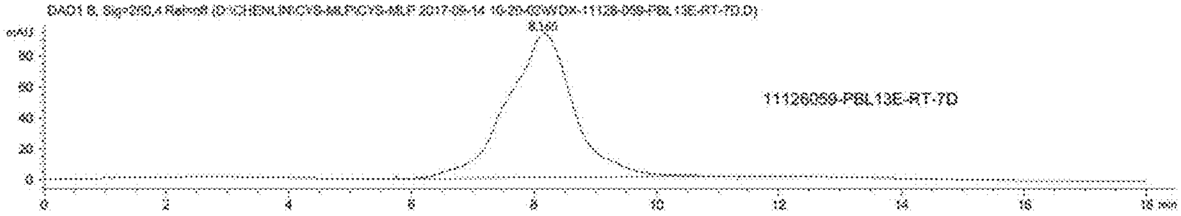
Figures 1, 19:
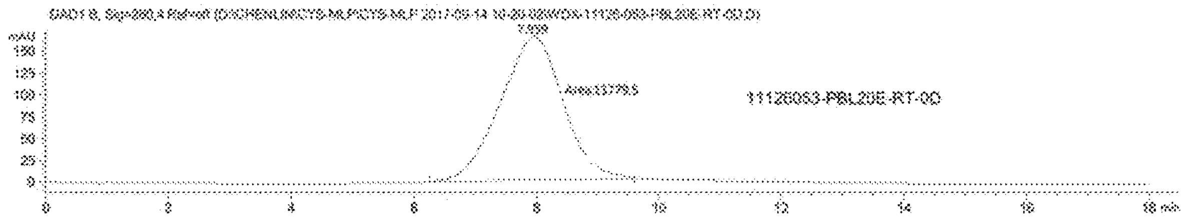
Figures 2, 19:
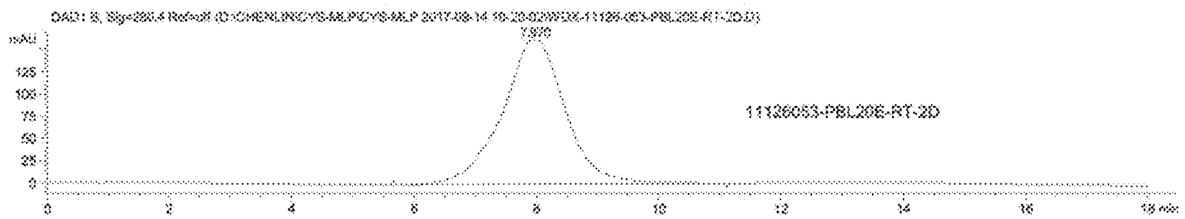
Figures 3, 19:
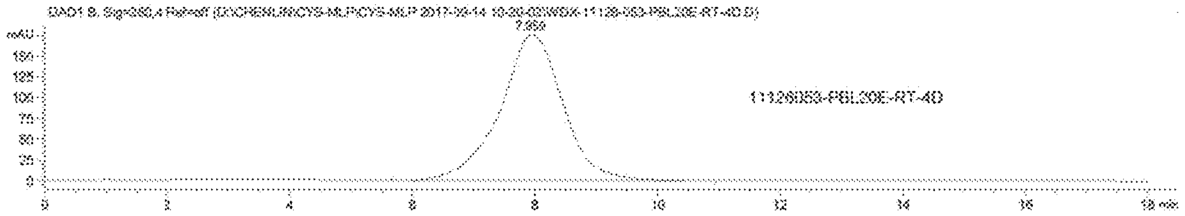
Figures 4, 19:
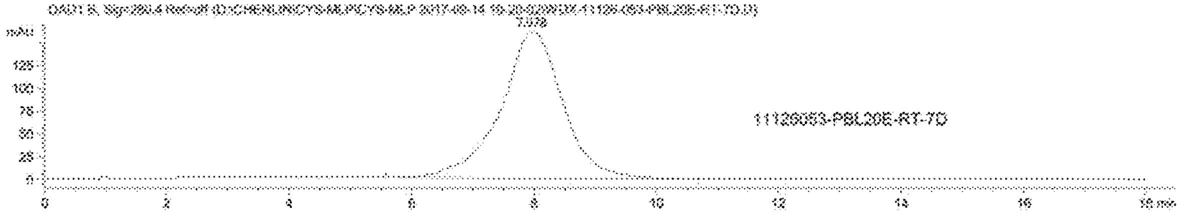
Figure 20:
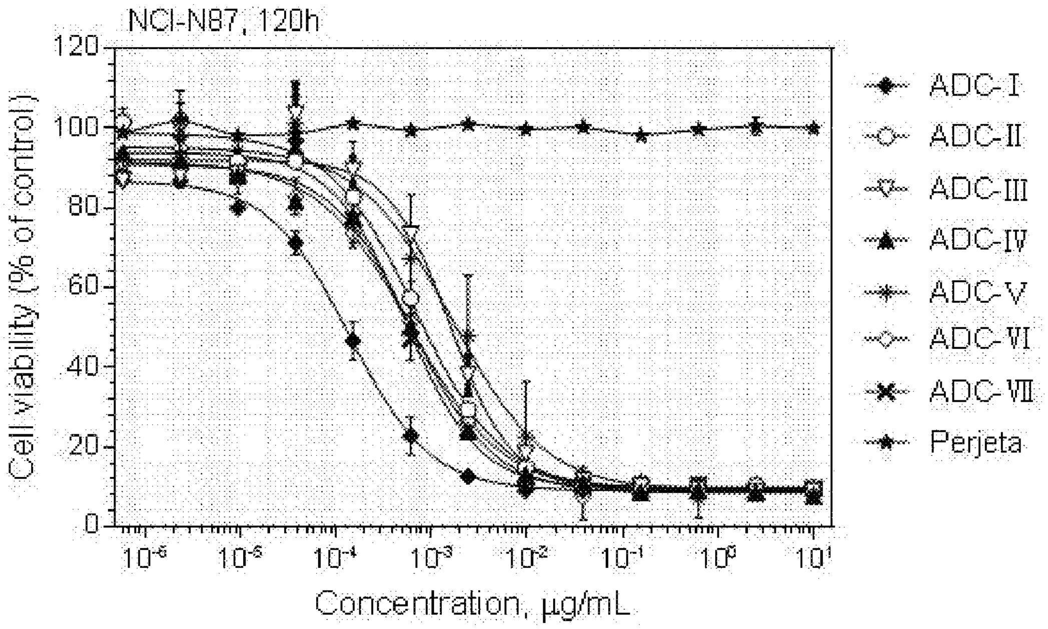
FIG. 20 shows experiment results of proliferation inhibition of ADC-I, ADC-II, ADC-III, ADC-IV, ADC-V, ADC-VI, ADC-VII and Pertuzumab (Perjeta) on human gastric cancer cells NIC-N87.
Figure 21:
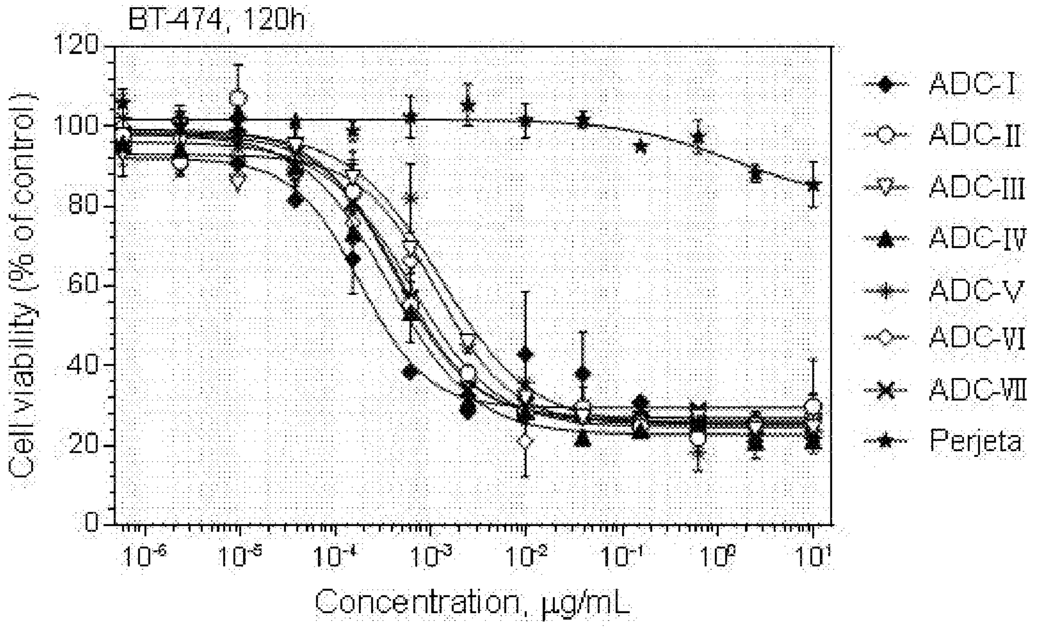
FIG. 21 shows experiment results of proliferation inhibition of ADC-I, ADC-II, ADC-III, ADC-IV, ADC-V, ADC-VI, ADC-VII and Pertuzumab (Perjeta) on human breast cancer cells BT-474.
Figure 22:
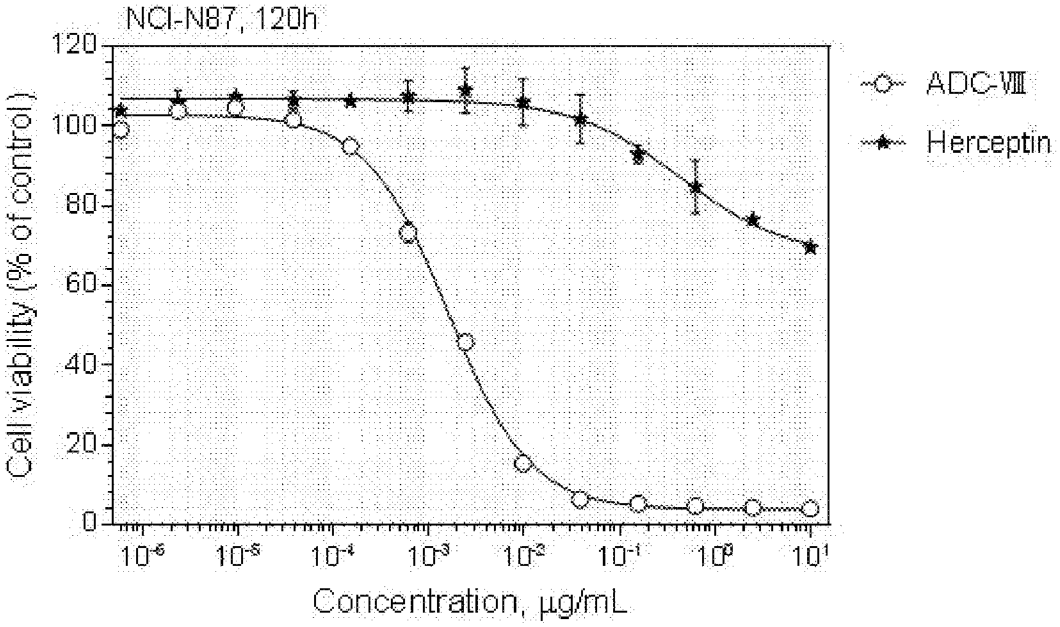
FIG. 22 shows experiment results of proliferation inhibition of ADC-VIII and Trastuzumab (Herceptin) on human gastric cancer cells NIC-N87.
Figure 23:
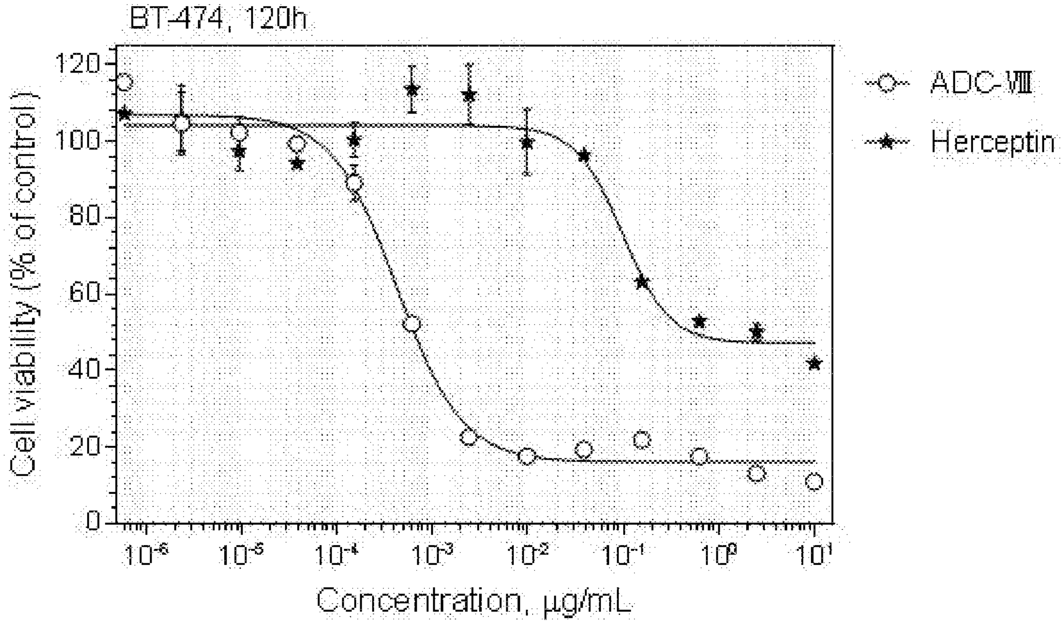
FIG. 23 shows experiment results of proliferation inhibition of ADC-VIII and Trastuzumab (Herceptin) on human breast cancer cells BT-474.

In addition, the changes of each ADC sample on day 0, 2, 4, and 7 were also determined by HIC. As can be seen from FIGS. 16-1 to 16-4, in the chromatogram of the control ADC sampled on day 7, an impurity peak appeared at the position where the retention time was 6.904. However, as shown in FIGS. 17-1 to 17-4, FIGS. 18-1 to 18-4, and FIGS. 19-1 to 19-4, the chromatograms of the ADC-I, ADC-II, and ADC-VII samples that sampled from day 0 to 7 showed no substantial changes.

The Fifth Group of Examples: Biological Detections of the Antibody Drug Conjugate 1. Biological Activity Assay of Cell Proliferation In Vitro Experimental materials used in the following experiment: DMEM, DMEM/F12K, RPMI 1640 medium, 0.25% trypsin-EDTA, fetal bovine serum, 100× sodium pyruvate and 100× penicillin-streptomycin were purchased from Gibco; sulforhodamine B (SRB) was purchased from Sigma; and NCI-N87 human gastric cancer cells and BT-474 human breast cancer cells were purchased from Kunming Cell Bank of Chinese Academy of Sciences. All other reagents used were analytical grade. 96-well Flat Bottom Polystyrene (Corning, catalog No. 3599) and Synergy 2 Microplate Reader (Bio-Tek) were used.

In this Example, effects of ADC-I, ADC-II, ADC-III, ADC-IV, ADC-V, ADC-VI, ADC-VII and ADC-VIII on the proliferation of tumor cell lines were investigated.

Sulforhodamine B (SRB)-based colorimetric method was used in this Example to evaluate the anti-proliferative effect of the drugs. SRB is a pink anionic dye which is easily soluble in water and can specifically bind to basic amino acids of proteins in cells under an acidic condition. It provides an absorption peak at 510 nm, and the absorbance is linearly and positively correlated with the amount of cells. In this regard, the method can be used in a quantitative detection of cell number.

Cell lines used in this Example are: BT-474 human breast cancer cells and NCI-N87 human gastric cancer cells.

BT-474 and NCI-N87 cells in RPMI 1640 medium containing 10% fetal bovine serum were incubated to logarithmic growth phase in a 5% CO2 incubator at 37° C. The above cells in the logarithmic growth phase were inoculated into 96-well plates at a density of $2\times10^3$ to $9\times10^3$ cells per well, 100 μL per well, cultured for 24 hours and then different concentrations of drugs were added thereto for 5 days. Specifically, each drug was prepared into nine concentrations by diluting in 3, 4 or 5-fold, each concentration was set in duplicate wells, and corresponding concentration of vehicle control wells and control wells without cells were set too. At the end of drug action, culture solutions were decanted, and 100 μl of a pre-cooled trichloroacetic acid solution (30%, w/v) at 4° C. was added to each well and the cells were fixed at 4° C. for 1 hour. Subsequently, the cells were washed with deionized water for 5 times, and dried at room temperature, and then 100 μL of 0.4% (w/v) SRB dye (Sigma, prepared with 1% glacial acetic acid) was added per well. After being incubated and stained at room temperature for 30 minutes, the cells were washed with 1% glacial acetic acid for 4 times to remove unbound dyes, and then dried at room temperature. Afterwards, 100 μL of 10 mM Tris solution was added per well. After being incubated and stained at room temperature for 15 minutes, the cells was washed with 1% glacial acetic acid for 5 times to remove unbound SRB, and then dried at room temperature. Dyes bound to the proteins in cells were dissolved by addition of 10 mM Tris buffer (pH=10.5) per well, and the absorbance (OD value) was measured at wavelengths of 510 nm and 690 nm using Synergy 2 Microplate Reader (Bio-Tek). $A=OD_{510}-OD_{690}$.

$$\text{Inhibition rate } (\%)=(A_{control}-A_{drug})/A_{control}\times100\%$$

In this experiment, effects of ADC-I, ADC-II, ADC-III, ADC-IV, ADC-V, ADC-VI, ADC-VII, and ADC-VIII on the proliferation of various Her2 highly expressing tumor cell lines in vitro cultured were investigated. As shown in following Table, proliferation of Her2 highly expressing NCI-N87 human gastric cancer cells and BT-474 human breast cancer cells were significantly inhibited after being treated with ADC-I, ADC-II, ADC-III, ADC-IV, ADC-V, ADC-VI, ADC-VII, and ADC-VIII compared to that treated with naked antibodies Perjeta and Herceptin. Corresponding proliferation inhibition curves are shown in FIG. 20-23.

| | $IC_{50}$, μg/mL, 120 h | |
|---|---|---|
| Sample | NCI-N87 | BT-474 |
| Perjeta | >10 | >10 |
| Herceptin | 0.440 | 0.0986 |
| ADC-I | 0.000140 | 0.000183 |
| ADC-II | 0.000690 | 0.000469 |
| ADC-III | 0.001562 | 0.000905 |
| ADC-IV | 0.000623 | 0.000364 |
| ADC-V | 0.001645 | 0.001255 |
| ADC-VI | 0.000612 | 0.000607 |
| ADC-VII | 0.000534 | 0.000421 |
| ADC-VIII | 0.00159 | 0.000431 |

2. In Vivo Anti-Tumor Efficacy Assay

Efficacy of the conjugates of the present invention can be detected in vivo. In brief, an allograft or xenograft of cancer cells can be implanted into rodents and then the implanted tumors are treated with the conjugates. Tested mice can be administered drug treatment or control treatment, monitored for weeks or longer to observe tumor doubling time, log-killing, and tumor suppression.

1) Experimental Animals 6-7 weeks BALB/cA-nude mice (♀) were purchased from Shanghai Lingchang Biotechnology Co., Ltd. Production license number: SCXK (Shanghai) 2013-0018; animal certificate number: 2013001815683; and feeding environment: SPF level.

2) Experimental Steps

Those nude mice were subcutaneously inoculated with $6\times10^6$ human gastric cancer NCI-N87 cells, and after the tumors grew to 100-250 $mm^3$, the mice were divided into groups (D0) according to tumor volumes. The mice were injected intravenously (IV), each with an administration volume 10 mL/kg; mice in vehicle control group was administered with the same volume of "vehicle" (physiological saline containing 0.1% BSA). Doses and regimen of administration are provided in FIG. 24. Tumor volume was measured 2 times a week, the mice were weighed, and corresponding data were recorded.

The purpose of this experiment was to investigate the effect of the drugs on tumor growth using specific indicators T/C % or tumor growth inhibition value (TGI) (%).

Tumor diameters were measured twice a week with a vernier caliper. The tumor volume (V) was calculated as:

$$V=\tfrac{1}{2}\times a\times b^2;$$

in which a and b represent length and width respectively.

$$T/C(\%)=(T-T0)/(C-C0)\times100,$$

in which T and C represent the tumor volumes at the end of the experiment; T0 and C0 represent the tumor volumes at the beginning of the experiment.

The tumor growth inhibition value (TGI) (%)=100−T/C (%).

When tumor regresses, the tumor growth inhibition value (TGI) (%)=100−(T−−T0)/T0×100.

If the tumor had a smaller volume than it initially had, i.e. T<T0 or C<C0, it was defined partially regressed (PR); whereas if the tumor completely disappeared, it was defined completely regressed (CR).

When the experiment was finished (D21), when the end of the experiment was reached, or when the volume of a tumor reached 15000 $mm^3$, the corresponding mouse was sacrificed with carbon dioxide narcosis, and dissected, and the tumor was removed and photographed.

3) Experiment Results

Figure 24:
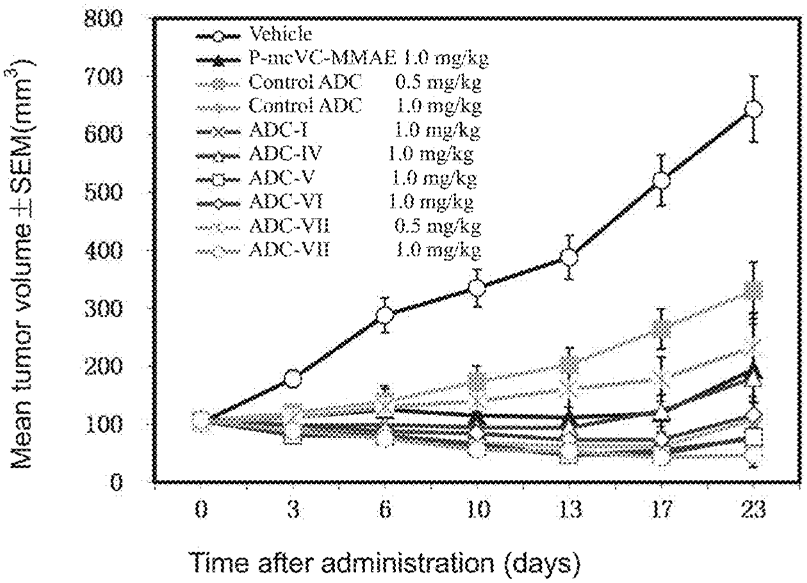
FIG. 24 shows results of study on inhibition activity of P-mcVC-MMAE (1.0 mg/kg), ADC control (0.5, 1.0 mg/kg), ADC-I (1.0 mg/kg), ADC-IV (1.0 mg/kg), ADC-V (1.0 mg/kg), ADC-VI (1.0 mg/kg) and ADC-VII (0.5, 1.0 mg/kg) on human gastric cancer NCI-N87 subcutaneous xenograft tumor in nude mice.

Efficacies of the drugs on the human gastric cancer NCI-N87 subcutaneous xenografts in nude mice were shown in the following Table and FIG. 24. What's more, those tumor-bearing mice had good tolerance to the drugs, and no symptom such as weight loss occurred.

| Group | | Administration | Route | Mean tumor volume (mm3) D 0 | SEM | Mean tumor volume (mm3) D 23 | SEM | % T/C D 23 | % TGI D 23 | p value D 23 | Partial regression | complete regression | number of mice per group at the beginning of the experiment | number of mice per group at the end of the experiment |
|---|---|---|---|---|---|---|---|---|---|---|---|---|---|---|
| vehicle control | | D 0 | IV | 102.3 | ±1.1 | 643.6 | ±57.1 | — | — | — | 0 | 0 | 12 | 12 |
| P-mcVC-MMAE | 1.0 mg/kg | D 0 | IV | 103.5 | ±3.1 | 194.6 | ±77.7 | 17 | 83 | 0.000 | 3 | 0 | 6 | 6 |
| Control ADC | 0.5 mg/kg | D 0 | IV | 105.4 | ±3.9 | 330.5 | ±48.5 | 42 | 58 | 0.003 | 0 | 0 | 6 | 6 |
| Control ADC | 1.0 mg/kg | D 0 | IV | 107.6 | ±4.6 | 107.8 | ±40.5 | 0 | 100 | 0.000 | 3 | 1 | 6 | 6 |
| ADC-I | 1.0 mg/kg | D 0 | IV | 103.6 | ±3.8 | 74.6 | ±32.8 | −28 | 128 | 0.000 | 3 | 2 | 6 | 6 |
| ADC-IV | 1.0 mg/kg | D 0 | IV | 109.5 | ±4.0 | 180.1 | ±42.6 | 13 | 87 | 0.000 | 1 | 0 | 6 | 6 |
| ADC-V | 1.0 mg/kg | D 0 | IV | 105.8 | ±1.0 | 78.7 | ±17.3 | −26 | 126 | 0.000 | 3 | 1 | 6 | 6 |
| ADC-VI | 1.0 mg/kg | D 0 | IV | 107.9 | ±3.7 | 116.0 | ±22.5 | 1 | 99 | 0.000 | 3 | 0 | 6 | 6 |
| ADC-VII | 0.5 mg/kg | D 0 | IV | 104.2 | ±2.2 | 233.2 | ±58.1 | 24 | 76 | 0.000 | 2 | 0 | 6 | 6 |
| ADC-VII | 1.0 mg/kg | D 0 | IV | 107.0 | ±3.6 | 46.8 | ±20.8 | −56 | 156 | 0.000 | 3 | 2 | 6 | 6 |

All the documents mentioned in the present invention are incorporated by reference in the present application, as if each document is incorporated by reference alone. In addition, it should be understood that after reading the above-mentioned teachings of the present invention, those skilled in the art would be able to make various modifications or amendments to the present invention, and these equivalents likewise fall within the scope defined by the appended claims of the present application.

What is claimed is:

1. A substituted maleamide linker as shown in Formula Ia, (Ia)

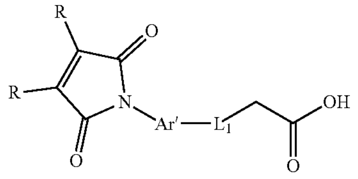

wherein, R is X or ArS-,

X is selected from halogen;

Ar is selected from the group consisting of substituted or unsubstituted $C_6$-$C_{10}$ aryl and substituted or unsubstituted 5-12 membered heteroaryl;

Ar' is selected from the group consisting of substituted or unsubstituted $C_6$-$C_{10}$ arylene, and substituted or unsubstituted 5-12 membered heteroarylene; and $L_1$ is —$O(CH_2CH_2O)_n$— linked to Ar', in which n is any integer between 1 and 20.

2. The substituted maleamide linker according to claim 1, wherein

Ar is selected from the group consisting of phenyl, halogen-substituted phenyl, $C_1$-$C_4$ alkylphenyl, $C_1$-$C_4$ alkoxyphenyl, 4-methylphenyl, 4-methoxyphenyl, 2-pyridyl, 2-pyrimidinyl, 1-methylimidazol-2-yl, and

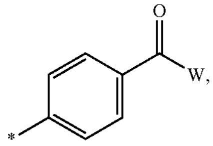

in which W is amido $R^1$ attached to carbonyl, and $R^1$ is selected from the group consisting of —$NH_2$,

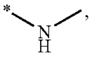, 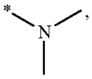, 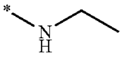,

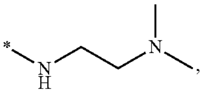, 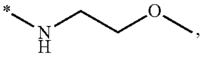,

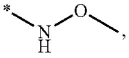, 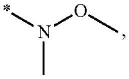, 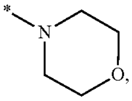

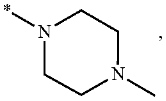, and 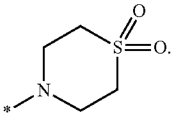

3. The substituted maleamide linker according to claim 1, wherein Ar' is selected from substituted phenylene and pyridyl, and the substitution means that hydrogen atom on the group is substituted by one or more substituents selected from the group consisting of: halogen, $C_1$-$C_4$ alkyl, $C_1$-$C_4$ alkoxy, trifluoromethyl, cyano, and amide group.

4. The substituted maleamide linker according to claim 1, wherein the linker has a structure selected from the group consisting of:

Formula 1
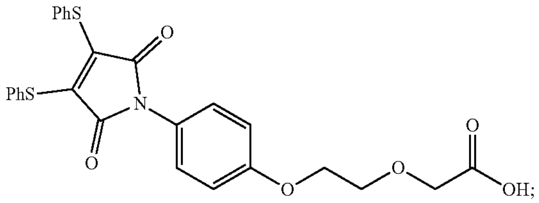
Formula 2
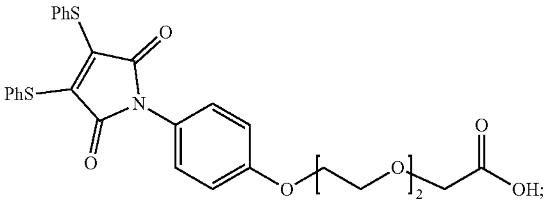
Formula 3
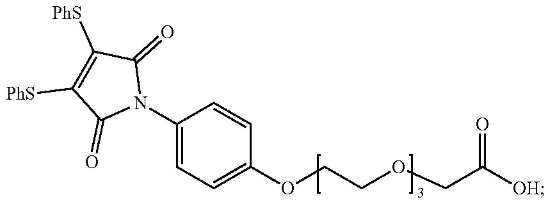
Formula 4
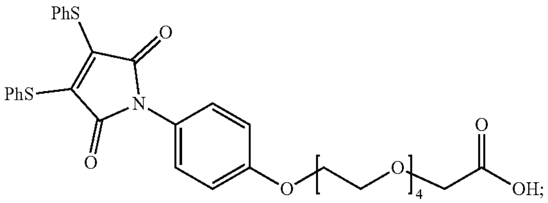
Formula 5
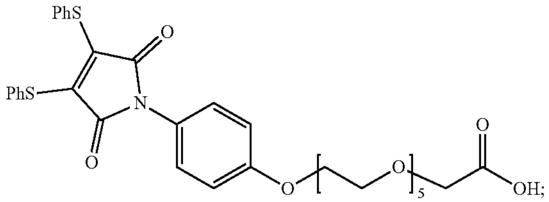
Formula 6
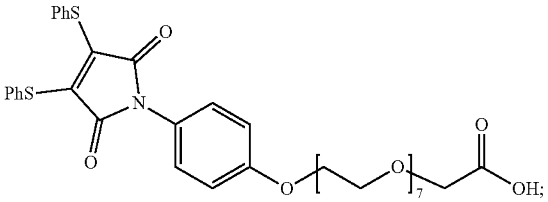
Formula 7
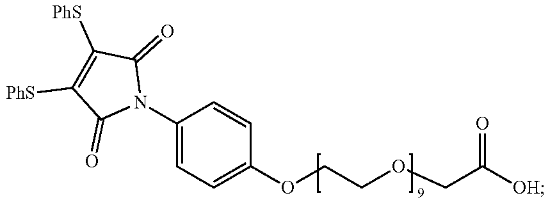
Formula 8
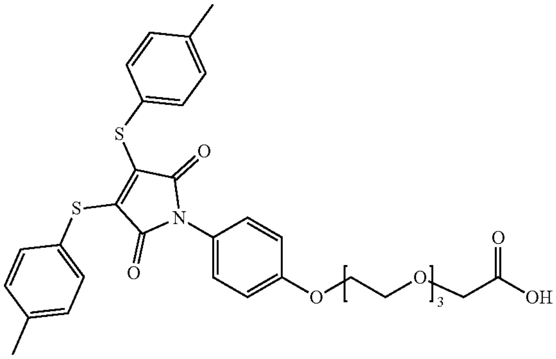
;
Formula 9
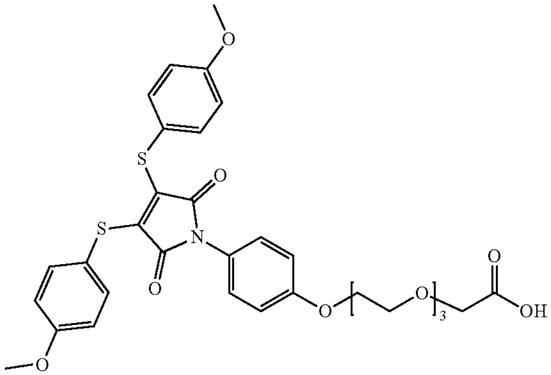
;
Formula 10
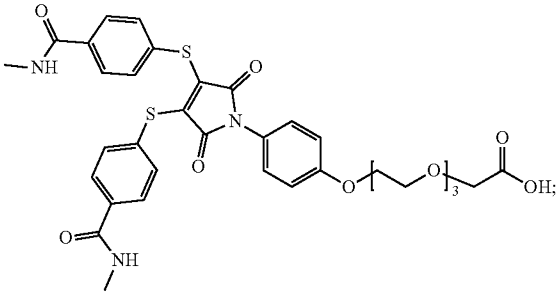

-continued
Formula 11
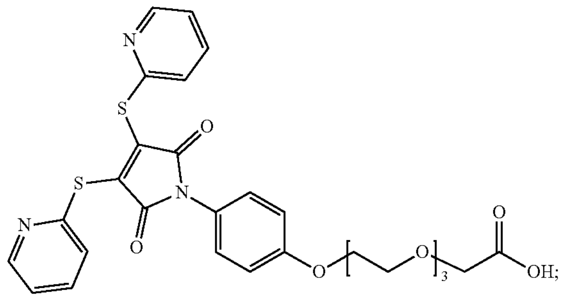
Formula 12
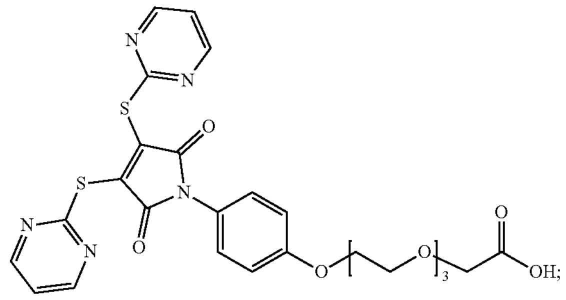
Formula 13
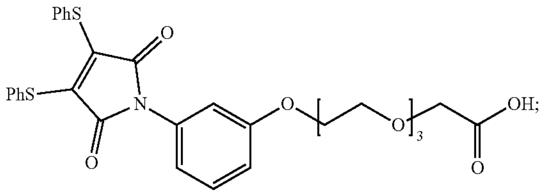
Formula 14
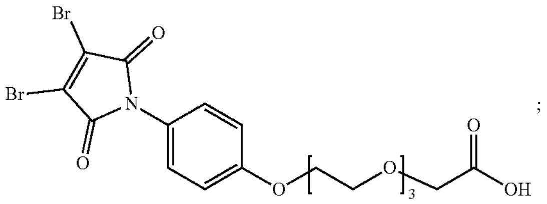
Formula 15
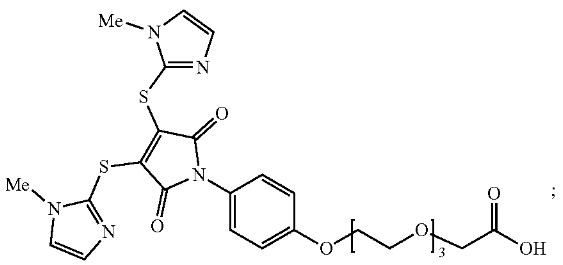
Formula 16
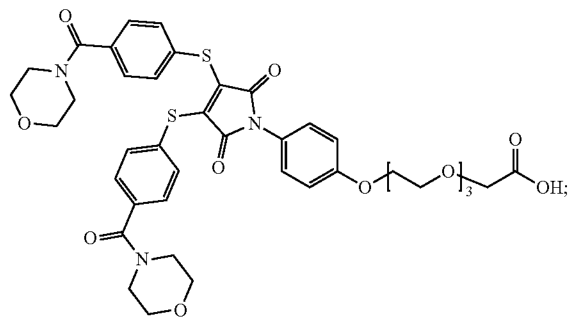
Formula 17
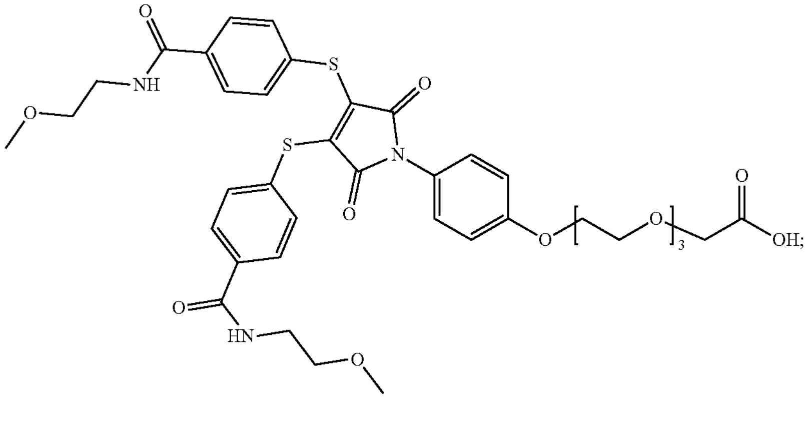

-continued
Formula 18
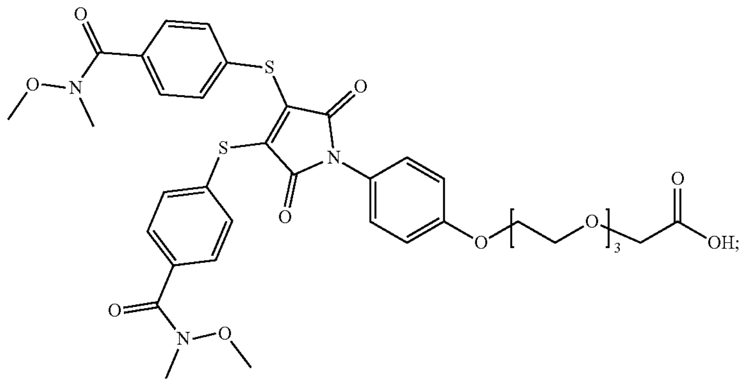
Ia-1
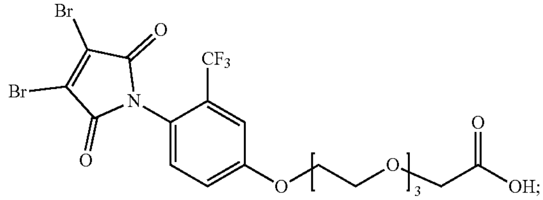
Ia-2
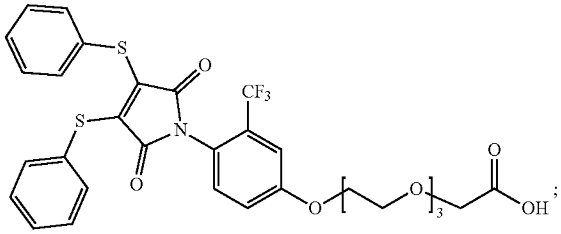
Ia-3
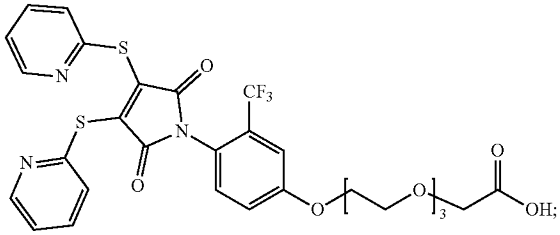
Ia-4
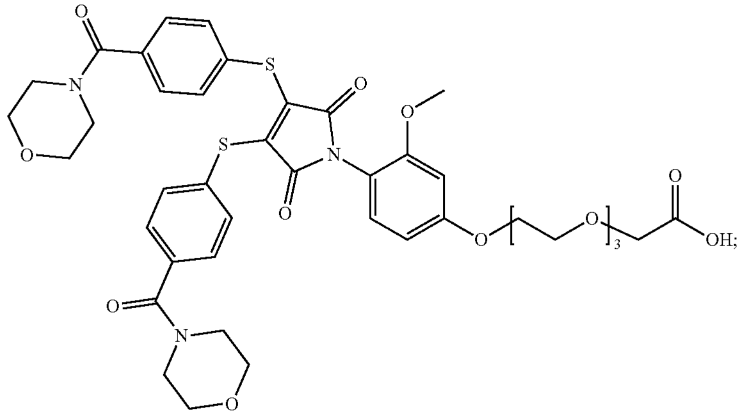

-continued
Ia-5
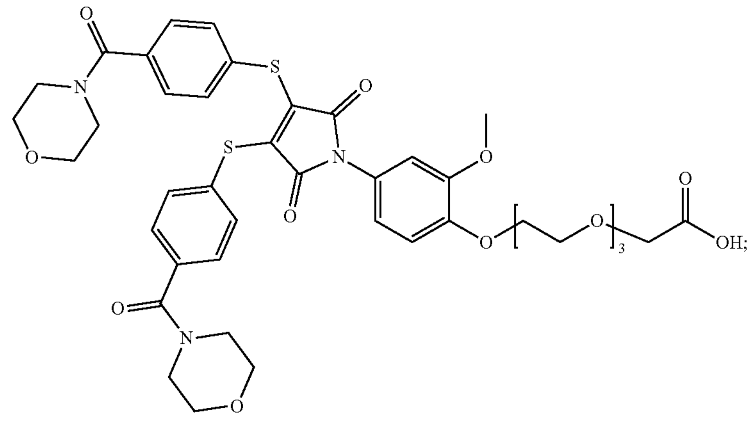
Ia-6
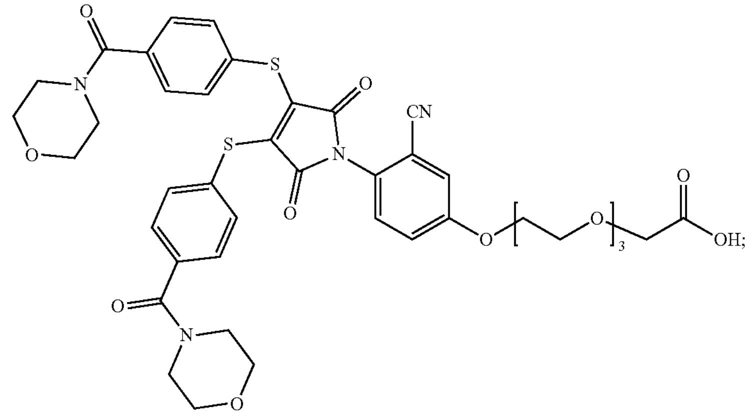
Ia-7
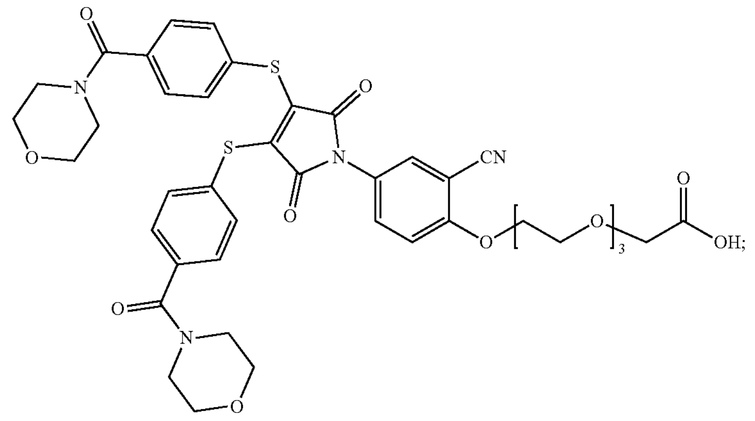

-continued
Ia-8
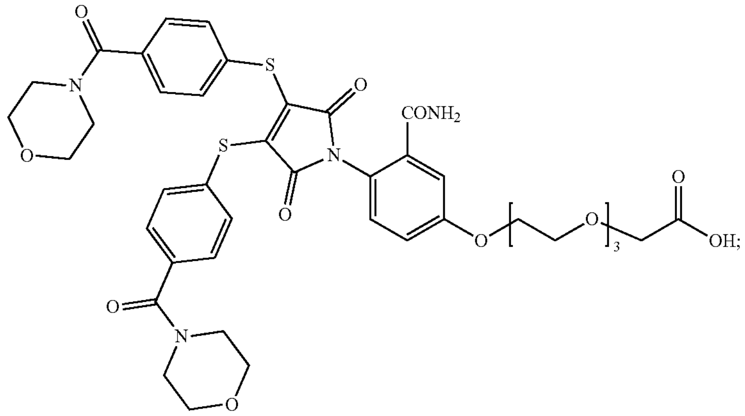
Ia-9
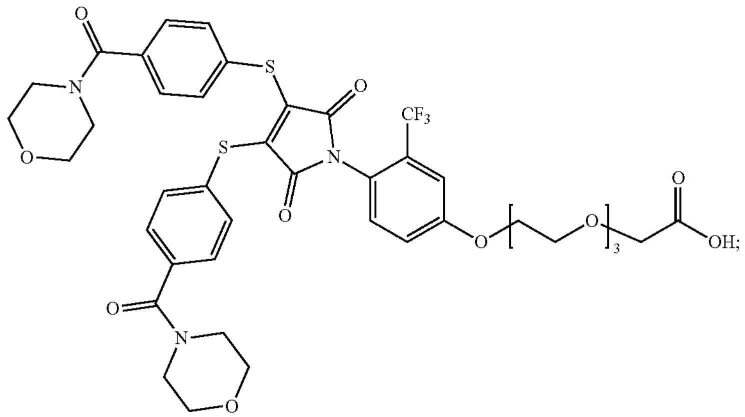
Ia-10
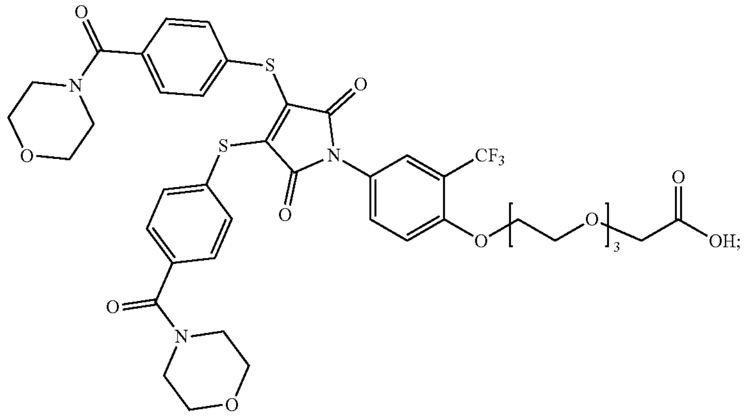

-continued
Ia-11
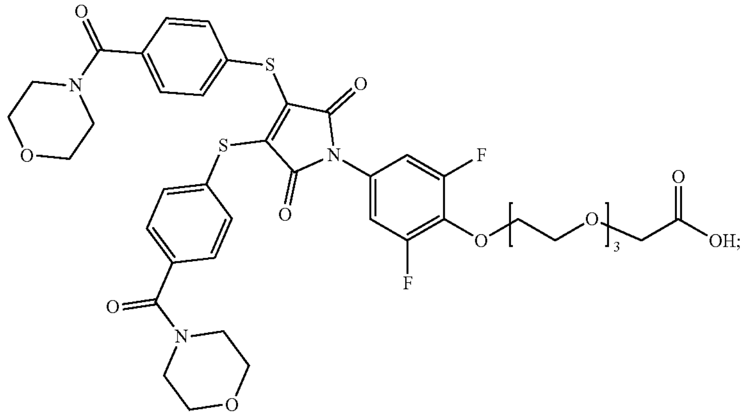
Ia-12
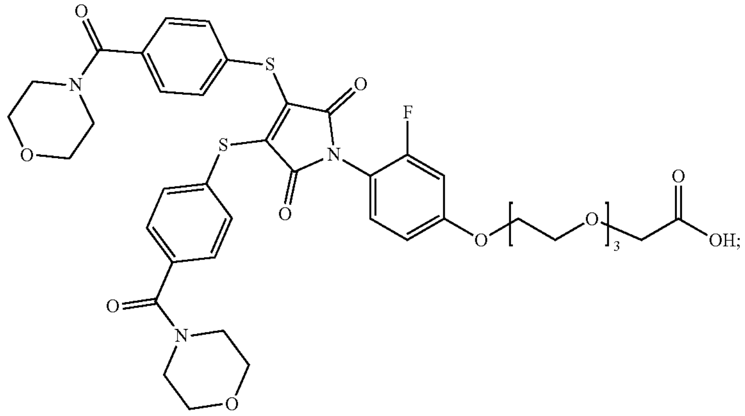
Ia-13
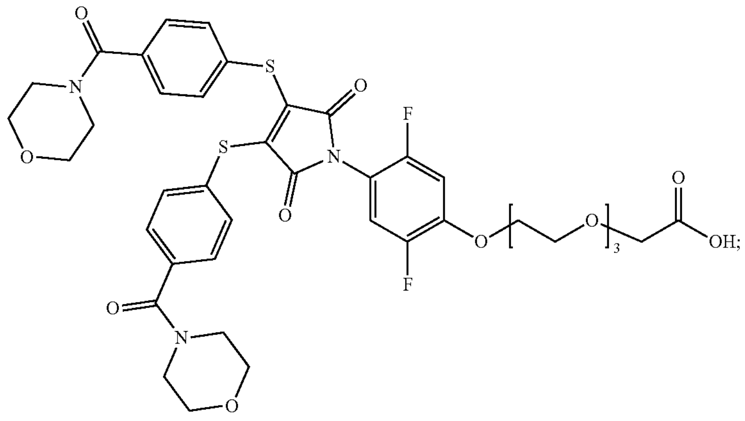

-continued
Ia-14
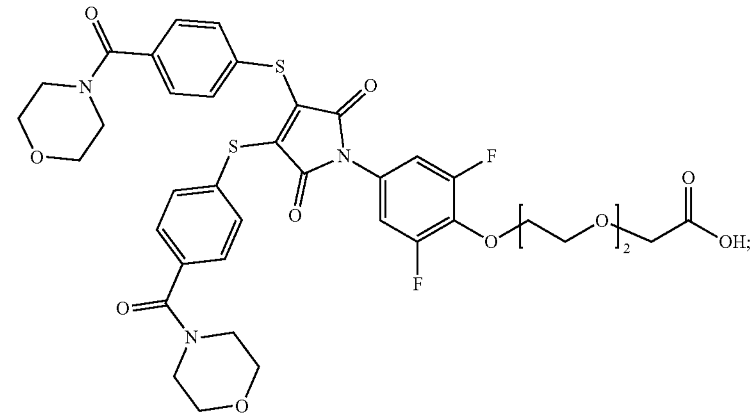
Ia-15
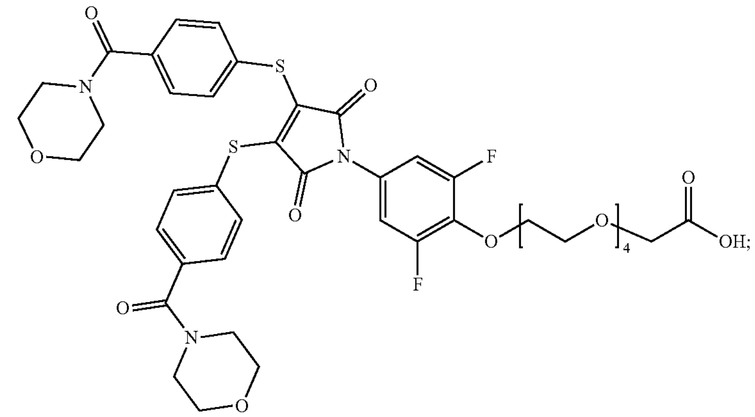
Ia-16
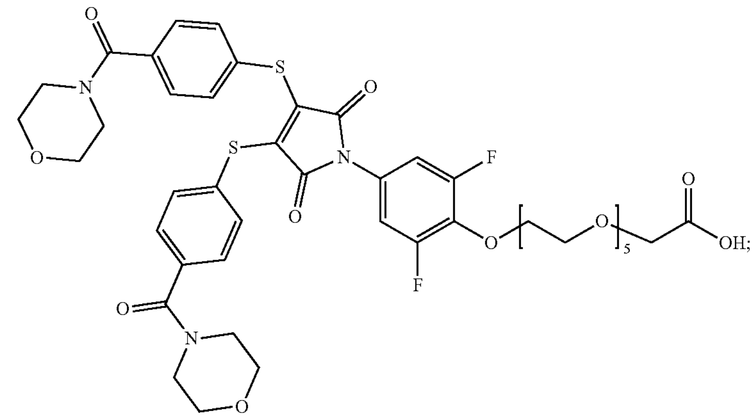

-continued
Ia-17
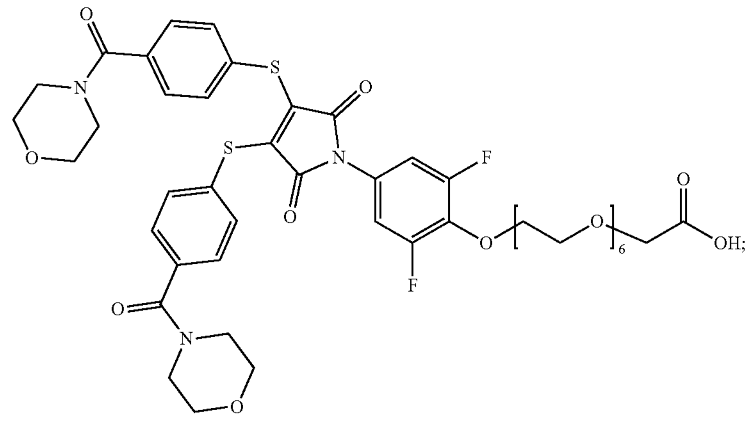
Ia-18
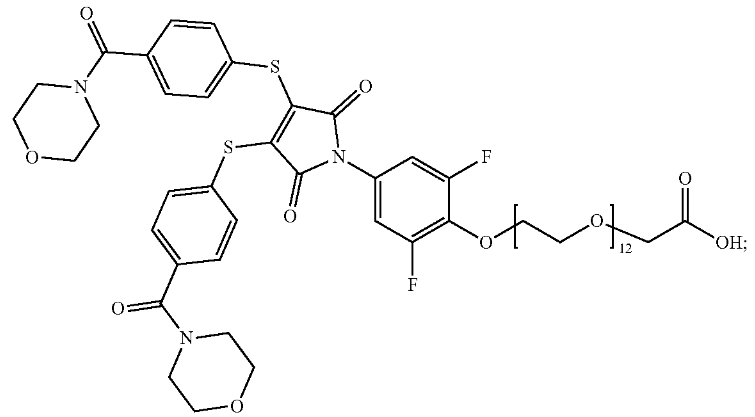
Ia-19
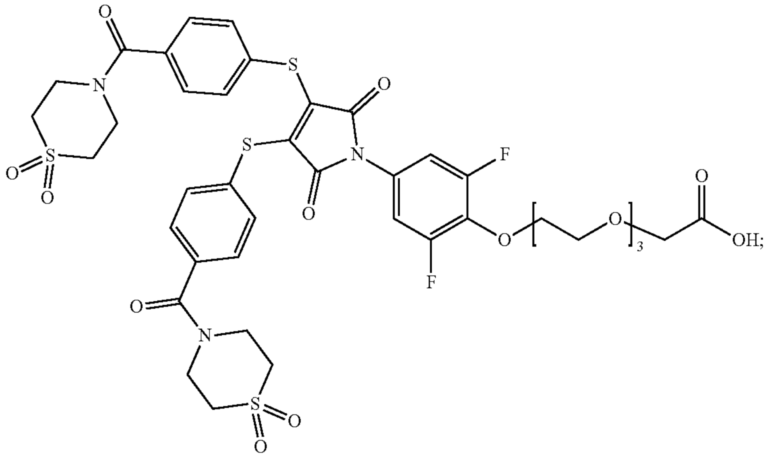

-continued

Ia-20

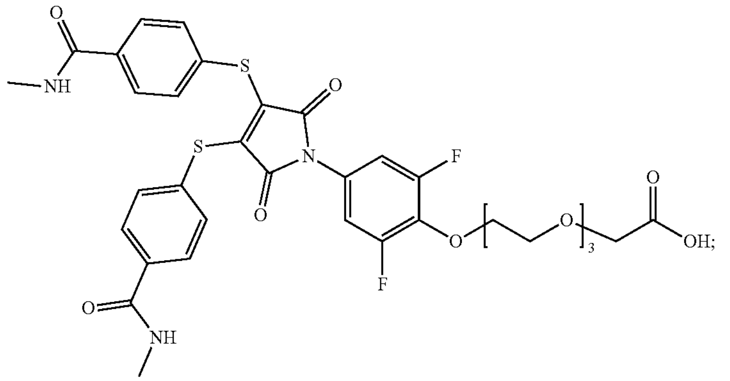

Ia-21

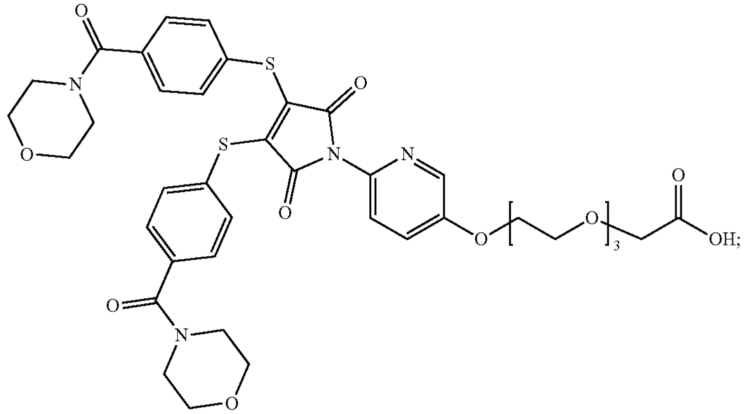

and

Ia-22

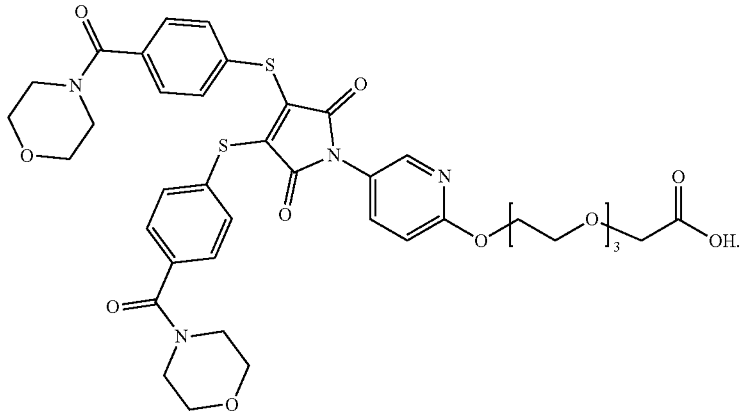

5. A substituted maleamide linker-drug conjugate, a pharmaceutically acceptable salt or solvate thereof, the conjugate having a structure as shown in Formula Ib:

(Ib)

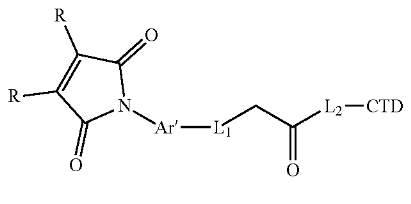

wherein R is X or ArS-;

X is selected from halogen;

Ar is selected from the group consisting of substituted or unsubstituted $C_6$-$C_{10}$ aryl and substituted or unsubstituted 5-12 membered heteroaryl;

Ar' is selected from the group consisting of substituted or unsubstituted $C_6$-$C_{10}$ arylene, and substituted or unsubstituted 5-12 membered heteroarylene;

$L_1$ is —$O(CH_2CH_2O)_n$— linked to Ar', in which n is any integer between 1 and 20;

$L_2$ is a chemical bond or has a structure of AA-PAB, in which AA is a dipeptide or tripeptide fragment, and PAB is p-aminobenzylcarbamoyl; and CTD is a cytotoxic small molecule drug and/or a drug for treating autoimmune disease and/or inflammation, which is bonded to $L_2$ via an amide bond.

6. The substituted maleamide linker-drug conjugate, a pharmaceutically acceptable salt or solvate thereof according to claim 5, wherein AA is selected from the group consisting of Val-Cit, Val-Ala, Phe-Lys, Ala-Ala-Asn, and D-Ala-Phe-Lys.

7. The substituted maleamide linker-drug conjugate, a pharmaceutically acceptable salt or solvate thereof according to claim 5, wherein the CTD is selected from the group consisting of tubulin inhibitor, topoisomerase inhibitor and DNA binding agent.

8. The substituted maleamide linker-drug conjugate, a pharmaceutically acceptable salt or solvate thereof according to claim 7, wherein the tubulin inhibitor is selected from the group consisting of maytansine or its derivatives, Monomethyl auristatin E, Monomethylauristatin F, Monomethyl Dolastatin 10, Tubulysin or its derivatives, Cryptophycin or its derivatives, and Taltobulin.

9. The substituted maleamide linker-drug conjugate, a pharmaceutically acceptable salt or solvate thereof according to claim 7, wherein the DNA binding agent is selected from the group consisting of PBD or its derivatives and duocarmycin or its derivatives.

10. The substituted maleamide linker-drug conjugate, a pharmaceutically acceptable salt or solvate thereof according to claim 7, wherein the topoisomerase inhibitor is selected from the group consisting of metabolite PNU-159682 of Doxorubicin or its derivatives, metabolite SN38 of irinotecan or its derivatives, and Exatecan.

11. The substituted maleamide linker-drug conjugate, a pharmaceutically acceptable salt or solvate thereof according to claim 5, wherein the CTD has a structure selected from the group consisting of D1-D13':

D1

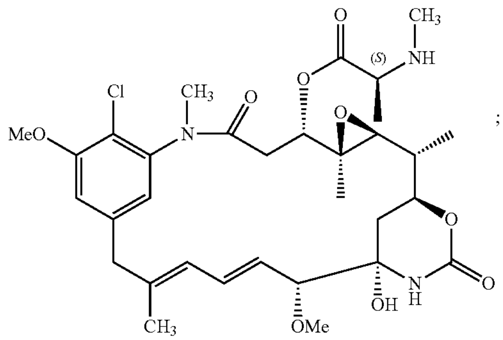

;

D2

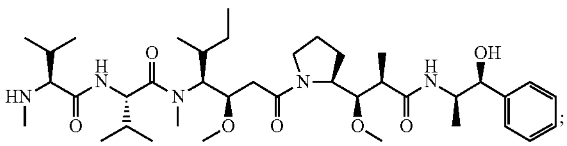

;

D3

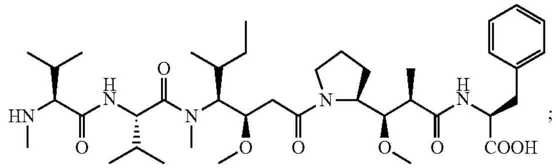

;

D4

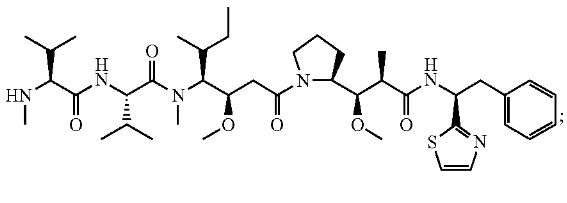

;

D5

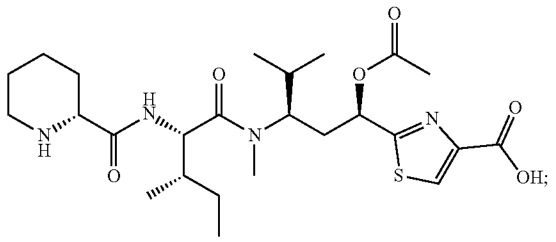

;

D6

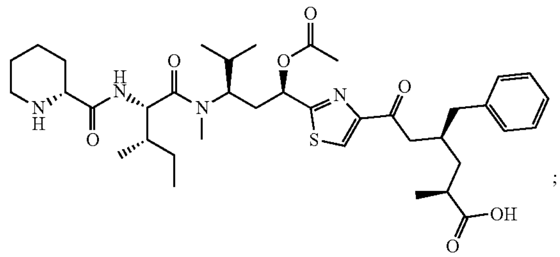

;

D7

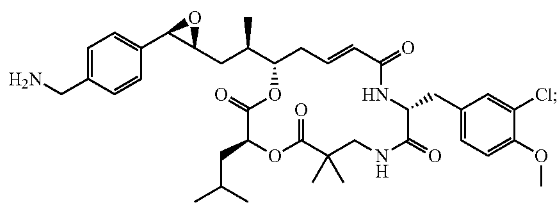

;

D8

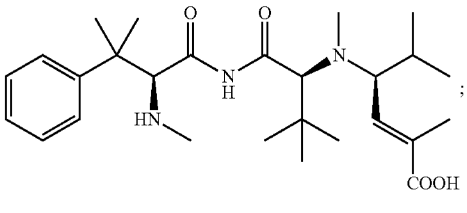

;

-continued
D9
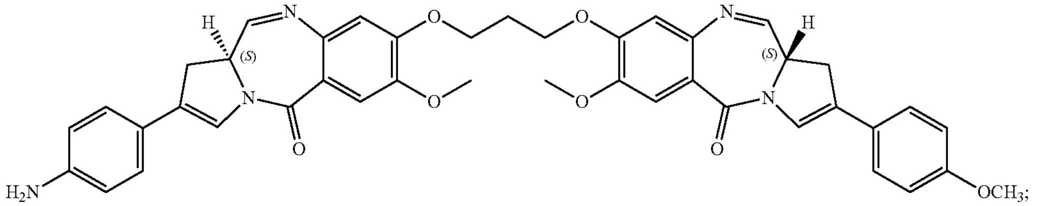
D10
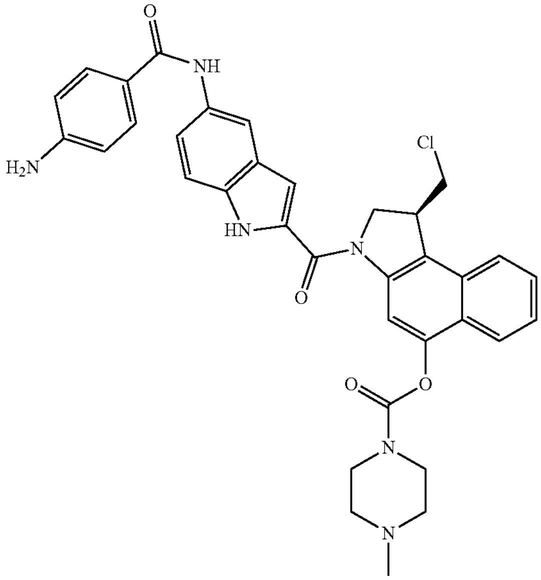
;
D11
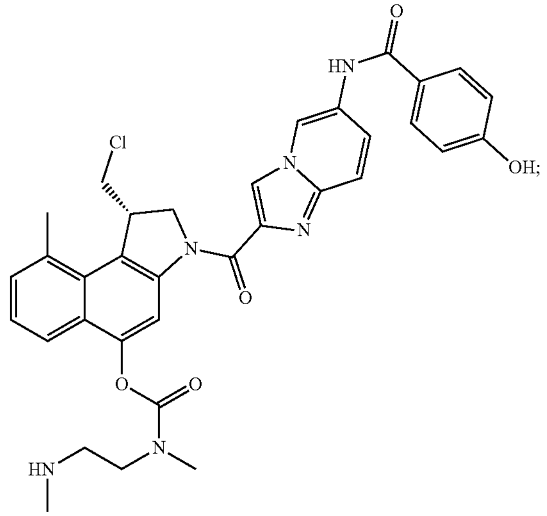
D12
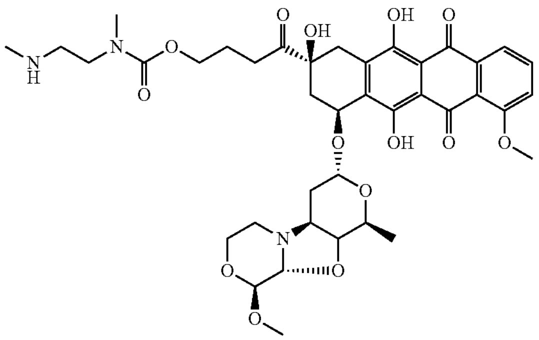
;
D13
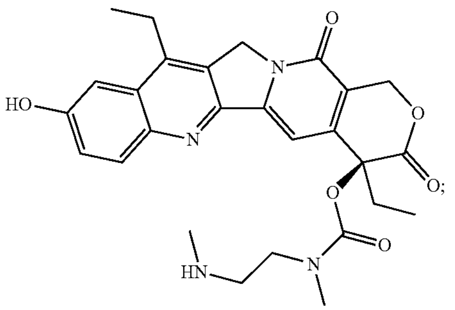
and
D13′
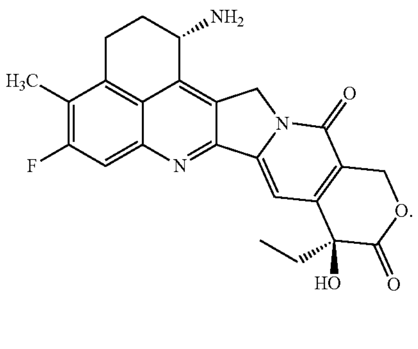

12. The substituted maleamide linker-drug conjugate, a pharmaceutically acceptable salt or solvate thereof according to claim 5, wherein the conjugate as shown in Formula Ib is selected from the group consisting of:
Formula 19
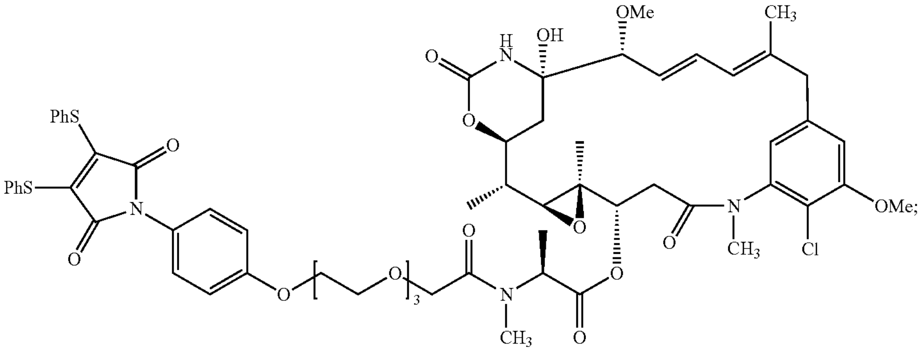
Formula 20
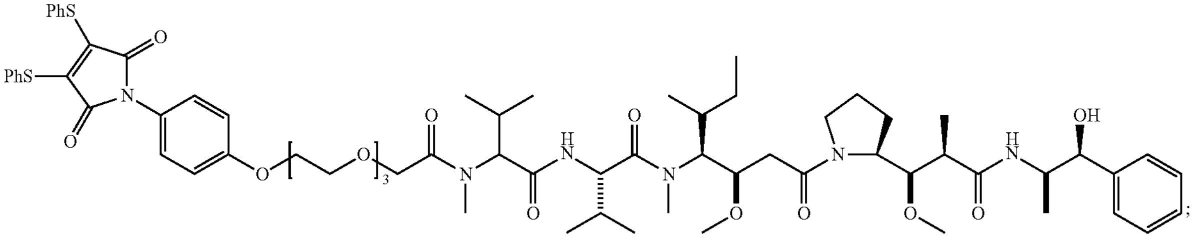
Formula 21
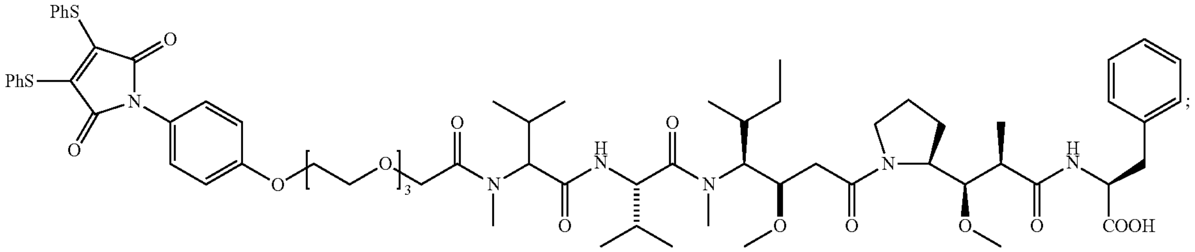
Formula 22
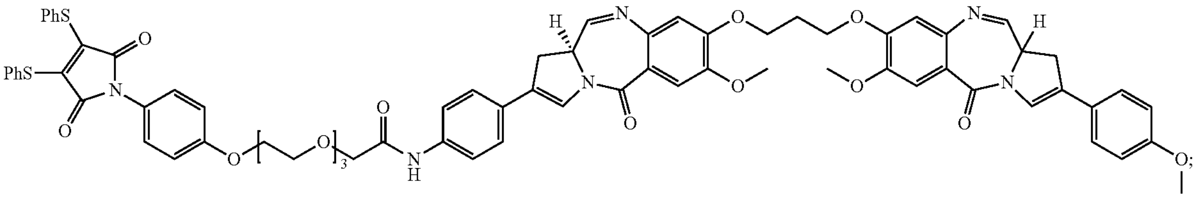
Formula 23
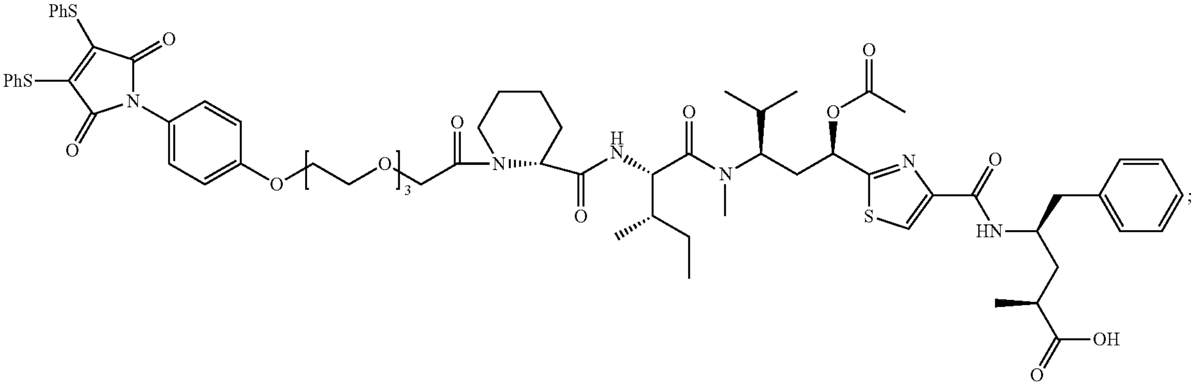

-continued
Formula 24
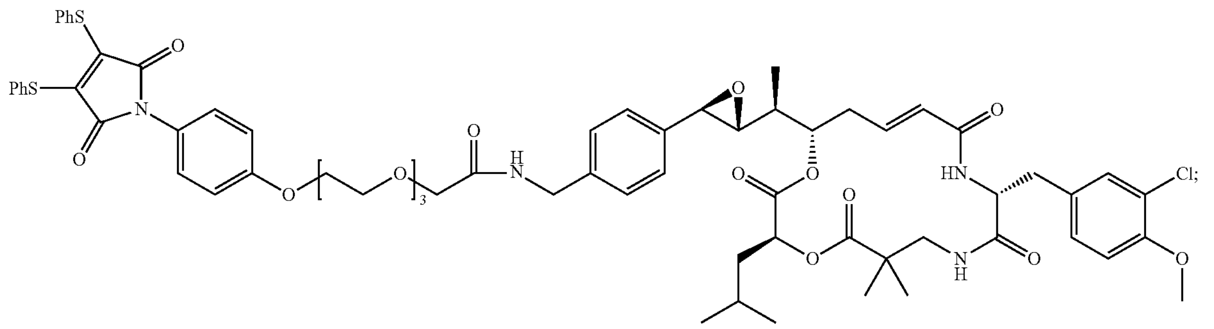
Formula 25
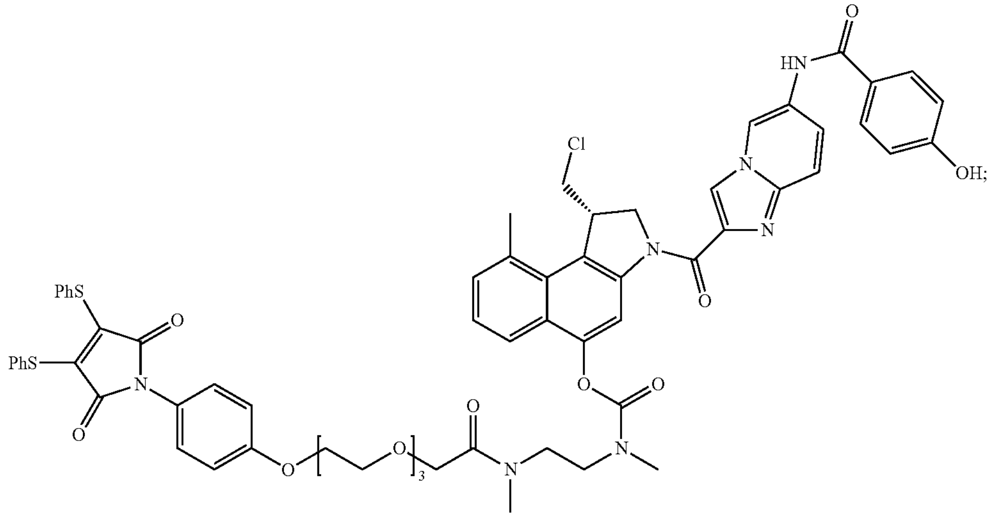
Formula 26
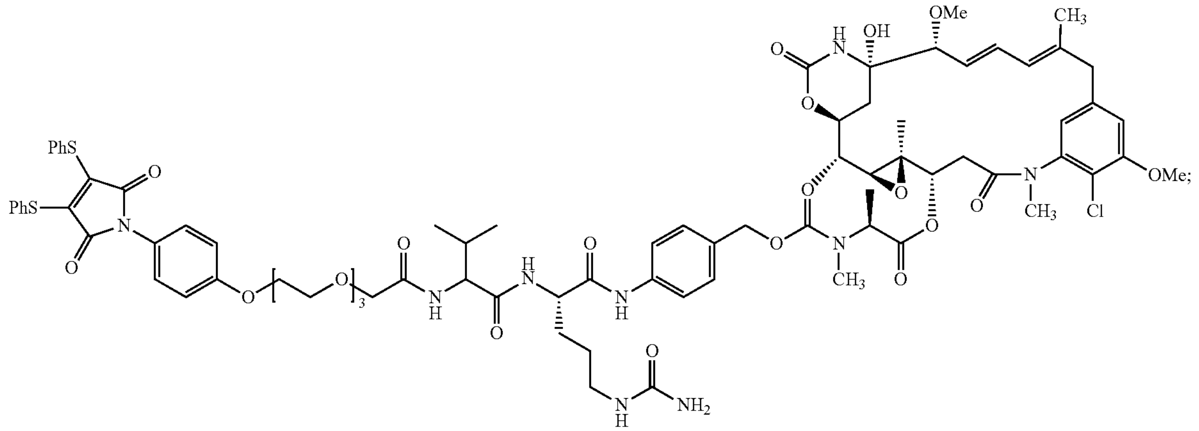
Formula 27
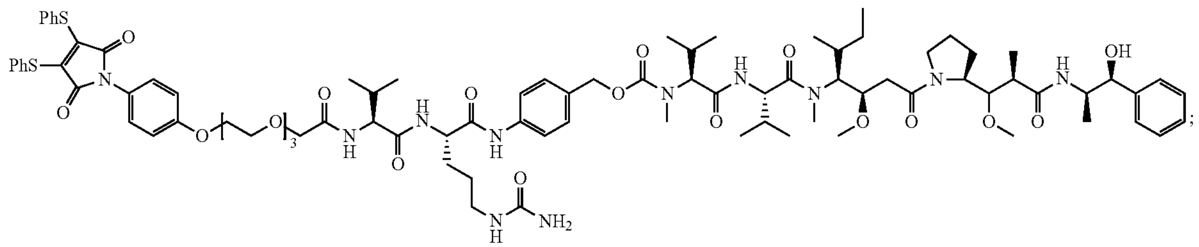

-continued
Formula 28
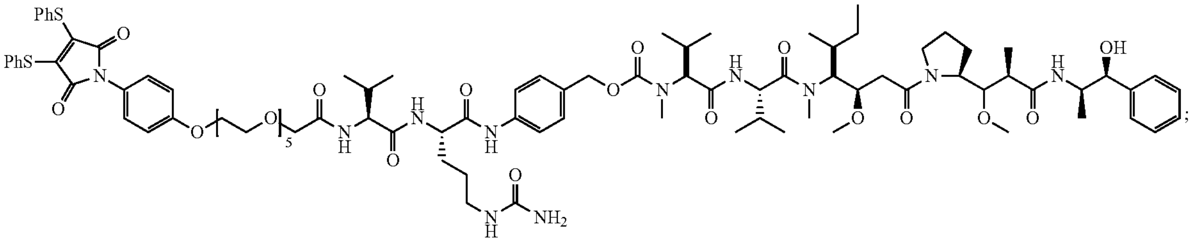
Formula 29
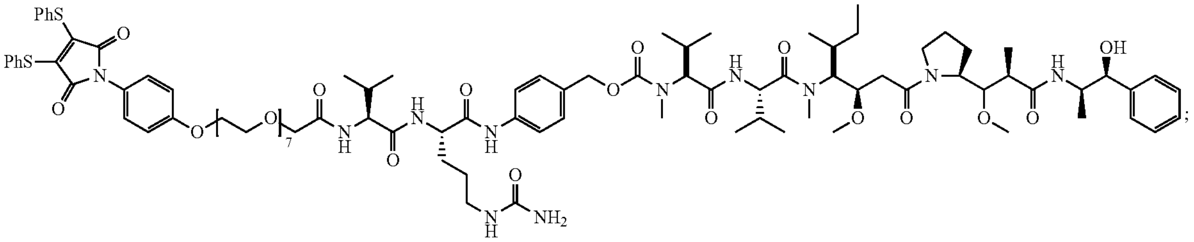
Formula 30
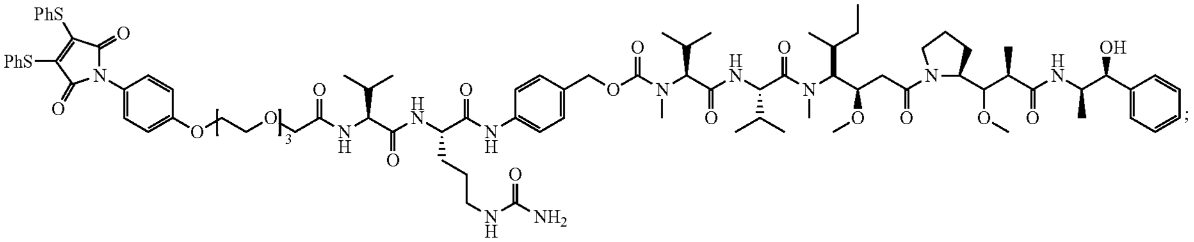
Formula 31
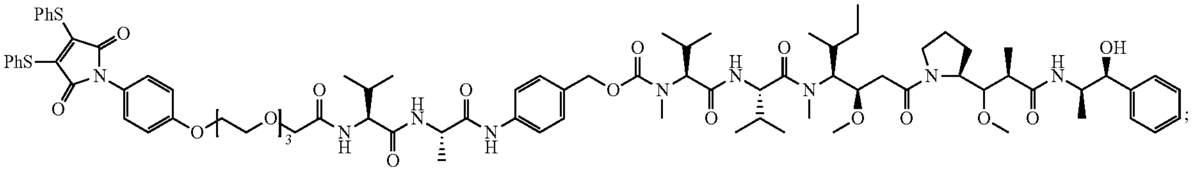
Formula 32
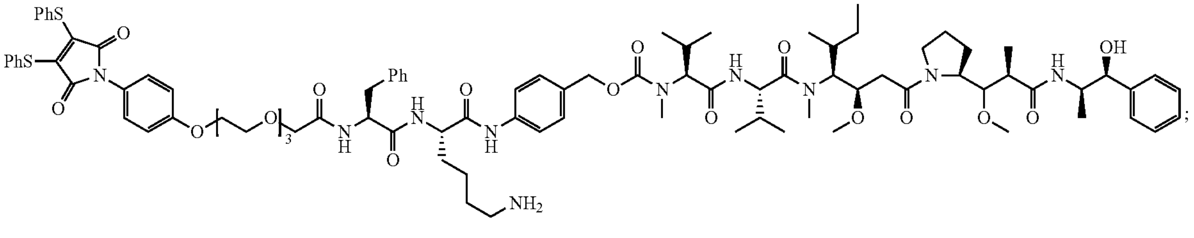
Formula 33
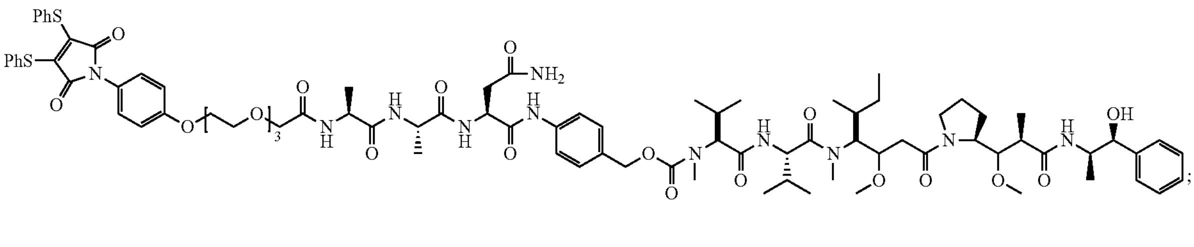

-continued
Formula 34
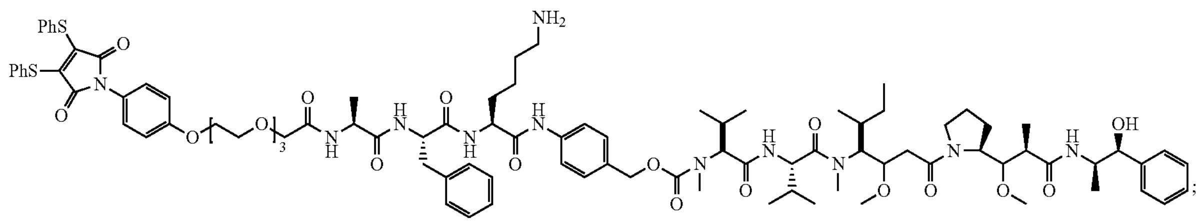
Formula 35
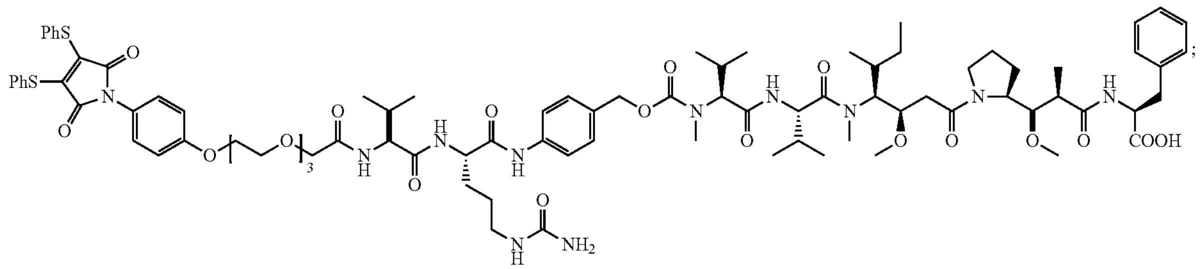
Formula 36
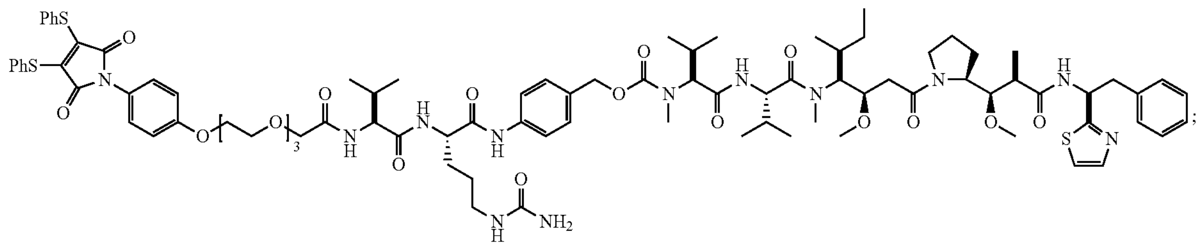
Formula 37
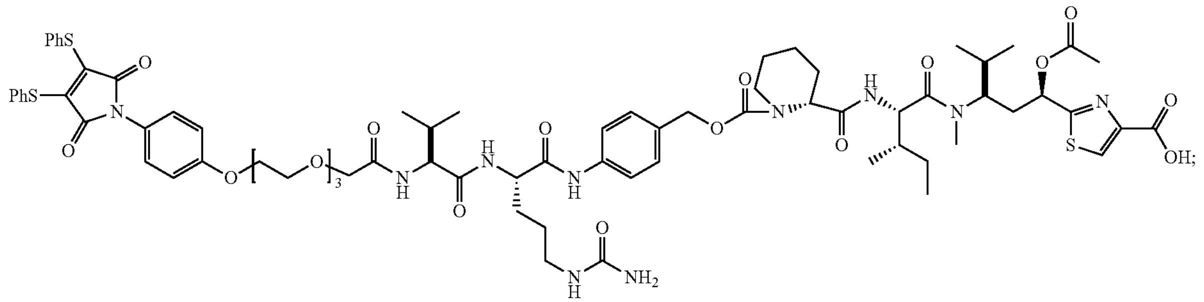
Formula 38
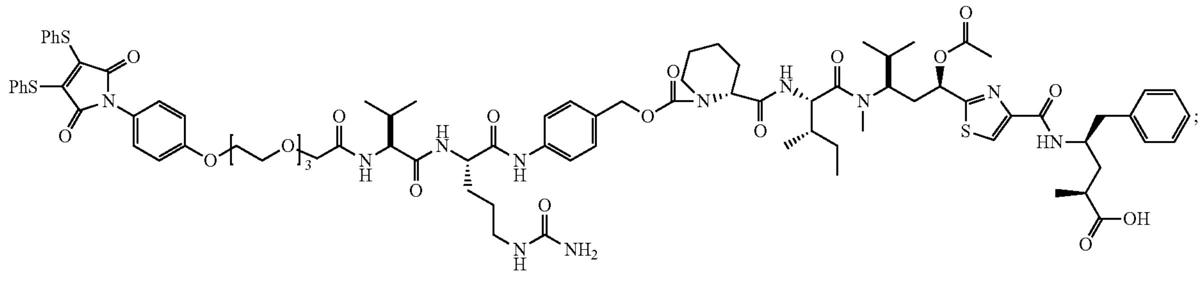

-continued
Formula 39
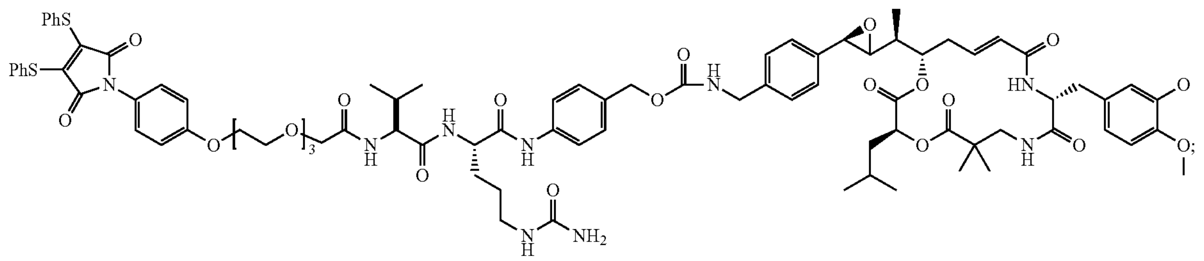
Formula 40
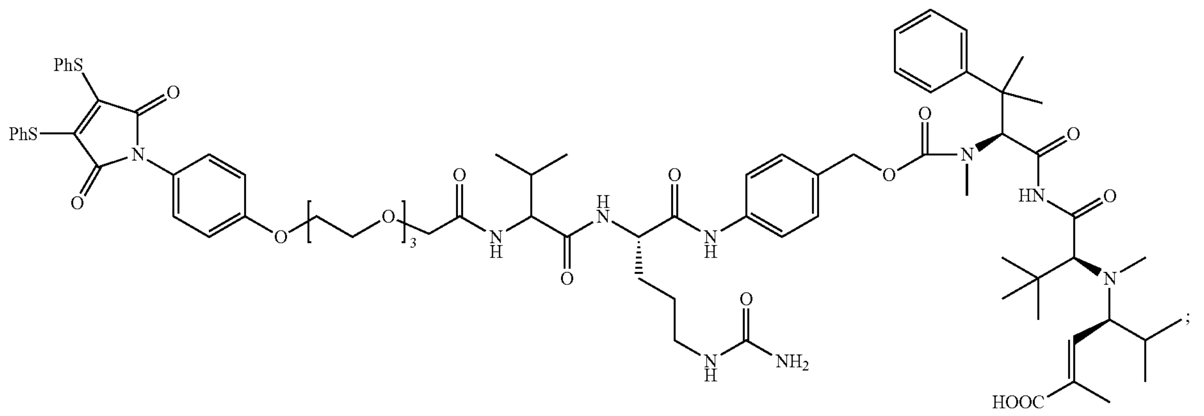
Formula 41
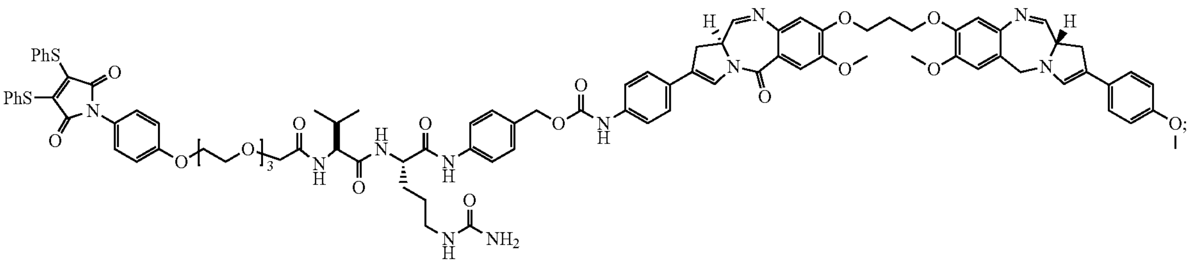
Formula 42
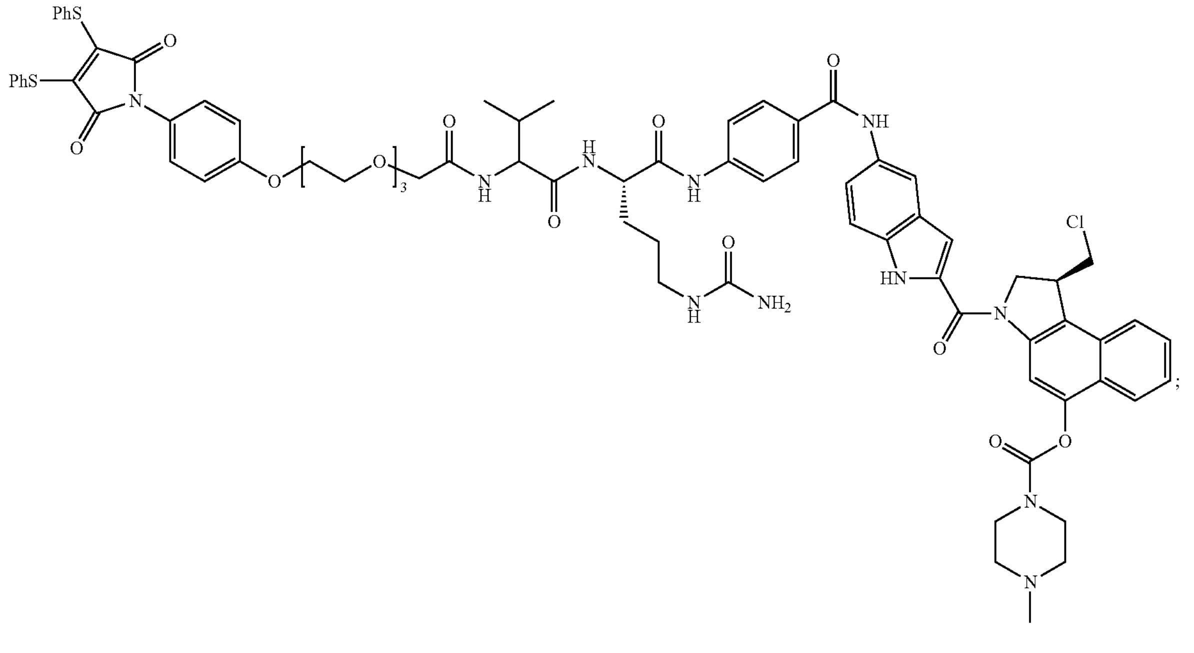

-continued
Formula 43
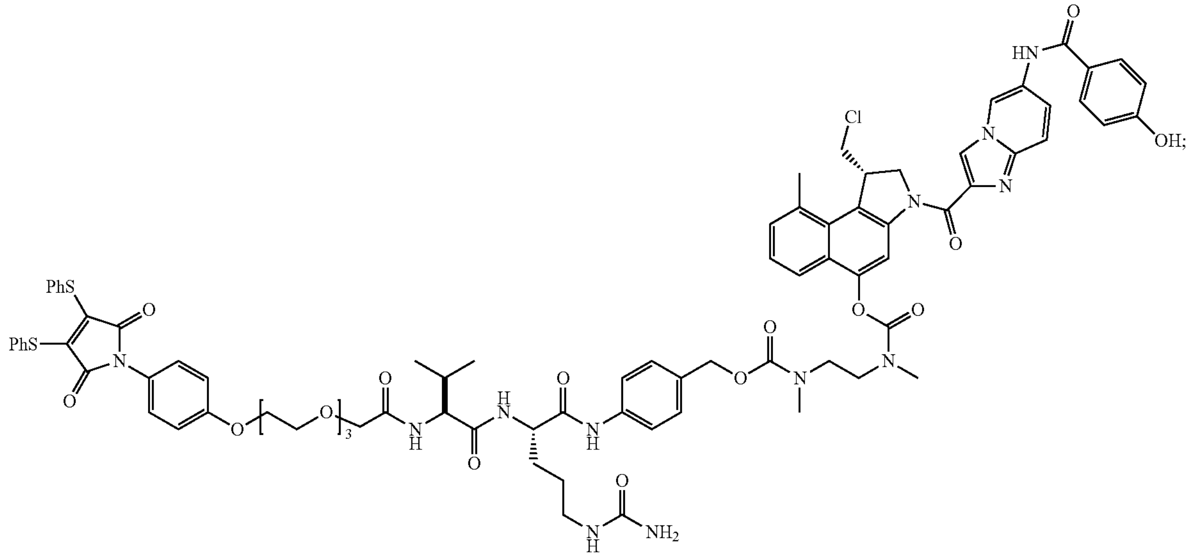
Formula 44
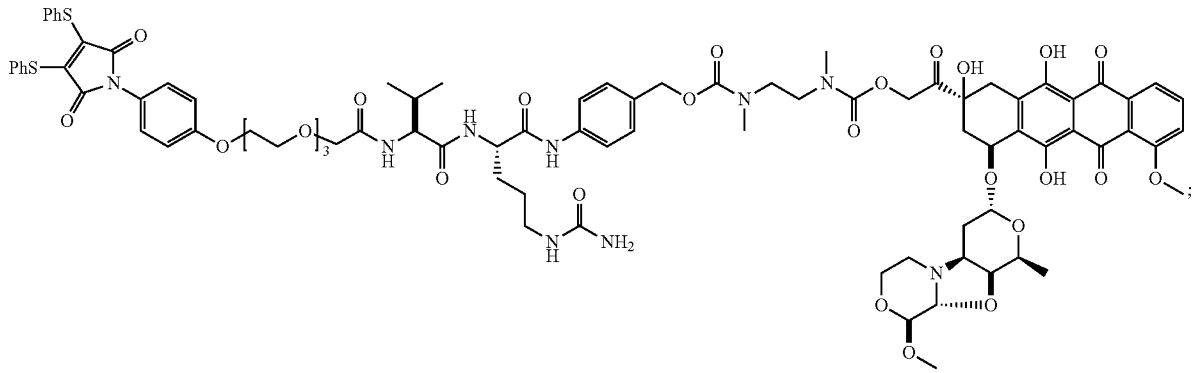
Formula 45
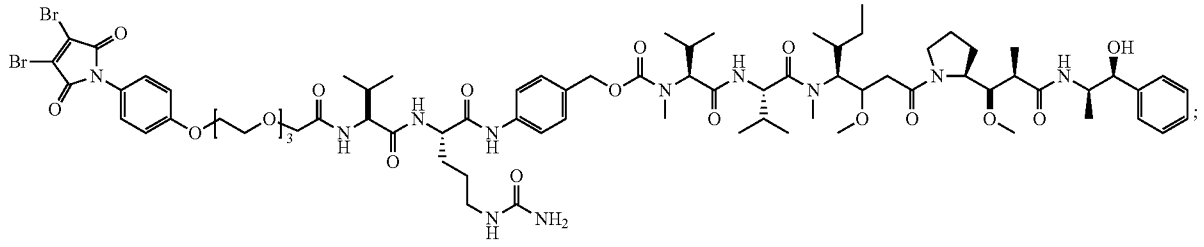
Formula 46
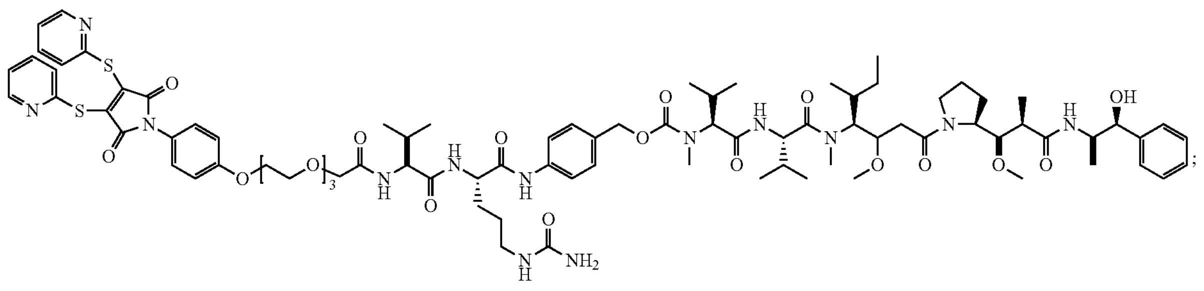

-continued
Formula 47
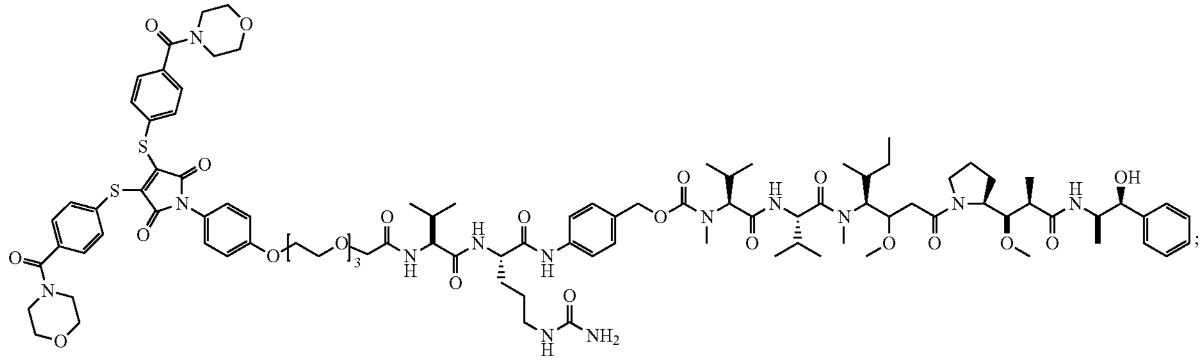
Formula 48
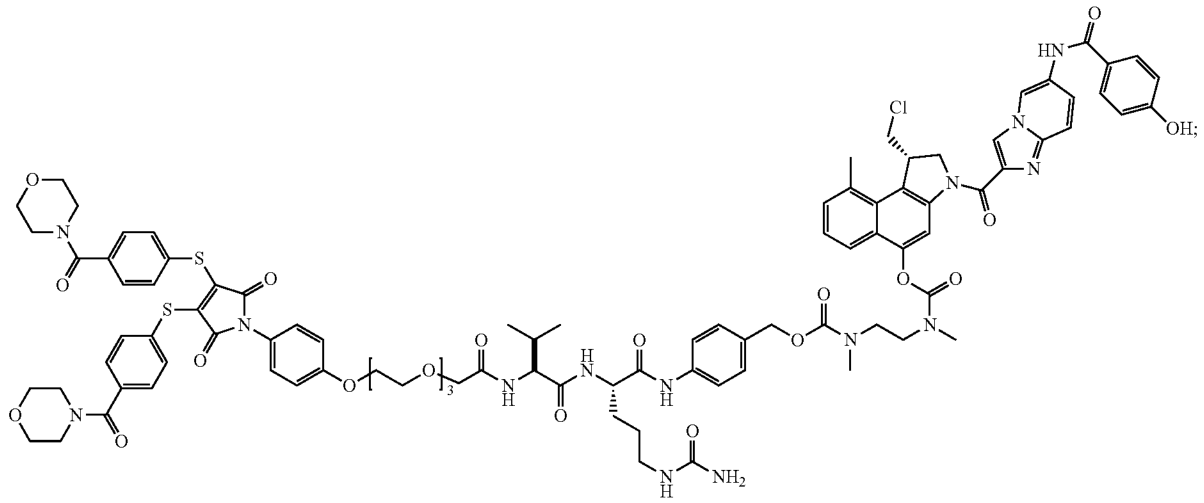
Formula 49
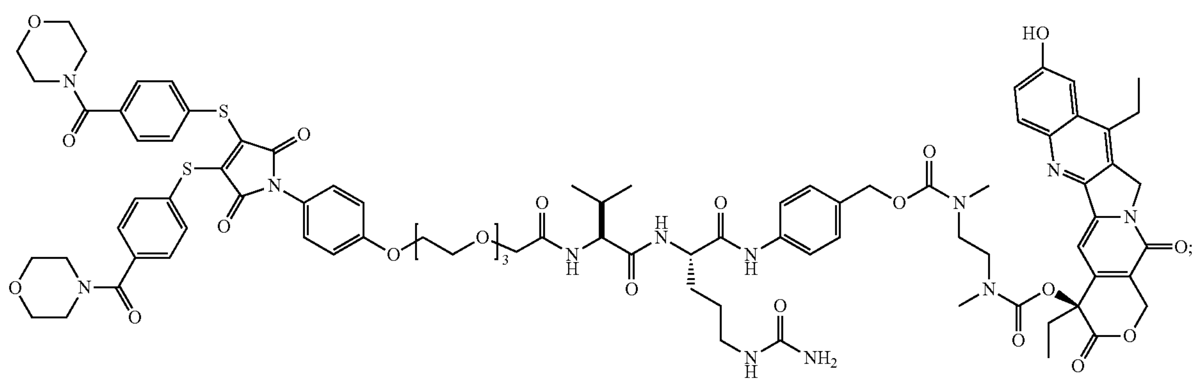

-continued
Ib-1
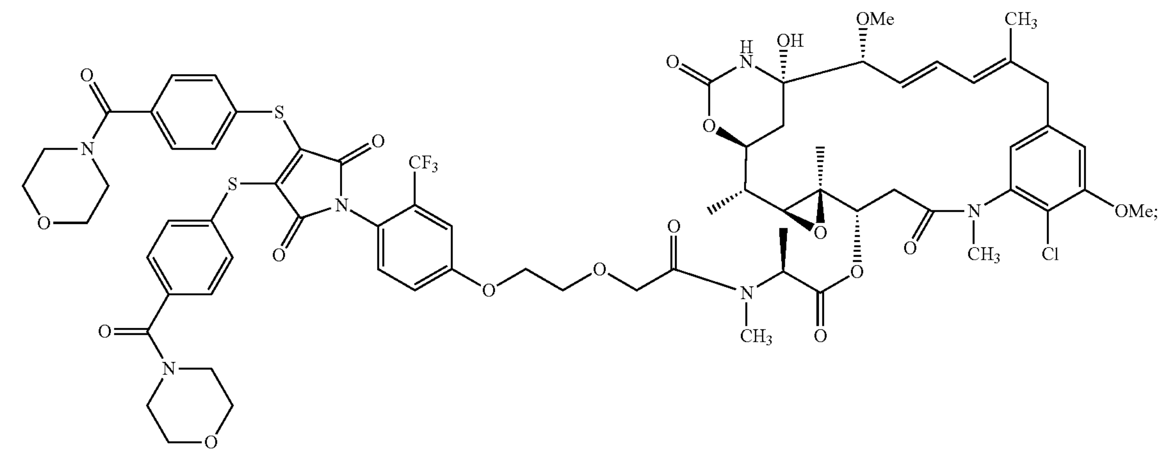
Ib-2
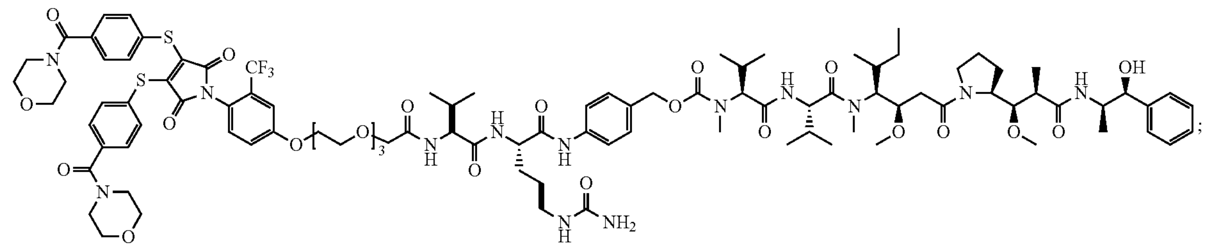
Ib-3
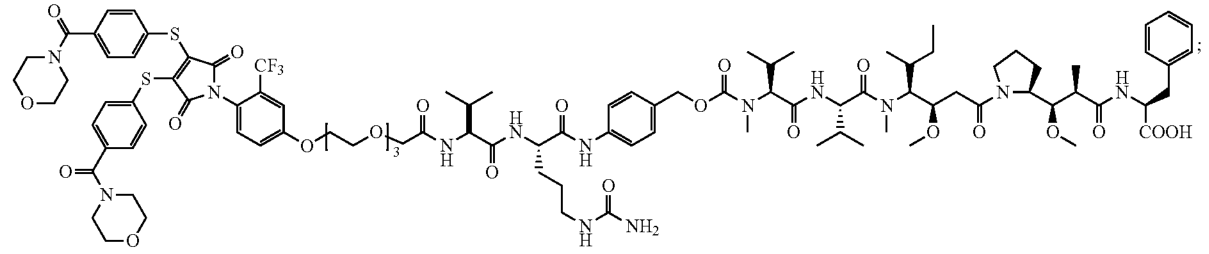
Ib-4
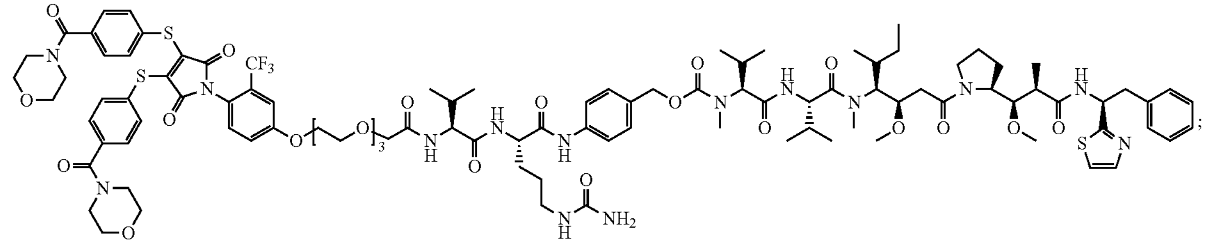
Ib-5
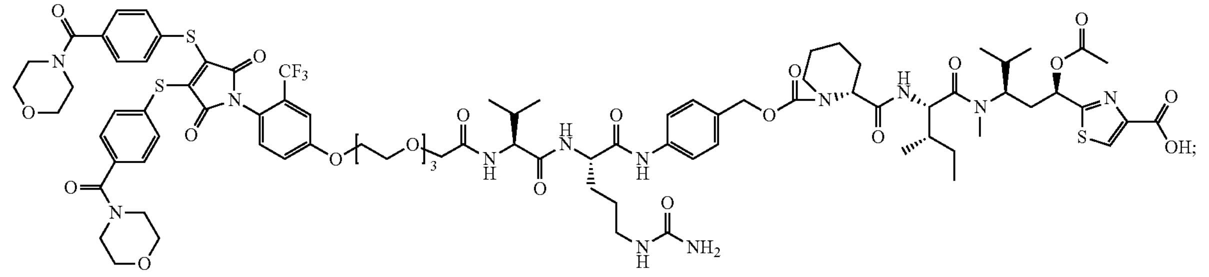

-continued
Ib-6
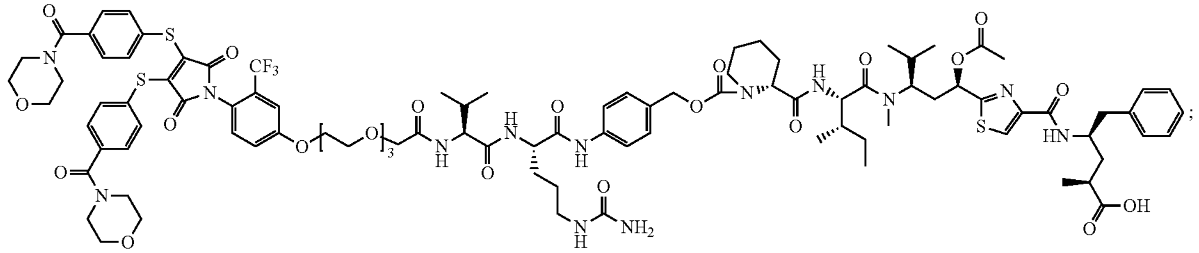
Ib-7
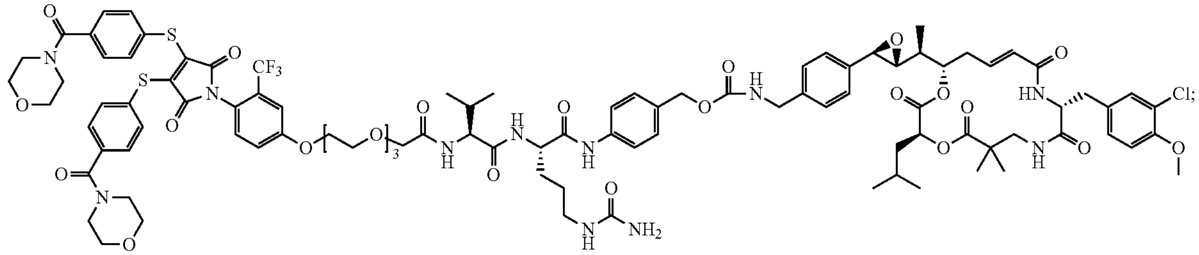
Ib-8
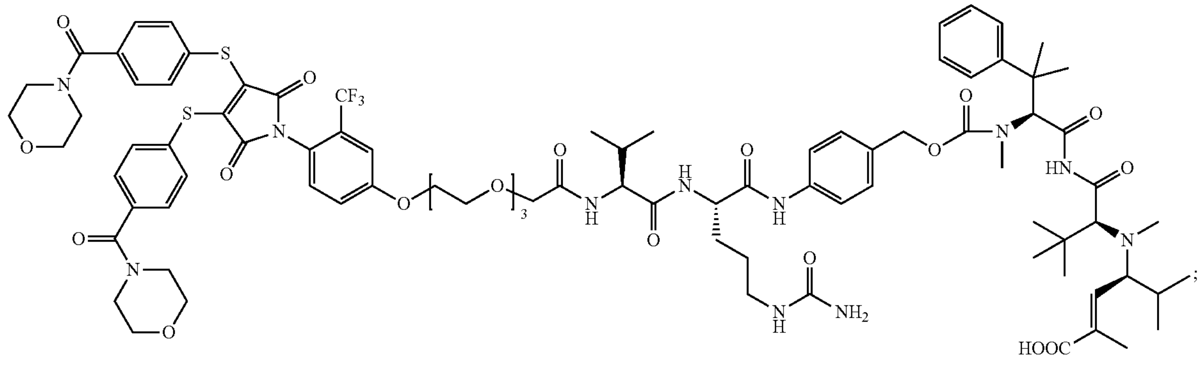
Ib-9
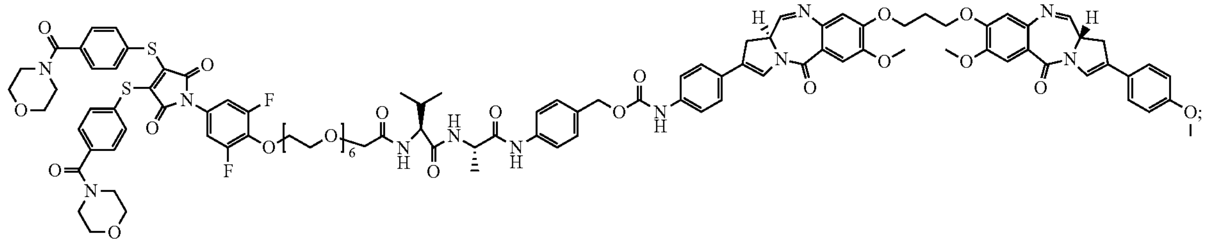

-continued
Ib-10
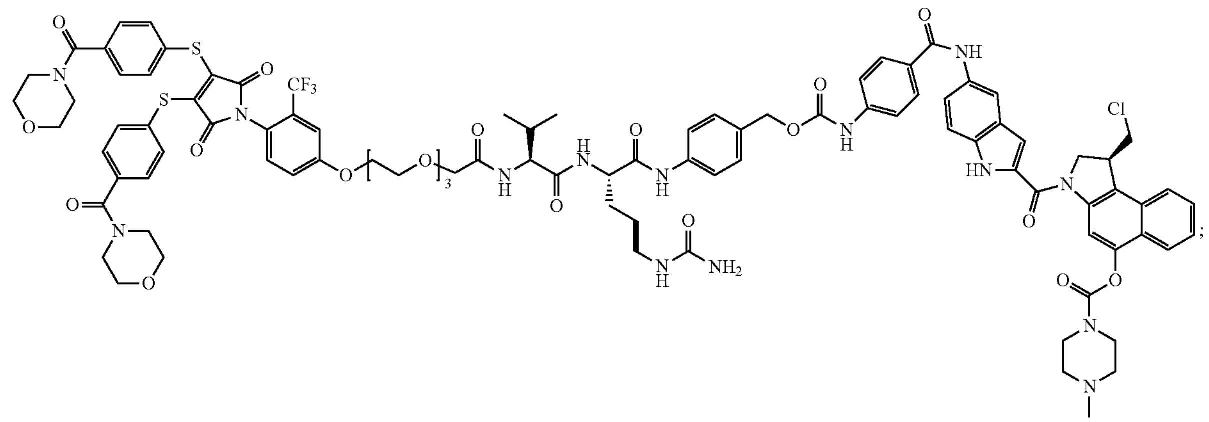
Ib-11
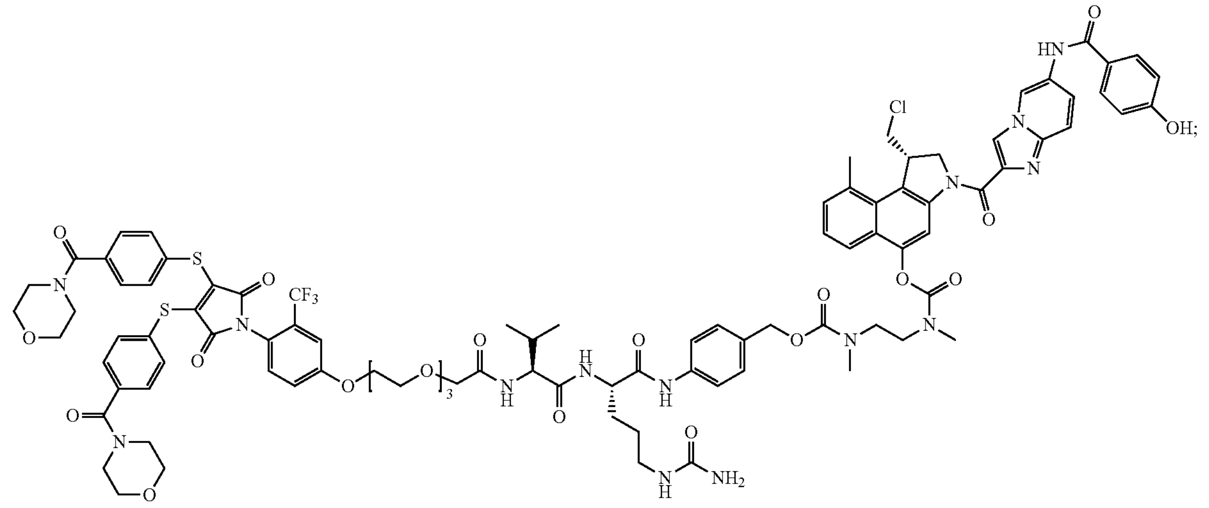
Ib-12
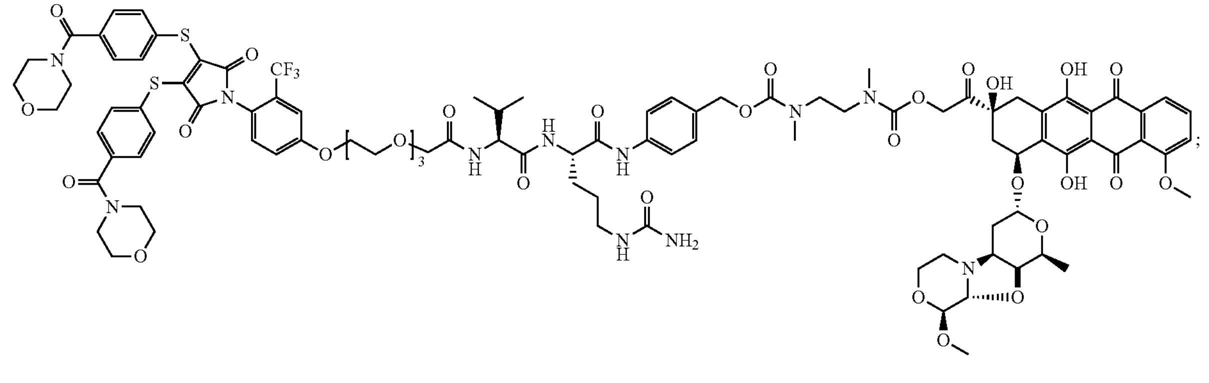

-continued
Ib-13
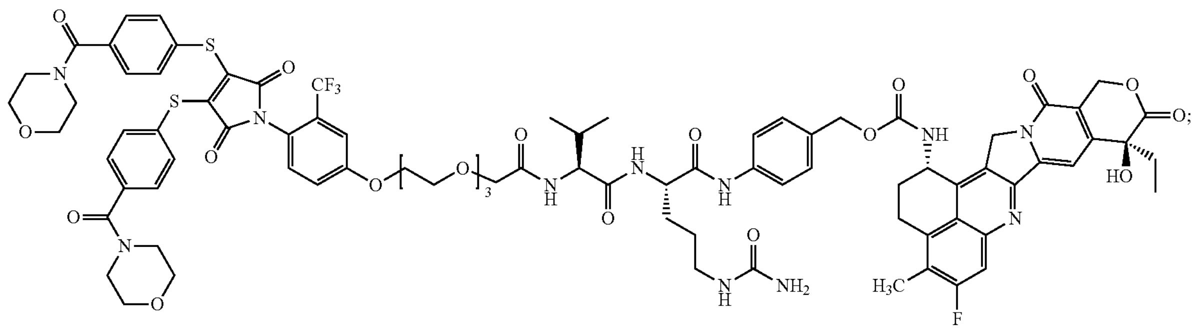
Ib-14
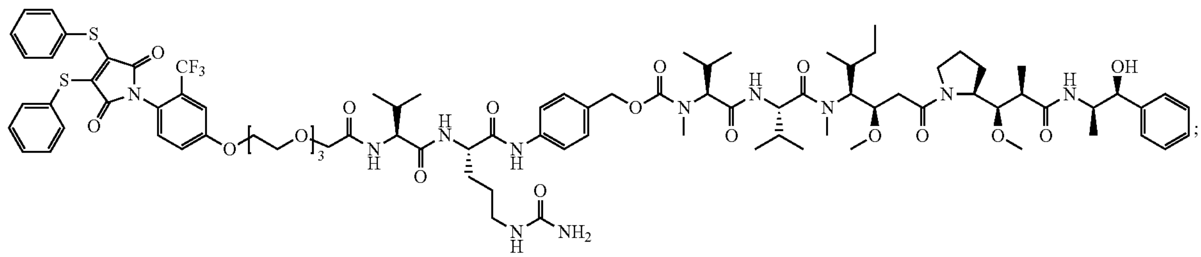
Ib-15
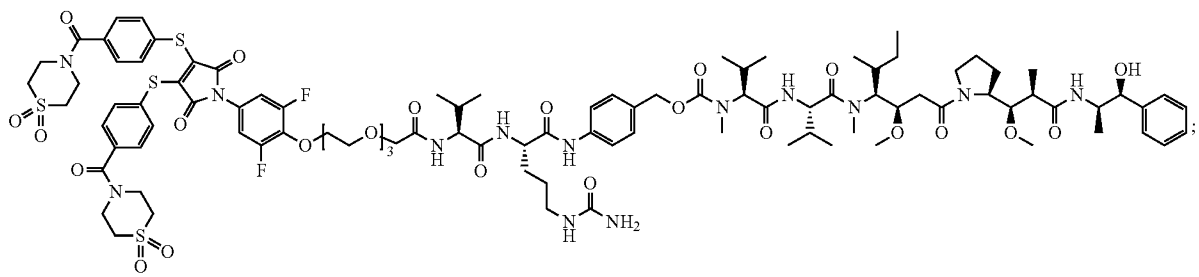
Ib-16
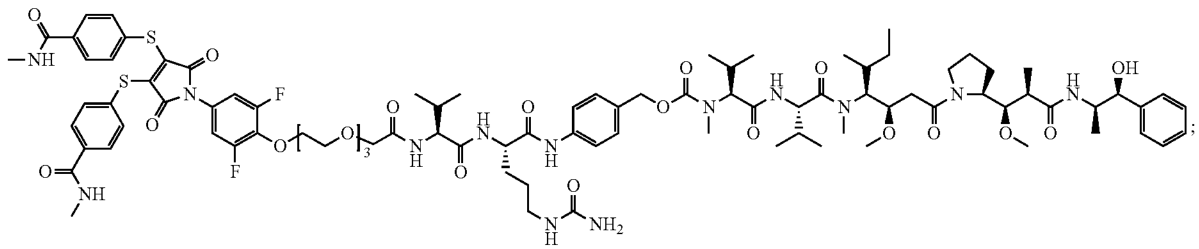
Ib-17
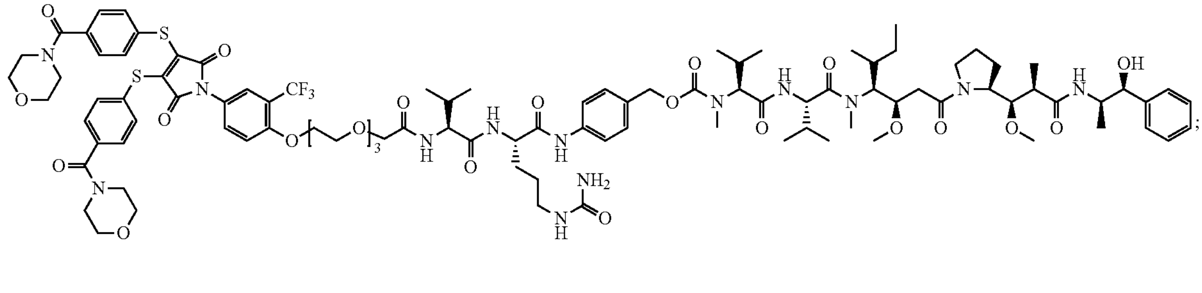

-continued
Ib-18
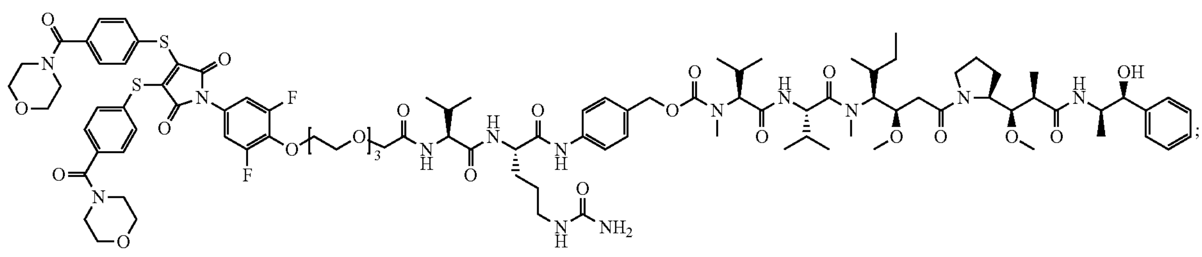
;
Ib-19
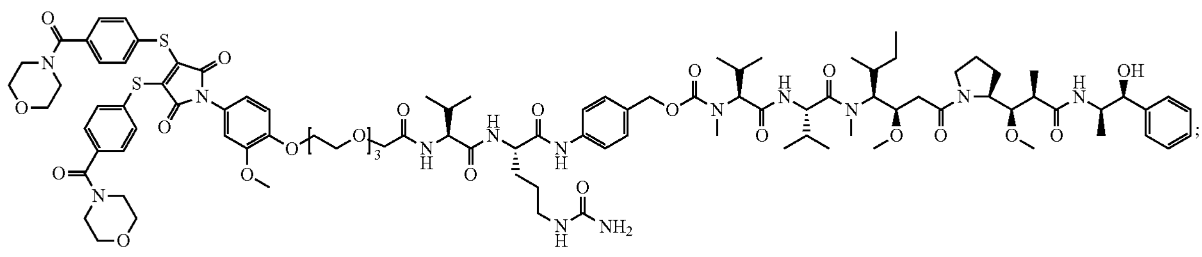
;
Ib-20
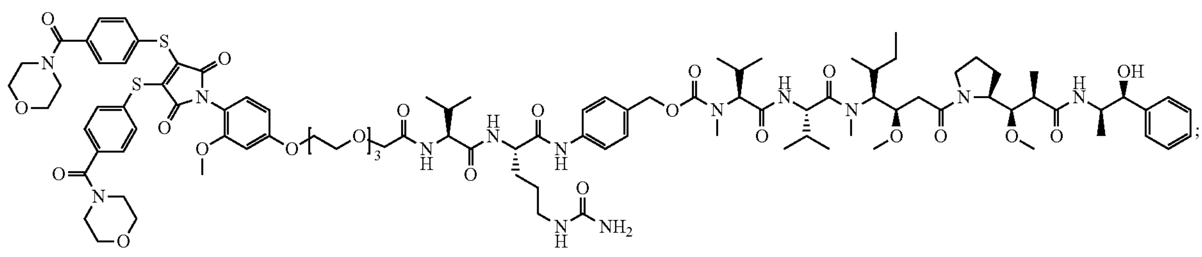
;
Ib-21
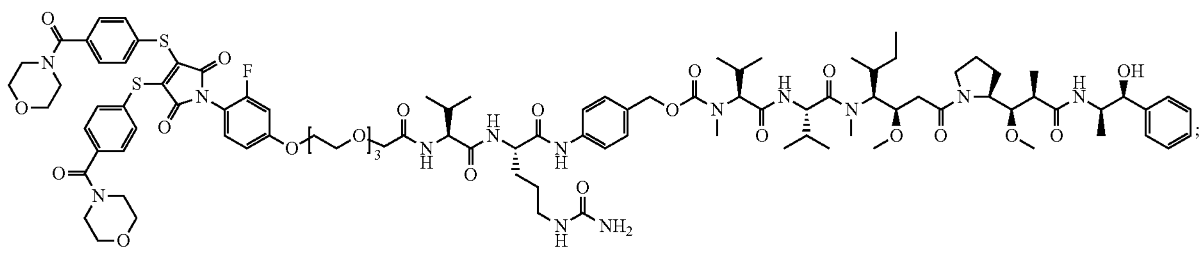
;
Ib-22
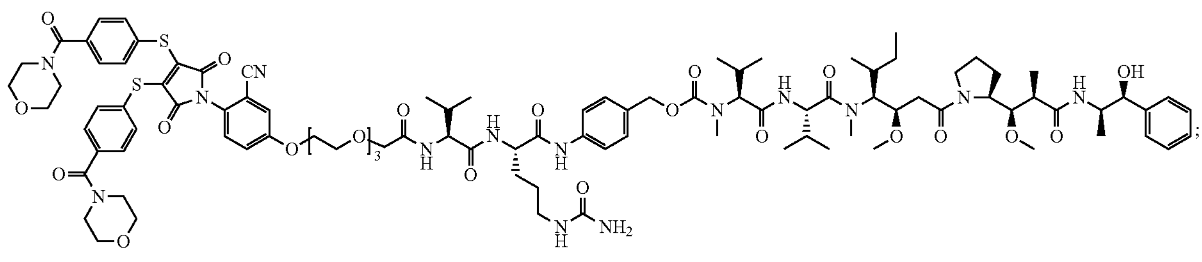
;

-continued

Ib-23

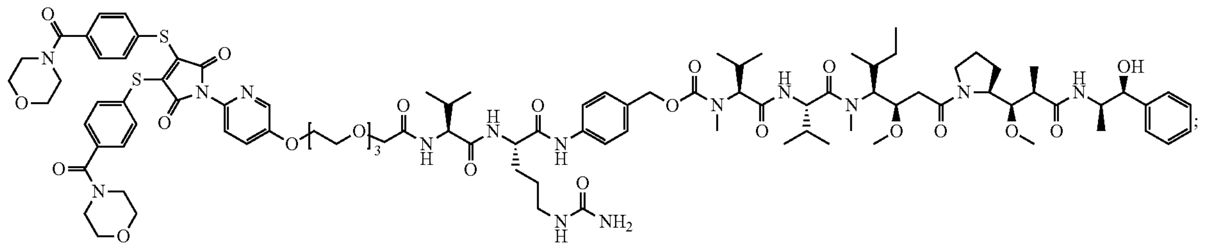

and

Ib-24

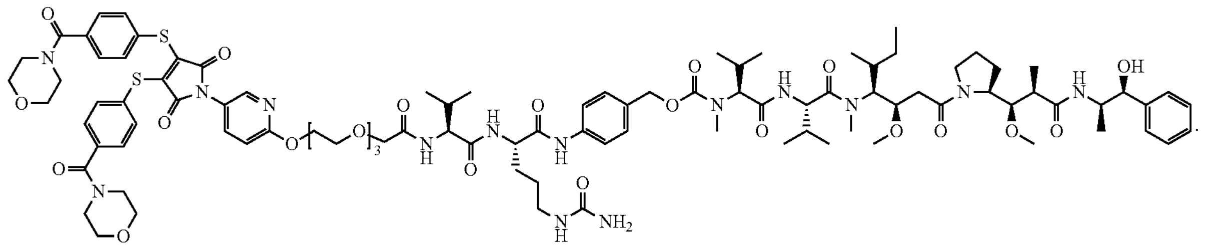

13. An antibody-drug conjugate, formed by coupling an antibody with the substituted maleamide linker-drug conjugate, a pharmaceutically acceptable salt or solvate thereof according to claim 5.

14. The antibody-drug conjugate according to claim 13, wherein the conjugate has a structure as shown in Formula Ic and/or Formula Id:

(Ic)

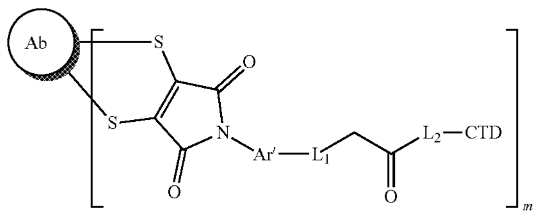

(Id)

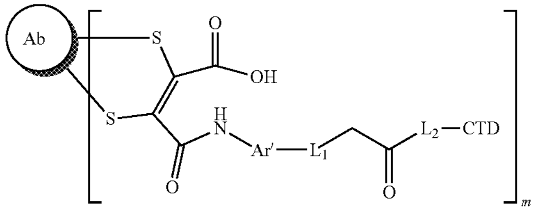

Ar', $L_1$, $L_2$, and CTD are defined as claim 5;
m=1.0-5.0;
Ab is selected from the group consisting of protein, enzyme, antibody, antibody fragment, and peptide.

15. The antibody-drug conjugate according to claim 13, wherein the antibody is selected from the group consisting of monoclonal antibody, bispecific antibody, chimeric antibody, humanized antibody and antibody fragment.

16. The antibody-drug conjugate according to claim 13, wherein the antibody is that capable of binding to a tumor-associated antigen selected from the group consisting of HER2, HER3, CD19, CD20, CD22, CD30, CD33, CD37, CD45, CD56, CD66e, CD70, CD74, CD79b, CD138, CD147, CD223, EpCAM, Mucin 1, STEAP1, GPNMB, FGF2, FOLR1, EGFR, EGFRvIII, Tissue factor, c-MET, Nectin 4, AGS-16, Guanylyl cyclase C, Mesothelin, SLC44A4, PSMA, EphA2, AGS-5, GPC-3, c-KIT, RoR1, PD-L1, CD27L, 5T4, Mucin 16, NaPi2b, STEAP, SLITRK6, ETBR, BCMA, Trop-2, CEACAM5, SC-16, SLC39A6, Delta-like protein3, and Claudin 18.2.

17. The antibody-drug conjugate according to claim 16, wherein the HER2 antibody is selected from Trastuzumab or Pertuzumab; or the EGFR antibody is selected from Erbitux or Vectibix.

18. A pharmaceutical composition, comprising: (a) the antibody-drug conjugate according to claim 13; and (b) a pharmaceutically acceptable diluent, carrier or excipient.

19. A use of the antibody-drug conjugate according to claim 13 for manufacturing a medicament for the treatment of a tumor.

20. A method for preparing the antibody-drug conjugate according to claim 13, the method including the following steps:

(1) reacting an antibody with a reducing reagent in a buffer solution to obtain a reduced antibody;

(2) cross-linking a linker-drug conjugate with the reduced antibody obtained in step (1) in a mixture solution of a buffer solution and an organic solvent to obtain the antibody-drug conjugate.

21. The method for preparing the antibody-drug conjugate according to claim 20, wherein synthesis scheme of the method is as follows:

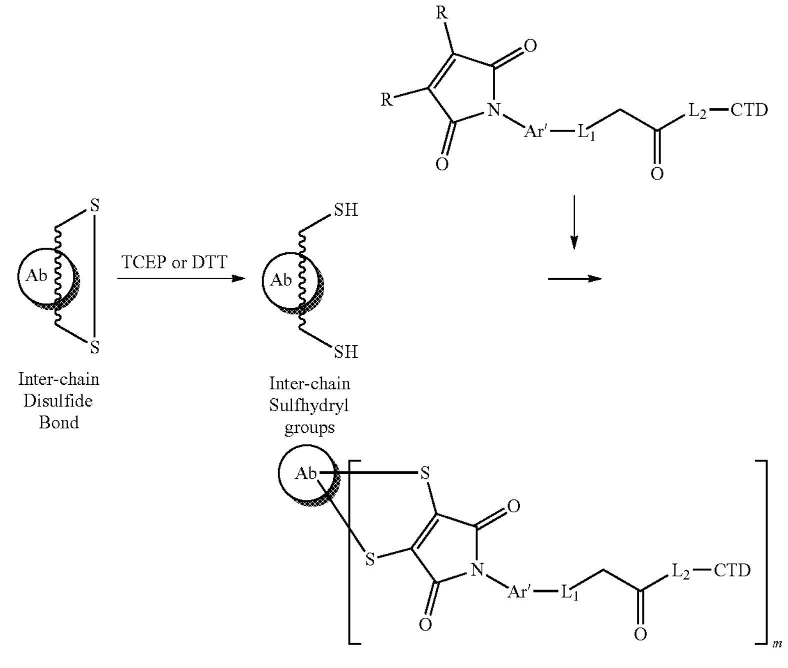

and/or

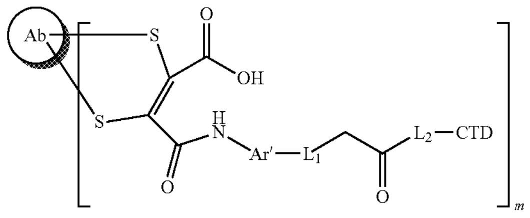

wherein R, Ab, Ar', $L_1$, $L_2$, CTD, and m are defined as claim 14.

22. A method for preparing the substituted maleamide linker according to claim 1, the method including the following steps:

performing a cyclization reaction of intermediate C and maleic anhydride dihalide to generate intermediate D, and performing a substitution reaction of intermediate D with aryl thiophenol to generate a linker as shown in Formula E, and synthesis scheme is as follows:

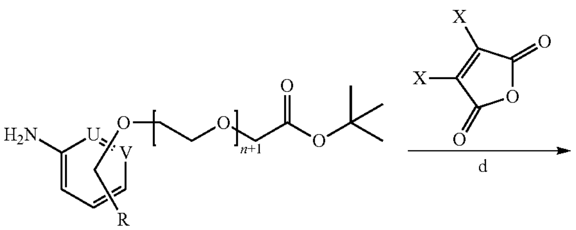

C

-continued

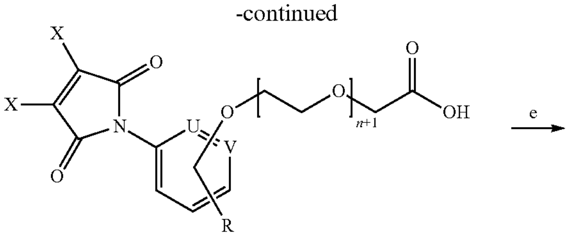

D

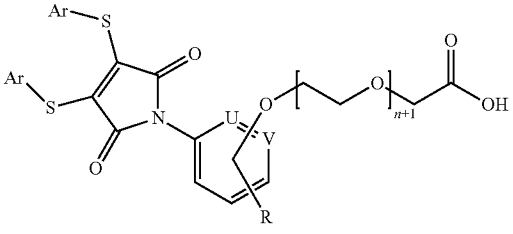

E wherein R and n are defined as claim 1; X represents halogen; and U and V are independently N or C.

23. The method for preparing the substituted maleamide linker according to claim 22, wherein intermediate C is obtained by reducing intermediate B, and synthesis scheme is as follows:

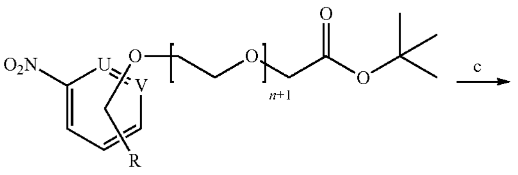

B

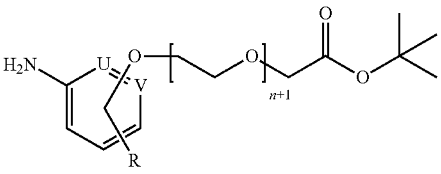

C wherein R, n, U, and V are defined as claim 22.

24. The method for preparing the substituted maleamide linker according to claim 23, wherein intermediate B is obtained by a substitution reaction of compound A with fluoronitrobenzene, and synthesis scheme is as follows:

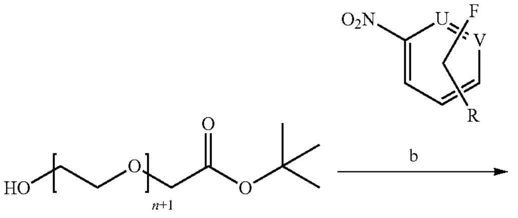

A

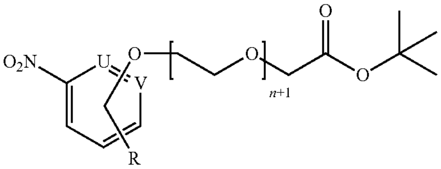

B wherein R, n, U, and V are defined as claim 22.

25. The method for preparing the substituted maleamide linker according to claim 24, wherein intermediate B is prepared as follows:

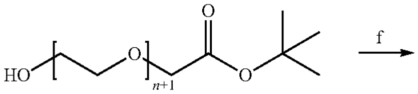

A

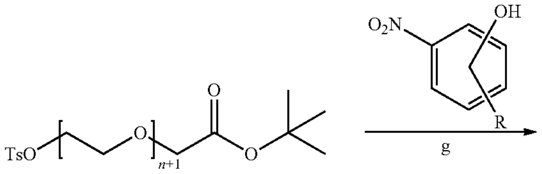

-continued

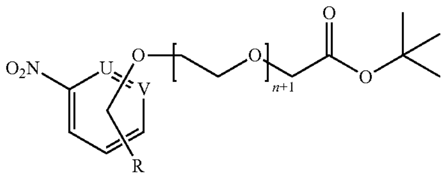

B wherein R, n, U, and V are defined as claim 22.

26. The method for preparing the substituted maleamide linker according to claim 25, wherein compound A is obtained by reacting n-ethylene glycol with tert-butyl haloacetate, and synthesis scheme is as follows:

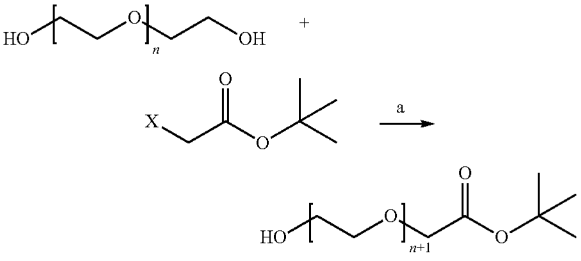

A wherein n and X are defined as claim 22.

27. A method for preparing the substituted maleamide linker-drug conjugate according to claim 5, the method including: performing a condensation reaction of a substituted maleimide linker and CTD containing a dipeptide/tripeptide-PAB to generate F1 or F'1 respectively; and synthesis schemes are as follows:

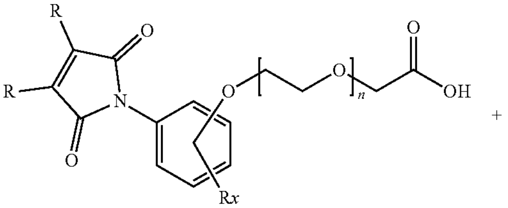

Ea

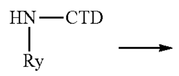

D1

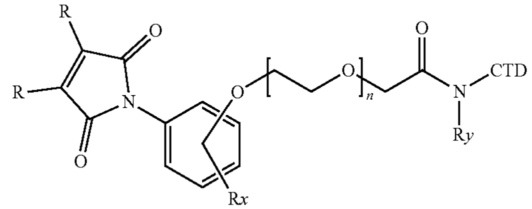

F1

-continued
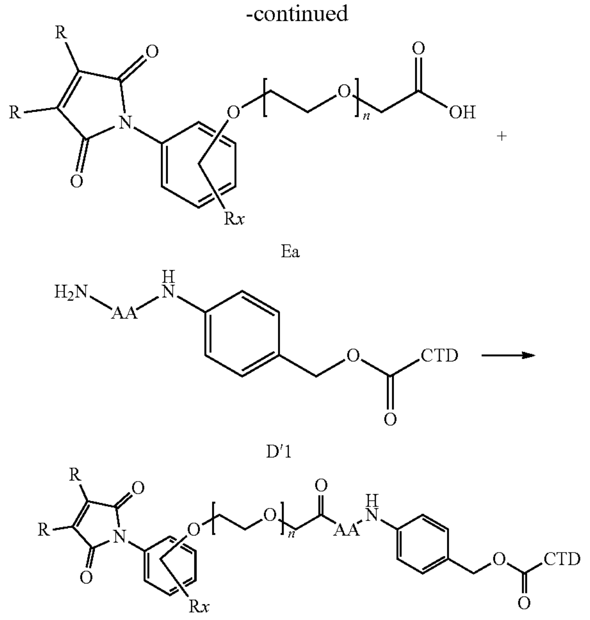
Ea
D'1
F'1
wherein R is defined as claim 1, Rx represents halogen, $C_1$-$C_4$ alkyl, $C_1$-$C_4$ alkoxy, trifluoromethyl, cyano, or amide group, and Ry represents H or alkyl.
28. The method for preparing the substituted maleamide linker according to claim 22, wherein X is Br or Cl.
* * * * *